US012502369B2

(12) United States Patent
Chen et al.

(10) Patent No.: US 12,502,369 B2
(45) Date of Patent: Dec. 23, 2025

(54) METHODS OF CANCER TREATMENT

(71) Applicant: K-GEN, INC., Burlingame, CA (US)

(72) Inventors: Ruihong Chen, Burlingame, CA (US); Chun Jiang, Hillsborough, CA (US)

( * ) Notice: Subject to any disclaimer, the term of this patent is extended or adjusted under 35 U.S.C. 154(b) by 0 days.

(21) Appl. No.: 15/765,124

(22) PCT Filed: Nov. 11, 2016

(86) PCT No.: PCT/US2016/061711
§ 371 (c)(1),
(2) Date: Mar. 30, 2018

(87) PCT Pub. No.: WO2017/083783
PCT Pub. Date: May 18, 2017

(65) Prior Publication Data

US 2018/0271819 A1 Sep. 27, 2018

Related U.S. Application Data

(60) Provisional application No. 62/306,019, filed on Mar. 9, 2016, provisional application No. 62/253,701, filed on Nov. 11, 2015.

(51) Int. Cl.

| | |
|---|---|
| ***A61K 31/215*** | (2006.01) |
| ***A61K 31/122*** | (2006.01) |
| ***A61K 31/336*** | (2006.01) |
| ***A61K 31/35*** | (2006.01) |
| ***A61P 35/00*** | (2006.01) |
| ***G01N 33/50*** | (2006.01) |

(52) U.S. Cl.
CPC .......... *A61K 31/215* (2013.01); *A61K 31/122* (2013.01); *A61K 31/336* (2013.01); *A61K 31/35* (2013.01); *G01N 33/5011* (2013.01); *G01N 2333/912* (2013.01)

(58) Field of Classification Search
CPC .. A61K 31/215; A61K 31/122; A61K 31/336; A61K 31/35; G01N 33/5011; G01N 2333/912; A61P 35/00
See application file for complete search history.

(56) References Cited

U.S. PATENT DOCUMENTS

| | | | |
|---|---|---|---|
| 4,716,179 | A | 12/1987 | Hecker |
| 5,145,842 | A | 9/1992 | Driedger |
| 6,268,395 | B1 | 7/2001 | Hattori |
| 6,432,452 | B1 | 8/2002 | Aylward |
| 8,022,103 | B2 | 9/2011 | Xu |
| 8,067,632 | B2 | 11/2011 | Wender |
| 8,106,092 | B2 | 1/2012 | Ogbourne |
| 8,431,612 | B2 | 4/2013 | Xu |
| 8,536,378 | B2 | 9/2013 | Wender |
| 8,816,122 | B2 | 8/2014 | Wender |
| 8,901,356 | B2 | 12/2014 | Hogburg |
| 9,102,687 | B2 | 8/2015 | Grue-SøRensen |
| 9,314,458 | B2 | 4/2016 | Aylward |
| 10,099,996 | B2 | 10/2018 | Han |
| 10,278,934 | B2 | 5/2019 | Han |
| 2008/0069809 | A1 | 3/2008 | Ogbourne |
| 2009/0187046 | A1 | 7/2009 | Wender |
| 2010/0204318 | A1 | 8/2010 | Obgourne |
| 2011/0014699 | A1 | 1/2011 | Wender |
| 2012/0101283 | A1 | 4/2012 | Wender |
| 2013/0324600 | A1 | 12/2013 | Grue-Sørensen |
| 2013/0331446 | A1 | 12/2013 | Grue-Sørensen |
| 2014/0018329 | A1 * | 1/2014 | Han ..................... A61K 31/215 514/160 |
| 2014/0371311 | A1 | 12/2014 | Oh |
| 2015/0175622 | A1 | 6/2015 | Laing |

FOREIGN PATENT DOCUMENTS

| | | | |
|---|---|---|---|
| WO | 2013182688 | A1 | 12/2013 |
| WO | 2014066967 | A1 | 8/2014 |

OTHER PUBLICATIONS

Ersvaer et al (Toxins, 2010; 2:174-194) (Year: 2010).*
Smanski et al (Methods in Enzymology, 2012; 515:163-186) (Year: 2012).*
Gura et al (Science, 1997, 278:1041-1042); (Year: 1997).*
Johnson et al (British Journal of Cancer, 2001, 84:1424-1431); and (Year: 2001).*
Mochly-Rosen et al (Nat Rev Drug Discov, 2012; 11:937-957) (Year: 2012).*
Ochi et al (J Cell Physiol, 2011; 226:1074-1081) (Year: 2011).*
Azmi (Future Med Chem, 2012; 4(8),939-941) (Year: 2012).*
Dawson (Science, 2017; 355:1147-1152) (Year: 2017).*
Hunger-Glaser (JBC, 2003; 278(25):22631-22643) (Year: 2003).*
Brändlin et al (JBC, 2002; 277(8):6490-6496) (Year: 2002).*
Ali, et al., "Protein kinases C isozymes are differentially expressed in human breast carcinomas," Life Sci. 2009; 84(21-22):766-771.
Antal et al., "Cancer-Associated Protein Kinase C Mutations Reveal Kinase's Role as Tumor Suppressor," Cell, 2015; 160:489-502.
Barcelo et al., "Phosphorylation at Ser-181 of Oncogenic KRAS Is Required for Tumor Growth," Cancer Res., 2014; 74(4):1190-1199.
Basu "The Potential of Protein Kinase C as a Target for Anticancer Treatment," Pharmac Ther., 1993; 59(3):257-280. Entire Document.
Beans et al., "Highly potent, synthetically accessible prostratin analogs induce latent HIV expression in vitro and ex vivo," Proc Natl Acad Sci USA., 2013; 110(29):11698-11703.
Bentley et al., "Accurate Whole Human Genome Sequencing using Reversible Terminator Chemistry," Nature, 2008; 456(7218): 53-59.
Bond et al., "Cytotoxic Action of Phorbol Esters on Human Pancreatic Cancer CellsInt J Cancer.," 2007; 121(7):1445-54.
Cariello et al., "Resolution of a missense mutant in human genomic DNA by denaturing gradient gel electrophoresis and direct sequencing using in vitro DNA amplification: HPRT Munich," Am J Hum Genet., 1988; 42(5):726-734.

(Continued)

*Primary Examiner* — Rayna Rodriguez

(57) ABSTRACT

This present disclosure is directed to a method of selecting a cancer for treatment with protein kinase C (PKC) activators, and corresponding methods of treating the cancer with PKC activators.

21 Claims, 42 Drawing Sheets

(56) References Cited

OTHER PUBLICATIONS

Chen et al., "Absolute quantitation of endogenous proteins with precision and accuracy using a capillary Western system," Anal Biochem., 2013; 442(1):97-103
Chen et al., "An Overview of Cancer Drugs Approved by the US Food and Drug Administration Based on the Surrogate End Point of Response Rate," JAMA Intern Med., 2019; 179(7):915-921.
Chin et al., "Nonhybrid, finished microbial genome assemblies from long-read SMRT sequencing data," Nat Methods, 2013; 10(6):563-569.
Clark, et al., "Altered protein kinase C (PKC) isoforms in non-small cell lung cancer cells: PKCdelta promotes cellular survival and chemotherapeutic resistance," Cancer Res., 2003; 63(4):780-786.
Cotton et al., "Reactivity of cytosine and thymine in single-base-pair mismatches with hydroxylamine and osmium tetroxide and its application to the study of mutations," Proc Natl Acad Sci USA., 1988; 85(12):4397-4401.
Drmanac et al., "Human genome sequencing using unchained base reads on self-assembling DNA nanoarrays," Science, 2010; 327(5961):78-81.
Elisabah et al., "Immunohistochemical assay for detection of K-ras protein expression in metastatic colorectal cancer," 2013; J Egypt Natl Cancer Inst 25(1):51-56.
Ersvaer et al., "The Protein Kinase C Agonist PEP005 (Ingenol 3-Angelate) in the Treatment of Human Cancer: A Balance between Efficacy and Toxicity," Toxins, 2010; 2:174-194, abstract; p. 178, para 4 to p. 179, Para 1; pp. 176-177, Tables 1 and 2; p. 175, para 2.
Garczarczyk et al., "Protein kinase Cγ in colon cancer cells: Expression, $Thr^{514}$ phophorylation and sensitivity to butyrate-mediated upregulation as related to the degree of differentiation," Chem Biol Interact., 2010; 185(1):25-32.
Genbank Database [Online] (Oct. 17, 2008) "*Homo sapiens*K-ras oncogene protein (KRAS) mRNA, complete cds," Accession No. M54968.1 Accessible on the Internet at URL: http://www.ncbi.nlm.nih.gov/nuccore/M54968.1.
Genbank Database [Online] (Dec. 29, 2018) "GTPase Nras [*Homo sapiens*]," Accession No. NP_002515 Accessible on the Internet at URL: http://www.ncbi.nlm.nih.gov/protein/np_002515.
Genbank Database [Online] (Oct. 23, 2008) "Human N-ras Mrna and flanking regions," Accession No. X02751.1 Accessible on the Internet at URL: http://www.ncbi.nlm.nih.gov/nuccore/X02751.
Hamilton et al., "Constitutive Association of c-N-Ras with c-Raf-1 and Protein Kinase Cε in Latent Signaling Modules," J Biol Chem., 2001; 276(31):29079-29090.
Han, et al., "Expression and function of classical protein kinase C isoenzymes in gastric cancer cell line and its drug-resistant sublines," World J Gastroenterol., 2002; 8(3):441-445.
Iori et al., "In situ protein Kinase C activity is increased in cultured fibroblasts from Type 1 diabetic patients with nephropathy," Diabetolgia, 2003; 46(4):524-530.
Igumenova, "Dynamics and membrane interactions of protein kinase C," Biochemistry, 2015; 54(32):4953-4968.
Jarvius et al., "In Situ Detection of Phosphorylated Platelet-derived Growth Factor Receptor β Using a Generalized Proximity Ligation Method," 2007; Method Mol Cell Proteomics 6(9):1500-1509.
Kawamura et al., "Nineteen-step total synthesis of (+)-phorbol," Nature, 2016; 532:90-93.
Karabacak et al., "Microfluidic, marker-free isolation of circulating tumor cells from blood samples," Nat Protoc., 2014; 9(3):694-710.
Kazanietz et al., "Residues in the Second Cysteine-rich Region of Protein Kinase C δ Relevant to Phorbol Ester Binding as Revealed by Site-directed Mutagenesis," J Biol Chem., 1995; 270(37):21852-21859.
Kornev et al., "Surface comparison of active and inactive protein kinases identifies a conserved activation mechanism," Proc Natl Acad Sci USA., 2006; 103(47): 17783-17788.
Lu et al., "Tumor Promotion by Depleting Cells of Protein Kinase Cδ," Mol Cell Biol., 1997; 17(6):3418-3428.
Manzow, et al., "Evidence against a role of general protein kinase C downregulation in skin tumor promotion," Int J Cancer., 2000; 85(4): 503-507.
Marguiles et al., "Genome sequencing in microfabricated high-density picolitre reactors," Nature, 2005; 437(7057):376-380.
Mullin et al., "Increased Tight Junction Permeability Can Result from Protein Kinase C Activation/Translocation and Act as a Tumor Promotional Event in Epithelial Cancers," Adv Drug Deliv Rev; Annals of the New York Academy of Sciences, 2000; 915(1):231-236.
Newton, "Protein kinase C: poised to signal," Am J Physiol Endocrinol Metab., 2010; 298:E395-E402.
Nishikawa et al., "Determination of the Specific Substrate Sequence Motifs of Protein Kinase C Isozymes," J Biol Chem., 1997; 272(2):952-960.
Niu et al., "In vitro human cell line models to predict clinical response to anticancer drugs," Pharmacogenomics., 2015; 16(3):273-285.
Picato—Highlights of Prescribing Information, Revised 2017 (11 pages).
Shenk et al., "Biochemical method for mapping mutational alterations in DNA with S1 nuclease: the location of deletions and temperature-sensitive mutations in simian virus 40," Proc Natl Acad Sci USA., 1975; 72(3):989-993.
Steinberg, "Structural Basis of Protein Kinase C Isoform Function," Physiol Rev., 2008; 88(4): 1341-1378.
Stott et al., "Isolation of circulating tumor cells using a microvortex-generating herringbone-chip," Proc Natl Acad Sci USA., 2010; 107(43):18392-18397.
Toomik et al., "A potent and highly selective peptide substrate for protein kinase C assay," Biochem J., 1997; 322(2):455-460.
Tsai et al., "Isolation of Phorbol Esters from Euphorbia grandicornis and Evaluation of Protein Kinase C- and Human Platelet-Activating Effects of Euphorbiacease Diterpenes," J Nat Prod., 2016; 79(10):2658-2666.
Van de Stolpe et al., "Circulating tumor cell isolation and diagnostics: toward routine clinical use," Cancer Res., 2011; 71(18):5955-5960.
Vila-Petroff et al., "$Ca^{2+}$/calmodulin-dependent protein kinase II contributes to intracellular pH recovery from acidosis via $Na^+/H^+$ exchanger activation," J Mol Cell Cardiol., 2010; 49(1):106-112.
Wang et al., "Role of Hydrophobic Residues in the C1b Domain of Protein Kinase C δ on Ligand and Phospholipid Interactions," J Biol Chem., 2001; 276(22):19580-19587.
Wang et al., "Substrate Recognition Mechanism of Atypical Protein Kinase Cs Revealed by the Structure of PKCι in Complex with a Substrate Peptide from Par-3," Structure, 2012; 20(6):791-801.
Wang et al., "K-Ras Promotes Tumorigenicity Through Suppression of Non-canonical Wnt Signaling," Cell, 2015; 163:1237-1251.
Wender et al., "Practical Synthesis of Prostratin, DPP, and Their Analogs, Adjuvant Leads Against Latent HIV," Science, 2008; 320(5876):649-652.
Wender et al., "A Gateway Synthesis, PKC Affinities and Cell Growth Activities of Daphnane Congeners," Nat Chem., 2011; 3(8):615-619.
Winter et al., "A method to detect and characterize point mutations in transcribed genes: amplification and overexpression of the mutant c-Ki-ras allele in human tumor cells," Proc Natl Acad Sci USA., 1985; 82(22):7575-7579.
Yin et al., "Tumor-Initiating Cells and FZD8 Play a Major Role in Drug Resistance in Triple-Negative Breast Cancer," Mol Cancer Ther., 2013; 2013 12(4):491-498.
Yoshida et al., "Antitumor activity of daphnane-type diterpene gnidimacrin isolated from Stellera chamaejasme L" Int J Cancer, 1996; 66(2):268-273.
Yu, et al., "Circulating tumor cells: approaches to isolation and characterization," J Cell Biol., 2011; 192(3):373-382.
Zhang et al., "Phosphoprotein analysis using antibodies broadly reactive against phosphorylated motifs," J Biol Chem., 2002; 277(42):39379-39387.
Zheng et al., "Effects of 12-O-tetradecanoylphorbol-13-acetate (TPA) in Combination With Paclitaxel (Taxol) on Prostate Cancer LNCaP

(56) References Cited

OTHER PUBLICATIONS

Cells Cultured in Vitro or Grown as Xenograft Tumors in Immunodeficient Mice," Clin Cancer Res., 2006; 12(11):3444-51.
International Preliminary Report on Patentability for International patent application PCT/US2016/0611711, dated May 15, 2018.
International Search Report for International patent application PCT/US2016/0611711, dated May 26, 2017 (3 pages).
Collier et al., 2014 "Ingenol mebutate: a novel treatment for actinic keratosis," Clin Pract 11(3):295-306.
Chen et al., "An Overview of Cancer Drugs Approved by the US Food and Drug Administration Based on the Surrogate End Point of Response Rate," JAMA Intern Med., 2019; 179(7):915-921. doi:10.1001/jamainternmed.2019.0583.
Kulkosky, et al., "Prostratin: activation of latent HIV-1 expression suggests a potential inductive adjuvant therapy for HAART," Blood, 2001, 98(10):3006-3015.

* cited by examiner

| Soft Agar Assay IC50(µM) | |
|---|---|
| Cpd-ID | A549 |
| 101A | 0.0367 |
| 101E | 0.2556 |
| 102 | 0.0025 |
| 103 | <0.00008 |
| STS | 0.0024 |

A.

B.

A.

B.

C.

A.

B.

C

A.

B.

A.

B.

C.

A.

B.

C.

A.

B.

C.

A.

B.

C.

A.

B.

METHODS OF CANCER TREATMENT

1. CROSS-REFERENCE TO RELATED APPLICATIONS

This application is a National Stage of International Application No. PCT/US2016/061711, filed Nov. 11, 2016, which claims the benefit under 35 U.S.C. § 119 (e) of U.S. provisional application Ser. No. 62/253,701 filed Nov. 11, 2015 and U.S. provisional application Ser. No. 62/306,019, filed Mar. 9, 2016, the contents of which are incorporated herein by reference in their entireties.

2. BACKGROUND

The identification of protein kinase C (PKC) as the receptor for phorbol esters known to have tumor promoting properties has resulted in targeting of PKC for development of anti-cancer therapeutics. Evidence of overexpression or activation of PKC activity in association with tumor formation or progression in a variety of cancer types has led to development of PKC inhibitors as candidate therapeutics for treating different types of cancers (see, e.g., Mullin et al., 2000, Ann. N. Y. Acad. Sci. 915:231-236). However, clinical studies have not shown that PKC inhibitors have the expected therapeutic effect. Confounding the targeting of PKC based on inhibition of its activity is the observation that compounds that activate PKC activity also display anti-cancer properties (see, e.g. Ersvaer et al., 2010, Toxins (Basel). 2(1): 174-94). While the presence of different isoforms has been cited to explain the differential roles of PKC in tumor formation or inhibition, the activation of the same PKC has been implicated in tumor cell proliferation while in other contexts its activation is correlated with anti-tumor effects. These and other uncertainties on the role of PKC have impeded development and use of therapeutics that target PKC activity in the treatment of cancers.

3. SUMMARY

Diterpenoid PKC activating compounds, such as tigliane, ingenane and daphnane class of PKC activating compounds, display inhibitory effects on cancer cell growth. However some cancer cell types are found to be insensitive to these PKC activators and in some instances, the PKC activators are associated with tumor promotion rather than tumor growth inhibition. The present disclosure provides a method of selecting cancers that are likely sensitive to PKC activators and its inhibitory effect on cell proliferation, and thus selection of a cancer that would benefit from treatment with a PKC activator.

In one aspect, a method of selecting a cancer sensitive to treatment with a PKC activator comprises determining the PKC activation potential of the cancer for the PKC activator, and selecting the cancer determined to have an effective PKC activation potential for treatment with the PKC activator. In some embodiments, the PKC activation potential can comprise: (i) measuring the basal level of PKC activity in the cancer, and/or (ii) measuring the increase in PKC activity during and/or following treatment of the cancer with the PKC activator. In some embodiments, the PKC activation potential of a cancer is determined or measured for total PKC activity. In some embodiments, the PKC activation potential is determined or measured for one or more of PKC isoforms selected from PKC α, β, γ, δ, ε, η, θ, ι/λ, μ, and ζ, particularly PKCμ and PKCδ. In some embodiments, the PKC activation potential is determined or measured by detecting the level of phosphorylation of the PKC enzyme, such as phosphorylation sites in the protein kinase domain and/or autophosphorylation sites in the PKC enzyme. In some embodiments, phosphorylation is determined or measured for PKCμ at Ser910. In some embodiments, phosphorylation is determined or measured for PKCδ at Tyr311. In some embodiments, the PKC activation potential of a cancer is determined for a diterpenoid PKC activator.

In some embodiments, an assessment of the PKC activation potential can be based on determining or identifying in the cancer the presence or absence of an inactivating or activity-attenuating deletion or partial deletion or other loss-of-function mutations in the genes encoding the PKC enzymes. In some embodiments, the determination of the presence or absence of a loss-of-function mutation is carried out for one or more of the genes encoding PKC isoforms selected from PKC α, β, γ, δ, ε, η, θ, ι/λ, μ, and ζ. In some embodiments, a cancer determined as having a loss-of-function mutation in one or more of PKC isoforms selected from PKC α, β, γ, δ, ε, η, θ, ι/λ, μ, and ζ is not selected for treatment with a PKC activator. In some embodiments, a method of selecting a cancer for treatment with a diterpenoid PKC activator comprises determining the presence or absence of an inactivating or activity-attenuating deletion or partial deletion or other loss-of-function mutations in the genes encoding one or more of PKC isoforms selected from PKC α, β, γ, δ, ε, η, θ, ι/λ, μ, and ζ, selecting the cancer negative for the loss-of-function mutation for treatment with the PKC activator.

In some embodiments, a method of treating a subject with cancer comprises administering to a subject in need thereof a therapeutically effective amount of a diterpenoid PKC activator, wherein the cancer is determined to have an effective PKC activation potential. In some embodiments, the cancer is determined as being negative for a loss-function-mutation in one or more of PKC isoforms selected from PKC α, β, γ, δ, ε, η, θ, ι/λ, μ, and ζ.

In another aspect, a method of selecting a cancer sensitive to treatment with a PKC activator comprises determining the absence or presence in the cancer of an oncogenic or activating K-ras and/or N-ras activity, and selecting the cancer determined to have an oncogenic or activating K-ras and/or N-ras activity for treatment with the PKC activator. In some embodiments, the oncogenic or activating K-ras activity is an oncogenic or activating K-ras mutation. In some embodiments, the oncogenic or activating N-ras activity is an oncogenic or activating N-ras mutation. Selection of cancers for treatment with a diterpenoid PKC activator by determining the presence or absence of an oncogenic or activating K-ras and/or N-ras mutation is based on diterpenoid PKC activator induced phosphorylation of K-ras, a modification event which inhibits the activity of K-ras. In some embodiments, a method of treating a subject with cancer comprises administering to a subject in need thereof a therapeutically effective amount of a diterpenoid PKC activator, wherein the cancer is determined or identified as having an oncogenic or activating K-ras and/or N-ras activity, particularly an oncogenic or activating K-ras and/or N-ras mutation.

In some embodiments, the method of selecting a cancer sensitive to a PKC activator is based on the PKC activation potential, and the presence or absence of an oncogenic or activating K-ras and/or N-ras activity. Thus, in some embodiments, a cancer determined or identified as having an effective PKC activation potential and an oncogenic or activating K-ras activity is selected for treatment with the PKC activator. In some embodiments, a method of treating a subject with a cancer comprises administering to a subject in need thereof a therapeutically effective amount of a diterpenoid PKC activator, wherein the cancer is determined or identified as having an effective PKC activation potential for the diterpenoid PKC activator, and the cancer is further determined or identified as having an oncogenic or activating K-ras and/or N-ras activity, particularly an oncogenic or activating K-ras and/or N-ras mutation.

In some embodiments, in the method of selecting a cancer for treatment with a PKC activator based on determining the PKC activation potential, determining the presence or absence of an oncogenic or activating K-ras and/or N-ras mutation, or a combination thereof, an assessment can also be made on the effects of the PKC activator on one or more downstream elements of the PKC signaling pathway for additional selection and treatment criteria. In some embodiments, these additional selection criteria include, among others, assessment of one or more of: (i) levels of K-ras phosphorylation; (ii) expression levels of Frizzled protein, particularly Frizzled 8 (Fzd8); (iii) levels of calmodulin-dependent protein kinase II (CaMKii) phosphorylation; (iv) expression levels of leukemia inhibitory factor (LIF); (v) inhibition of Wnt signaling; and (vi) levels of extracellular signal-regulated kinase 1/2 (Erk1/2) phosphorylation.

In some embodiments, a variety of cancers can be selected and treated according to the methods herein. In some embodiments, the cancer is selected from cancer of the pancreas, lung, colon, head and neck, stomach (gastric), biliary tract, endometrium, ovary, small intestine, urinary tract, liver, cervix, breast, brain, renal, skin, bone, and kidney, as well as hematological cancers, where the cancer selected has one or more characteristics described herein.

In some embodiments, the selection and/or treatment of hematological cancers include selection and/or treatment of lymphomas and leukemias. Lymphomas include Hodgkin's lymphoma and non-Hodgkin's lymphoma, such as diffuse large B-cell lymphoma, follicular large cell lymphoma, anaplastic large cell lymphoma, T-cell lymphoma, lymphomatoid granulomatosis, peripheral T-cell lymphoma, Burkitt's lymphoma, and lymphoblastic lymphoma. Leukemias include, among others, acute myeloid leukemia, chronic myeloid leukemia, acute lymphoblastic leukemia, juvenile myelomonocytic leukemia, chronic myelomonocytic leukemia, myelodysplastic syndrome, myeloproliferative neoplasia, and multiple myeloma.

Suitable PKC activator compounds for use in the methods herein include any PKC compound having the effects described in the detailed description. In some embodiments, the PKC activating compounds comprise diterpenoid PKC activating compounds, particularly the PKC activating compounds within the class of tiglianes (e.g., phorbols and deoxyphorbols), ingenanes (e.g., ingenols), and daphnanes, including derivatives and analogs thereof, and salts, hydrates and solvates thereof. In some embodiments, the PKC activating compounds are prodrug forms of the PKC activating tiglianes (e.g., phorbols, deoxyphorbols), ingenanes (e.g., ingenols), and daphnanes. In some embodiments, the PKC activating tiglianes (e.g., phorbols, deoxyphorbols), ingenanes (e.g., ingenols), and daphnanes have a biohydrolyzable ester, biohydrolyzable amide, biohydrolyzable carbonate, biohydrolyzable ureide, or a biohydrolyzable phosphate progroup.

Pharmaceutical formulations, administration of PKC activating compounds or formulations, and dosing of the PKC activator compounds for treating the cancer are further provided in the detailed description that follow.

4. BRIEF DESCRIPTION OF THE FIGURES

Figure 9:
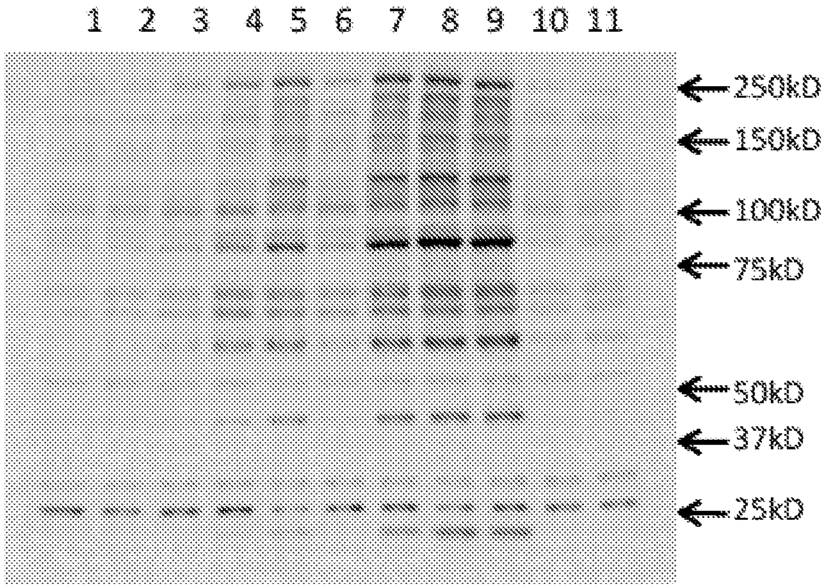
Figure 9:
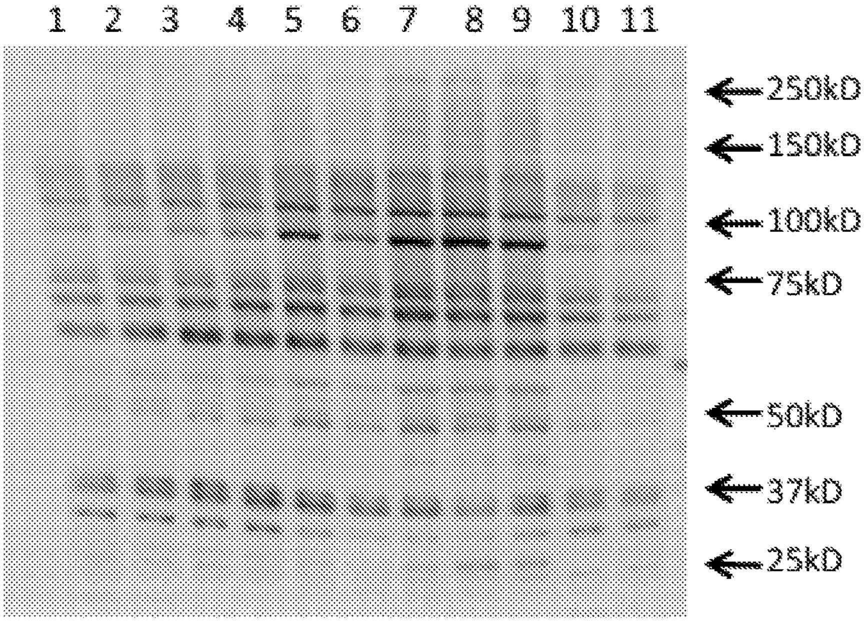

FIG. 9 shows global phosphorylation in cancer cell line A549 (Panel A) and Panc2.13 (Panel B) treated with PKC activators as assessed by probing a Western Blot of whole cell extracts separated by PAGE. Panel A shows a Western blot probed with the antibody that binds to phosphorylated amino acid sequence motif R/KXpSX(R/K) MultiMab™. Panel B shows a Western blot probed with an antibody that recognizes phosphorylated cellular PKC substrate proteins. Panel A: Lane 1, 0.2% DMSO; Lane 2, 0.2% DMSO; Lane 3, 0.1 μM K101A; Lane 4, 0.5 μM K101A; Lane 5, 2.5 μM K101A; Lane 6, 2.5 μM K101E; Lane 7, 0.1 μM K102; Lane 8, 0.5 μM K102; Lane 9, 0.05 μM K103; Lane 10, 1 μM Ref1; and Lane 11, 0.05 μM Ref2. Panel B: Lane 1, 0.2% DMSO; Lane 2, 0.2% DMSO; Lane 3, 0.1 μM K101A; Lane 4, 0.5 μM K101A; Lane 5, 2.5 μM K101A; Lane 6, 2.5 μM K101E; Lane 7, 0.1 μM K102; Lane 8, 0.5 μM K102; Lane 9, 0.05 μM K103; Lane 10, 1 μM Ref1; and Lane 11, 0.05 μM Ref2.

Figure 10:
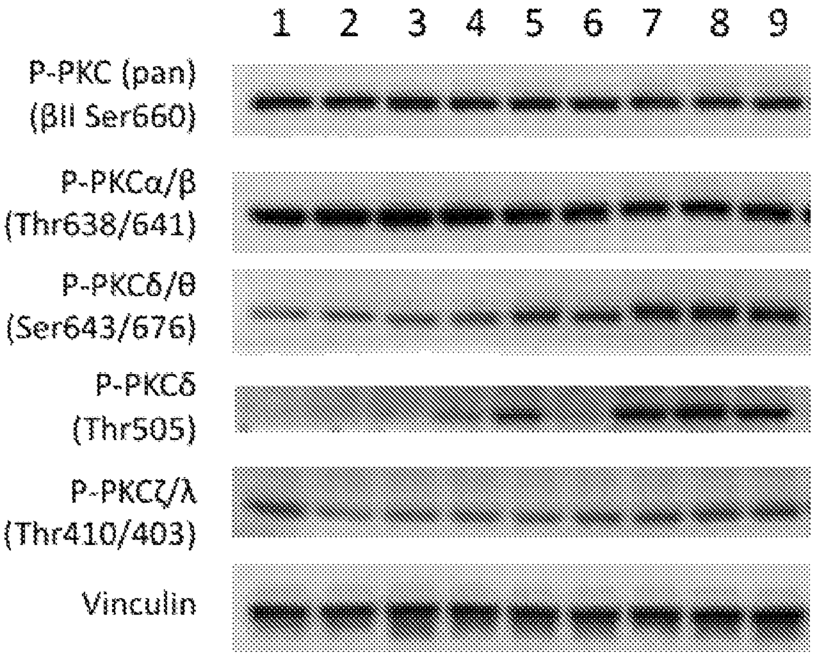

FIG. 10 shows effect of PKC activation by PKC activators as assessed by Western Blot probed with different antibodies that bind to phosphorylated amino acids in PKC enzymes PKCβII (Ser660), PKCα/β (Thr638/641), PKCδ/θ (Ser643/676), PKCδ (Thr505), PKCζ/λ (Thr410/403) in lung cancer cell line A549 treated for 30 minutes with the following: Lane 1, DMSO; Lane 2, DMSO; Lane 3, 0.1 μM K101A; Lane 4, 0.5 μM K101A; Lane 5, 2.5 μM K101A; Lane 6, 2.5 μM K101E; Lane 7, 0.1 μM K102; Lane 8, 0.5 μM K102; and Lane 9, 0.05 μM K103. PKCδ shows the largest changes in PKC activation as assessed by detection of phosphorylation at Thr505 and Ser643.

Figure 11:
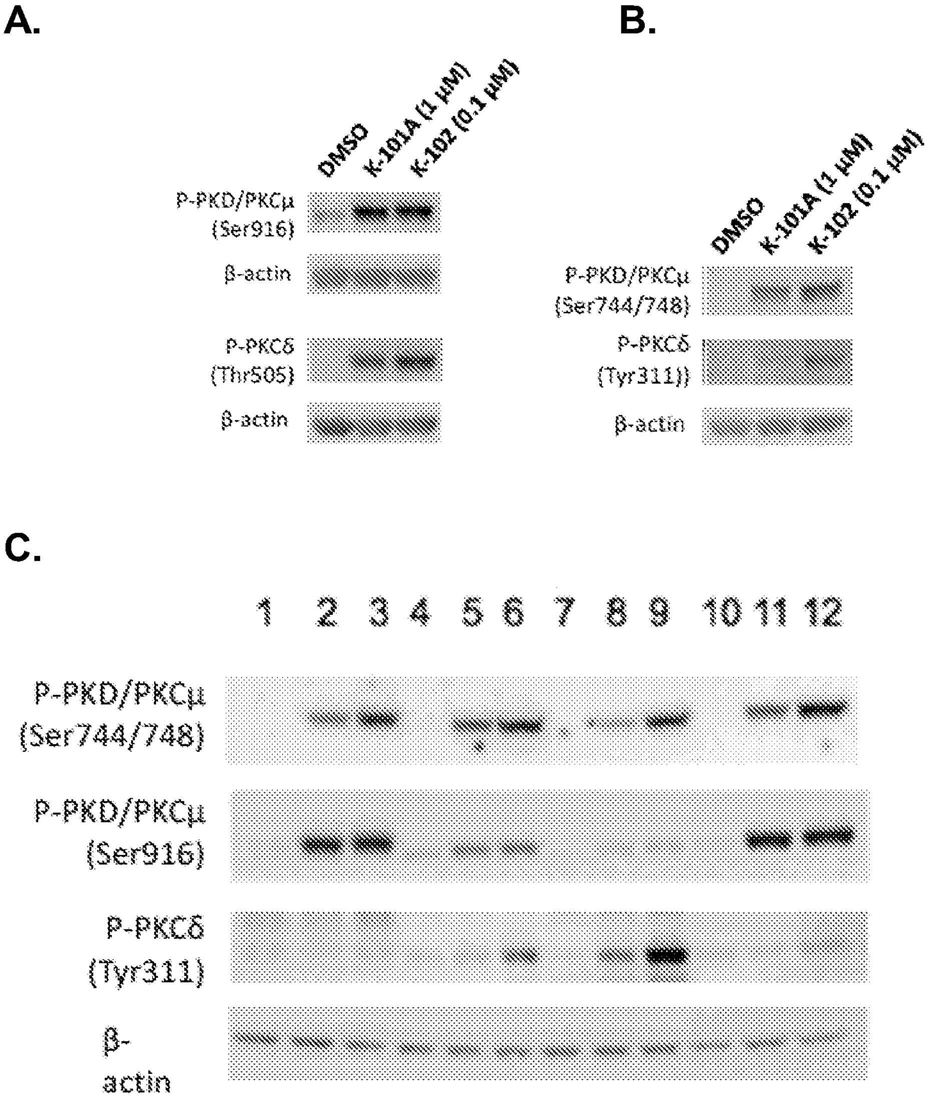

FIG. 11, Panel A and Panel B show effect of PKC activation by prostratin (K101A) or ingenol-3-angelate (K102) in normal human lung fibroblast cells HFL-1 as assessed by Western Blot probed with antibodies that bind to different phosphorylated amino acids in PKCμ (Ser916, Ser744/748) and PKCδ (Tyr311, Thr505). Ser916, Ser744, and Ser748, which are the amino acid positions in mouse, are equivalent to Ser910, Ser738, and Ser742, respectively, in human PKCμ. Anti-phospho antibodies which bind to Ser916 in mouse also bind to Ser910 in human PKCμ. Anti-phospho antibodies which bind to Ser744/748 in mouse also bind to Ser738/742 in human PKCμ. Loading control is β-actin. Panel C shows effect of PKC activation by prostratin (K101A) as assessed by Western Blot probed with antibodies that bind to different phosphorylated amino acids in PKC enzymes in four different cancer cell lines (A549, HCT116, SW620, Pan 02,13) treated for 30 minutes with the following: Lane 1, A549 cells treated with DMSO; Lane 2, A549 cells treated with 0.5 μM K101A; Lane 3, A549 cells treated with 1 μM K101A; Lane 4, HCT116 cells treated with DMSO; Lane 5, HCT116 cells treated with 0.5 μM K101A; Lane 6, HCT116 cells treated with 2.5 μM K101A; Lane 7, SW620 cells treated with DMSO; Lane 8, SW620 cells treated with 0.5 μM K101A; Lane 9, SW620 cells treated with 2.5 μM K101A; Lane 10, Pan 02,13 cells treated with DMSO, Lane 11, Pan 02,13 cells treated with 0.5 μM K101A; and Lane 12, Pan 02,13 cells treated with 2.5 μM K101A. PKCμ activation with K101A is observed for all four cancer cell lines as assessed by detecting phosphorylation at Ser744/748 while PKCμ activation is observed primarily in cell lines A549 and Pan 02,13 cells when assessed by detecting phosphorylation at Ser916. PKCδ activation by K101A is observed for cell lines HCT116 and SW620 but not as significantly for cell lines A549 and Pan 02,13 cells when assessed by detecting phosphorylation at Tyr311. HCT116 and SW620 are insensitive while A549 and Pan 02,13 are sensitive to the anti-cell proliferative effects of prostratin K101A.

Figure 12:
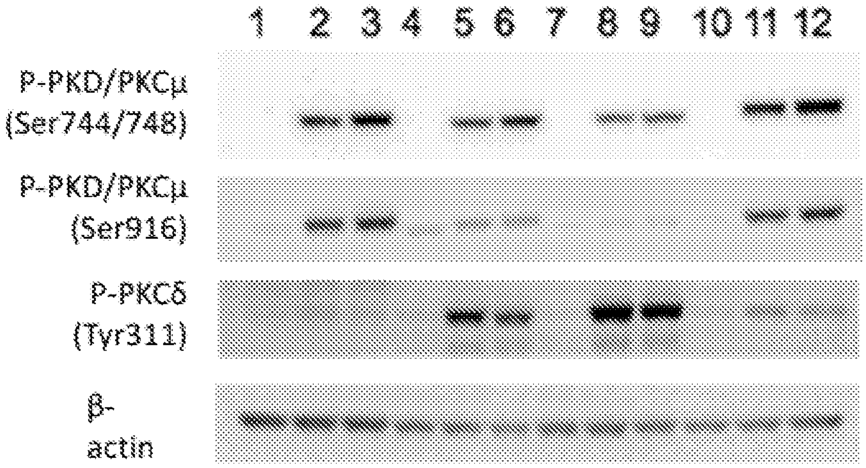

FIG. 12 shows effect of PKC activation by ingenol-3-angelate (K102) or PMA (K103) as assessed by Western Blot probed with antibodies that bind to phosphorylated amino acids in PKC enzymes PKCμ and PKCδ in four different cancer cell lines (A549, HCT116, SW620, Pan 02,13) treated for 30 minutes as follows: Lane 1, A549 cells treated with DMSO; Lane 2, A549 cells treated with 0.1 μM K102; Lane 3, A549 cells treated with 0.05 μM K103; Lane 4, HCT116 cells treated with DMSO; Lane 5, HCT116 cells treated with 0.5 μM K102; Lane 6, HCT116 cells treated with 0.05 μM K103; Lane 7, SW620 cells treated with DMSO; Lane 8, SW620 cells treated with 0.1 μM K102; Lane 9, SW620 cells treated with 0.05 μM K103; Lane 10, Pan 02,13 cells treated with DMSO, Lane 11, Pan 02,13 cells treated with 0.1 μM K102; and Lane 12, Pan 02,13 cells treated with 0.05 μM K103. PKCμ activation by PKC activators K102 and K103 is observed for all four cancer cell lines as assessed by detecting phosphorylation at Ser744/748 while PKCμ activation is observed primarily in cell lines A549 and Pan 02,13 cells when assessed by detecting phosphorylation at Ser916. PKCδ activation by PKC activators K102 and K103 is observed for PKC activator insensitive cell lines HCT116 and SW620 but not as significantly for sensitive cell lines A549 and Pan 02,13 cells when assessed by detecting phosphorylation at Tyr311.

Figure 13:
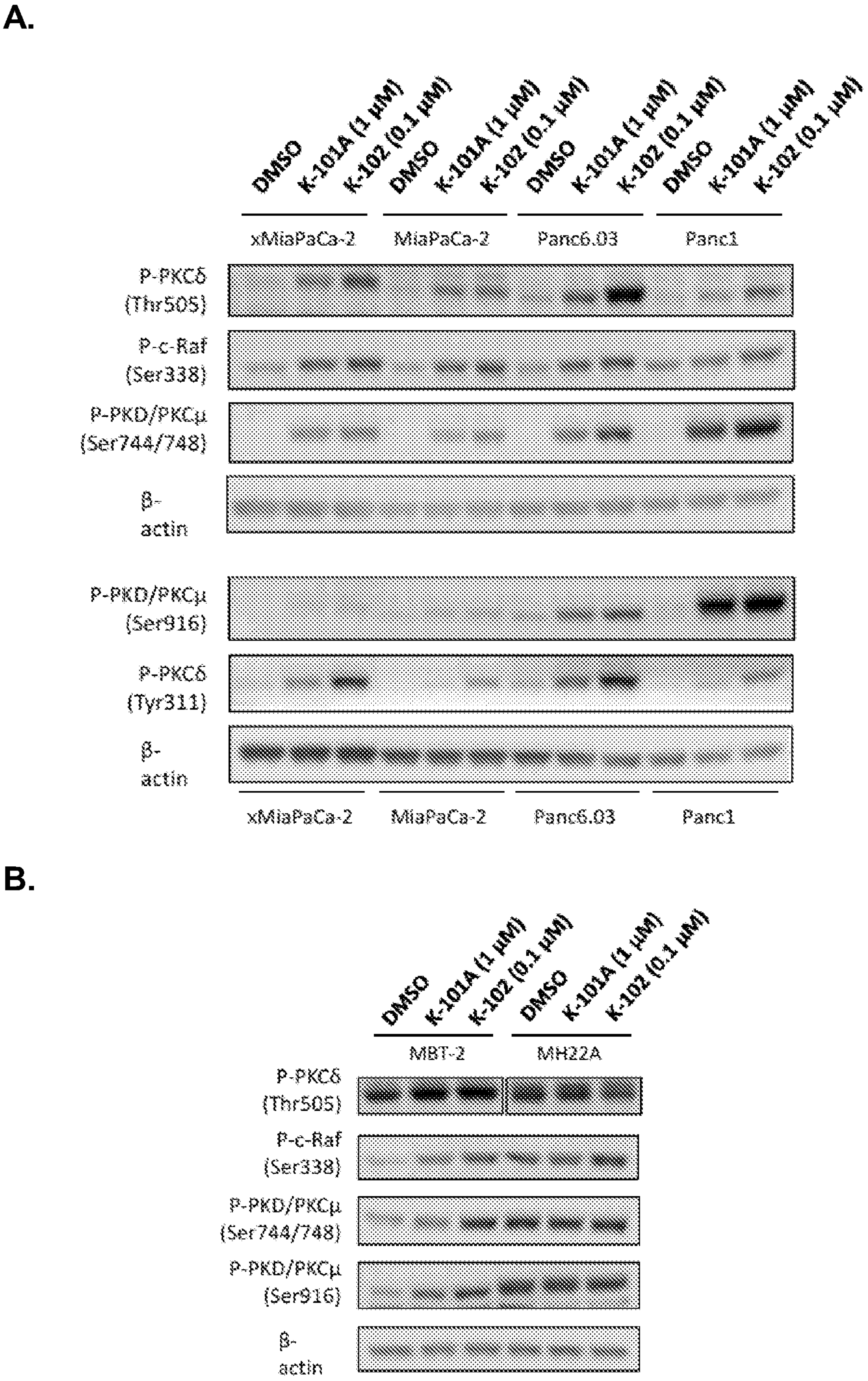

FIG. 13 shows effect of PKC activation of PKCμ and PKCδ by diterpenoid PKC activators prostratin (K101A) or ingenol-3-angelate (K102) as assessed by Western Blot probed with antibodies that bind to phosphorylated amino acids in the PKC enzymes PKCμ and PKCδ in four different pancreatic cancer cell lines, xMiaPaCa-2, MiaPaCa-2, Panc6.03, and Panc1 (Panel A), and mouse bladder carcinoma cell line MBT-2 and mouse hepatoma cell line MH-22A (Panel B).

Figure 14:
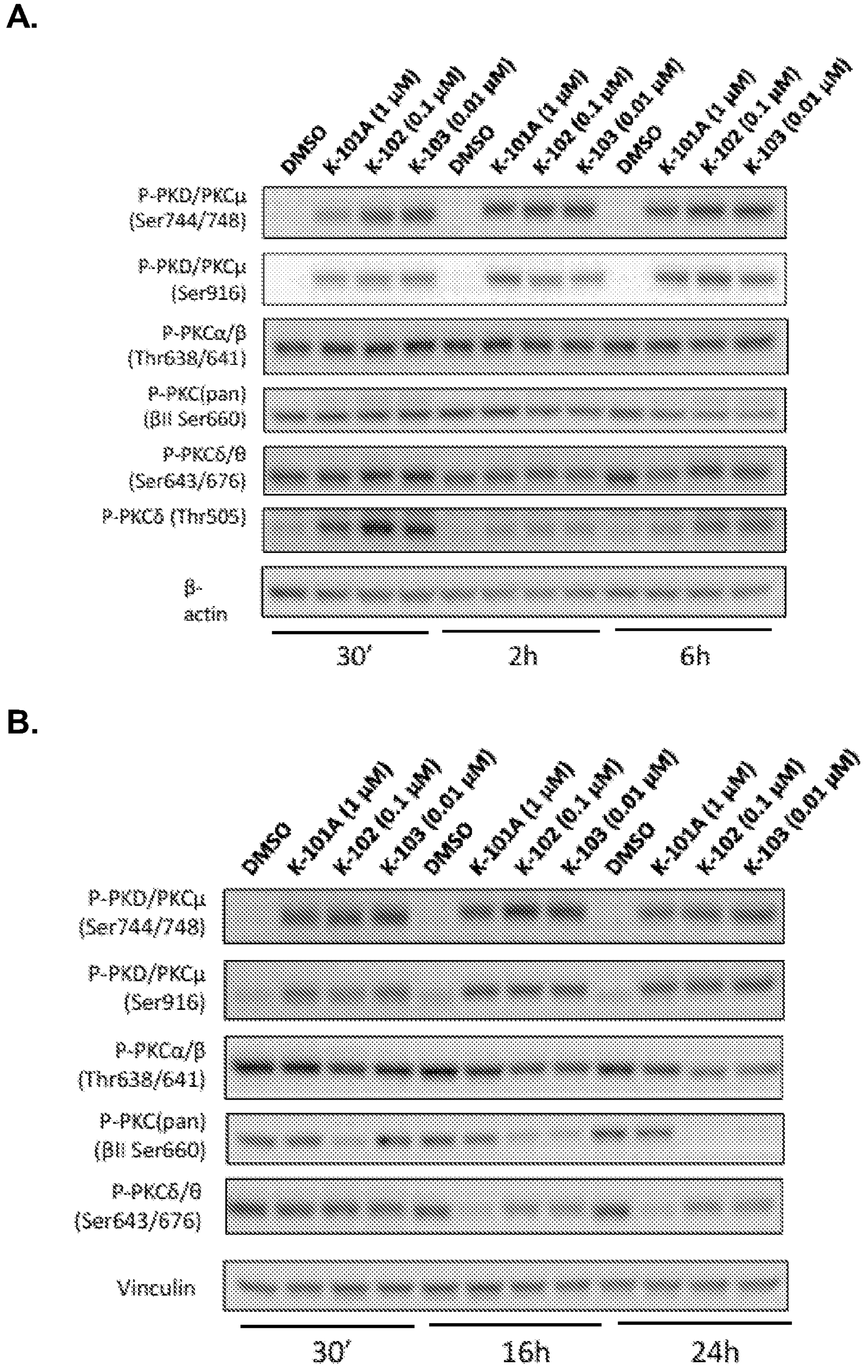

FIG. 14 shows time course of PKC activation by PKC activators prostratin (K101A), ingenol-3-angelate (K102) and PMA (K103) as assessed by Western Blot probed with antibodies that bind to phosphorylated amino acids in the PKC enzymes PKCμ, PKCα/β, PKCβII and PKCδ/θ in cancer cell line Panc2.13 for time periods of 30 min, 2 h, and 6 h (Panel A); and 30 min, 16 h and 24 h (Panel B). Antibodies detected phosphorylation at Ser744/748 or Ser916 for PKCμ; phosphorylation at Thr638/641 for PKCα/β; phosphorylation at Ser660 for PKCβII; phosphorylation at Ser643/676 for PKCδ/θ; and phosphorylation at Thr505 for PKCδ. Extended activation by the diterpenoid PKC activators are observed for PKCμ and PKCδ, and possibly for PKCθ.

Figure 15:
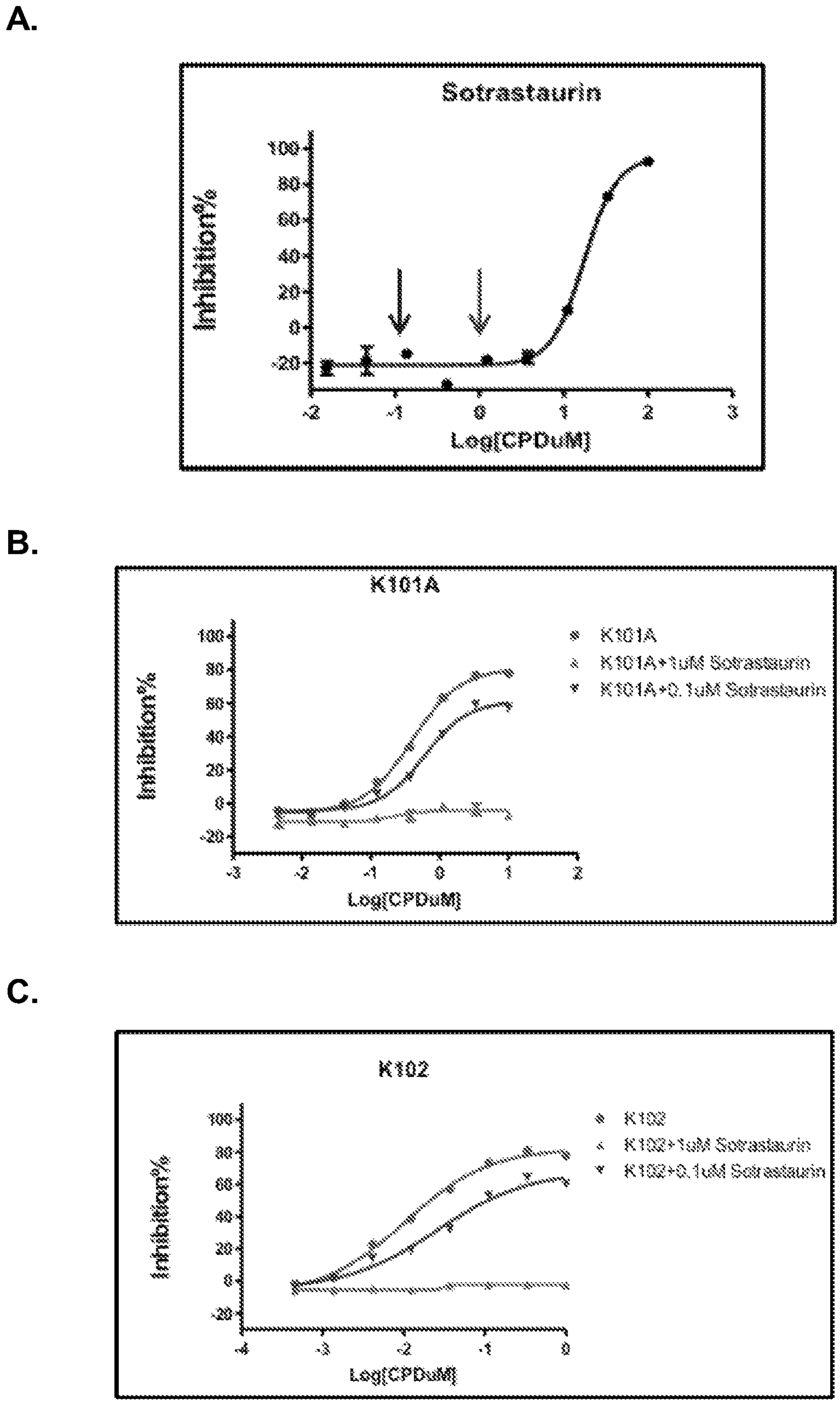

FIG. 15 shows the effect of broad spectrum PKC inhibitor sotrastaurin in abrogating cell proliferation inhibitory effect of prostratin (K101A) or ingenol-3-angelate (K102) in lung cancer cell line A549 at concentrations of sotrastaurin (1 μM and 0.1 μM) that do not affect cell viability: Panel A, sotrastaurin alone; Panel B, K101A alone, or K101A in presence of sotrastaurin at 1 μM or 0.1 μM; and Panel C, K102 alone, or K102 in presence of sotrastaurin at 1 μM or 0.1 μM.

Figure 16:
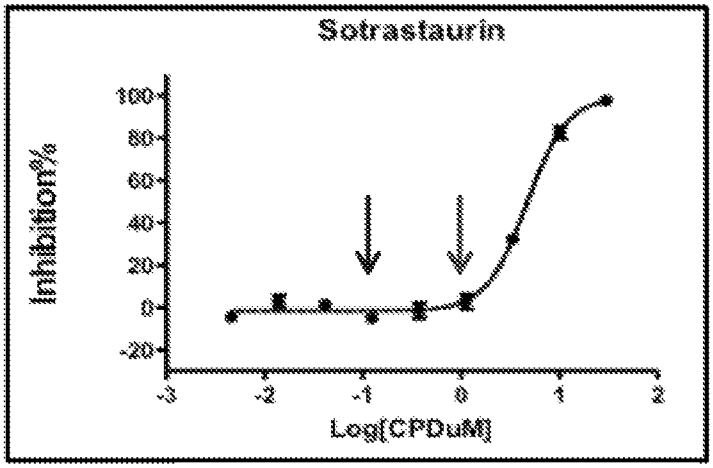
Figure 16:
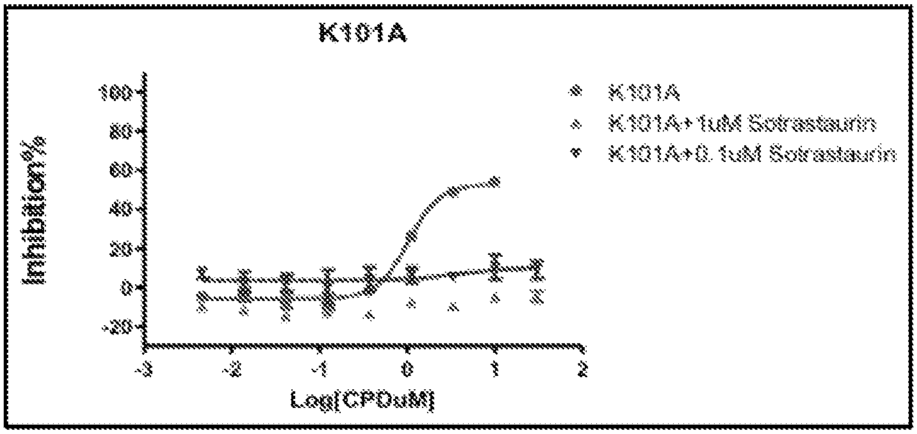
Figure 16:
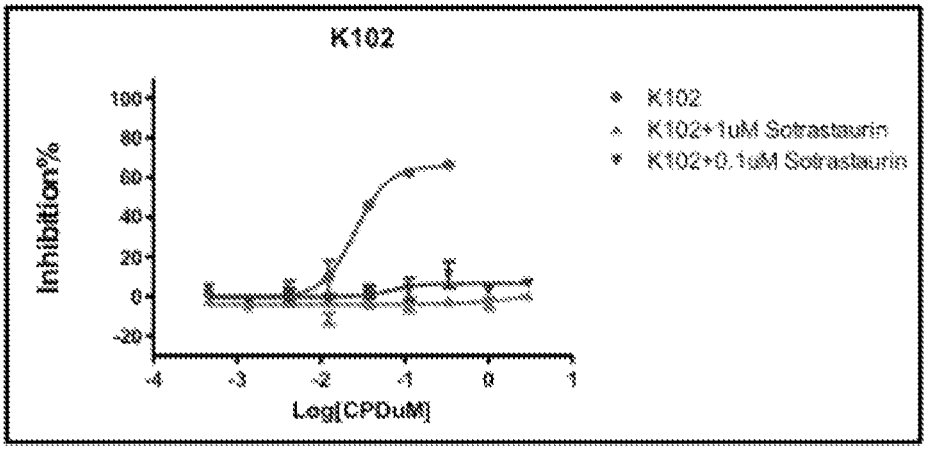

FIG. 16 shows the effect of broad spectrum PKC inhibitor sotrastaurin in abrogating cell proliferation inhibitory effect of prostratin (K101A) and ingenol-3-angelate (K102) in pancreatic cancer cell line MiaPaCa-2 at concentrations of sotrastaurin (1 μM and 0.1 μM) that do not affect cell viability: Panel A, sotrastaurin alone; Panel B, K101A alone, or K101A in presence of sotrastaurin at 1 μM or 0.1 μM; and Panel C, K102 alone, or K102 in presence of sotrastaurin at 1 μM or 0.1 μM.

Figure 17:
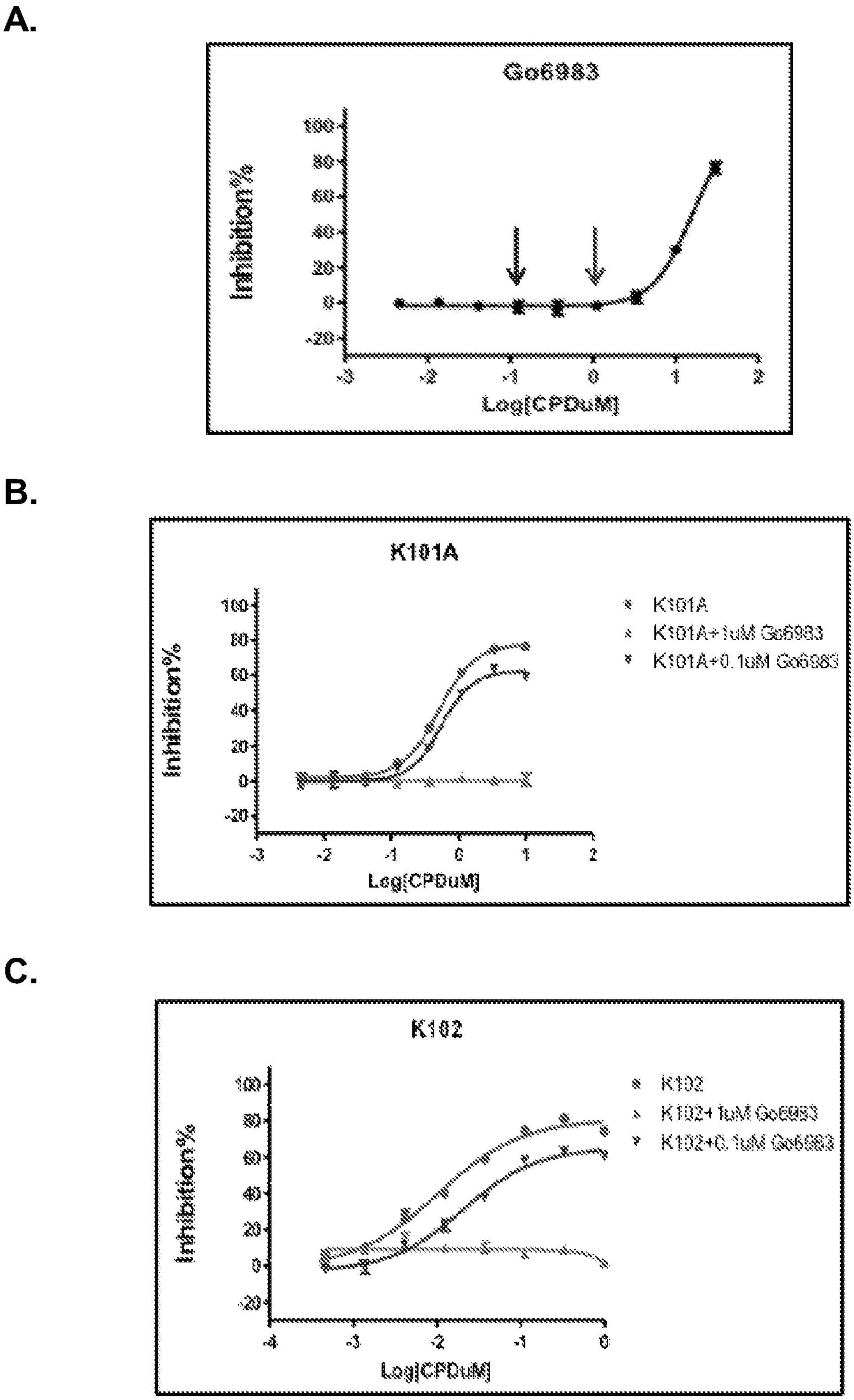

FIG. 17 shows the effect of pan-PKC inhibitor Go6983 in abrogating cell proliferation inhibitory effect of prostratin (K101A) and ingenol-3-angelate (K102) in lung cancer cell line A549 at concentrations of sotrastaurin (1 μM and 0.1 μM) that do not affect cell viability: Panel A, Go6983 alone; Panel B, K101A alone, or K101A in presence of Go6983 at 1 μM or 0.1 μM; and Panel C, K102 alone, or K102 in presence of Go6983 at 1 μM or 0.1 μM.

Figure 18:
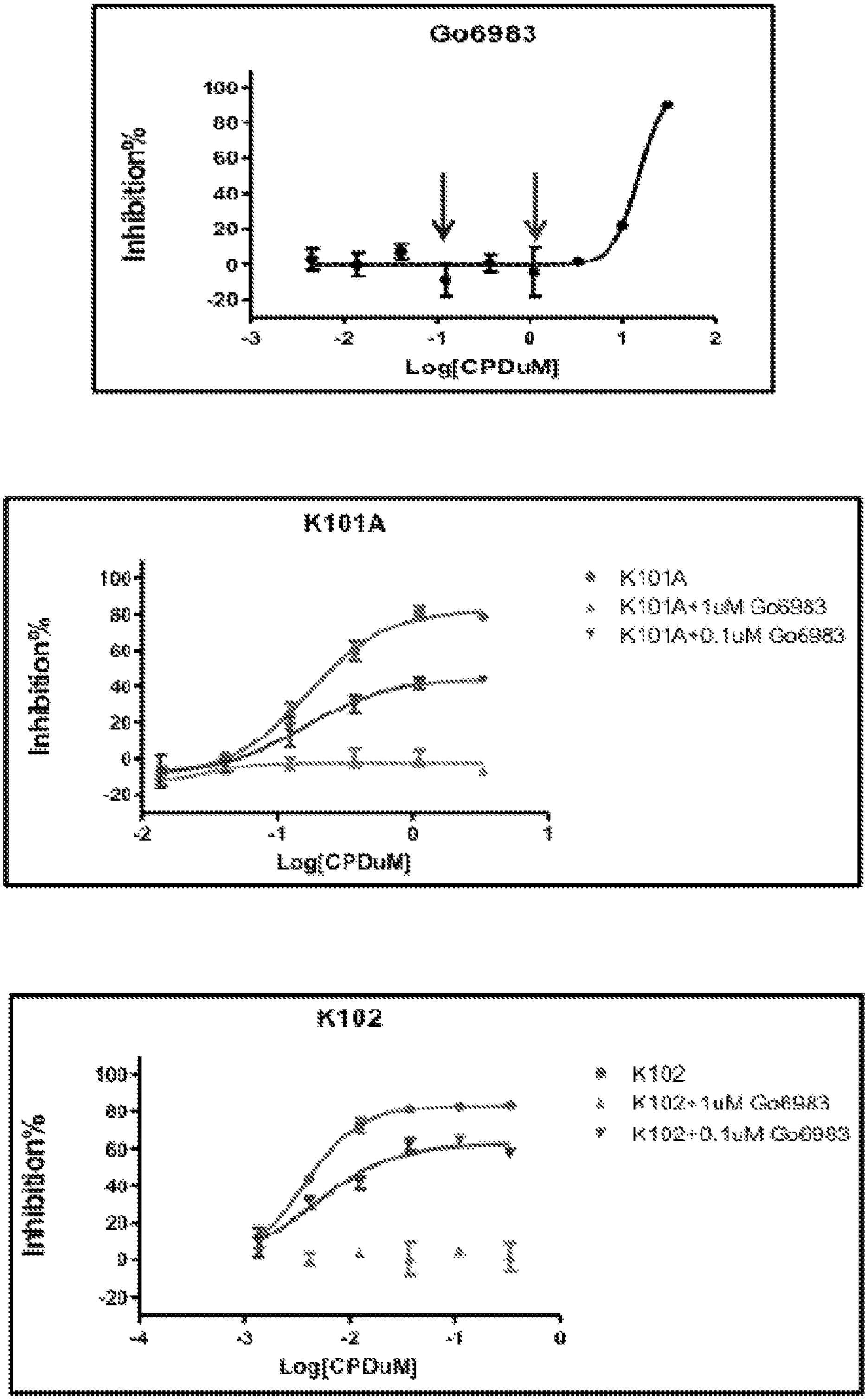

FIG. 18 shows the effect of broad spectrum PKC inhibitor Go6983 in abrogating cell proliferation inhibitory effect of prostratin (K101A) or ingenol-3-angelate (K102) in pancreatic cancer cell line MiaPaCa-2 at concentrations of Go6983 (1 μM and 0.1 μM) that do not affect cell viability: Panel A, Go6983 alone; Panel B, K101A alone, or K101A in presence of Go6983 at 1 μM or 0.1 μM; and Panel C, K102 alone, or K102 in presence of Go6983 at 1 μM or 0.1 μM.

Figure 19:
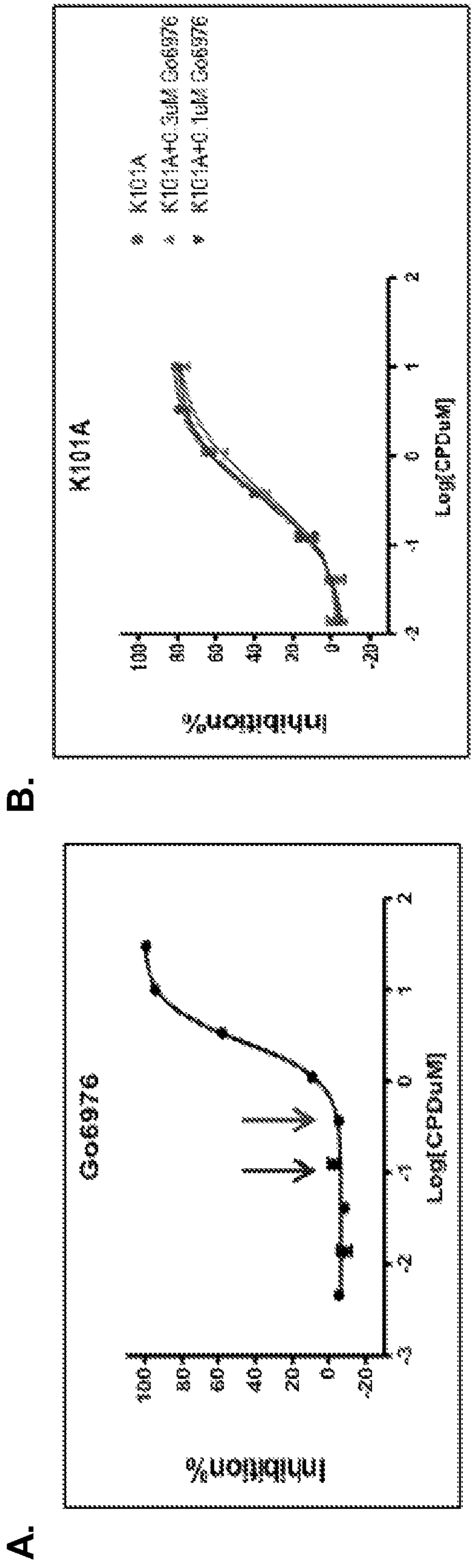

FIG. 19 shows the effect of PKC α/β inhibitor Go6976 on cell proliferation inhibitory effect of prostratin (K101A) in lung cancer cell line A549 at concentrations of Go6976 (0.3 μM and 0.1 μM) that do not affect cell viability: Panel A, Go6976 alone; and Panel B, K101A alone, or K101A in presence of Go6976 at 0.3 μM or 0.1 μM.

Figure 20:
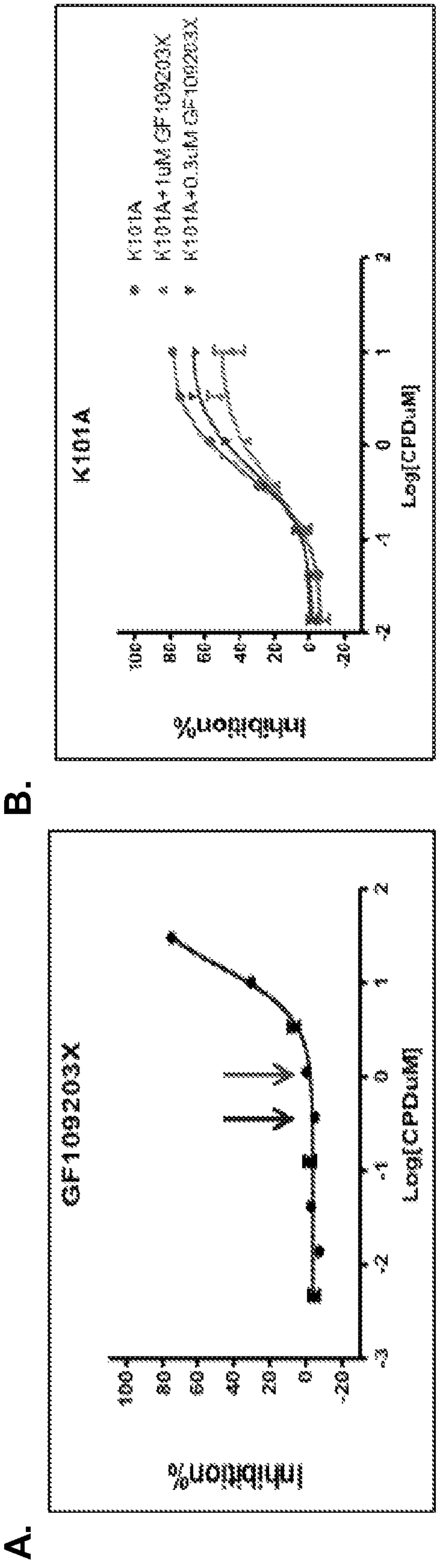

FIG. 20 shows the effect of PKC α/β/γ inhibitor GF109203X on cell proliferation inhibitory effect of prostratin (K101A) in lung cancer cell line A549 at concentrations of GF109203X (1 μM and 0.3 M) that do not affect cell viability: Panel A, GF109203X alone; and Panel B, K101A alone or K101A in presence of GF109203X at 1 μM or 0.3 μM.

Figure 21:
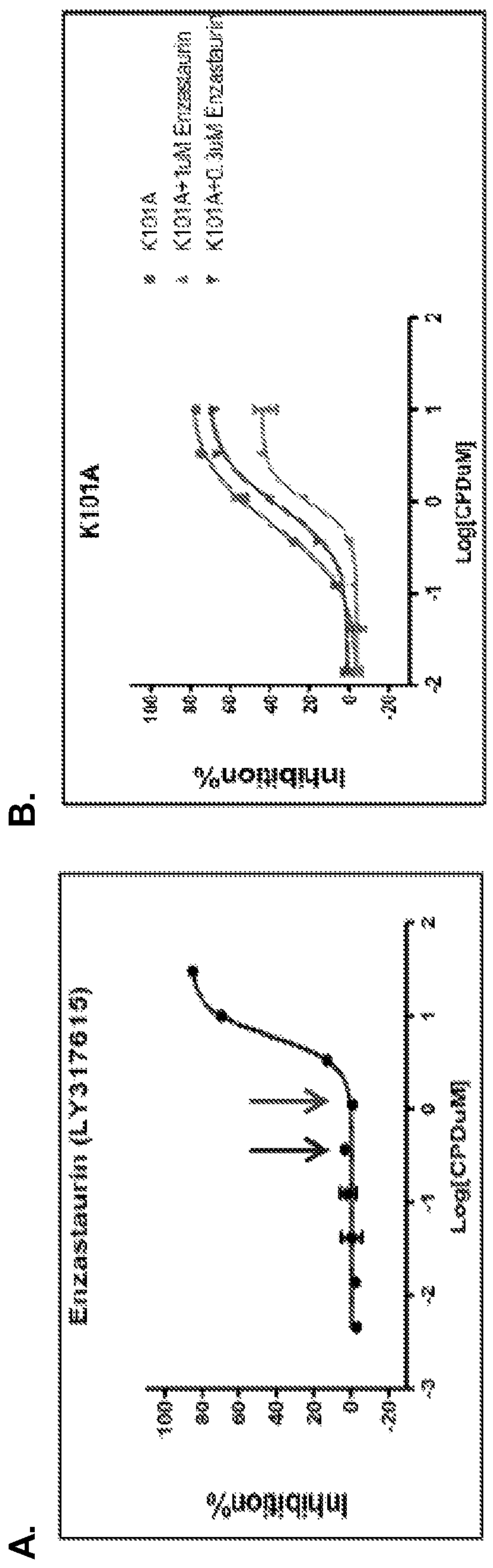

FIG. 21 shows the effect of PKC α/β/γ/ε inhibitor Enzastaurin on cell proliferation inhibitory effect of prostratin K101A in lung cancer cell line A549 at concentrations of Enzastaurin (1 μM and 0.3 M) that do not affect cell viability: Panel A, Enzastaurin alone; and Panel B, K101A alone or K101A in presence of Enzastaurin at 1 μM or 0.3 μM.

Figure 22:
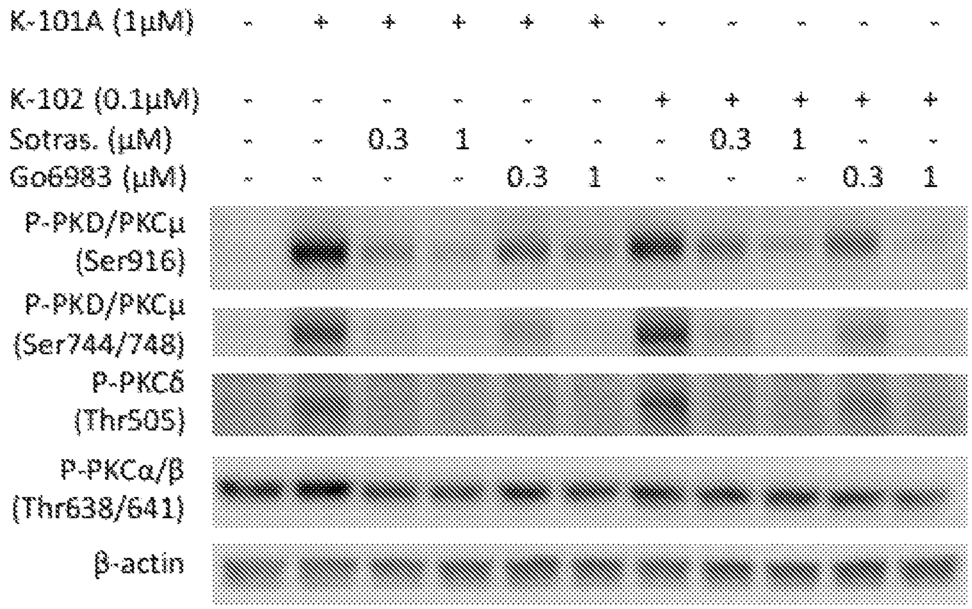
Figure 22:
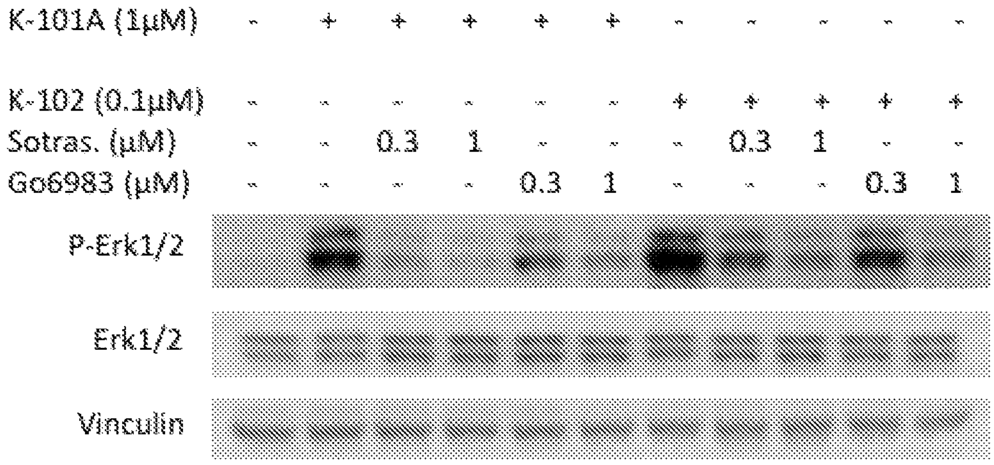

FIG. 22, Panel A shows a photograph of a Western Blot probed with antibodies that bind phosphorylated amino acids in the specified PKC enzymes in lung cancer cell line A549 treated with prostratin (K101A) or ingenol-3-angelate (K102) for 30 minutes in presence (pre-treatment for 30 minutes) or absence of general PKC inhibitor sotrastaurin or pan-PKC inhibitor Go6983. Antibodies detected phosphorylation at Ser744/748 or Ser916 for PKCμ; phosphorylation at Thr638/641 for PKCα/β, and phosphorylation at Thr505 for PKCδ. Panel B shows a photograph of a Western Blot probed with antibodies that bind to phosphorylated amino acids in the downstream target Erk1/2 in lung cancer cell line A549 treated with prostratin (K101A) or ingenol-3-angelate (K102) for 30 minutes in presence of different PKC inhibitors (pre-treatment for 30 minutes).

Figure 23:
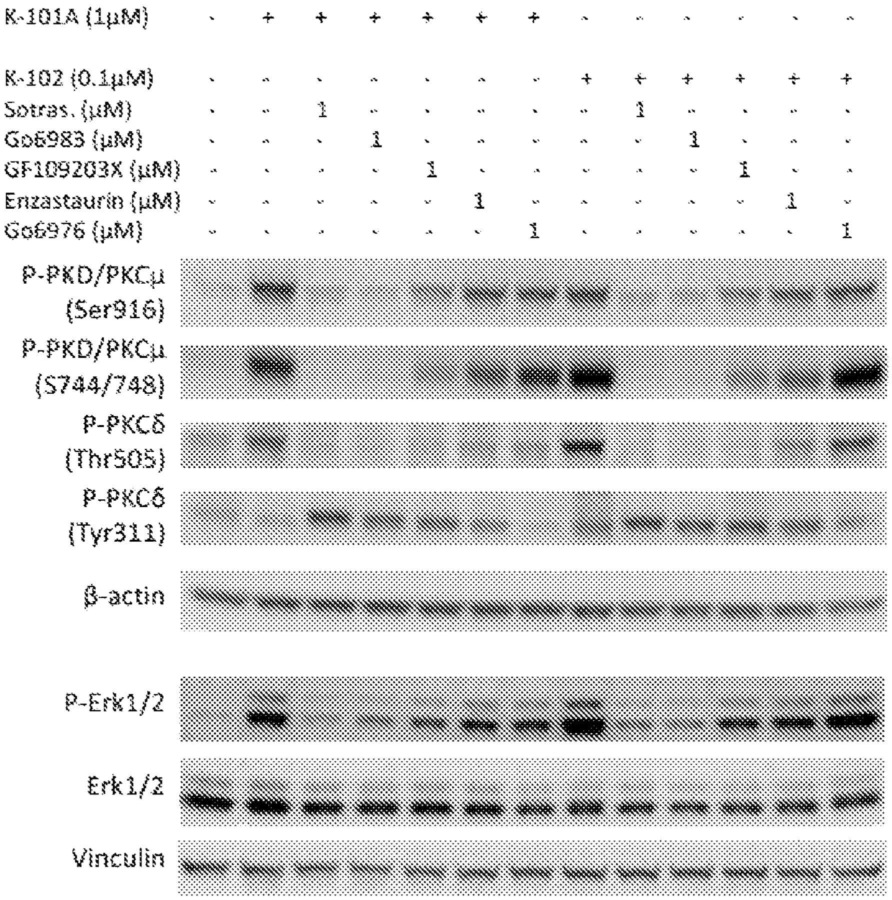

FIG. 23 shows effect of different PKC inhibitors on PKC activation by prostratin (K101A) or ingenol-3-angelate (K102) in lung cancer cell line A549 as assessed by Western Blot probed with antibodies that bind phosphorylated amino acids in the specified PKC enzyme. Also shown is a photograph of a Western Blot probed with antibodies that bind to phosphorylated amino acids in the downstream target Erk1/2 in lung cancer cell line A549 treated similarly as for the PKC enzyme.

Figure 24A:
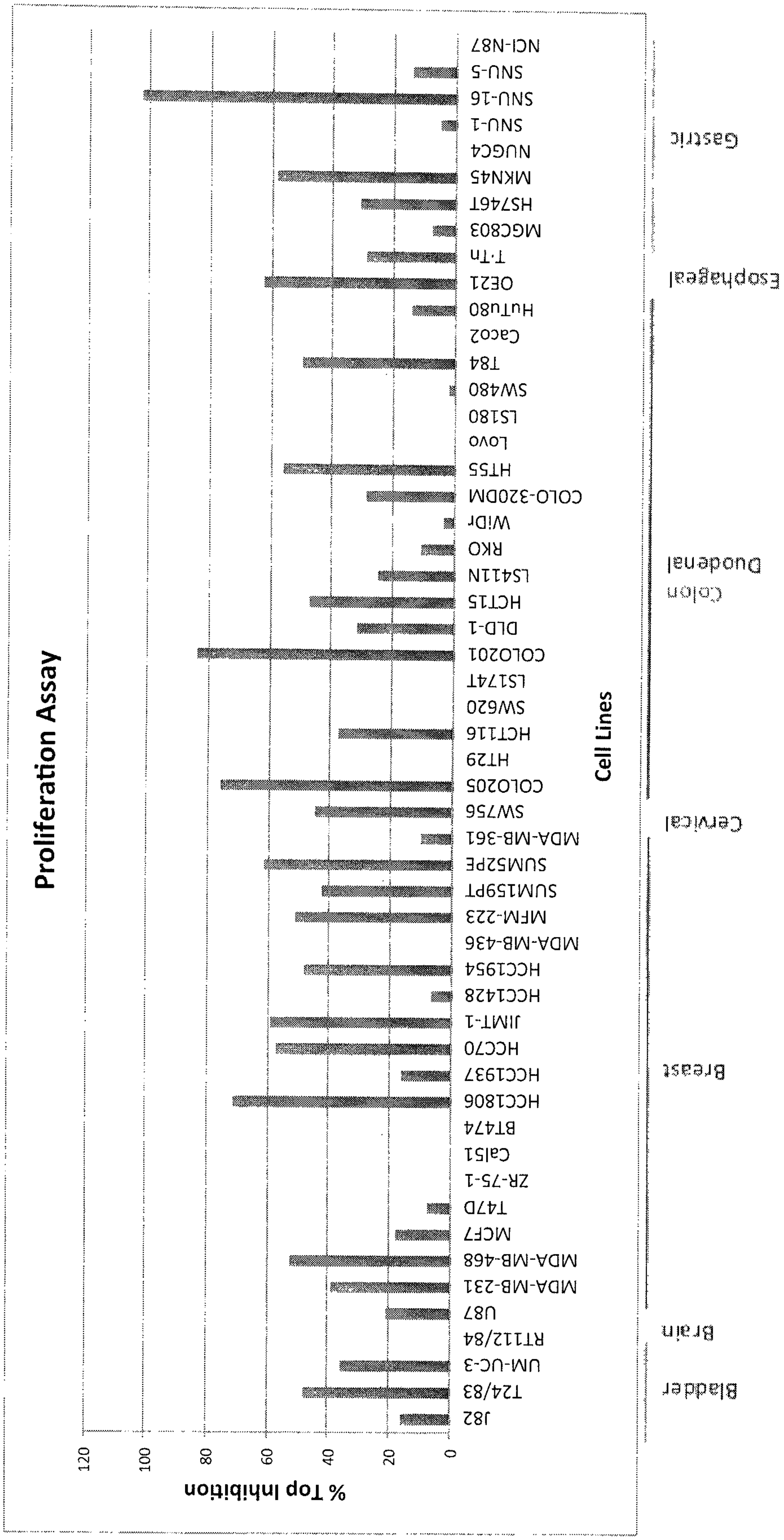
Figure 24B:
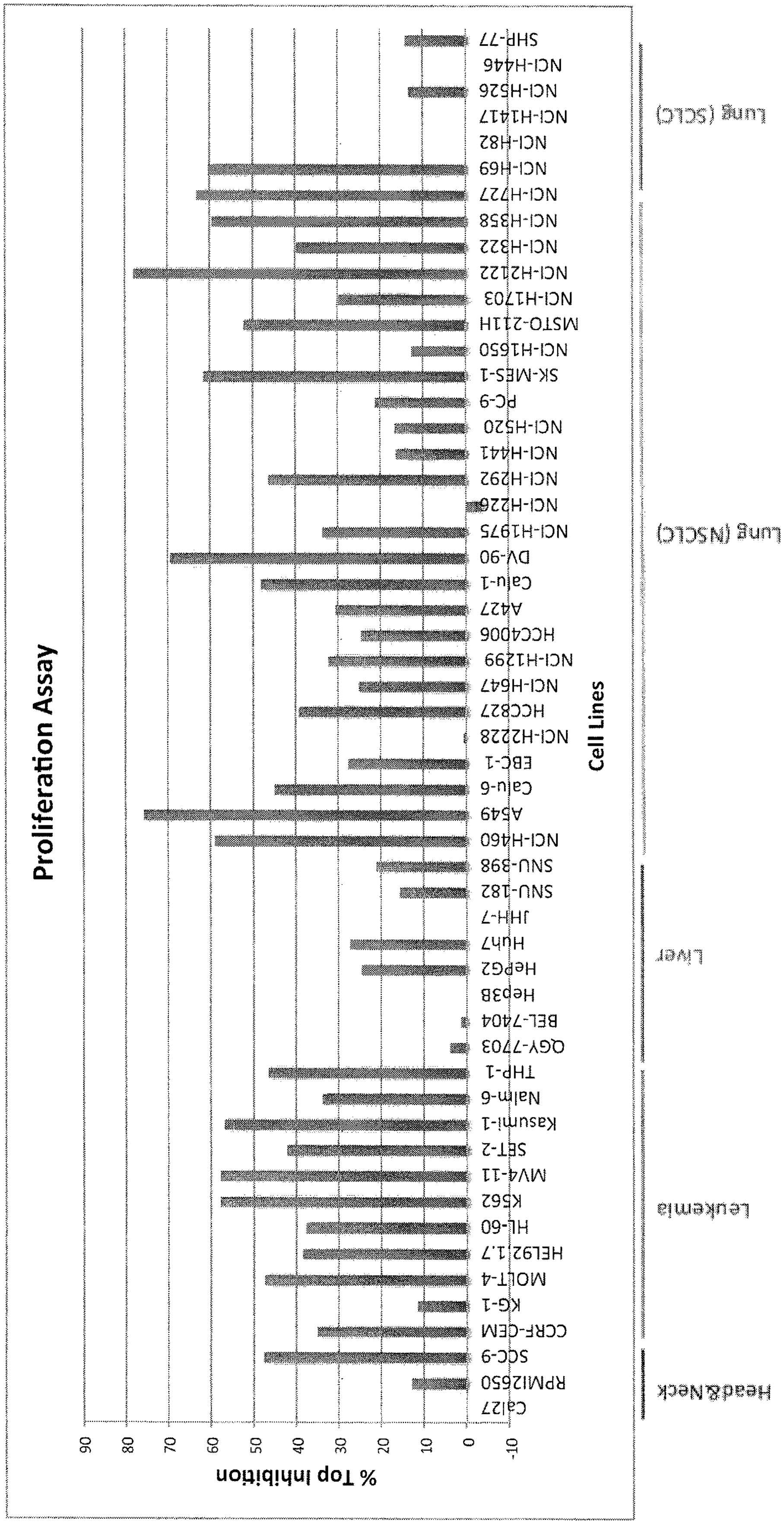
Figure 24C:
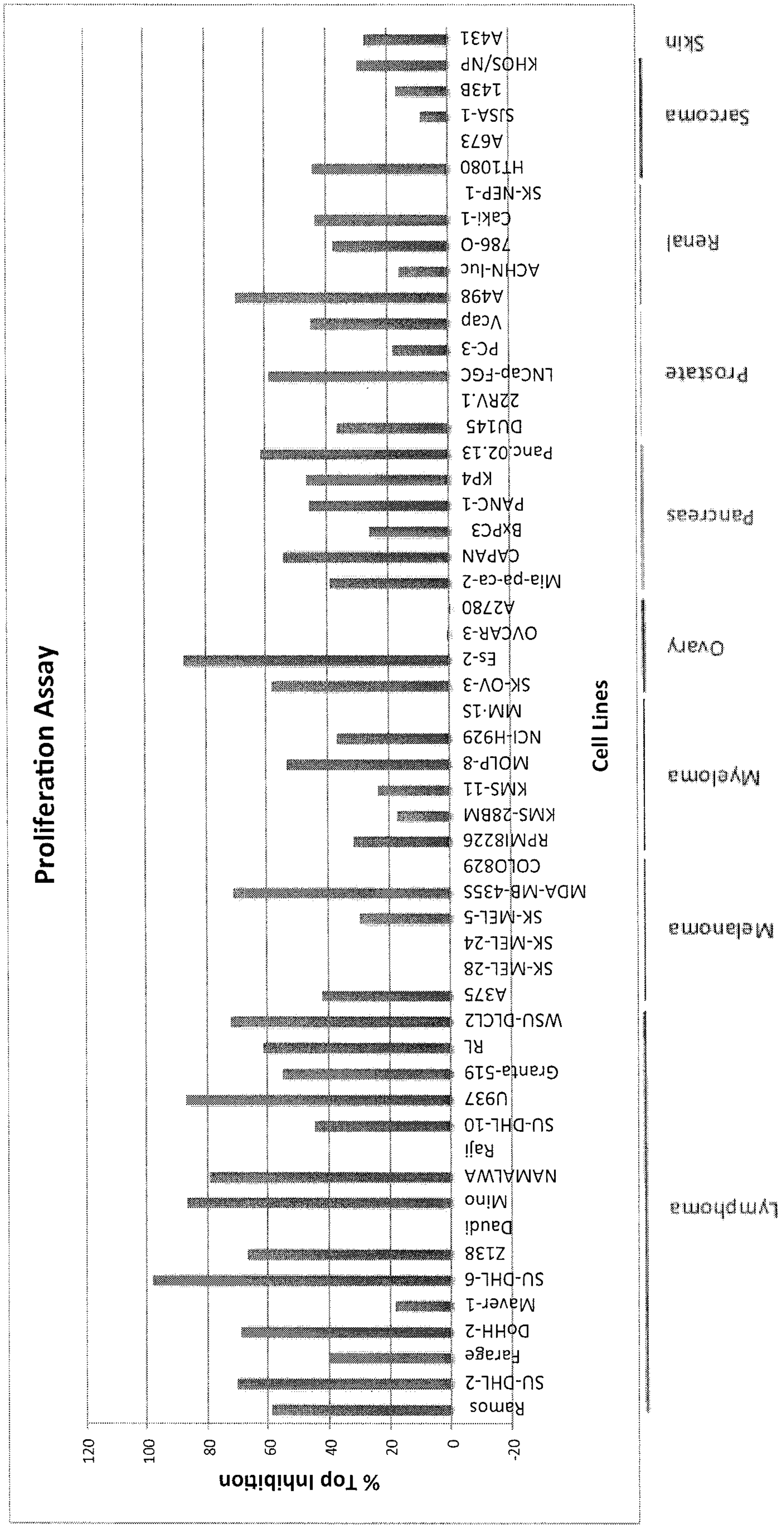

FIG. 24A, FIG. 24B and FIG. 24C illustrate cell proliferation inhibitory effect of prostratin (K101A) on various cancer cell lines. Cell lines from leukemia, non-small cell lung cancer, lymphoma, ovarian cancer, and pancreatic cancer were most sensitive while cell lines from liver cancer and small-cell lung cancer were the least sensitive to K101A.

Figure 25A:
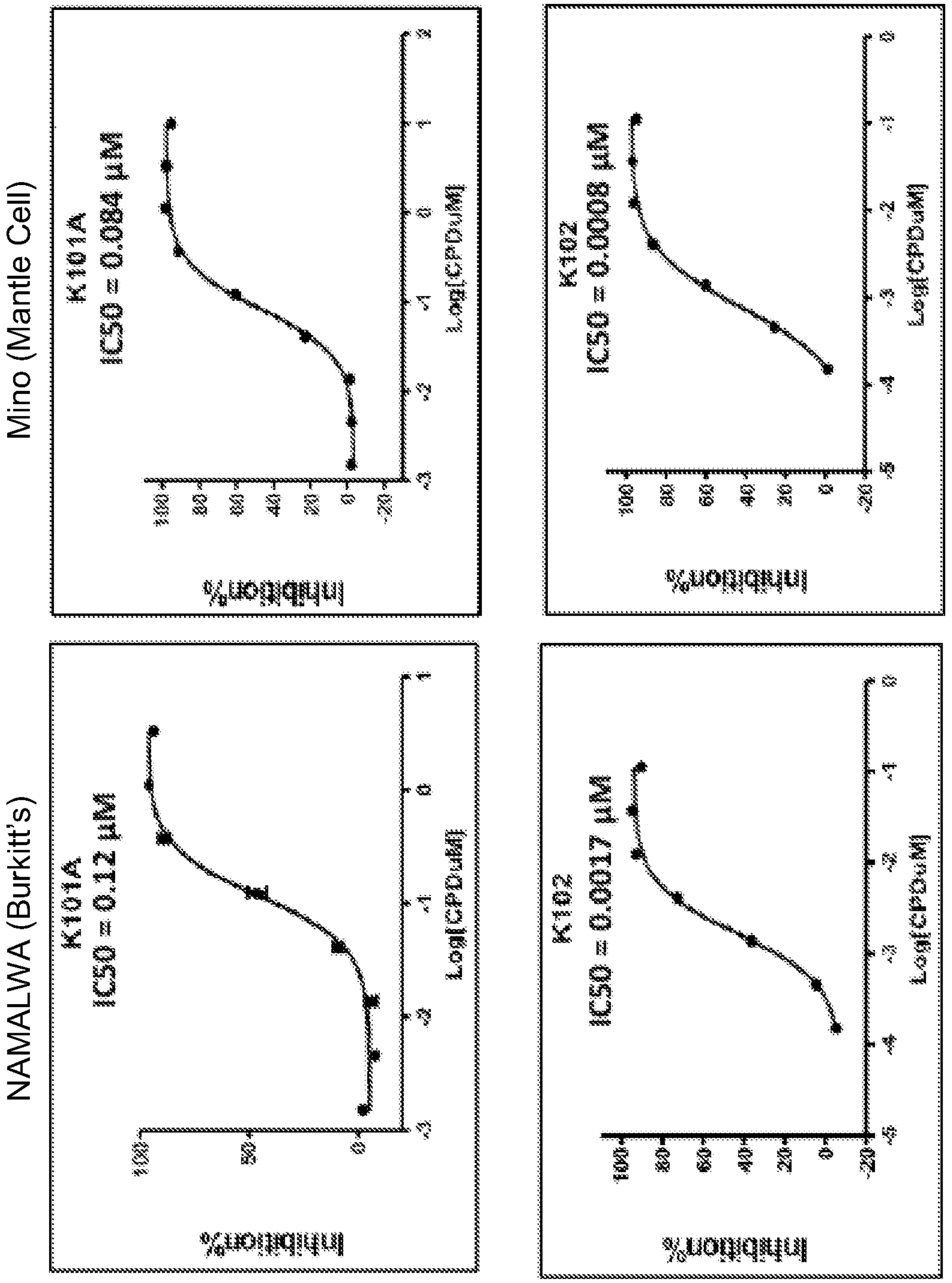
Figure 25B:
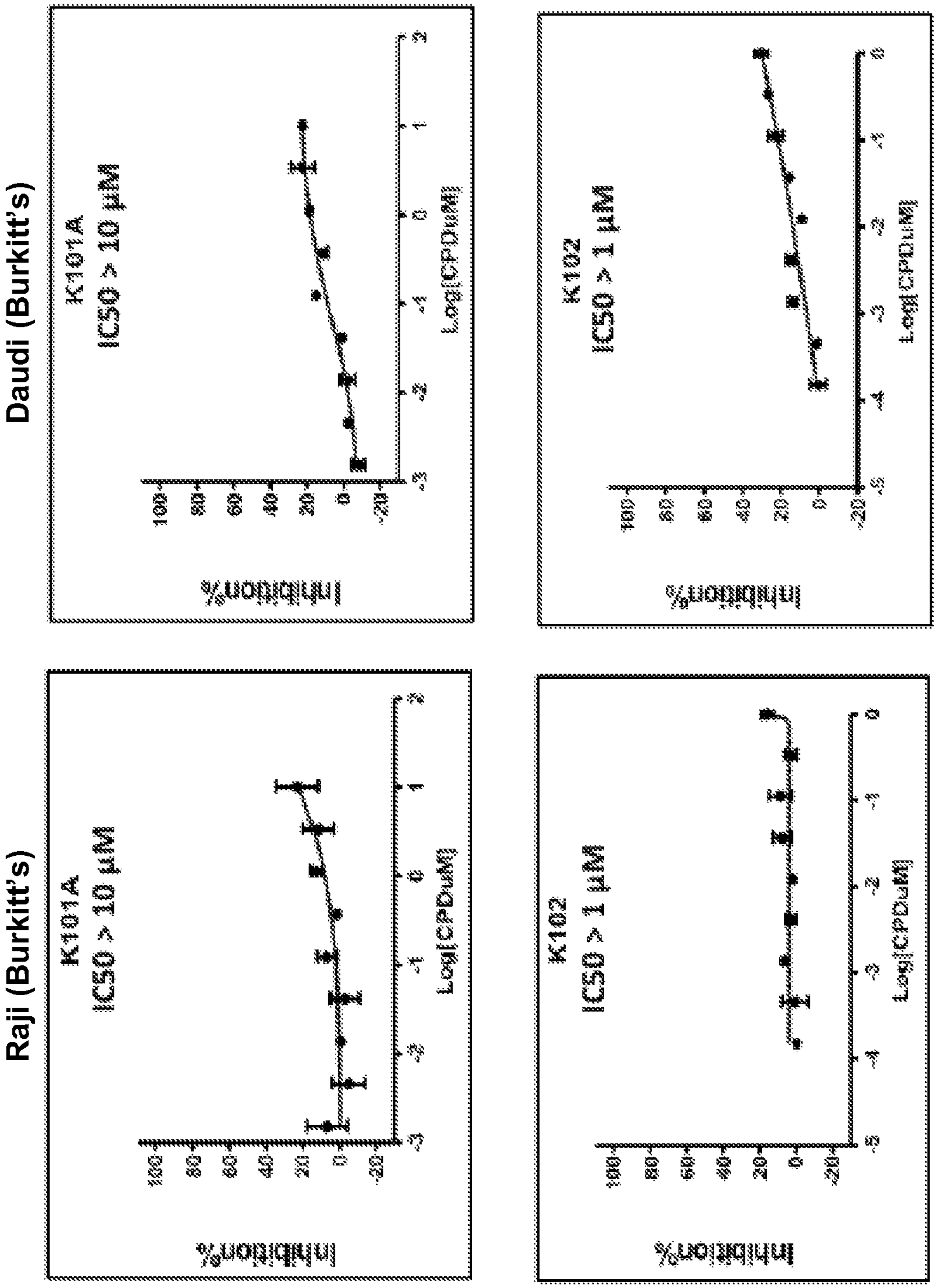
Figure 25C:
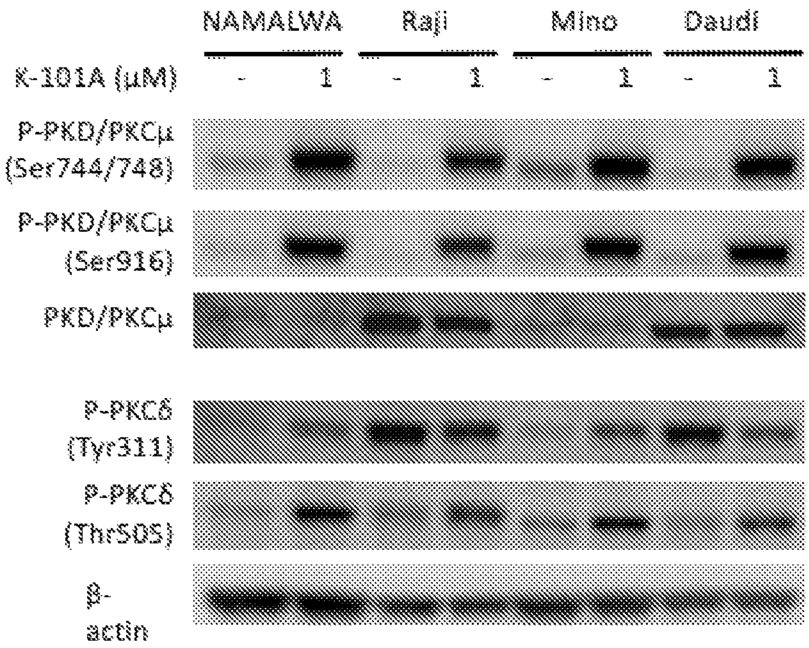

FIG. 25A, and FIG. 25B illustrate sensitivity of lymphoma cell lines (Namalwa, Mino, Raji and Daudi) to inhibition by prostratin (K101A) and ingenol 3 angelate (K102). FIG. 25C illustrates activation of PKC isoforms upon treatment with K101A in four lymphoma cell lines as assessed by Western Blot probed with antibodies that bind phosphorylated amino acids in the specified PKC enzyme. Namalwa and Mino cell lines are sensitive while the Raji and Daudi cell lines are insensitive to cell growth inhibition effects of the PKC activator.

Figure 26:
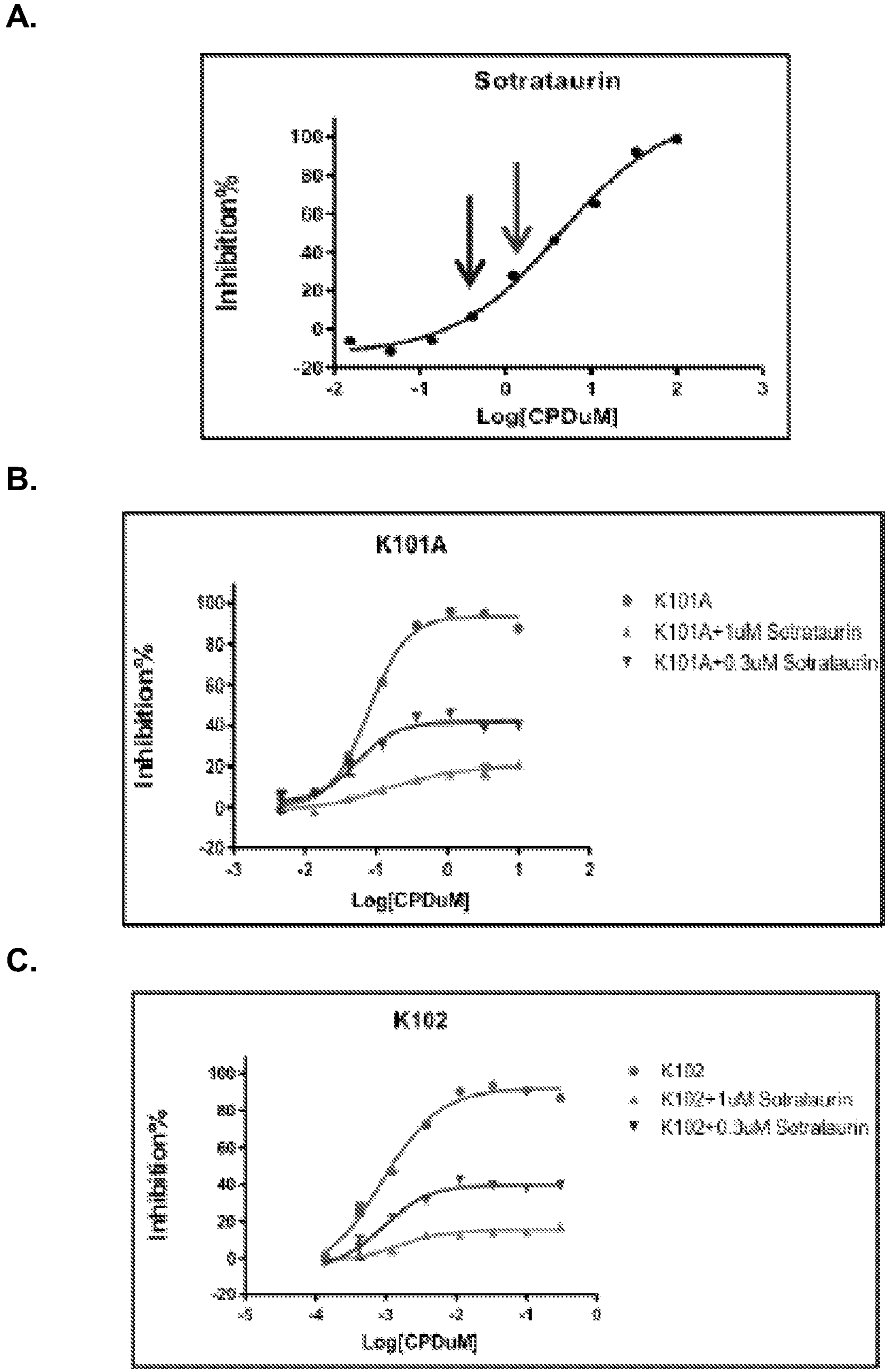

FIG. 26 shows effect of PKC inhibitor sotrastaurin on cell proliferation inhibitory effect of PKC activator prostratin (K101A) or ingenol-3-angelate (K102) in lymphoma cell line Mino. Panel A, sotrastaurin alone, where arrows indicate concentrations of sotrastaurin used for studies with PKC activators. Panel B, K101A alone, or K101A in presence of sotrastaurin at 1 μM or 0.3 μM. Panel C, K102 alone or K102 in presence of sotrastaurin at 1 μM or 0.3 μM.

Figure 27:
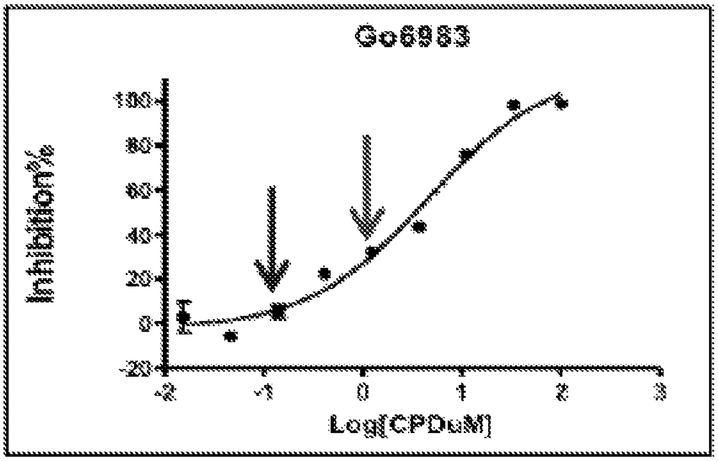
Figure 27:
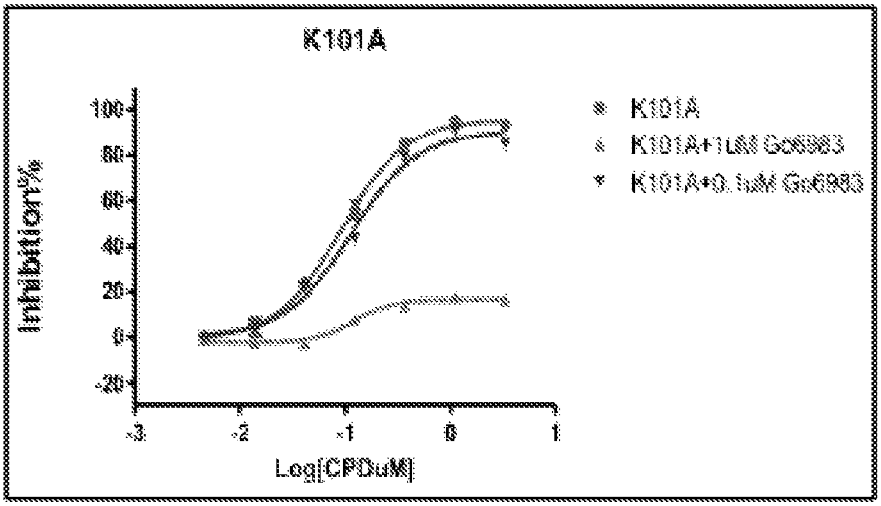
Figure 27:
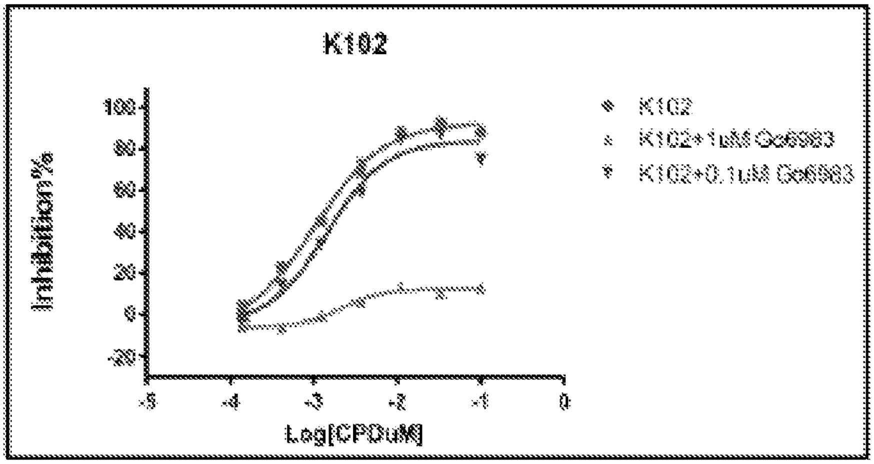

FIG. 27 shows effect of PKC inhibitor Go6983 on cell proliferation inhibitory effect of PKC activator prostratin (K101A) or ingenol-3-angelate (K102) in lymphoma cell line MINO. Panel A, Go6983 alone, where arrows indicate concentrations of Go6983 used for studies with PKC activators. Panel B, K101A alone, or K101A in presence of Go6983 at 1 μM or 0.1 μM. Panel C, K102 alone or K102 in presence of Go6983 at 1 μM or 0.1 μM.

Figure 28:
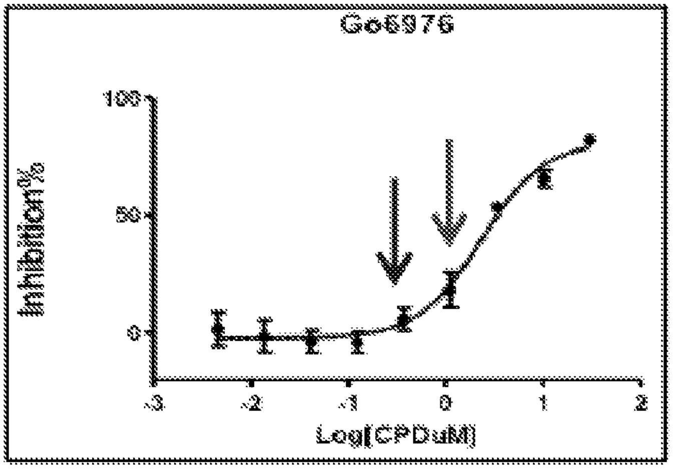
Figure 28:
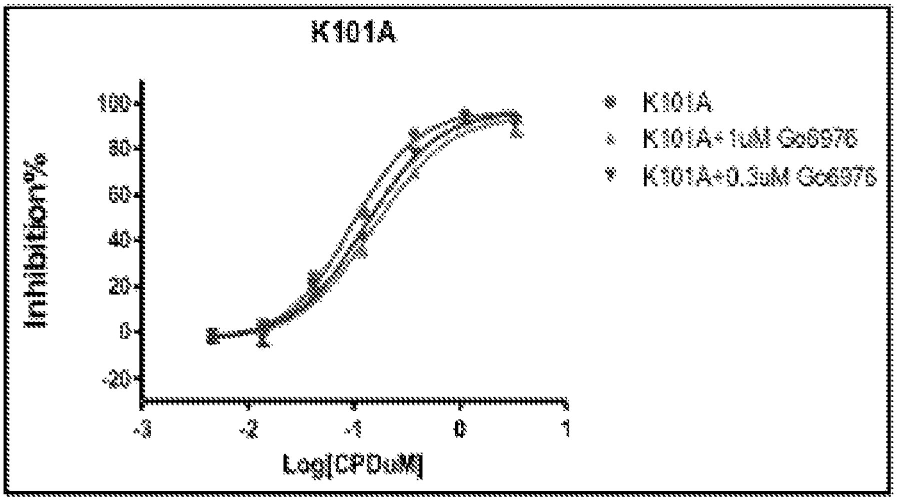
Figure 28:
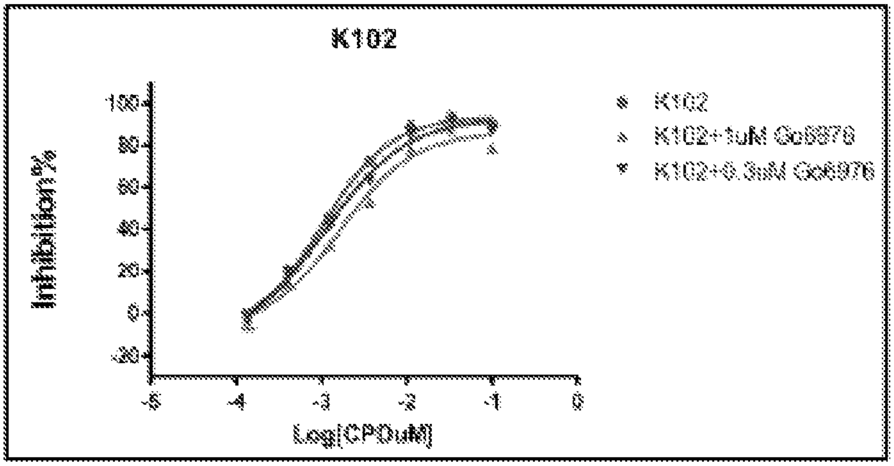

FIG. 28 shows effect of PKC inhibitor Go6976 on cell proliferation inhibitory effect of PKC activator prostratin (K101A) or ingenol-3-angelate (K102) in lymphoma cell line Mino. Panel A, Go6976 alone, where arrows indicate concentrations of Go6976 used for studies with PKC activators. Panel B, K101A alone, or K101A in presence of Go6976 at 1 μM or 0.3 μM. Panel C, K102 alone or K102 in presence of Go6983 at 1 μM or 0.3 μM.

Figure 29:
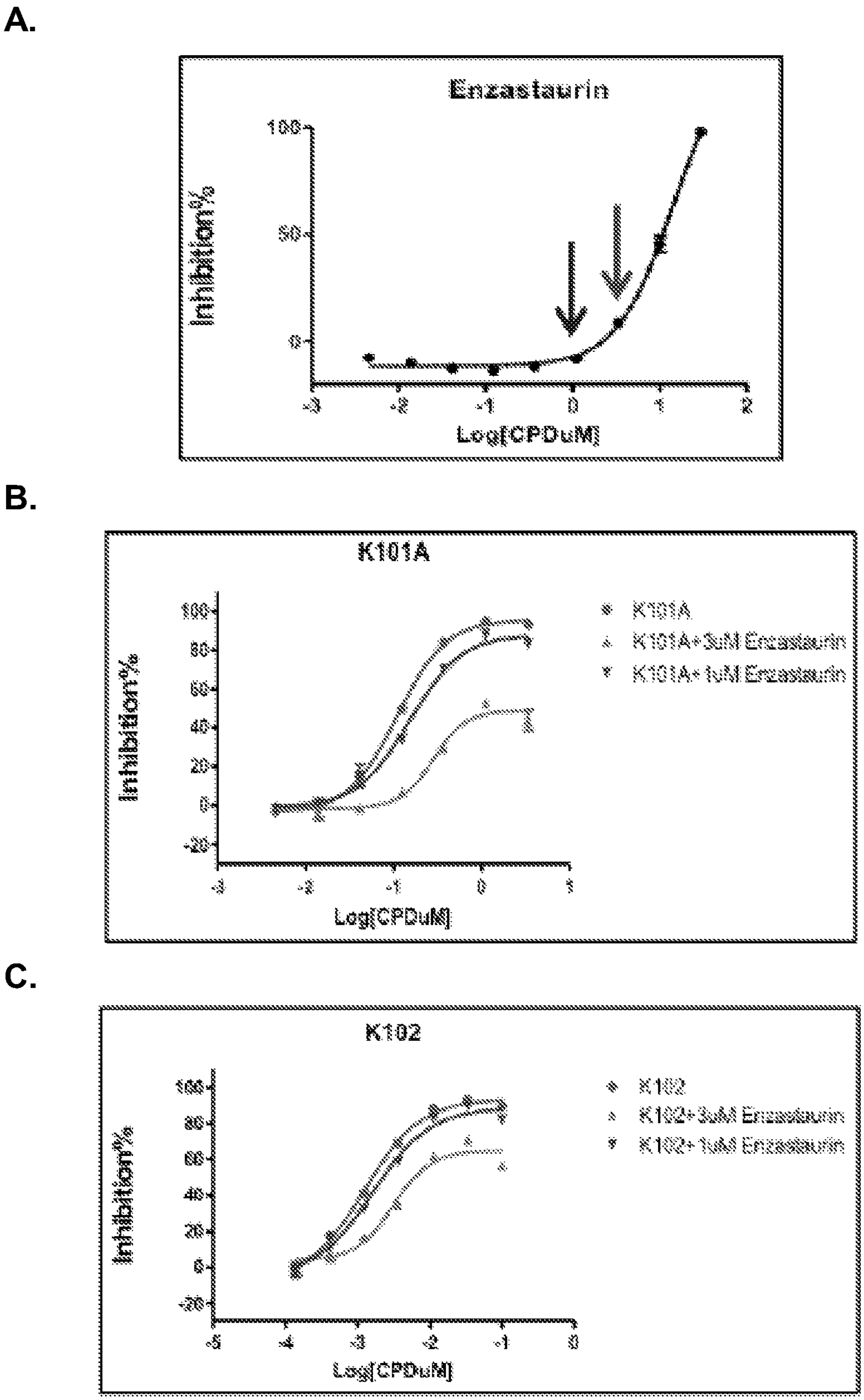

FIG. 29 shows effect of PKC inhibitor Enzastaurin on cell proliferation inhibitory effect of PKC activator prostratin (K101A) or ingenol-3-angelate (K102) in lymphoma cell line Mino. Panel A, Enzastaurin alone, where arrows indicate concentrations of Enzastaurin used for studies with PKC activators. Panel B, K101A alone, or K101A in presence of Enzastaurin at 3 μM or 1 μM. Panel C, K102 alone or K102 in presence of Enzastaurin at 3 μM or 1 μM.

Figure 30:
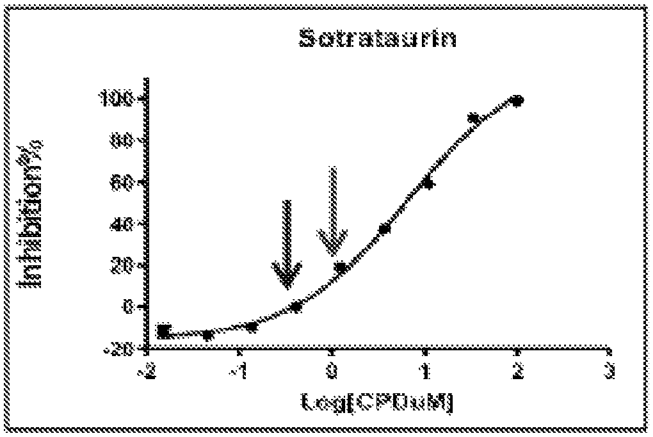
Figure 30:
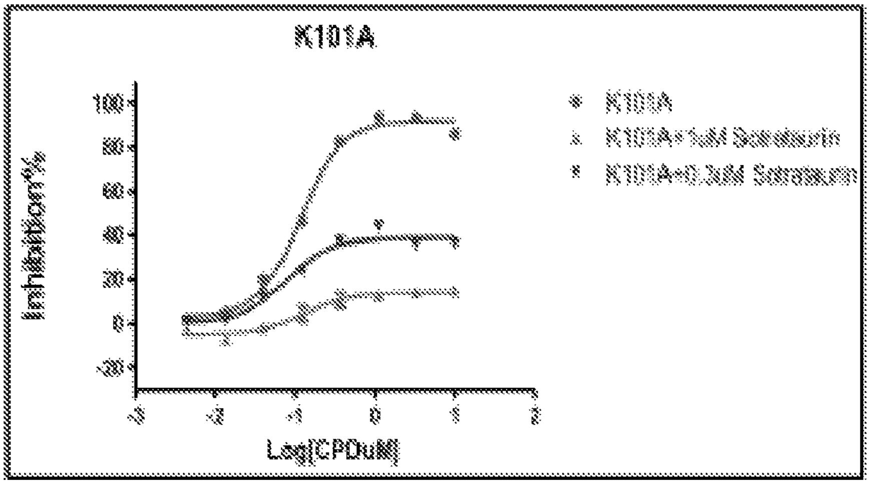
Figure 30:
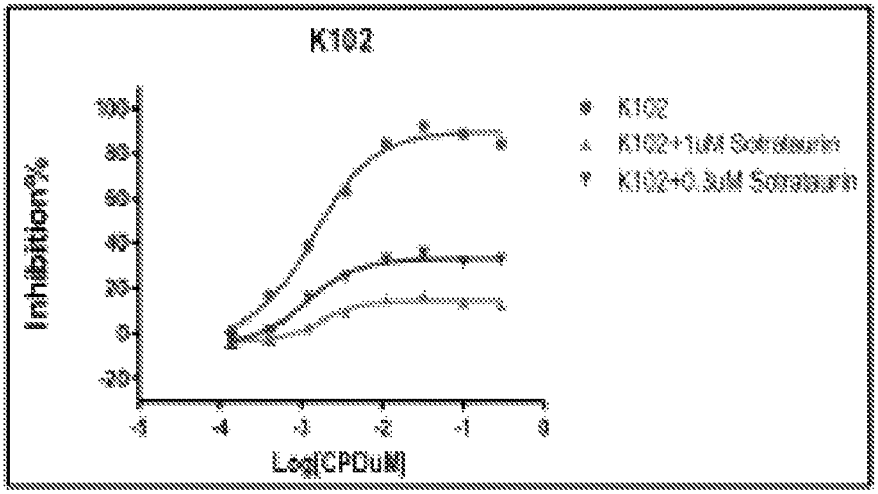

FIG. 30 shows effect of PKC inhibitor sotrastaurin on cell proliferation inhibitory effect of PKC activator prostratin (K101A) or ingenol-3-angelate (K102) in lymphoma cell line Namalwa. Panel A, sotrastaurin alone, where arrows indicate concentrations of sotrastaurin used for studies with PKC activators. Panel B, K101A alone, or K101A in presence of sotrastaurin at 1 μM or 0.3 μM. Panel C, K102 alone or K102 in presence of sotrastaurin at 1 μM or 0.3 μM.

Figure 31:
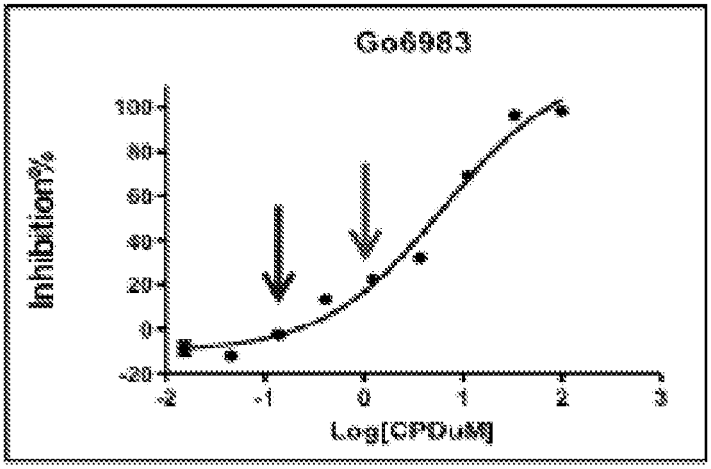
Figure 31:
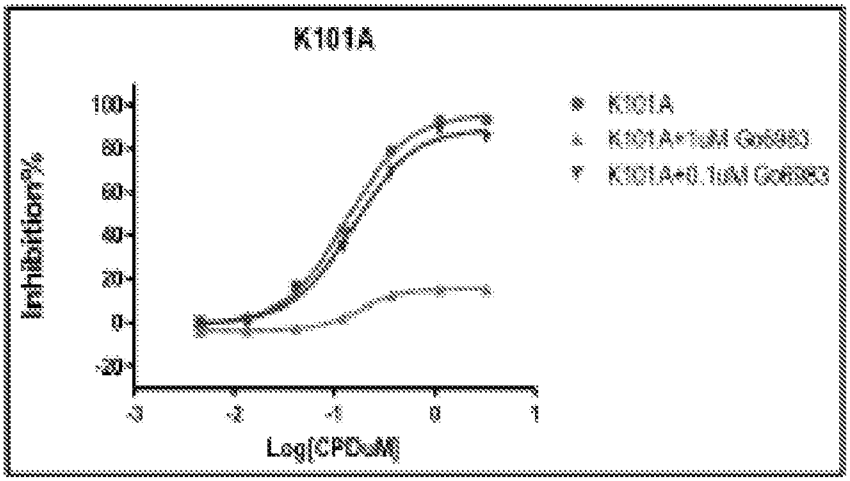
Figure 31:
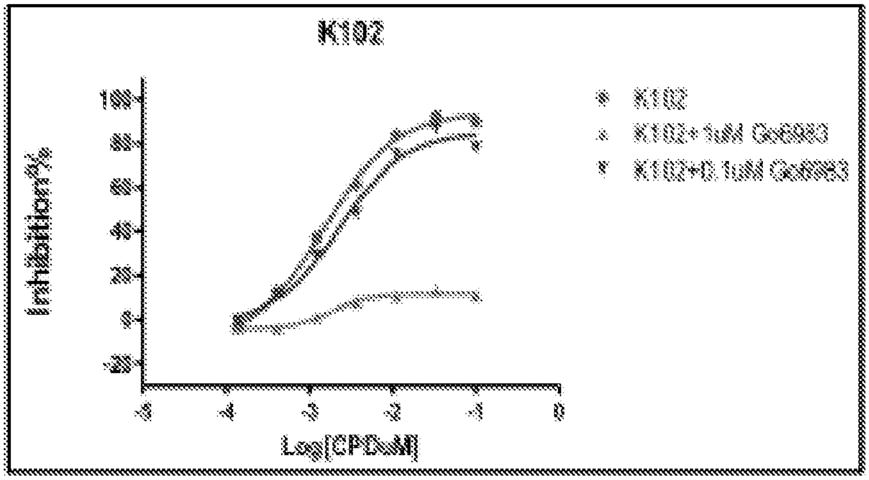

FIG. 31 shows effect of PKC inhibitor Go6983 on cell proliferation inhibitory effect of PKC activators prostratin (K101A) or ingenol-3-angelate (K102) in lymphoma cell line Namalwa. Panel A, Go6983 alone, where arrows indicate concentrations of Go6983 used for studies with PKC activators. Panel B, K101A alone, or K101A in presence of Go6983 at 1 μM or 0.1 μM. Panel C, K102 alone or K102 in presence of Go6983 at 1 μM or 0.1 μM.

Figure 32:
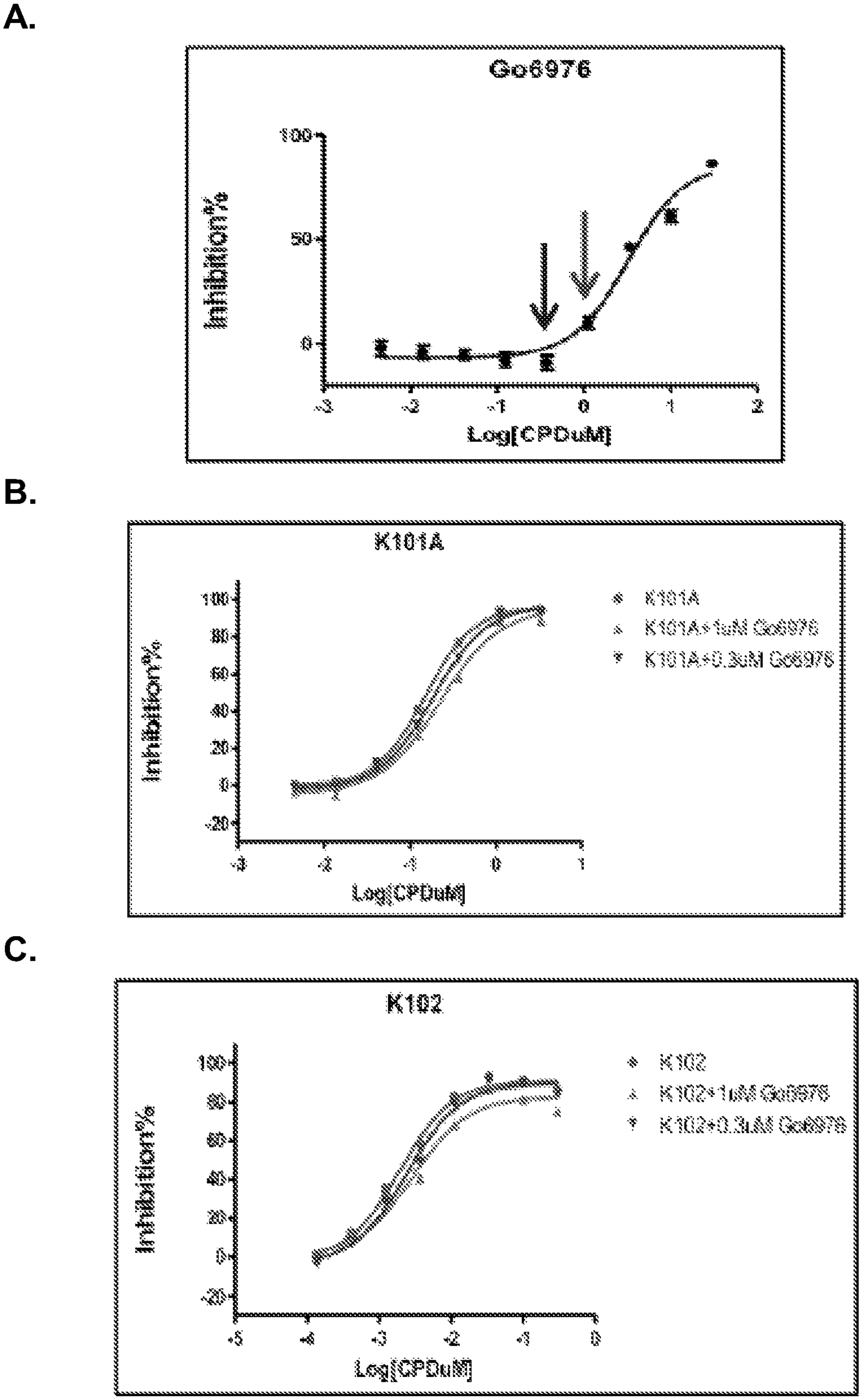

FIG. 32 shows effect of PKC inhibitor Go6976 on cell proliferation inhibitory effect of PKC activator prostratin (K101A) or ingenol-3-angelate (K102) in lymphoma cell line Namalwa. Panel A, Go6976 alone, where arrows indicate concentrations of Go6976 used for studies with PKC activators. Panel B, K101A alone, or K101A in presence of Go6976 at 1 μM or 0.3 μM. Panel C, K102 alone or K102 in presence of Go6983 at 1 μM or 0.3 μM.

Figure 33:
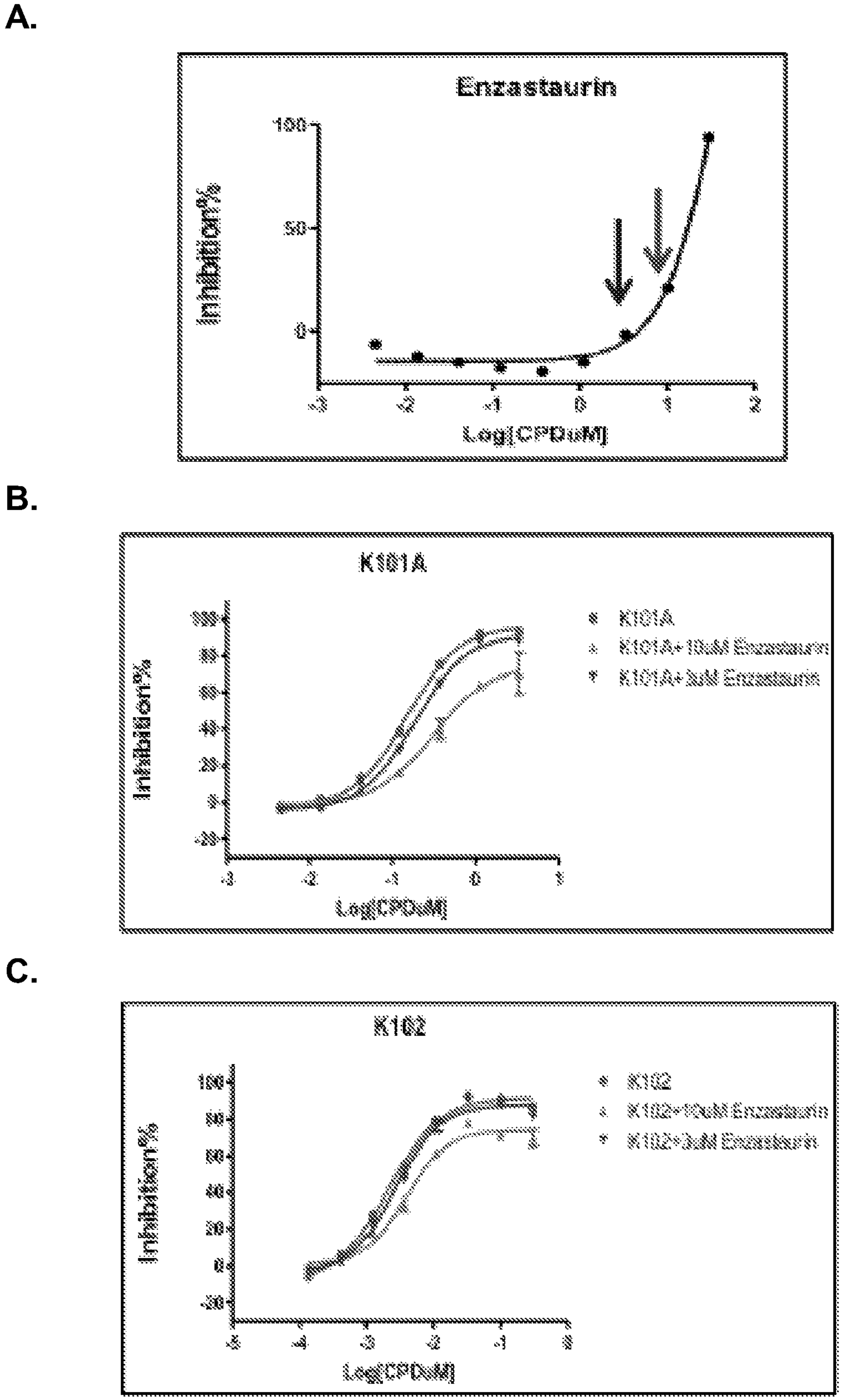

FIG. 33 shows effect of PKC inhibitor Enzastaurin on cell proliferation inhibitory effect of PKC activator prostratin (K101A) or ingenol-3-angelate (K102) in lymphoma cell line Namalwa. Panel A, Enzastaurin alone, where arrows indicate concentrations of Enzastaurin used for studies with PKC activators. Panel B, K101A alone, or K101A in presence of Enzastaurin at 3 μM or 1 μM. Panel C, K102 alone or K102 in presence of Enzastaurin at 3 μM or 1 μM.

Figure 34:
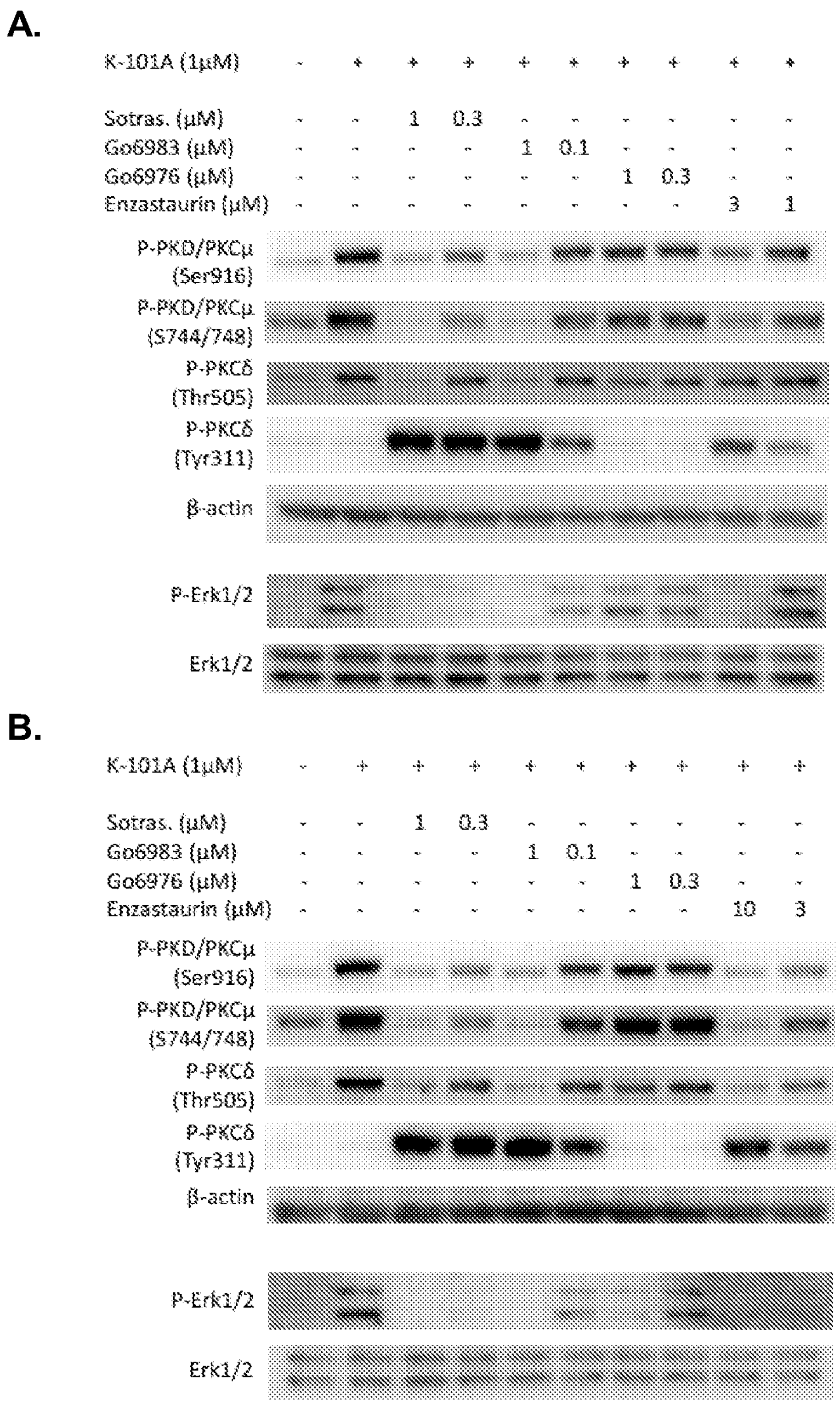

FIG. 34 shows effect of different PKC inhibitors on PKC activation by prostratin (K101A) in lymphoma cell lines Mino (Panel A) and Namalwa (Panel B) as assessed by Western Blot probed with antibodies that bind phosphorylated amino acids in PKCμ (Ser744/748, Ser 916) and PKCδ (Tyr311/505), and Erk1/2. Cells were pre-treated with the indicated amount of PKC inhibitors (Sotrastaurin, Go6983, Go6976, or Enzastaurin) for 30 minutes before adding K101A for another 30 minutes.

Figure 35:
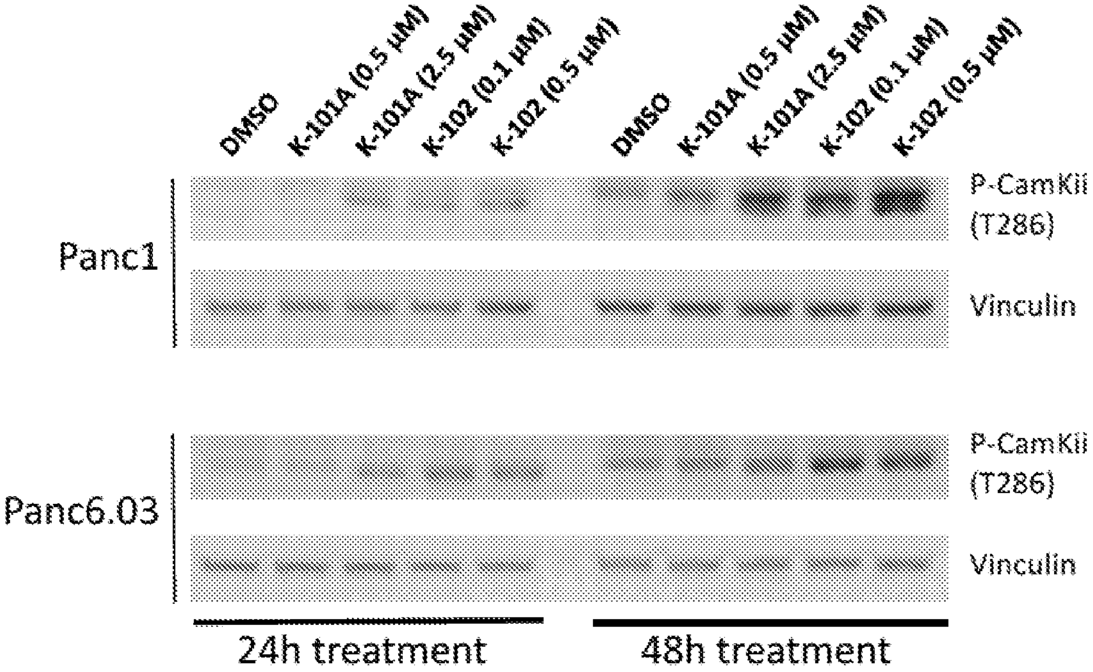

FIG. 35 shows effect of PKC activator prostratin (K101A) or ingenol-3-angelate (K102) on CaMKii phosphorylation at Thr286 in two pancreatic cancer cell lines, Panc1 and Panc6.03. PKC activation by the diterpenoid PKC activators result in increased phosphorylation at Thr286 of CaMKii.

Figure 36:
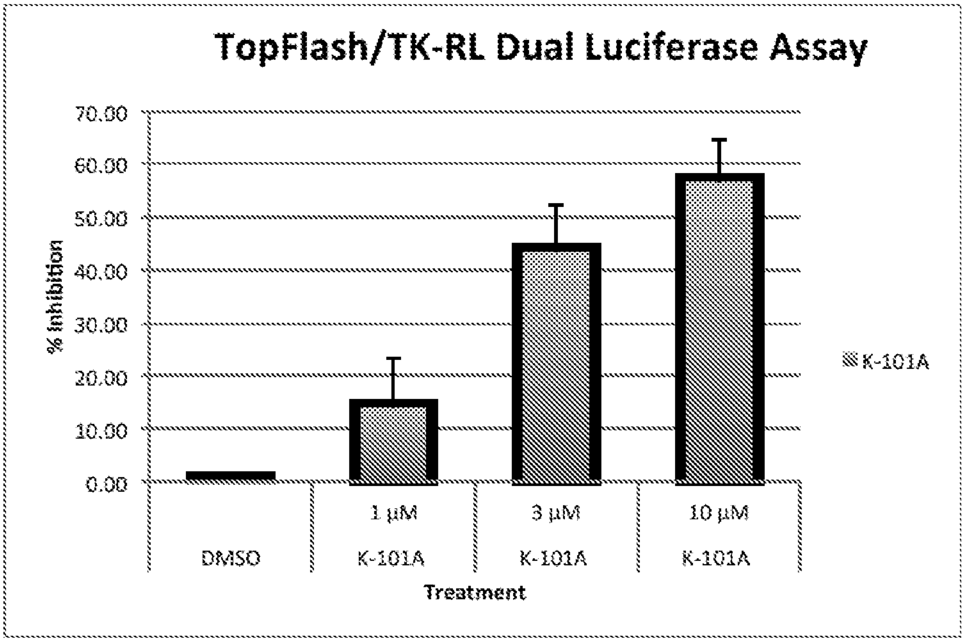
Figure 36:
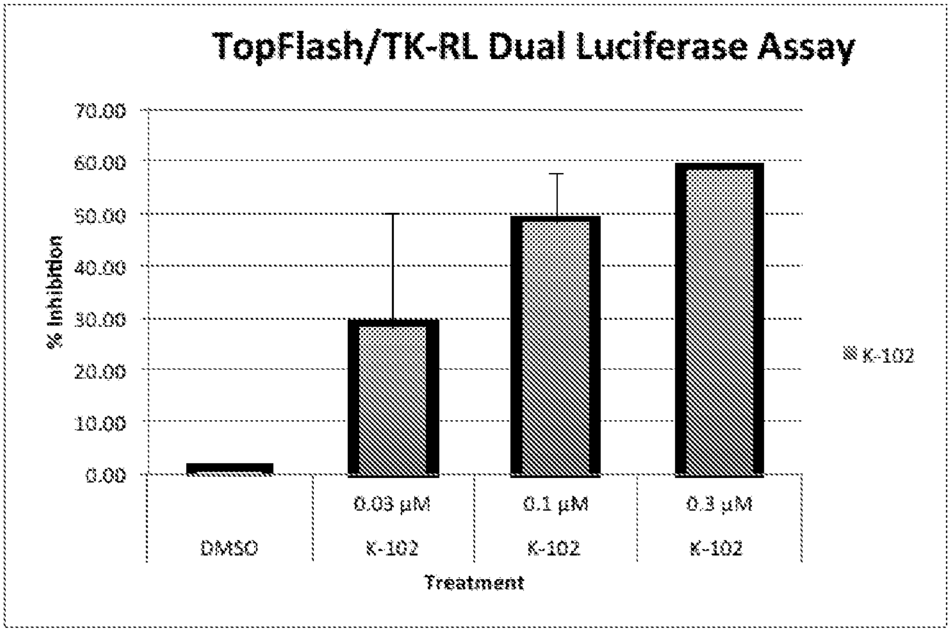

FIG. 36 illustrates the results of a TopFlash and TK-RL (internal control) Dual Luciferase assay, which measures the activation of Wnt signaling pathway via beta-catenin protein association with transcription factors TCF/LEF and their translocation to the nucleus for activation of Wnt target genes. Panel A illustrates results of TopFlash and TK-RL Dual Luciferase assay in A549 cells treated with prostratin (K101A). Panel B illustrates results of TopFlash TK-RL Luciferase assay in A549 cells treated with of ingenol-3-angelate (K102).

5. DETAILED DESCRIPTION

As used in this specification and the appended claims, the singular forms “a”, “an” and “the” include plural referents unless the context clearly indicates otherwise. Thus, for example, reference to "a protein" includes more than one protein, and reference to "a compound" refers to more than one compound.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure. The section headings used herein are for organizational purposes only and not to be construed as limiting the subject matter described.

5.1. Definitions

In reference to the present disclosure, the technical and scientific terms used in the descriptions herein will have the meanings commonly understood by one of ordinary skill in the art, unless specifically defined otherwise. Accordingly, the following terms are intended to have the meanings as described below.

"Polypeptide," "peptide" and "protein" are used interchangeably herein to denote a polymer of at least two amino acids covalently linked by an amide bond, regardless of length or modification, e.g., post-translational modification such as glycosylation, phosphorylation, lipidation, myristoylation, ubiquitination, etc.

"Amino acid position" and "amino acid residue" are used interchangeably to refer to the position of an amino acid in a polypeptide chain. In some embodiments, the amino acid residue can be represented as "XN", where X represents the amino acid and the N represents its position in the polypeptide chain. Where two or more variations, e.g., polymorphisms, occur at the same amino acid position, the variations can be represented with a "/" separating the variations. A substitution of one amino acid residue with another amino acid residue, such as a mutation, at a specified residue position can be represented by "XNY", where X represents the original amino acid, N represents the position in the polypeptide chain, and Y represents the replacement or substitute amino acid. In some embodiments, the amino acids can be represented by the standard three letter code or one letter code (e.g., Ser, Thr, Tyr and S, T, Y, respectively).

"Polynucleotide" or "nucleic acid" refers to two or more nucleosides that are covalently linked together. The polynucleotide may be wholly comprised ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more non-standard linkages. Non-limiting examples of such non-standard linkages include phosphoramidates, phosphorothioates, O-methylphosphodiesters, positively-charged linkages and non-ionic linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. Preferably, such modified or synthetic nucleobases will be encoding nucleobases.

"Protein Kinase C" or "PKC" refers to a family of protein kinases involved in signal transduction systems. Structurally, the typical PKC comprises a regulatory domain and a catalytic domain separated by a hinge region. PKC enzymes can be characterized by conserved domains, e.g., C1 to C4, each domain having different properties. In many PKC enzymes, the C1 domain interacts with diacylglycerol/phorbol esters; the C2 domain contains the recognition site for acidic lipids, and in some isozymes the $Ca^{+2}$ binding site; and the C3 and C4 domains form the ATP and substrate binding site. The C3 and C4 domain are part of the protein kinase domain. Some PKC enzymes differ in the C1 domain, and may not respond to phorbol esters. PKC proteins can be present as various isozymes and include, without limitation, α, βI, βII, γ, δ, ε, η, θ, ι/λ, μ, and ζ.

"Domain" and "region" are used interchangeably herein and refer to a contiguous sequence of amino acids within a defined protein, such as a PKC protein, typically characterized by being either conserved or variable.

"Protein kinase C activator" or "PKC activator" or "PKC activating compound" or "PKC agonist" refers to a moiety that enhances the activity of one or more PKC enzymes. The moiety can be, without limitation, a small molecule, a peptide, lipid, or carbohydrate. While PKC activation can be direct or indirect, unless otherwise specified, a PKC activator as used herein refers to a moiety that interacts with the PKC enzyme.

"Protein kinase activation potential" or "PKC activation potential" refers to the degree in which PKC activity can be increased by treatment with a PKC activator and/or the total PKC activity that can be achieved by treatment with a PKC activator.

"K-ras" refers to Kirsten rat sarcoma viral oncogene homolog, a small GTPase and a member of the ras family of proteins involved in signal transduction. Exemplary human K-ras gene and protein sequences are provided in GenBank Nos. M54968.1 and AAB414942.1, respectively. "K-ras" as used herein encompasses variants, including orthologs and interspecies homologs, of the human K-ras protein.

"Mutant K-ras polypeptide", "mutant K-ras protein", "mutant K-ras" and "K-ras mutation" are used interchangeably and refer to a K-ras polypeptide comprising at least one K-ras mutation as compared to the corresponding wild-type K-ras sequence. Certain exemplary mutant K-ras polypeptides include, but are not limited to, allelic variants, splice variants, derivative variants, substitution variants, deletion variants, insertion variants, and fusion polypeptides.

"N-ras" refers to Neuroblastoma RAS Viral (V-Ras) oncogene homolog, a small GTPase and a member of the ras family of proteins involved in signal transduction. Exemplary human N-ras gene and protein sequences are provided in NCBI Accession No. NP_002515 and GenBank Accession No. X02751, respectively. "N-ras" as used herein encompasses variants, including orthologs and interspecies homologs of the human N-ras protein.

"Mutant N-ras polypeptide", "mutant N-ras protein," "mutant N-ras" and "N-ras mutation" are used interchangeably and refer to an N-ras polypeptide comprising at least one N-ras mutation as compared to the corresponding wild-type N-ras sequence. Certain exemplary mutant N-ras polypeptides include, but are not limited to, allelic variants, splice variants, derivative variants, substitution variants, deletion variants, insertion variants, and fusion polypeptides.

"Activating K-ras" refers to a form of K-ras that has increased activity compared to wild-type K-ras. The activation of K-ras activity can result from a mutation or in some embodiments, overexpression of the K-ras protein. Oncogenic K-ras refers to forms of K-ras associated with cancers and/or tumorigenesis.

"Activating N-ras" refers to a form of N-ras that has increased activity compared to wild-type N-ras. The activation of N-ras activity can result from a mutation, or in some embodiments, overexpression of the N-ras protein. Oncogenic N-ras refers to forms of N-ras associated with cancers and/or tumorigenesis.

"Mutation" or "mutant" refers to an amino acid or polynucleotide sequence which has been altered by substitution, insertion, and/or deletion. In some embodiments, a mutant or variant sequence can have increased, decreased, or substantially similar activities or properties in comparison to the parental sequence.

"Gain-of-function" refers to enhancement of activity or acquisition of a new or abnormal activity of a nucleic acid or protein. "Gain-of-function mutation" in the context of a protein refers to an altered form of the protein that has enhanced activity or acquires a new or abnormal protein activity.

"Loss-of-function" refers to reduced or abolished activity (e.g., partially or wholly inactivated) of a nucleic acid or protein. "Loss-of-function mutation" in the context of a protein generally refers to a mutation that results in reduced or abolished protein function.

"Dominant negative" refers to the effect of an alteration in a gene that results in negation or attenuation of the effect of the normal or wild-type copy of the gene. The dominant negative effect may result from an expression product of the gene, such as an expressed RNA or expressed protein. By way of example and not limitation, a mutated, dominant negative PKC resulting in loss or attenuation of PKC activity can further lead to loss or attenuation of PKC activity of the normal or wild-type PKC, or in some instances, loss or attenuation of PKC activity of other PKC isoforms.

"Dominant negative mutation" refers to a change in an amino acid or polynucleotide sequence which has been altered by substitution, insertion, and/or deletion, and results in the "dominant negative" effect on a biological process, for example a signal transduction pathway.

"Identified" or "determined" refers to analyzing for, detection of, or carrying out a process for detecting the presence or absence of one or more specified characteristics, or one or more analytes.

"Frizzled protein" or "Frizzled" or "Fzd" refers to members of the family of G-protein coupled receptor proteins involved in the Wnt signaling pathway. As such, Frizzled belongs to the seven transmembrane class of receptors. Human frizzled proteins include, without limitation, Frizzled-1, Frizzled-2, Frizzled-3, Frizzled-4, Frizzled-5, Frizzled-6, Frizzled-7, and Frizzled-8.

"Ca2+/calmodulin-dependent protein kinase II" or "CaM kinase II" and "CaMKii" are used interchangeably herein and refer to serine/threonine-specific protein kinase that is regulated by the Ca2+/calmodulin complex. General structure of CaMKii includes a catalytic domain, an autoinhibitory domain, a variable segment, and a self-association domain. Phosphorylation at amino acid Thr286 in human CaMKii activates the kinase and regulates autoinhibition.

"Leukemia inhibitory factor" or "LIF" refers to an interleukin 6 class cytokine that affects cell growth by inhibiting differentiation. Of the several biological activities of LIF, it induces the terminal differentiation of myeloid leukemic cells. Exemplary human LIF protein sequence is provided as UniProtKB/Swiss-Prot. Accession No. P15018.1.

"Extracellular signal-regulated kinase 1/2," "Erk1/2," "Mitogen-activated protein kinase 1/2," and "MAPK1/2" refer to members of protein-serine/threonine kinases that participate in the Ras-Raf-MEK-ERK signal transduction cascade. Human ERK1 and ERK2 are 84% identical in sequence and share many biological functions. ERK1/2 are proline-directed kinases that preferentially catalyze the phosphorylation of substrates containing a Pro-Xxx-Ser/Thr-Pro sequence.

"β-catenin" refers to a protein containing armadillo repeat elements which fold together into a rigid protein domain having an elongated shape referred to as armadillo (ARM) domain. The protein regulates cell-cell adhesion and gene transcription. β-catenin can interact with transcription factors, such as LEF1, TCF1, TCF2 or TCF3, to form a complex, which activates transcription of several target genes. The human β-catenin is encoded by the CTNNB1 gene. Exemplary human β-catenin protein sequence is provided as UniProtKB/Swiss-Prot. Accession No. P35222.

"Wild-type" or "naturally occurring" refers to the form found in nature. For example, a naturally occurring or wild-type polypeptide or polynucleotide sequence is a sequence present in an organism that can be isolated from a source in nature and which has not been intentionally modified by human manipulation.

"Control" or "control sample" or "control group" refers to a sample or group that is compared to another sample or group, where generally the control sample or group are the same as a comparison group except for one or more factors being compared.

"Selecting" refers to the process of determining that a disease condition or a subject with a condition will receive an agent to treat the occurrence of the condition. Selecting can be based on susceptibility to a particular disease or condition due to, for example, presence of an identifying cellular, physiological or environment factor or factors. In some embodiments, selecting can be based on determining or identifying whether that subject or disease condition will be responsive to an agent, for example as assessed by identifying the presence of a biomarker and/or drug target marker that makes the subject or disease sensitive, insensitive, responsive, or unresponsive to an agent or treatment.

"Biological sample" refers to any sample including a biomolecule, such as a protein, a peptide, a nucleic acid, a lipid, a carbohydrate or a combination thereof, that is obtained from an organism, particularly a mammal. Examples of mammals include humans; veterinary animals like cats, dogs, horses, cattle, and swine; and laboratory animals like mice, rats and primates. In some embodiments, a human subject in the clinical setting is referred to as a patient. Biological samples include tissue samples (such as tissue sections and needle biopsies of tissue), cell samples (for example, cytological smears such as Pap or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, milk, vaginal fluid, saliva, swabs (such as buccal swabs), or any material containing biomolecules that is derived from a first biological sample. In particular embodiments, the biological sample is a "cell free sample", such as cell free or extracellular polynucleotides, and cell free or extracellular proteins. In some embodiments, cell free DNA or cfDNA refers to extracellular DNA obtained from blood, particularly the serum.

"Subject" as used herein refers to a mammal, for example a dog, a cat, a horse, or a rabbit. In some embodiments, the subject is a non-human primate, for example a monkey, chimpanzee, or gorilla. In some embodiments, the subject is a human, sometimes referred to herein as a patient.

"Treating" or "treatment" of a disease, disorder, or syndrome, as used herein, includes (i) preventing the disease, disorder, or syndrome from occurring in a subject, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art, particularly in view of the guidance provided in the present disclosure.

"Therapeutically effective amount" refers to that amount which, when administered to an animal for treating a disease, is sufficient to effect such treatment for the disease, disorder, or condition.

"Alkyl" refers to straight or branched chain hydrocarbon groups of 1 to 20 carbon atoms, particularly 1 to 12 carbon atoms, and more particularly 1 to 8 carbon atoms. Exemplary "alkyl" includes, but are not limited to, methyl, ethyl, n-propyl, i-propyl, n-butyl, s-butyl, t-butyl, n-pentyl, and s-pentyl.

"Alkenyl" refers to straight or branched chain hydrocarbon group of 2 to 20 carbon atoms, particularly 2 to 12 carbon atoms, and most particularly 2 to 8 carbon atoms, having at least one double bond. Exemplary "alkenyl" includes, but are not limited to, vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

"Alkynyl" refers to a straight or branched chain hydrocarbon group of 2 to 12 carbon atoms, particularly 2 to 8 carbon atoms, containing at least one triple bond. Exemplary "alkynyl" includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Alkylene", "alkenylene" and "alkynylene" refers to a straight or branched chain divalent hydrocarbon radical of the corresponding alkyl, alkenyl, and alkynyl, respectively. The "alkylene", "alkenylene" and "alkynylene" may be optionally substituted, for example with alkyl, alkyloxy, hydroxyl, carbonyl, carboxyl, halo, nitro, and the like. In some embodiments, where an alkyl, alkenyl or alkynyl is appended to another chemical group, for example arylalkyl-, arylalkenyl-, and arylalkynyl-, the appended alkyl, alkenyl or alkynyl represents an alkylene, alkenylene and alkynylene, respectively.

"Lower" in reference to substituents refers to a group having between one and six carbon atoms.

"Cycloalkyl" refers to any stable monocyclic or polycyclic system which consists of carbon atoms, any ring of which being saturated. "Cycloalkenyl" refers to any stable monocyclic or polycyclic system which consists of carbon atoms, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, and bicycloalkyls.

"Heterocycloalkyl" or "heterocyclyl" refers to a substituted or unsubstituted 5 to 8 membered, mono- or bicyclic, non-aromatic hydrocarbon, wherein 1 to 3 carbon atoms are replaced by a heteroatom. Heteroatoms and/or heteroatomic groups which can replace the carbon atoms include, but are not limited to, —O—, —S—, —S—O—, —NR'—, —PH—, —S(O)—, $—S(O)_2—$, —S(O) NR'—, $—S(O)_2NR'—$, and the like, including combinations thereof, where each R' is independently hydrogen or lower alkyl. Examples include pyrrolidin-2-yl; pyrrolidin-3-yl; piperidinyl; morpholin-4-yl and the like.

"Aryl" refers to a six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Examples of "aryl" include phenyl, naphthyl, indanyl, and the like.

"Heteroaryl" refers to an aromatic heterocyclic ring, including both monocyclic and bicyclic ring systems, where at least one carbon atom of one or both of the rings is replaced with a heteroatom independently selected from N, O, and O, or at least two carbon atoms of one or both of the rings are replaced with a heteroatom independently selected from N, O, and S.

"Carbonyl" refers to —C(O)—. The carbonyl group may be further substituted with a variety of substituents to form different carbonyl groups including acids, acid halides, aldehydes, amides, esters, and ketones. For example, an —C(O)R', wherein R' is an alkyl is referred to as an alkylcarbonyl. In some embodiments, R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Halogen" or "halo" refers to fluorine, chlorine, bromine and iodine.

"Hydroxy" refers to —OH.

"Oxy" refer to group —O—, which may have various substituents to form different oxy groups, including ethers and esters. In some embodiments, the oxy group is an —OR', wherein R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Oxo" refers to =O.

"Alkyloxy" or "alkoxy" refers to —OR', wherein R' is an optionally substituted alkyl.

"Aryloxy" refers to —OR', wherein R' is an optionally substituted aryl.

"Carboxy" refers to $—COO^-$ or COOM, wherein M is H or a counterion.

"Carbamoyl" refers to —C(O)NR'R', wherein each R' is independently selected from H or an optionally substituted: alkyl, cycloalkyl, cycloalkylalkyl, heterocycloalkyl, heterocycloalkylalkyl, aryl, arylalkyl, heteroaryl, or heteroarylalkyl.

"Cyano" refers to —CN.

"Ester" refers to a group such as —C(=O)OR', wherein R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Thiol" refers to —SH.

"Sulfanyl" refers to —SR', wherein R' is selected from an optionally substituted: alkyl, cycloalkyl, cycloalkylalkyl, heterocycloalkyl, heterocycloalkylalkyl, aryl, arylalkyl, heteroaryl, and heteroarylalkyl. For example, —SR, wherein R is an alkyl is an alkylsulfanyl.

"Sulfonyl" refers to —$S(O)_2$—, which may have various substituents to form different sulfonyl groups including sulfonic acids, sulfonamides, sulfonate esters, and sulfones. For example, —$S(O)_2R'$, wherein R' is an alkyl refers to an alkylsulfonyl. In some embodiments of —$S(O)_2R'$, R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Sulfinyl" refers to —S(O)—, which may have various substituents to form different sulfinyl groups including sulfinic acids, sulfinamides, and sulfinyl esters. For example, —S(O)R', wherein R' is an alkyl refers to an alkylsulfinyl. In some embodiments of —S(O)R', R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Selenide" refers to Se, which may have various substituents, particularly alkyl groups. For example, —SeR', wherein R' is an alkyl group refers to an alkylselenide. In some embodiments, R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Phosphine" refers to —PR'R'R', wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Phosphate" refers to a group of formula —OP(=O)$(OR')_2$, wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Phosphono" refers to a group of formula —P(=O)$(OR')_2$, wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Phosphoramide" refers to a group of formula —OP(=O)R'R', wherein at least one of R' is an —NR"R", wherein each R" is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Phosphoramidite" refers to a group of formula —OP(OR')NR'R', wherein each R' is independently selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Phosphoramidate" refers to —OP(=O)(OR')NR'R, wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Phosphonate" refers to —P(=O)$(OR')_2$, wherein each R' is independently selected from H and an optionally substituted: alkyl, cycloalkyl, cycloalkylalkyl, heterocycloalkyl, heterocycloalkylalkyl, aryl, arylalkyl, heteroaryl and heteroarylalkyl.

"Ureide" refers to a cyclic or acyclic organic molecule of natural or synthetic origin that comprises one or more ureide moieties or derivatives thereof. Exemplary ureides include, among others, urea, uric acid, hydantoin, allantoin, imidazolidinyl urea (1,1'-methylenebis(3-[1-(hydroxymethyl)-2,5-dioxoimidazolidin-4-yl]urea), diazolydinyl urea (1,3-bis(hydroxymethyl)-1-(1,3,4-tris(hydroxymethyl)-2,5-dioxoimidazolidin-4-yl)urea), purines, and derivatives thereof.

"Urea" refers to a group such as —NHC(=O)NR'R', wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Amino" or "amine" refers to the group —NR'R' or —NR'R'R', wherein each R' is independently selected from H and an optionally substituted: alkyl, cycloalkyl, heterocycloalkyl, alkoxy, aryl, heteroaryl, heteroarylalkyl, acyl, alkyloxycarbonyl, sulfanyl, sulfinyl, sulfonyl, and the like. Exemplary amino groups include, but are not limited to, dimethylamino, diethylamino, trimethylammonium, triethylammonium, methylsulfonylamino, furanyl-oxy-sulfamino, and the like.

"Amide" refers to a group such as, —C(=O)NR'R', wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Sulfonamide" refers to —$S(O)_2NR'R'$, wherein each R' is independently selected from H and an optionally substituted: alkyl, heteroalkyl, heteroaryl, heterocycle, alkenyl, alkynyl, arylalkyl, heteroarylalkyl, heterocyclolalkyl, -alkylcarbonyl-, or alkylene-O—C(O)—OR", where R" is selected from H, alkyl, heteroalkyl, cyclolalkyl, heterocycloalkyl, aryl, heteroaryl, alkenyl, alkynyl, arylalkyl, heterocycloalkyl, heteroarylalkyl, amino, and sulfinyl.

"Guanidine" refers to —NR'C(=NR')NR'R', wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Optional" or "optionally" refers to a described event or circumstance may or may not occur, and that the description includes instances where the event or circumstance occurs and instances where the event or circumstance does not. For example, "optionally substituted alkyl" refers to an alkyl group that may or may not be substituted and that the description encompasses both substituted alkyl group and unsubstituted alkyl group.

"Optionally substituted" as used herein means one or more hydrogen atoms of the group can each be replaced with a substituent atom or group commonly used in pharmaceutical chemistry. Each substituent can be the same or different. Examples of suitable substituents include, but are not limited to, alkyl, alkenyl, alkynyl, cycloalkyl, aryl, arylalkyl, heterocycloalkyl, heteroaryl, OR' (e.g., hydroxyl, alkoxy (e.g., methoxy, ethoxy, and propoxy), aryloxy, heteroaryloxy, arylalkyloxy, ether, ester, carbamate, etc.), hydroxyalkyl, alkoxycarbonyl, alkoxyalkoxy, perhaloalkyl, alkoxyalkyl, SR' (e.g., thiol, alkylthio, arylthio, heteroarylthio, arylalkylthio, etc.), $S^+R'_2$, S(O)R', $SO_2R'$, NR'R" (e.g., primary amine (i.e., $NH_2$), secondary amine, tertiary amine, amide, carbamate, urea, etc.), hydrazide, halo, nitrile, nitro, sulfide, sulfoxide, sulfone, sulfonamide, thiol, carboxy, aldehyde, keto, carboxylic acid, ester, amide, imine, and imide, including seleno and thio derivatives thereof, wherein each of the substituents can be optionally further substituted. In embodiments in which a functional group with an aromatic carbon ring is substituted, such substitutions will typically number less than about 10 substitutions, more preferably about 1 to 5, with about 1 or 2 substitutions being preferred.

"Prodrug" refers to a derivative of an active compound (e.g., drug) that requires a transformation under the conditions of use, such as within the body or appropriate in vitro conditions, to release the active drug. Prodrugs are frequently, but not necessarily, pharmacologically inactive until converted into the active drug. Prodrugs can be obtained by masking a functional group in the drug believed to be in part required for activity with a progroup to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

Various progroups, as well as the resultant promoieties, suitable for masking functional groups in the active drugs to yield prodrugs can be used. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed, e.g., in vivo or under appropriate in vitro conditions, to provide the amino group. A carboxyl group may be masked as an ester (including silyl esters and thioesters), amide or hydrazide promoiety, which may be hydrolyzed in vivo to provide the carboxyl group. Included within the scope of prodrugs are, among others, "biohydrolyzable carbonate", "biohydrolyzable ureide", "biohydrolyzable carbamate", "biohydrolyzable ester", "biohydrolyzable amide", and "biohydrolyzable phosphate" groups.

"Biohydrolyzable carbonate", "biohydrolyzable ureide" and "biohydrolyzable carbamate" refers to a carbonate, ureide, or carbamate form, respectively, of a drug substance, such as the PKC activating compound of the disclosure, which (a) does not interfere with the biological activity of the parent substance but confers on that substance advantageous properties in vivo such as duration of action, onset of action, and the like, or (b) is biologically inactive but is readily converted in vivo by the subject to the biologically active principle.

"Biohydrolyzable ester" is an ester of a drug substance, such as the PKC activating compounds of the disclosure, which either a) does not interfere with the biological activity of the parent substance but confers on that substance advantageous properties in vivo such as duration of action, onset of action, and the like, or b) is biologically inactive but is readily converted in vivo by the subject to the biologically active principle. Examples include, by way of example, lower alkyl esters, lower acyloxy-alkyl esters, lower alkoxyacyloxyalkyl esters, alkoxyacyloxy esters, alkyl acylamino alkyl esters, and choline esters.

"Biohydrolyzable amide" refers to an amide of a drug substance, such as the PKC activating compounds of the disclosure, which either a) does not interfere with the biological activity of the parent substance but confers on that substance advantageous properties in vivo such as duration of action, onset of action, and the like, or b) is biologically inactive but is readily converted in vivo by the subject to the biologically active principle.

"Solvate" refers to a complex of variable stoichiometry formed by a solute, such as a PKC activator compound, and a solvent. Such solvents are selected to minimally interfere with the biological activity of the solute. Solvents may be, by way of example and not limitation, water, ethanol, or acetic acid.

"Hydrate" refers to a combination of water with a solute, such as a PKC activator compound, wherein the water retains its molecular state as water and is either absorbed, adsorbed or contained within a crystal lattice of the solute (e.g., PKC activating compound).

"Pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure may contain both basic and acidic functionalities that allow the compounds to be converted into either base or acid addition salts. Lists of suitable salts are found in Remington's Pharmaceutical Sciences, 17th Ed., Mack Publishing Company, Easton, Pa., (1985) and Journal of Pharmaceutical Science, 66:2 (1977), each of which is incorporated herein by reference in its entirety.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

5.2. Methods of Treating Cancers with Protein Kinase C (PKC) Activators

The present disclosure provides methods for treating cancer with a PKC activator. In various embodiments, the method is directed to selecting a cancer susceptible to PKC activation with a PKC activator, and treating the selected cancer with the PKC activator. In some embodiments, the method is directed to selecting a subject with cancer for treatment with a protein kinase C (PKC) activator, wherein the cancer is determined or identified as being susceptible to treatment with the PKC activator. In various embodiments, the PKC activator comprises a diterpenoid compound having PKC activating properties, as further described below.

In one aspect, the present disclosure provides a method of determining the sensitivity or insensitivity (e.g., resistance) of a cancer to a PKC activator. In some embodiments, the sensitivity or resistance of a cancer to a PKC activator can be determined based on the protein kinase C activation potential (PKC activation potential), which as used herein refers to the degree to which the PKC activity can be increased and/or maintained by treatment with a PKC activator. It is to be understood that some cancers are likely to have an attenuated or no response to the PKC activator because of, for example, inactivating mutations in the PKC itself, including deletion or partial deletion of the gene encoding the PKC, loss-of-function mutations, and/or mutations affecting downstream signaling elements. In this regards, it has been observed that a significant percentage of cancers have loss-of-function mutations in PKC and that the loss of PKC activity is associated with tumor formation and/or progression (see, e.g., Antal et al., 2015, Cell, 160: 489-502). Knowledge of the PKC activation potential, which allows an assessment of the ability of a cancer to respond to a PKC activator, provides a basis for determining the sensitivity or insensitivity of the cancer to a PKC activator and thus the likely effectiveness of the PKC activator in treatment of the cancer.

Accordingly, in some embodiments, a method of determining the sensitivity or insensitivity of a cancer to a PKC activator comprises contacting a cancer cell with a PKC activator, and determining the level of activation of PKC activity, wherein a cancer determined to have an effective PKC activation potential is likely sensitive to the PKC activator. As further described herein, the level of activation can be determined for total PKC activity or the activity of one or more PKC isoforms selected from PKC α, β, γ, δ, ε, η, ι/λ, ζ, μ, and θ.

In some embodiments, a method of selecting a cancer for treatment with a PKC activator comprises determining a PKC activation potential of the cancer for the PKC activator, and selecting the cancer having an effective PKC activation potential for the PKC activator for treatment with the PKC activator. In some embodiments, a method of selecting a cancer for treatment with a PKC activator comprises: contacting a cancer cell with a PKC activator, determining the level of activation of one or more PKC enzymes, and selecting the cancer having an effective PKC activation of the one or more PKC enzymes for treatment with the PKC activator.

In some embodiments, a method of selecting a subject with cancer for treatment with a PKC activator comprises: determining or identifying a PKC activation potential of the cancer for the PKC activator, and selecting the subject with a cancer determined to have an effective PKC activation potential for the PKC activator for treatment with the PKC activator. In some embodiments, a method of selecting a subject with a cancer for treatment with a PKC activator comprises: contacting a cancer cell from the subject with a PKC activator, determining the level of activation of one or more PKC enzymes, and selecting the subject with a cancer determined to have an effective PKC activation potential for treatment with the PKC activator.

In some embodiments, a method of treating a cancer with a PKC activator comprises: determining a PKC activation potential of the cancer for the PKC activator, and treating a cancer determined to have an effective PKC activation potential with an effective amount of the PKC activator. In some embodiments, a method of treating a subject with cancer comprises determining or identifying a PKC activation potential of the cancer for a PKC activator, and administering to the subject having a cancer determined to have an effective PKC activation potential a therapeutically effective amount of the PKC activator. In some embodiments, a method of treating a subject with cancer comprises administering to a subject in need thereof a therapeutically effective amount of a PKC activator, wherein the cancer has been determined or identified as having an effective PKC activation potential for the PKC activator.

In some embodiments, the PKC activation potential can take into account (a) the basal level of PKC activity present in the cancer cell, and/or (b) the increase in PKC activity upon contacting the cancer cell or upon treatment of the cancer with the PKC activator. Without being bound by theory, a low basal level of PKC activity may result in insufficient level of PKC activity even upon treatment with a PKC activator to affect cell proliferation, thus resulting in an insignificant therapeutic effect. A low basal level of PKC activity can arise from, among others, down-regulation of PKC expression, mutations affecting expression control of the PKC gene, and/or inactivating or activity-attenuation mutations in the PKC enzyme itself. Moreover, PKC activity that is not or ineffectively activated upon treatment with a PKC activator would also likely result in ineffective increase in PKC activity to affect cell proliferation, thus resulting in insufficient therapeutic benefit. In some embodiments, the PKC activity can be determined or measured for global PKC activity (i.e., total PKC activity), or determined or measured for one or more specific PKC isoforms in the cancer cell.

The presence of an effective PKC activation potential for a PKC activator can be determined by various methods. In some embodiments, the effective PKC activation potential can be determined by measuring the level of PKC activation in cancer cells sensitive to the PKC activator, e.g., based on inhibition of cell proliferation. For example, the level of PKC activation associated with 50% inhibition of cell proliferation ($IC_{50}$) by a PKC activator can be used as an effective PKC activation potential for the PKC activator. In some embodiments, a cancer cell insensitive or resistant to the PKC activator, e.g., insignificant effect on cell proliferation at concentration of PKC activator sufficient to inhibit proliferation of PKC-activator sensitive cells (e.g., $IC_{50}$), can be used to identify the PKC enzyme activated by the PKC activator in sensitive cancer cells. In some embodiments, the basal level of PKC activity in PKC activator sensitive cells as compared to level of PKC activity in PKC activator insensitive cells can be used to determine a basal level of PKC activity, either as total PKC activity or activity of one or more specific PKC isoforms associated with sensitivity to the PKC activator.

In some embodiments, the effective PKC activation potential for a PKC activator can be determined by the use of a PKC inhibitor. The PKC inhibitor can be a broad spectrum inhibitor or a specific inhibitor targeting one or a limited set of the PKC isoforms. In some embodiments, a cancer cell sensitive to a PKC activator can be treated with different concentrations of a PKC inhibitor and then treated with the PKC activator. The reduction in PKC activator-mediated inhibition of cell proliferation by treatment with the PKC inhibitor and the associated level of PKC activation can provide a measure of the level of effective PKC activation sufficient for inhibiting cell proliferation. In some embodiments, the PKC inhibitor used is an inhibitor specific to a PKC isoform or specific to a limited set of PKC isoforms.

In some embodiments, a cancer with a basal level of total PKC activity of at least 20%, 30%, 40%, 50%, 60%, 70%, 80%, 90% or more of the basal PKC activity present in a suitable control, for example non-cancerous cells or tissues or normal cells or tissues, can provide an indication of sensitivity to a PKC activator, and thus a basis for selection of the cancer for treatment with the PKC activator.

In some embodiments, a cancer which displays an increase in total PKC activity of at least 30%, 40% 50%, 60%, 70%, 80%, 90%, 100%, 150%, 200% or more above the PKC activity of untreated cancer cells, in presence of or following treatment with the PKC activator indicates sensitivity to the PKC activator and thus a basis for selection of the cancer for treatment with the PKC activator.

In some embodiments, a cancer which has increased total PKC activity upon treatment with the PKC activator, such as in the foregoing, and in which the total PKC activity following treatment is at least 30%, 40%, 50%, 60%, 70%, 80%, 90%, 100%, 150%, 200% or more of the PKC activity of control non-cancerous cells or tissue indicates sensitivity to the PKC activator and thus a basis for selection of the cancer for treatment with the PKC activator.

In some embodiments, the selection of a cancer for treatment with a PKC activator is based on the PKC activation potential for one or more of PKC isoforms. In some embodiments, the PKC activation potential is determined or measured for one or more of PKC isoforms selected from PKC α, β, γ, δ, ε, η, θ, ι/λ, μ and ζ. In some embodiments, the PKC activation potential is determined or measured for one or more classical PKCs. Exemplary classical PKCs include PKC α, β (e.g., βI, βII), and γ. In some embodiments, the PKC activation potential is determined or measured for one or more novel PKCs. Exemplary novel PKCs include δ, ε, η, and θ. In some embodiments, the PKC activation potential is determined or measured for one or more atypical PKCs. Exemplary atypical PKCs include ι/λ and ζ. In some embodiments, the PKC activation potential is determined or measured for PKCμ, which is a member of the protein kinase D (PKD) family.

In some embodiments, a cancer with a basal level of PKC activity of at least 20%, 30%, 40%, 50%, 60%, 70%, 80%, 90% or more of the basal PKC activity for one or more of PKC isoforms selected from PKC α, β, γ, δ, ε, η, θ, ι/λ, μ and ζ as compared to a suitable control level, for example the basal level in non-cancerous cells or tissues (e.g., normal cells or tissues), can provide an indication of sensitivity to a PKC activator, and thus a basis for selection of the cancer for treatment with the PKC activator. In some embodiments, the determination of a basal level of PKC activity can be useful where the PKC activity is known to be expressed in the control cells or tissues in the absence of treatment with the PKC activator.

In some embodiments, a cancer which displays or is capable of an increase in one or more of PKC α, β, γ, δ, ε, η, θ, ι/λ, μ and ζ activity of at least 30%, 40%, 50%, 60%, 70%, 80%, 90%, 100%, 150%, 200% or more above the PKC α, β, γ, δ, ε, η, θ, ι/λ, μ and ζ activity, respectively, of a control level, e.g., untreated cancer cells, in presence of or following treatment with the PKC activator is selected for treatment with the PKC activator.

In some embodiments, the PKC activation potential is measured for one or more of PKC α, β, and γ. In some embodiments, a cancer with a basal level of PKC α, β, or γ activity of at least 20%, 30%, 40%, 50%, 60%, 70%, 80%, 90% or more of the basal PKC α, β, or γ activity, respectively, of a control level, e.g., normal cells or normal tissue, is indicated for treatment with the PKC activator. In some embodiments, a cancer which displays or is capable of an increase in one or more of PKC α, β, and γ activity of at least 30%, 40%, 50%, 60%, 70%, 80%, 90%, 100%, 150%, 200% or more above the PKC α, β, or γ activity, respectively, of a control level, e.g., untreated cancer cells, in presence of or following treatment with the PKC activator is selected for treatment with the PKC activator. In some embodiments, a cancer which displays or is capable of an increase in PKC α, β, or γ activity upon treatment with the PKC activator, such as in the foregoing, and in which the total PKC α, β, or γ activity is at least 30%, 40%, 50%, 60%, 70%, 80%, 90%, 100%, 150%, 200% or more of the PKC activity of a control level, e.g., untreated cells, in presence of or following treatment with the PKC activator is selected for treatment with the PKC activator.

In some embodiments, the PKC activation potential is measured for one or more of PKC δ, ε, η, or θ. In some embodiments, a cancer with a basal level of PKC δ, ε, η, or θ activity of at least 20%, 30%, 40%, 50%, 60%, 70%, 80%, 90% or more of the basal PKC δ, ε, η, or θ activity, respectively, of a control level, e.g., normal cells or normal tissue, is indicated for treatment with the PKC activator. In some embodiments, a cancer which displays or is capable of an increase in one or more of PKC δ, ε, η, or θ activity of at least 30%, 40%, 50%, 60%, 70%, 80%, 90%, 100%, 150%, 200% or more above the PKC δ, ε, η, or θ activity, respectively, of a control level, e.g., untreated cancer cells, in presence of or following treatment with the PKC activator is selected for treatment with the PKC activator. In some embodiments, a cancer which displays or is capable of an increase in PKC δ, ε, η, or θ activity upon treatment with the PKC activator, such as in the foregoing, and in which the total PKC δ, ε, η, or θ activity is at least 30%, 40%, 50%, 60%, 70%, 80%, 90%, 100%, 150%, 200% or more of the PKC activity of a control level, e.g., untreated cells, in presence of or following treatment with the PKC activator is selected for treatment with the PKC activator.

In some embodiments, the PKC activation potential is measured for one or more of PKC ι/λ, μ or ζ. In some embodiments, a cancer with a basal level of PKC ι/λ, μ or ζ activity of at least 20%, 30%, 40%, 50%, 60%, 70%, 80%, 90% or more of the basal PKC ι/λ, μ or ζ activity, respectively, of a control level, e.g., normal cells or normal tissue, is indicated for treatment with the PKC activator. In some embodiments, a cancer which displays or is capable of an increase in one or more of PKC ι/λ, μ or ζ activity of at least 30%, 40%, 50%, 60%, 70%, 80%, 90%, 100%, 150%, 200% or more above the PKC ι/λ, μ or ζ activity, respectively, of a control level, e.g., untreated cancer cells, in presence of or following treatment with the PKC activator is selected for treatment with the PKC activator. In some embodiments, a cancer which displays or is capable of an increase in PKC ι/λ, μ or ζ activity upon treatment with the PKC activator, such as in the foregoing, and in which the total PKC ι/λ, μ or ζ activity is at least 30%, 40%, 50%, 60%, 70%, 80%, 90%, 100%, 150%, 200% or more of the PKC activity of a control level, e.g., untreated cells, in presence of or following treatment with the PKC activator is selected for treatment with the PKC activator.

As further described herein, the PKC activation potential can be measured by various methods. In some embodiments, the PKC activation potential can be assessed by detecting or measuring one or more phosphorylated amino acid sequences in the PKC enzyme, particularly phosphorylation associated with activation or activity of the PKC enzyme. In some embodiments, the phosphorylated amino acid sequence detected has (i) increased phosphorylation induced by the PKC activator in a control, e.g., normal cells, and/or (ii) increased phosphorylation in control PKC activator-sensitive cancer cells but not in control PKC activator insensitive cancer cells. Determining the PKC activation potential can be based on identified phosphorylated amino acid sequences in one or more of PKC α, β (e.g., βI or βII,), γ, δ, ε, η, θ, ι/λ, μ, and ζ, particularly phosphorylated amino acid sequences localized in the protein kinase domain and carboxy terminal tail of the PKC, also referred to as the C3 and C4 domains (see, e.g., Newton, A. C., 2010, Am J Physiol Endocrinol Metab. 298:E395-E402; Steinberg, S. F., 2008, Physiol Rev. 88(4):1341-1378; incorporated herein by reference). Compilation of phosphorylated sites in each of the PKC enzymes is available at PhosphoSitePlus® at world wide web (www) at phosphosite.org.

In some embodiments, determining PKC activation potential for human PKCα can measure phosphorylation at one or more of S226, T228, T497, T638, S657 and Y658, particularly T497, T638, S657 and Y658.

In some embodiments, determining PKC activation potential for human PKCβ (βI/βII) can measure phosphorylation at one or more of Y368, T500, T504, Y507, Y515, Y518, T635, T642(641), and S661(660), particularly T500, T642(641), and S661(660).

In some embodiments, determining PKC activation potential for human PKCγ can measure phosphorylation at one or more of T514, T518, Y521, Y529, Y532, T655, T674 and S687, particularly T514 and T674.

In some embodiments, determining PKC activation potential for human PKCδ can measure phosphorylation at one or more of Y64, T141, Y187, T295, S299, Y313, Y374, S503, T505, S506, T507, T511, Y514, Y567, Y630, S643, S645, Y646, S647, S658, and S664, particularly Y64, Y187, Y313, T505, T507, T511, Y514, Y567, Y630, S643, S645, Y646, S647, S658, and S664.

In some embodiments, determining PKC activation potential for human PKCε can measure phosphorylation at one or more of Y250, T309, S329, S337, S346, S350, S368, S388, T566, T710, and S729, particularly T566, T710, and S729.

In some embodiments, determining PKC activation potential for human PKCη can measure phosphorylation at one or more of S28, S32, Y94, S317, S327, Y381, T656, S676, S685, S695, and S675, particularly S327, Y381, T656, and S675.

In some embodiments, determining PKC activation potential for human PKCθ can measure phosphorylation at one or more of Y90, T219, T307, T536, T538, Y545, S676, S685, and S695, particularly Y90, T538, S676, S685 and S695.

In some embodiments, determining PKC activation potential for human PKCι/λ can measure phosphorylation at one or more of Y136, T403, T409, T410, S411, T412, S459, T555, T557, T564, Y584, and S591, particularly T403, T409, T410, S411, T412, S459, T555, T557, T564, Y584, and S591.

In some embodiments, determining PKC activation potential for human PKCμ can measure phosphorylation at one or more of Y95, S205, S208, S219, S223, Y463, S738, S742, T746, S748, and S910, particularly Y95, Y463, S738, S742, S744, T746, S748, and S910, more particularly S910. The S910, Ser738, and Ser742 in human PKCμ are equivalent to Ser916, Ser744, and Ser748, respectively, in mouse PKCμ.

In some embodiments, determining PKC activation potential for human PKCζ can measure phosphorylation at one or more of S262, Y263, R375, T410, Y417, Y428, S520, T560, and S591, particularly T410, Y417, Y428, S520, T560, and S591.

In some embodiments, the PKC activation potential is determined by measuring phosphorylation at the kinase domain activation loop, the turn motif, and/or the hydrophobic motif of the PKC. In some embodiments, the PKC activation potential is determined by detecting phosphorylation at the kinase domain activation loop. Exemplary phosphorylations occurring at the activation loop of human PKCs include T497 for PKCα, T500 for PKCβ, T514 for PKCγ, T505 for PKCδ, T538 for PKCθ, T566 for PKCε, T512 for PKC η, T410 for PKCζ, T403 for PKCι/λ, and S738/S742 for PKCμ.

In some embodiments, the PKC activation potential is determined by measuring phosphorylation at the kinase domain turn motif. Exemplary phosphorylations occurring at the turn motif of PKCs include S638 for PKCα, T641 for PKCβ (βII and βII), T655 for PKCγ, T643 for PKCδ, S676 for PKCθ, T710 for PKCε, T645 for PKC η, and T560 for PKCζ.

In some embodiments, the PKC activation potential is determined by measuring phosphorylation at the kinase domain hydrophobic motif and/or carboxy terminal domain. Exemplary phosphorylations occurring at the hydrophobic motif and/or carboxy terminal domain include S657 for PKCα, S660 for PKCβ (βII and βII), S674 for PKCγ, S662 for PKCδ, S695 for PKCθ, S729 for PKCε, S664 for PKC η, and S910 for PKCμ.

In some embodiments, the PKC activation potential is determined by measuring phosphorylation at one or more autophosphorylation sites in the PKC enzyme. Exemplary autophosphorylation sites include: S638 for PKCα, T641 for PKCβ, T141/T295/T514 for PKCγ, T295/T505 for PKCδ, T219/T538/S676/S695 for PKCθ, S729 for PKCε, T655 for PKCη, T560 for PKCζ, and S738/S742/S910 for PKCμ.

In some embodiments, the PKC activation potential is determined for phosphorylation of PKCμ at Ser910, which is equivalent to Ser916 in mouse. In some embodiments, a method of determining the sensitivity of a cancer or selecting a cancer for treatment with a PKC activator includes determining the level of phosphorylated PKCμ at Ser910 in the cancer, wherein an elevated level of phosphorylated PKCμ at Ser910 upon treatment with the PKC activator indicates sensitivity of the cancer to the PKC activator. In some embodiments, a cancer or a subject with cancer is selected for treatment with a PKC activator if the cancer is determined to have (i) an elevated level of phosphorylated PKCμ at Ser910 upon treatment of the cancer with the PKC activator, or (ii) an elevated level of phosphorylated PKCμ at Ser910 upon treatment of the cancer with the PKC activator as compared to a control level, e.g., basal level in untreated cancer or normal cells or tissues. In some embodiments, a method of treating a subject with cancer comprises administering to a subject in need thereof a therapeutically effective amount of a PKC activator, e.g., a diterpenoid PKC activator, wherein the cancer is determined to have an elevated level of phosphorylated PKCμ at Ser910 upon treatment of the cancer with the PKC activator.

It is to be understood that in some embodiments, phosphorylation of a PKC can be correlated with insensitivity of a cancer to a PKC activator, in contrast to phosphorylation of a PKC that is correlated with sensitivity to the PKC activator. In some embodiments, the phosphorylated PKC can be present endogenously in the absence of treatment with a PKC activator, where presence of the phosphorylated PKC correlates with insensitivity to the PKC activator. In some embodiments, the phosphorylation of the PKC correlated with insensitivity to the PKC activator occurs in response to treatment of the cancer with a PKC activator. In some embodiments, the phosphorylation correlated with insensitivity to a PKC activator is phosphorylation of PKCδ, particularly phosphorylation of PKCδ at Tyr311. In some embodiments, a method of determining the sensitivity of a cancer or selecting a cancer for treatment with a PKC activator includes determining the level of phosphorylated PKCδ at Tyr311 in the cancer, wherein (i) an absence of phosphorylated PKCδ at Tyr311, or (ii) a basal level of phosphorylated PKCδ at Tyr311 as compared to a control level, e.g., basal level in control PKC activator sensitive cancer, indicates sensitivity of the cancer to the PKC activator. A basal level as used in this context refers to the level of phosphorylated PKCδ at Tyr311 in control PKC activator sensitive cancer cells, with or without treatment with the PKC activator. In some embodiments, a cancer or a subject with a cancer is selected for treatment with a PKC activator if the cancer has: (i) an absence of phosphorylated PKCδ at Tyr311, or (ii) a basal level of phosphorylated PKCδ at Tyr311 as compared to a control level. In some embodiments, a method of treating a subject with cancer comprises administering to the subject in need thereof a therapeutically effective amount of a PKC activator, e.g., a diterpenoid PKC activator, wherein the cancer is determined to have: (i) an absence of phosphorylated PKCδ at Tyr311, and/or (ii) a basal level of phosphorylated PKCδ at Tyr311 as compared to a control level, e.g., basal level in control PKC activator sensitive cancer cells or tissues.

In some embodiments, a cancer or a subject with cancer is not selected for treatment with a PKC activator if the cancer is determined to have (i) phosphorylated PKCδ at Tyr311, and/or (ii) an elevated level of phosphorylated PKCδ at Tyr311 as compared to a basal control level, e.g., level in control PKC activator sensitive cancer cells or tissues, or normal cells or tissue. In some embodiments, a cancer or a subject with cancer is not selected for treatment with a PKC activator when the level of phosphorylated PKCδ at Tyr311 is elevated compared to a control basal level, e.g., basal level in PKC activator sensitive cancer cells or tissues, or normal cells or tissues.

In some embodiments, the sensitivity or insensitivity of a cancer to a PKC activator can be based on assessment of the level of phosphorylated PKCμ at Ser910 (Ser916), and the level of phosphorylated PKCδ at Tyr311. In some embodiments, a method of determining the sensitivity of a cancer or selecting a cancer for treatment with a PKC activator includes: determining the level of phosphorylated PKCμ at Ser910, and the level of phosphorylated PKCδ at Tyr311, wherein (i) an elevated level of phosphorylated PKCμ at Ser910, and (ii) an absence or a basal level of phosphorylated PKCδ at Tyr311 upon treatment with the PKC inhibitor indicates sensitivity of the cancer to the PKC inhibitor. In some embodiments, a cancer or a subject with a cancer is selected for treatment with a PKC activator if the cancer is determined to have (i) an elevated level of phosphorylated PKCμ at Ser910 upon treatment with the PKC inhibitor, and (ii) an absence or a basal level of phosphorylated PKCδ at Tyr311 as compared to a control level. In some embodiments, a method of treating a subject with cancer comprises administering to the subject in need thereof a therapeutically effective amount of a PKC activator, e.g., a diterpenoid PKC activator, wherein the cancer is determined to have: (i) an elevated level of phosphorylated PKCμ at Ser910 upon treatment with the PKC inhibitor, and (ii) an absence or a basal level of phosphorylated PKCδ at Tyr311 as compared to a control level.

In some embodiments, the PKC activation potential can be assessed by determining the presence or absence of mutations in the gene encoding a PKC enzyme, where the mutations result in inactivation or attenuation of PKC activity, such as gene deletions and other loss-of-function mutations. The presence of such mutations in the PKC gene may result in low or no basal level of PKC activity and also display ineffective PKC activation upon treatment with the PKC activator. Accordingly, in some embodiments, the PKC activation potential is assessed by identifying or determining in the cancer the presence or absence of one or more loss-of-function mutations (e.g., inactivating or activity-attenuating) in the gene encoding the PKC enzyme. In various embodiments, a cancer determined or identified as being negative for loss-of-function mutations in one or more of PKC enzymes is selected for treatment with the PKC activator. In some embodiments, cancer determined or identified as being negative for two or more, three or more, four or more, or five or more loss-of-function mutations is selected for treatment with the PKC activator. In some embodiments, a cancer is not selected for treatment if it is determined or identified as having loss-of-function mutations in one or more PKC enzymes. In some embodiments, a cancer is not selected for treatment if it is determined or identified as having two or more, three or more, four or more, or five or more loss-of-function mutations. In view of the presence of various PKC isoforms, in some embodiments, the cancer is not selected for treatment with the PKC activator if two or more, three or more, four or more, or five or more PKC isoforms are determined or identified as having a loss-of-function mutation. In some embodiments, a cancer assessed for presence of a loss-of-function PKC mutation and measured for activation potential identifies the basis for selecting the cancer for treatment with a PKC activator. In some embodiments, assessment based on identification of or absence of a loss-of-function mutation alone is used as the basis for selecting or not selecting the cancer for treatment with a PKC activator.

In some embodiments, the loss-of-function mutation is assessed for one or more of PKC isoforms selected from PKC α, β, γ, δ, ε, η, θ, ι/λ, μ and ζ. In some embodiments, the loss-of-function mutation is assessed for one or more classical PKCs, including PKC α, β (e.g., βI, βII), and γ. In some embodiments, the loss-of-function mutation is assessed for one or more novel PKCs, including PKC δ, ε, η, and θ. In some embodiments, the loss-of-function mutation is assessed for one or more atypical PKCs, including PKC ι/λ and ζ. In some embodiments, the loss-of-function mutation is assessed for PKCμ.

In some embodiments, the loss-of-function mutation is assessed for one or more PKC isoforms selected from PKC α, β, and γ.

In some embodiments, the PKC is PKCα, and the loss-of-function mutation is an inactivating or activity-attenuating deletion or partial deletion of the gene encoding PKCα, or a loss-of-function mutation at one or more of codon 58, codon 61, codon 63, codon 75, codon 257, codon 435, codon 444, codon 481, codon 506, and codon 508. In some embodiments, the loss-of-function mutation in PKCα is one or more of αW58L, αG61W, αQ63H, αH75Q, αG257V, αF435C, αA444V, αD481E, αA506V, αA506T, and αE508K.

In some embodiments, the PKC is PKCβ, and the loss-of-function mutation is an inactivating or activity-attenuating deletion or partial deletion of the gene encoding PKCβ, or a loss-of-function mutation at one or more of codon 61, codon 353, codon 417, codon 484, codon 509, codon 523, codon 561, codon 585, and codon 619. In some embodiments, the loss-of-function mutation in PKCβ is one or more of βG61W, βF353L, βY417H, βD484N, βA509V, βA509T, βD523N, βP561H, βG585S, and βP619Q.

In some embodiments, the PKC is PKCγ, and the loss-of-function mutation is an inactivating or activity-attenuating deletion or partial deletion of the gene encoding PKCγ, or a loss-of-function mutation at one or more of codon 23, codon 57, codon 193, codon 218, codon 254, codon 362, codon 431, codon 450, codon 461, codon 498, codon 524, codon 537, and codon 575. In some embodiments, the loss-of-function mutation in PKCγ is one or more of γG23E, γG23W, γW57splice, γD193N, γT218M, γT218R, γD254N, γF362fs, γF362L, γG450C, γY431F, γA461T, γA461V, γD498N, γP524L, γP524R, γD537G, γD537Y, and γP575H.

In some embodiments, the loss-of-function mutation is assessed for one or more PKC isoforms selected from PKC δ, ε, η, or θ.

In some embodiments, the PKC is PKCδ, and the loss-of-function mutation is an inactivating or activity-attenuating deletion or partial deletion of the gene encoding PKCδ, or a loss-of-function mutation at one or more of codon 146, codon 454, codon 517, codon 530, and codon 568. In some embodiments, the loss-of-function mutation in PKCδ is one or more of δG146R, δA454V, δP517S, δD530G, δP568A, and δP568S.

In some embodiments, the PKC is PKCε, and the loss-of-function mutation is an inactivating or activity-attenuating deletion or partial deletion of the gene encoding PKCε, or a loss-of-function mutation at one or more of codon 162, codon 197, codon 502, and codon 576. In some embodiments, the loss-of-function mutation in PKCε is one or more of εR162H, εQ197P, εR502X, and εP576S.

In some embodiments, the PKC is PKCη, and the loss-of-function mutation is an inactivating or activity-attenuating deletion or partial deletion of the gene encoding PKCη, or a loss-of-function mutation at one or more of codon 284, codon 591, codon 596, and codon 598. In some embodiments, the loss-of-function mutation in PKCη is one or more of ηH284Y, ηK591E, ηK591N, ηR596H, and ηG598V.

In some embodiments, the PKC is PKCθ, and the loss-of-function mutation is an inactivating or activity-attenuating deletion or partial deletion of the gene encoding PKC θ, or a loss-of-function mutation at one or more of codon 171, codon 485, codon 548, and codon 616. In some embodiments, the loss-of-function mutation in PKCθ is one or more of θW171X, θA485T, θP548S, and θR616Q.

In some embodiments, the loss-of-function mutation is assessed for one or more PKC isoforms selected from PKCι/λ, μ and ζ.

In some embodiments, the PKC is PKCι/λ, and the loss-of-function mutation is an inactivating or activity-attenuating deletion or partial deletion of the gene encoding PKCι/λ, or a loss-of-function mutation at one or more of codon 179, codon 359, codon 396, and codon 423. In some embodiments, the loss-of-function mutation in PKCι/λ is one or more of ιH179Y, ιS359, ιD396E, and ιE423D.

In some embodiments, the PKC is PKCμ, and the loss-of-function mutation is an inactivating or activity-attenuating deletion or partial deletion of the gene encoding PKCμ, or a loss-of-function mutation at one or more of the mutations found in breast and colon cancer (see, e.g., Kan et al., 2010, Nature 466:869-873).

In some embodiments, the PKC is PKCζ, and the loss-of-function mutation is an inactivating or activity-attenuating deletion or partial deletion of the gene encoding PKCζ, or a loss-of-function mutation at codon 421. In some embodiments, the loss-of-function mutation in PKCζ is ζE421K.

In some embodiments, the PKC loss-of-function mutation is in the kinase domain of PKC, which sequence is conserved in eukaryotic PKCs (see, e.g., Kornev et al., 2006, Proc Natl Acad Sci. USA 103:17783-17788, incorporated herein by reference). In some embodiments, the PKC loss-of-function mutation is a loss-of-function mutation in the activation loop, the turn motif, and/or the hydrophobic motif of the PKC kinase domain.

In some embodiments, the PKC mutations are dominant negative mutations, particularly dominant negative mutations which result in attenuated global PKC activity in the cancer cell and which can attenuate activation by PKC activators. In some embodiments, the dominant negative mutation is one or more of PKCα (e.g., H75Q), PKCγ (e.g., P524R), and PKCβ (e.g., A509V). In some embodiments, a subject with a cancer which is determined or identified as having one or more dominant negative PKC mutations is not selected for treatment with the PKC activator. In some embodiments, a subject with a cancer which is determined or identified as being negative for at least one, at least two or more, at least three or more, or at least for or more dominant negative mutations in PKC are selected for treatment with the PKC activator.

In some embodiments, the PKC activation potential can be assessed by determining or identifying in the cancer the presence or absence of mutations affecting interaction of the PKC enzyme with the PKC activator, particularly a diterpenoid PKC activator. In some embodiments, a cancer with identified mutations occurring in the C1 domain of PKC and affecting interaction with a diterpenoid PKC activator with the PKC is not selected for treatment with the PKC activator. For example, exemplary mutations affecting the interaction of PKC with phorbol PKC activator are described in, for example, Wang et al., 2001, J Biol Chem. 276:19580-19587; and Kazanietz et al, 1995, J Biol Chem. 270:21852-21859; incorporated herein by reference. In some embodiments, a cancer determined or identified as negative for mutations affecting interaction of a PKC activator with the PKC protein is indicated for treatment with the PKC activator.

In some embodiments, the assessment of the PKC activation potential of the cancer can also include determining or identifying the expression level of the PKC enzyme during or following treatment with the PKC activator. In some embodiments, the determining or identifying the expression level of the PKC enzyme is carried out as an adjunct to assessment of the PKC activation potential based on PKC activity, e.g., PKC phosphorylation. In some embodiments, the expression level of the PKC enzyme is determined for one or more PKC isoforms α, β (e.g., βI or βII,), γ, δ, ε, η, θ, ι/λ, μ, and ζ. In some embodiments, an assessment of the PKC activation potential includes determining or identifying the expression level of one or more of PKC isoforms α, β (e.g., βI or βII,), and γ. In some embodiments, an assessment of the PKC activation potential includes determining or identifying the expression level of one or more of PKC isoforms δ, ε, η, and θ. In some embodiments, an assessment of the PKC activation potential includes determining or identifying the expression level of one or more of PKC isoforms ι/λ, μ, and ζ. In various embodiments, the measured expression level of the PKC enzyme is compared to a control or reference level, such as the level of PKC in the cancer prior to treatment with the PKC activator and/or the level of PKC in non-cancerous cell or tissue, e.g., normal cell or tissue. In some embodiments, the measured expression level of PKC enzyme is compared to the level in the cancer prior to treatment with the PKC activator. In some embodiments, the expression level of the PKC enzyme is determined at the protein level or at the level of mRNA. In some embodiments, a cancer having an effective PKC activation potential and elevated expression of PKC enzymes is selected for treatment with the PKC activator.

In some embodiments, cancers for selection and treatment based on its PKC activation potential includes, among others, cancer of the pancreas, lung, colon, head and neck, stomach (gastric), biliary tract, endometrium, ovary, small intestine, urinary tract, liver, cervix, breast, brain, renal, skin, bone, and kidney, and hematologic cancers, such as lymphomas and leukemias. In some embodiments, the PKC activation potential in the cancer is determined for one or more of PKC isoforms selected from PKC α, β, γ, δ, ε, η, θ, ι/λ, and ζ.

In some embodiments, the cancer selected based on PKC activation potential is pancreatic cancer. In some embodiments, the pancreatic cancer is pancreatic adenocarcinoma or metastatic pancreatic cancer. In some embodiments, the PKC activation potential in the pancreatic cancer is determined for one or more of PKC isoforms selected from PKC α, β, γ, δ, ε, η, θ, ι/λ, μ and ζ. In some embodiments, the pancreatic cancer is selected for treatment with a PKC activator if the cancer is identified as being negative for loss-of-function mutations in one or more of PKC γ, δ, ε, μ, and θ. In some embodiments, the pancreatic cancer is not selected for treatment with a PKC activator if the cancer is determined or identified as having a loss-of-function mutations in one or more of PKC γ, δ, ε, μ and θ.

In some embodiments, the cancer selected based on PKC activation potential is colon cancer. In some embodiments, the colon cancer is a colon adenocarcinoma or a metastatic colon cancer. In some embodiments, the PKC activation potential in the colon cancer is determined for one or more of PKC isoforms selected from PKC α, β, γ, δ, ε, η, θ, ι/λ, μ and ζ. In some embodiments, the colon cancer is selected for treatment with a PKC activator if the cancer is determined or identified as being negative for loss-of-function mutations in one or more of PKC α, β, γ, δ, η, μ and ι/λ. In some embodiments, the colon cancer is not selected for treatment with a PKC activator if the cancer is determined or identified as having loss-of-function mutations in one or more of PKC α, β, γ, δ, η, μ and ι/λ.

In some embodiments, the cancer selected based on PKC activation potential is lung cancer. In some embodiments, the lung cancer is small cell lung cancer. In some embodiments, the lung cancer is non-small cell lung cancer. In some embodiments, the non-small cell lung cancer is an adenocarcinoma, squamous cell carcinoma, or large cell carcinoma. In some embodiments, the lung cancer is metastatic lung cancer. In some embodiments, the PKC activation potential in the lung cancer is determined for one or more of PKC isoforms selected from PKC α, β, γ, δ, ε, η, θ, ι/λ, μ and ζ. In some embodiments, the lung cancer is selected for treatment with a PKC activator if the cancer is determined or identified as being negative for loss-of-function mutations in one or more of PKC γ, β, α, δ, ε, μ and η. In some embodiments, the lung cancer is not selected for treatment with a PKC activator if the cancer is determined or identified as having loss-of-function mutations in one or more of PKC γ, β, α, δ, ε, μ and η.

In some embodiments, the cancer selected based on PKC activation potential is stomach or gastric cancer. In some embodiments, the PKC activation potential in the stomach or gastric cancer is determined for one or more of PKC isoforms selected from PKC α, β, γ, δ, ε, η, θ, ι/λ, μ and ζ. In some embodiments, the stomach or gastric cancer is selected for treatment with a PKC activator if the cancer is determined or identified as being negative for loss-of-function mutations in one or more of PKC γ, δ and μ. In some embodiments, the stomach or gastric cancer is not selected for treatment with a PKC activator if the cancer is determined or identified as having loss-of-function mutations in one or more of PKC γ, δ and μ.

In some embodiments, the cancer selected based on PKC activation potential is endometrial or ovarian cancer. In some embodiments, the PKC activation potential in the endometrial or ovarian cancer is determined for one or more of PKC isoforms selected from PKC α, β, γ, δ, ε, η, θ, ι/λ, μ and ζ. In some embodiments, the endometrial or ovarian cancer is selected for treatment with a PKC activator if the cancer is determined or identified as being negative for loss-of-function mutations in one or more of PKC α, β, γ, δ, ε, η, ι/λ, μ and θ. In some embodiments, the endometrial or ovarian cancer is not selected for treatment with a PKC activator if the cancer is determined or identified as having loss-of-function mutations in one or more of PKC α, β, γ, δ, ε, η, ι/λ, μ and θ.

In some embodiments, the cancer selected based on PKC activation potential is breast cancer. In some embodiments, the breast cancer is metastatic breast cancer. In some embodiments, the breast cancer is estrogen receptor negative breast cancer. In some embodiments, the breast cancer is Her2 negative breast cancer. In some embodiments, the breast cancer is estrogen receptor positive breast cancer. In some embodiments, the breast cancer is Her2 positive breast cancer. In some embodiments, the breast cancer is selected for treatment with a PKC activator if the cancer is determined or identified as being negative for loss-of-function mutations in one or more of PKC α, β, γ, δ, ε, η, ι/λ, μ and θ. In some embodiments, the breast cancer is not selected for treatment with a PKC activator if the cancer is determined or identified as having loss-of-function mutations in one or more of PKC α, β, γ, δ, ε, η, ι/λ, μ and θ.

In some embodiments, the cancer selected based on PKC activation potential is head and neck cancer. In some embodiments, the head and neck cancer is selected for treatment with a PKC activator if the cancer is determined or identified as being negative for loss-of-function mutations in one or more of PKC α, β, γ, δ, η, μ and ι/λ. In some embodiments, the head and neck cancer is not selected for treatment with a PKC activator if the cancer is determined or identified as having loss-of-function mutations in one or more of PKC α, β, γ, δ, η, μ and ι/λ.

In another aspect, the selection of a cancer for sensitivity to a PKC activator can be based on the presence or absence of an oncogenic or activating K-ras and/or N-ras mutation in the cancer (see, e.g., Hamilton et al., 2001, J Biol Chem. 276(31):29079-90). In some embodiments, consideration of the K-ras and/or N-ras mutation status in determining the sensitivity of a cancer to a PKC activator can be done independently of or in combination with the assessment of the PKC activation potential describe above.

In some embodiments, a method of determining the sensitivity of a cancer to a PKC activator comprises: determining the presence or absence of an oncogenic or activating K-ras and/or N-ras activity, wherein the presence of an oncogenic or activating K-ras and/or N-ras activity identifies the cancer as being sensitive to the PKC activator. In some embodiments, a method of selecting a cancer for treatment with a PKC activator comprises: determining the presence or absence of an oncogenic or activating K-ras and/or N-ras activity, and selecting the cancer determined to have an oncogenic or activating K-ras and/or N-ras activity for treatment with the PKC activator.

In some embodiments, a method of selecting a subject with cancer for treatment with a PKC activator comprises: determining the absence or presence of an oncogenic or activating K-ras activity, and selecting the subject having a cancer determined to have an oncogenic or activating K-ras activity for treatment with a PKC activator. In some embodiments, the method of treating a subject with cancer comprises: determining the presence or absence of an oncogenic or activating K-ras activity; and administering to the subject with the cancer determined to have an oncogenic or activating K-ras activity a therapeutically effective amount of a PKC activator. In some embodiments, the method of treating cancer comprises administering to a subject in need thereof a therapeutically effective amount of a PKC activator, wherein the cancer is determined to have an oncogenic or activating K-ras activity.

As noted above, in some embodiments, determining the sensitivity of a cancer to a PKC activator can use a combination of an assessment of the PKC activation potential and presence or absence of the oncogenic or activating K-ras and/or N-ras activity. In some embodiments, a method of determining sensitivity of a cancer to a PKC activator comprises: determining or measuring a PKC activation potential of the cancer for the PKC activator, and determining the absence or presence of an oncogenic or activating K-ras and/or N-ras mutation, wherein the cancer determined to have an effective activation potential and an oncogenic or activating K-ras and/or N-ras mutation identifies the cancer as being sensitive to the PKC activator.

In some embodiments, a method of selecting a cancer for treatment with a PKC activator comprises: determining or measuring a PKC activation potential of the cancer for the PKC activator, determining the absence or presence of an oncogenic or activating K-ras and/or N-ras activity, and selecting the cancer determined to have an effective PKC activation potential and an oncogenic or activating K-ras and/or N-ras activity for treatment with the PKC activator.

In some embodiments, a method of selecting a subject with cancer for treatment with a PKC activator comprises: determining or measuring a PKC activation potential of the cancer for the PKC activator, determining the absence or presence of an oncogenic or activating K-ras and/or N-ras activity, and selecting the subject having a cancer determined to have an effective PKC activation potential and an oncogenic or activating K-ras and/or N-ras activity for treatment with the PKC activator.

In some embodiments, a method of treating a subject with cancer comprises: determining or measuring a PKC activation potential of the cancer for the PKC activator, determining the absence or presence of an oncogenic or activating K-ras and/or N-ras activity; and administering to the subject with the cancer determined to have an effective PKC activation potential and an oncogenic or activating K-ras and/or N-ras activity a therapeutically effective amount of a PKC activator. In some embodiments, the method of treating cancer comprises administering to a subject in need thereof a therapeutically effective amount of a PKC activator, wherein the cancer is determined to have an effective PKC activation potential and an oncogenic or activating K-ras and/or N-ras activity.

In some embodiments, the oncogenic or activating form of K-ras or N-ras can be a normally occurring K-ras or N-ras respectively, e.g., wild-type, which is expressed at elevated levels in the cancer as compared to a reference cell or tissue, such as a non-cancerous cell or tissue. In some embodiments, activity levels of K-ras, and ras in general, can be measured by determining the Ras-GTP form, e.g., based on binding of the Ras-binding domain of Ras effector Raf. Affinity isolated Ras-GTP can be detected immunologically, such as by ELISA or Western Blotting. In some embodiments, the expression level of K-ras is determined at the protein level, at the level of mRNA expression, and/or gene copy number, as further described herein.

In some embodiments, the oncogenic or activating K-ras or N-ras activity is an oncogenic or activating K-ras or N-ras mutation, respectively. Thus, in some embodiments, determining the sensitivity of a cancer to a PKC activator or selection of a cancer for treatment with a PKC activator can be based on determining the presence or absence of an oncogenic or activating K-ras and/or N-ras mutation. In some embodiments where K-ras mutation status is used, the oncogenic or activating K-ras mutation can be an oncogenic or activating mutation in human K-ras at one or more of codon 5, codon 9, codon 12, codon 13, codon 14, codon 18, codon 19, codon 22, codon 23, codon 24, codon 26, codon 33, codon 36, codon 57, codon 59, codon 61, codon 62, codon 63, codon 64, codon 68, codon 74, codon 84, codon 92, codon 35, codon 97, codon 110, codon 115, codon 117, codon 118, codon 119, codon 135, codon 138, codon 140, codon 146, codon 147, codon 153, codon 156, codon 160, codon 164, codon 171, codon 176, codon 185, and codon 188.

In some embodiments, the oncogenic or activation K-ras mutations include mutations in which: codon 5 is K5E; codon 9 is V91; codon 12 is G12A, G12C, G12D, G12F, G12R, G12S, G12V, or G12Y; codon 13 is G13C, G13D, or G13V; codon 14 is V14I or V14L; codon 18 is A18D; codon 19 is L19F; codon 22 is Q22K; codon 23 is L23R; codon 24 is I24N; codon 26 is N26K; codon 33 is D33E; codon 36 is I36L or I36M; codon 57 is D57N; codon 59 is A59E, A59G, or A59T; codon 61 is Q61H, Q61K, Q61L, or Q61R; codon 62 is E62G or E62K; codon 63 is E63K; codon 64 is Y64D, Y64H, or Y64N; codon 68 is R68S; codon 74 is T74P; codon 84 is I84T; codon 92 is D92Y; codon 97 is R97I; codon 110 is P110H or P110S; codon 115 is G115E; codon 117 is K117N; codon 118 is C118S; codon 119 is D119N; codon 135 is R135T; codon 138 is G138V; codon 140 is P140H; codon 146 is A146T or A146V; codon 147 is K147N; codon 153 is D153N; codon 156 is F156L; codon 160 is V160A; codon 164 is R164Q; codon 171 is I117M; codon 176 is K176Q; codon 185 is C185R or C185S; and codon 188 is M188V.

In particular, cancers with oncogenic or activating K-ras mutations at codon 12, codon 13 and/or codon 61 are selected for treatment with the PKC activator since the majority of activating K-ras mutations observed in certain cancers, such as pancreatic, colon, and lung cancer, occur in the three codons. In some embodiments, the oncogenic or activating K-ras mutation at codon 12 is G12A, G12C, G12D, G12F, G12R, G12S, G12V, or G12Y; at codon 13 is G13C, G13D, or G13V; and at codon 61 is Q61H, Q61K, Q61L, or Q61R. In some embodiments, the oncogenic or activating K-ras mutation is a combination of oncogenic or activating K-ras mutations at codon 12 and codon 13; codon 12 and codon 61; codon 13 and 61; or codon 12, codon 13 and codon 61.

In some embodiments where N-ras mutation status is used, the oncogenic or activating N-ras mutation is an activating mutation in human N-ras at one or more of codon 12, codon 13 and codon 61. In some embodiments, the oncogenic or activating N-ras mutation at codon 12 is G12A, G12C, G12D, G12R, G12S, or G12V. In some embodiments, the oncogenic or activating N-ras mutation at codon 13 is G13A, G13C, G13D, G13R, G13S, or G13V. In some embodiments, the oncogenic or activating N-ras mutation at codon 61 is Q61E, Q61H, Q61K, Q61L, Q61P, or Q61R. In some embodiments, the oncogenic or activating N-ras mutation is a combination of oncogenic or activating N-ras mutations at codon 12 and codon 13; codon 12 and codon 61; codon 13 and 61; or codon 12, codon 13 and codon 61.

In some embodiments, cancers having an identified oncogenic or activating K-ras and/or N-ras mutation can be a cancer of the pancreas, lung, colon, head and neck, stomach (gastric), biliary tract, endometrium, ovary, small intestine, urinary tract, liver, cervix, breast, brain, renal, skin, bone, or kidney, or a hematological cancer, such as leukemia or lymphoma.

In some embodiments, cancers characterized by high rates of oncogenic or activating K-ras and/or N-ras mutations are selected. Pancreatic cancer are known to have high rates of activating K-ras mutations. Thus, a pancreatic cancer having an identified oncogenic or activating K-ras mutation, in particular those described above, can be selected for treatment with the PKC activator. In some embodiments, the pancreatic cancer has an identified oncogenic or activating K-ras mutations in codon 12, codon 13, and/or codon 61.

In some embodiments, the pancreatic cancer is pancreatic adenocarcinoma or metastatic pancreatic cancer having an identified oncogenic or activating K-ras mutation. In some embodiments, the pancreatic cancer is pancreatic adenocarcinoma diagnosed as stage I, stage II, stage III, or stage IV, where the pancreatic adenocarcinoma has an identified oncogenic or activating K-ras mutation.

In some embodiments, the cancer is lung cancer determined or identified as having an oncogenic or activating K-ras mutation. In particular, lung cancer having an identified oncogenic or activating K-ras mutation, such as those specified above, can be selected for treatment with the PKC activator. In some embodiments, the lung cancer has an identified oncogenic or activating K-ras mutation in codon 12, codon 13, and/or codon 61.

In some embodiments, the lung cancer is small cell lung cancer determined or identified as having an oncogenic or activating K-ras mutation. In some embodiments, the lung cancer selected for treatment is non-small cell lung cancer determined or identified as having an oncogenic or activating K-ras mutation. In some embodiments, the non-small cell lung cancer selected for treatment is an adenocarcinoma, squamous cell carcinoma, or large cell carcinoma determined or identified as having an oncogenic or activating K-ras mutation. In some embodiments, the lung cancer selected for treatment is metastatic lung cancer determined or identified as having an oncogenic or activating K-ras mutation.

In some embodiments, the cancer is colon cancer determined or identified as having an oncogenic or activating K-ras mutation. In particular, colon cancer having an identified oncogenic or activating K-ras mutation, such as those specified above, can be selected for treatment with the PKC activator. In some embodiments, the colon cancer has an identified oncogenic or activating K-ras mutation in codon 12, codon 13, and/or codon 61. In some embodiments, the colon cancer is colon adenocarcinoma or metastatic colon cancer determined or identified as having an oncogenic or activating K-ras mutation.

In some embodiments, the cancer is a hematological cancer, particularly a lymphoma or leukemia, determined or identified as having an oncogenic or activating K-ras and/or N-ras mutation, particularly an oncogenic or activating N-ras mutation, which is present in a significant percentage of leukemias and lymphomas. Leukemias for the methods herein can be acute myeloid leukemia, chronic myeloid leukemia, acute lymphoblastic leukemia, juvenile myelomonocytic leukemia, chronic myelomonocytic leukemia, myelodysplastic syndrome, myeloproliferative neoplasia, multiple myeloma, and other types of leukemia determined or identified as having an activating K-ras or N-ras mutation. Lymphomas for the methods herein can be Hodgkin's lymphoma or non-Hodgkin's lymphoma, such as diffuse large B-cell lymphoma, follicular large cell lymphoma, anaplastic large cell lymphoma, T-cell lymphoma, lymphomatoid granulomatosis, peripheral T-cell lymphoma, Burkitt's lymphoma, lymphoblastic lymphoma or other types of lymphomas.

In some embodiments, targets of PKC and/or downstream elements of the K-ras signaling pathway can be analyzed to assess the sensitivity of the cancer to the PKC activator and/or effectiveness of the PKC activator. Analysis of the downstream elements can be done in conjunction with or independently of the assessment of the PKC activation potential and/or K-ras/N-ras activity status described above. In some embodiments, the cancer is assessed for levels of Frizzled (Fzd). Expression of some Fzd protein is increased in response to attenuation of K-ras activity, and decreases in response to oncogenic or activated K-ras activity. Treatment with a PKC activator compound that inhibits or attenuates the activity of K-ras should result in increased expression of certain Fzd proteins. In some embodiments, the Fzd protein is Frizzled-8 (Fzd8). In some embodiments, a method of determining the sensitivity of a cancer or selecting a cancer for treatment with a PKC activator includes determining the expression level of Fzd in a cancer treated with a PKC activator, wherein an elevated level of Fzd as compared to a control level, e.g., untreated cancer cells or tissues or normal cells or tissues, indicates sensitivity of the cancer to the PKC activator. In some embodiments, the cancer selected for treatment with a PKC activator is determined or identified as being capable of or having increased or elevated level of Fzd, particularly Fzd8 when the cancer is treated with the PKC activator. In some embodiments, the expression of Fzd protein in the cancer can be measured before, during and/or following treatment with the PKC activator.

Another component of the K-ras signaling pathway is CaMKii, which is a downstream effector of calmodulin and whose interaction with K-ras is affected by PKC activity. In some embodiments, a method of determining the sensitivity of a cancer or selecting a cancer for treatment with a PKC activator includes determining the level of phosphorylated CaMKii in a cancer treated with a PKC activator, wherein an elevated level of phosphorylated CaMKii as compared to a control level, e.g., untreated cancer cells or tissues, or normal cells or tissues, indicates sensitivity of the cancer to the PKC activator. In some embodiments, the cancer selected for treatment with a PKC activator is determined or identified as being capable of or having increased or elevated levels of phosphorylated CaMKii when the cancer is treated with the PKC activator. In some embodiments, the levels of phosphorylated CaMKii in the cancer can be measured before, during and/or following treatment with the PKC activator. In some embodiments, the phosphorylation of CaMKii at Tyr231, Thr286, and/or Thr305 can be detected to measure PKC activation levels.

In some embodiments, the cancer is assessed for levels of phosphorylated K-ras, which phosphorylation is mediated by PKC. In some embodiments, a method of determining the sensitivity of a cancer or selecting a cancer for treatment with a PKC activator includes determining the level of phosphorylated K-ras in a cancer treated with a PKC activator, wherein an elevated level of phosphorylated K-ras as compared to a control level, e.g., untreated cancer cells or tissues, or normal cells or tissues, indicates sensitivity of the cancer to the PKC activator. In some embodiments, the cancer selected for treatment with a PKC activator is determined or identified as being capable of or having increased or elevated levels of phosphorylated K-ras when the cancer is treated with the PKC activator. In some embodiments, the levels of phosphorylated K-ras in the cancer can be measured before, during and/or following treatment with the PKC activator. In some embodiments, the level of phosphorylation at amino acid residue 181 of human K-ras is measured. In some embodiments, the level of phosphorylation of a K-ras having an oncogenic or activating mutation, such as described herein, is measured.

In some embodiments, the cancer is assessed for levels of leukemia inhibitory factor (LIF), which functions in inducing differentiation of myeloid leukemic cells and is upregulated at the mRNA and protein level in cancers with oncogenic or activating K-ras mutations. Attenuating K-ras activity through activation of PKC by a PKC activator should result in a reduction in levels of LIF. In some embodiments, a method of determining the sensitivity of a cancer or selecting a cancer for treatment with a PKC activator includes determining the level of LIF in a cancer treated with a PKC activator, wherein an elevated level of LIF as compared to a control level, e.g., untreated cancer cells or tissues, or normal cells or tissues, indicates sensitivity of the cancer to the PKC activator. In some embodiments, the cancer selected for treatment with a PKC activator is determined or identified as being capable of or having increased or elevated levels of LIF when the cancer is treated with the PKC activator. In some embodiments, the levels of LIF in the cancer can be measured before, during and/or following treatment with the PKC activator. In some embodiments, the levels of LIF can be measured based on mRNA and/or protein.

In some embodiments, the cancer is assessed for effect on Wnt signaling pathway by measuring activity of beta-catenin, which is regulated by PKC. The beta-catenin protein is known to associate with transcription regulator TCF/LEF and translocates from the cytoplasm to the nucleus where it activates transcription of target genes. In some embodiments, a method of determining the sensitivity of a cancer or selecting a cancer for treatment with a PKC activator includes determining the level of beta-catenin in a cancer treated with a PKC activator, wherein a reduced level of beta-catenin as compared to a control level, e.g., untreated cancer cells or tissues, or normal cells or tissues, indicates sensitivity of the cancer to the PKC activator. In some embodiments, a method of determining the sensitivity of a cancer or selecting a cancer for treatment with a PKC activator includes determining the transcription of a target gene for TCF/LEF in a cancer treated with a PKC activator, wherein an reduced transcription of the target gene for TCF/LEF as compared to a control level, e.g., untreated cancer cells or tissues, or normal cells or tissues, indicates sensitivity of the cancer to the PKC activator.

In some embodiments, the cancer is assessed for levels of phosphorylated Erk1/2, which phosphorylation is mediated by PKC. In some embodiments, a method of determining the sensitivity of a cancer or selecting a cancer for treatment with a PKC activator includes determining the level of phosphorylated Erk1/2 in a cancer treated with a PKC activator, wherein an elevated level of phosphorylated Erk1/2 as compared to a control level, e.g., untreated cancer cells or tissues, or normal cells or tissues, indicates sensitivity of the cancer to the PKC activator. In some embodiments, the cancer selected for treatment with a PKC activator is determined or identified as being capable of or having increased or elevated levels of phosphorylated Erk1/2 when the cancer is treated with the PKC activator. In some embodiments, the levels of phosphorylated Erk1/2 in the cancer can be measured before, during and/or following treatment with the PKC activator.

In some embodiments, a cancer selected for treatment is characterized by at least one, or a combination of, or all of: (i) increased expression of Fzd protein, particularly Fzd8; (ii) elevated phosphorylation of CaMKii; (iii) increased phosphorylation levels of K-ras, particularly at amino acid residue 181; (iv) reduction in expression or levels of LIF; (v) inhibition of Wnt signaling, e.g., by reduction in beta-catenin or beta-catenin-TCF/LEF mediated transcriptional activity; and (vi) elevated phosphorylation levels of Erk1/2. In some embodiments, the forgoing factors can be measured before, during and/or following treatment with the PKC activator.

For the methods herein, the mutations in K-ras, N-ras, and PKC can be identified using various techniques available to the skilled artisan. In various embodiments, the presence or absence of a mutation can be determined by known DNA or RNA detection methods, for example, DNA sequencing, oligonucleotide hybridization, polymerase chain reaction (PCR) amplification with primers specific to the mutation, or protein detection methods, for example, immunoassays or biochemical assays to identify a mutated protein, such as mutated K-ras, N-ras and PKCs. In some embodiments, the nucleic acid or RNA in a sample can be detected by any suitable methods or techniques of detecting gene sequences. Such methods include, but are not limited to, PCR, reverse transcriptase-PCR (RT-PCR), in situ PCR, in situ hybridization, Southern blot, Northern blot, sequence analysis, microarray analysis, or other DNA/RNA hybridization platforms (see, e.g., Taso et al., 2010, Lung Cancer 68(1):51-7). In particular, detection of mutations can use samples obtained non-invasively, such as cell free nucleic acid (e.g., cfDNA) from blood.

In some embodiments, mutations can be detected using various Next-Gen sequencing (NGS) techniques, particularly high-throughput NGS techniques. Exemplary NGS techniques include, among others, Polony sequencing (see, e.g., Shendure et al., 2005, Science 309(5741):1728-32), IonTorrent sequencing (see, e.g., Rusk, N., 2011, Nat Meth 8(1):44-44), pyrosequencing (see, e.g., Marguiles et al., 2005, Nature 437(7057):376-380), reversible dye sequencing with colony sequencing (Bentley et al., 2008, Nature 456(7218):53-59; Illumina, CA, USA), sequencing by ligation (e.g., SOLid systems of Applied Biosystems; Valouev et al., 2008, Genome Res. 18(7):1051-1063), high throughput rolling circle "nanoball" sequencing (see, e.g., Drmanac et al., 2010, Science 327 (5961):78-81; Porreca, G. J., 2010, Nature Biotech. 28 (1):43-44), and zero-mode wave guide based sequencing (see, e.g., Chin et al., 2013, Nat Methods 10(6):563-569); all publications incorporated herein by reference. In some embodiments, massively parallel sequencing of target genes, such as genes encoding K-ras, N-ras, or PKCs can be carried out to detect or identify presence or absence of mutations in the cancer being assessed for treatment with a PKC activator.

In some embodiments, detection of point mutations in target nucleic acids can be accomplished by molecular cloning of the target nucleic acid molecules and sequencing the nucleic acid molecules using available techniques. Alternatively, amplification techniques such as PCR can be used to amplify target nucleic acid sequences directly from a genomic DNA preparation from a tumor tissue, cell sample, or cell free sample (e.g., cell free plasma from blood). The nucleic acid sequence of the amplified molecules can then be determined to identify mutations. Design and selection of appropriate primers are within the abilities of one of ordinary skill in the art.

In some embodiments, ligase chain reaction (Wu et al., 1989, Genomics 4:560-569) and allele-specific PCR (Ruano et al., 1989, Nucleic Acids Res. 17:8392) can also be used to amplify target nucleic acid sequences. Amplification by allele-specific PCR uses primers that hybridize at their 3' ends to a particular target nucleic acid mutation. If the particular mutation is not present, an amplification product is not observed. Insertions and deletions of genes can also be detected by cloning, sequencing and amplification. In addition, restriction fragment length polymorphism probes for the gene or surrounding marker genes can be used to score alteration of an allele or an insertion in a polymorphic fragment. Single stranded conformation polymorphism analysis can also be used to detect base change variants of an allele (Orita et al., 1989, Proc. Natl. Acad. Sci. USA 86:2766-2770). Other known techniques for detecting insertions and deletions can also be used with the claimed methods.

In some embodiments, mismatch detection can be used to detect point mutations in a target nucleic acid molecule, such as GRIN2A or TRRAP. Mismatches are hybridized nucleic acid duplexes which are not 100% complementary. The lack of total complementarity can be due to deletions, insertions, inversions, substitutions or frameshift mutations. An example of a mismatch cleavage technique is the RNase protection method, which is described in detail in Winter et al., 1985, Proc. Natl. Acad. Sci. USA 82:7575-7579, and Myers et al., 1985, Science 230:1242-1246. For example, detection of mutations in K-ras, N-ras or PKCs can involve the use of a labeled riboprobe that is complementary to wild-type K-ras, N-ras or PKC, respectively. The riboprobe and nucleic acid molecule to be tested (for example, obtained from a tumor sample) are annealed (hybridized) together and subsequently digested with the enzyme RNase A, which is able to detect mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid mRNA or gene, but can be a portion of the target nucleic acid, provided it encompasses the position suspected of being mutated. If the riboprobe comprises only a segment of the target nucleic acid mRNA or gene, it may be desirable to use a number of these probes to screen the whole target nucleic acid sequence for mismatches if desired.

In a similar manner, DNA probes can be used to detect mismatches, for example through enzymatic or chemical cleavage (Cotton et al., 1988, Proc. Natl. Acad. Sci. USA 85: 4397; Shenk et al., 1975, Proc. Natl. Acad. Sci. USA 72:989). Alternatively, mismatches can be detected by shifts in the electrophoretic mobility of mismatched duplexes relative to matched duplexes (see, e.g., Cariello et al., 1988, Human Genetics 42:726). With riboprobes or DNA probes, the target nucleic acid mRNA or DNA which may contain a mutation can be amplified before hybridization. Changes in target nucleic acid DNA can also be detected using Southern hybridization, especially if the changes are gross rearrangements, such as deletions and insertions.

In some embodiments, amplified nucleic acid sequences can also be screened using allele-specific probes. These probes are nucleic acid oligomers, each of which contains a region of the target nucleic acid gene harboring a known mutation. For example, one oligomer may be about 30 nucleotides in length, corresponding to a portion of the target gene sequence. By use of a plurality of such allele-specific probes, target nucleic acid amplification products can be screened to identify the presence of a previously identified mutation in the target gene. Hybridization of allele-specific probes with amplified target nucleic acid sequences can be performed, for example, on a nylon filter. Hybridization to a particular probe under stringent hybridization conditions indicates the presence of the same mutation in the tumor tissue as in the allele-specific probe.

In some embodiments, gene-specific primers are useful for determination of the nucleotide sequence of a target nucleic acid molecule using nucleic acid amplification techniques such as the polymerase chain reaction. Pairs of single stranded DNA primers can be annealed to sequences within or surrounding the target nucleic acid sequence in order to prime amplification of the target sequence. Allele-specific primers can also be used. Such primers anneal only to particular mutant target sequences, and thus will only amplify a product in the presence of the mutant target sequence as a template. In order to facilitate subsequent cloning of amplified sequences, primers may have restriction enzyme site sequences appended to their ends. Such enzymes and sites are well known in the art. The primers themselves can be synthesized using techniques known in the art.

In some embodiments, mutations in nucleic acid molecules can also be detected by screening for alterations of the corresponding protein. For example, monoclonal antibodies immunoreactive with a target gene product can be used to screen a tissue, for example an antibody that is known to bind to a particular mutated position of the gene product (protein). For example, a suitable antibody may be one that binds to a deleted exon or that binds to a conformational epitope comprising a deleted portion of the target protein. Lack of cognate antigen would indicate a mutation. Such immunological assays can be accomplished using any convenient format known in the art, such as Western blot, immunohistochemical assay and ELISA. For example, antibody-based detection of K-ras mutations is described in Elisabah et al., 2013, J Egypt Natl Cancer Inst. 25(1):51-6).

Mutations in a gene or encoded protein of interest can be evaluated using any technique described above, or any other method known in the art. For example, mutations in a gene or corresponding mRNA can be detecting by direct sequencing of a nucleic acid molecule, detection of an amplification product, microarray analysis or any other DNA/RNA hybridization platforms. For detection of mutant proteins, an immunoassay, biochemical assay or microarray can be used. Kits for detection of various mutations are available commercially (see, e.g., Anderson, S. M., 2011, Expert Rev. Mol Diagn. 11(6):635-643).

The expression of mRNA or proteins, such as expression of PKC or downstream elements, such as Frizzled, can use standard techniques available to the skilled artisan, including some of the methods described above. For example, the mRNA encoding a protein of interest can be detected by hybridization with nucleic acid probes, reverse transcription, polymerase chain reaction, and combinations thereof (e.g., RT-qPCR). In some embodiments, chip-based or bead-based microarrays containing nucleic acid probes hybridizing to the target sequence can be used. In some embodiments, mRNA expression can be detected directly in the target cells, such as by in-situ hybridization.

In some embodiments, the protein products can be detected directly. Direct detection can use a binding agent that binds specifically to the protein, such as antibodies or target-interacting proteins or small molecule reagents that bind specifically with the protein target of interest. For example antibodies to PKC enzymes are available or can be prepared by polyclonal production methods or by generation of monoclonal antibodies (see, e.g., Current Protocols in Immunology, Coligan et al., eds., John Wiley & Sons (updates to 2015); Immunoassays: A Practical Approach, Gosling, ed., Oxford University Press (2000)). In some embodiments, the protein product can be detected by immunological methods. Various immunoassays include, by way of example, enzyme immunoassays, enzyme-linked immunoassays, fluorescence polarization immunoassay, and chemiluminescence assay. For example, "Western Blot" based immunological detection of PKC enzymes are described in Chen et al., 2013, Anal Biochem. 442(1):97-103. Other references describing detection of PKC enzymes include, among others, Garaczarczyk et al., 2010, Chem Biol Interact. 181(1):25-32; Ali et al., 2009, Life Sci. 84(21-22):766-71; Stross et al., 2009, J Biol Chem. 390(3):235-44; Clark et al., 2003, Cancer Res. 63(4):780-786; Han et al., 2002, World J Gastroenterol 8(3):44-445; and Manzow et al., 2000, Int J Cancer 85(4):503-507; all publications incorporated herein by reference). Exemplary descriptions of antibodies to Frizzled protein, such as FZD8 is described in, among others, Yin et al., 2013, Mol Cancer Ther. 12:491-498 and Wang et al., 2012, Biochem Biophys Res Commun. 417(1):62-6.

For determining PKC activation potential, general methods for detecting PKC activity can be used, such as described in Protein Kinase C Protocols, Newton, A. C. ed., Humana Press, Totowa, N.J. USA (2003), incorporated herein by reference. In some embodiments, the assays for detecting kinase activity can use synthetic substrates or natural substrates that are the target of the PKC enzymes and detecting the phosphorylated substrate, for example by transfer of detectable phospho group (e.g., $^{32}$P-labeled or ligand labeled ATP) or detection of the phosphorylated product, such as with an antibody that binds the phosphorylated product (PegTag®, Promega, USA). In some embodiments, PKC activity can be detected in situ (see, e.g., Iori et al., 2003, Diabetologia. 46(4):524-30). Samples for examining PKC activity includes cells and tissues obtained from a patient, and/or circulating cancer cells obtained from the peripheral blood or lymph of patients (see, e.g., Karabacak et al., 2014, Nat Protoc. 9(3):694-710; van de Stolpe et al., 2011, Cancer Res. 71:5955-5960; Yu et al., 2011, J Cell Biol. 192(3):373-382; and Stott et al., 2010, Proc Natl Acad Sci. USA 107(43): 18392-18397; all publications incorporated herein by reference). In some embodiments, the PKC activity can be measured by use of synthetic peptide substrates. These synthetic peptide substrates can be based on amino acid sequences known to be phosphorylated naturally in a PKC enzyme. Substrates for PKCα, β and γ are described in Toomik et al., 1997, Biochem J. 322:455-460; substrates for PKCα, βI, δ, ζ, and μ are described in Nishikawa et al., J Biol Chem. 272(2):952-960; Chen et al., 1993, Biochem. 32(4):1032-1039; and Wang et al., 2012, Structure 20(6):791-801; incorporated herein by reference. PKC substrates are also available commercially (see, e.g., Abcam, MA, USA; Perkin Elmer, USA; ImmuneChem, BC, Canada; and Promega, USA).

Detection of phosphorylated proteins, such as phosphorylated PKC enzymes, K-ras, Erk1/2, or CaMKii can use standard techniques, such as antibodies that distinguish phosphorylated protein from non-phosphorylated protein or by detection of a labeled phosphate group (e.g., $^{32}$P) (see, e.g., Barcelo et al., 2014, Cancer Res. 74:1190-1190; Vila Petroff et al., 2010, J Mol Cell Cardiol. 9(1):106-112; Zhang et al., 2002, J Biol Chem. 277(42):39379-39387; Dissanayake et al., 2008, Methods Mol Biol. 468:187; all publications incorporated herein by reference). In some embodiments, antibodies that detect phosphorylated target proteins can be obtained commercially (see, e.g., Abcam, USA; Cell Signaling Technology, USA). In some embodiments, detecting or measuring phosphorylated proteins by use of anti-phospho antibodies can comprise: affinity isolating the PKC protein; and detecting phosphorylated protein with an anti-phospo antibody. In some embodiments, the affinity isolated PKC protein can be separated, such as by gel electrophoresis, the separated proteins bound onto a membrane substrate; and the membrane probed with an anti-phospho antibody. The binding of the anti-phospho antibody to phosphorylated protein can be detected with anti-phospho antibodies containing a detectable label, or by use of a secondary antibody directed against the primary anti-phospho antibody, where the secondary antibody contains a detectable label. The detectable label can be, by way of example and not limitation, a radioactive label, detectable enzyme (e.g., horseradish peroxidase); or fluorescent molecule. Exemplary antibodies for detecting phosphorylated sequences in PKC enzymes are provided below on Table A.

TABLE A

| Antibody Name | Vendor | Cat No. | Species | Dilution |
|---|---|---|---|---|
| GAPDH (loading control) | Millipore | MAB374 | Mouse | 1:10000 |
| β-Actin (loading control) | Sigma | A5441 | Mouse | 1:10000 |
| Vinculin (loading control) | Sigma | V9131 | Mouse | 1:20000 |
| Phospho-CaMKii (Thr286) | Abcam | ab32678 | Rabbit | 1:1000 |
| Phospho-PKC substrate Motif [(R/KXpSX(R/K)] MultiMab ™ | Cell Signaling | 6967 | Rabbit | 1:1000 |

TABLE A-continued

| Antibody Name | Vendor | Cat No. | Species | Dilution |
|---|---|---|---|---|
| Phospho(Ser)-PKC substrate | Cell Signaling | 2261 | Rabbit | 1:500 |
| Phospho-PKC(pan)(βII Ser660) | Cell Signaling | 9371 | Rabbit | 1:1000 |
| Phospho-PKCα/β (Thr638/641) | Cell Signaling | 9375 | Rabbit | 1:1000 |
| Phospho-PKCδ/θ (Ser643/676) | Cell Signaling | 9376 | Rabbit | 1:1000 |
| Phospho-PKD/PKCμ (Ser744/748) | Cell Signaling | 2054 | Rabbit | 1:1000 |
| Phospho-PKD/PKCμ (Ser916) | Cell Signaling | 2051 | Rabbit | 1:1000 |
| Phospho-PKCδ (Thr505) | Cell Signaling | 9374 | Rabbit | 1:1000 |
| Phospho-PKCδ(Tyr311) | Cell Signaling | 2055 | Rabbit | 1:1000 |
| Phospho-PKCζ/λ (Thr410/403) | Cell Signaling | 9378 | Rabbit | 1:1000 |
| PKD/PKCμ | Cell Signaling | 2052 | Rabbit | 1:1000 |
| P44/42 Erk1/2 | Cell Signaling | 9102 | Rabbit | 1:1000 |
| Phospho-p44/42 Erk1/2 (Thr202/Tyr204) | Cell Signaling | 9106 | Mouse | 1:1000 |
| Phospho-c-Raf (Ser338) | Cell Signaling | 9427 | Rabbit | 1:1000 |

In some embodiments, phosphorylation can be detected in situ in a cell, for example, using an antibody directed against the phosphorylated protein. In some embodiments, the technique of in situ proximity ligation assay can be used to detect phosphorylated proteins in situ (see, e.g., Soderberg et al., 2006, Nat Methods 3:995-1000; Jarvious et al., 2007, Method Mol Cell Proteomics 6:1500-1509). Other methods of in situ detection of phosphorylated proteins are described in, for example, Roche et al., "Detection of Protein Phosphorylation in Tissues and Cells," in Current Protocols in Neuroscience, John Wiley & Sons (2001); incorporated herein by reference.

Biological sample for the method herein include any samples are amenable to analysis herein, such as tissue or biopsy samples containing cancer cells, or any biological fluids that contain the material of interests (e.g., DNA), such as blood, plasma, saliva, tissue swabs, and intestinal fluids. In some embodiments, exosomes extruded by cancer cells and obtained from blood or other body fluids can be used to detect nucleic acids and proteins produced by the cancer cells.

General biological, biochemical, immunological and molecular biological methods applicable to the present disclosure are described in Sambrook et al., Molecular Cloning: A Laboratory Manual 2$^{nd}$ Ed. (1989) Cold Spring Harbor Laboratory Press, Cold Spring Harbor, NY; Current Protocols in Molecular Biology, Ausubel et al., ed., John Wiley & Sons (2015); Current Protocols in Immunology, Coligan, J E ed., John Wiley & Sons (2015); and Methods in Enzymology, Vol. 200, Abelson et al., ed., Academic Press (1991). All publications are incorporated herein by reference.

5.3. Protein Kinase C (PKC) Activating Compounds

The compounds for use in the methods described herein are PKC activating compounds. In some embodiments, the PKC activating compounds are capable of activating the activity of one or more of the PKC isoforms, including isoforms selected from PKC α, β, γ, δ, ε, η, θ, ι/λ, μ, and ζ. In some embodiments, the PKC activating compound is capable of activating PKCα. In some embodiments, the PKC activating compound is capable of activating PKCβ. In some embodiments, the PKC activating compound is capable of activating PKCγ. In some embodiments, the PKC activating compound is capable of activating PKCδ. In some embodiments, the PKC activating compound is capable of activating PKCε. In some embodiments, the PKC activating compound is capable of activating PKCη. In some embodiments, the PKC activating compound is capable of activating PKCθ. In some embodiments, the PKC activating compound is capable of activating PKCι/λ. In some embodiments, the PKC activating compound is capable of activating PKCμ. In some embodiments, the PKC activating compound is capable of activating PKCζ.

In some embodiments, the PKC activator is a diterpenoid PKC modulating compound. Various classes of diterpenoids modulating PKC activity include tigliane (e.g., phorbol, deoxyphorbol, etc.), ingenane (e.g., ingenol), and daphnane diterpenoids. In some embodiments, the PKC activator for use in the methods herein include PKC activating phorbol, deoxyphorbol, ingenol and daphnane compounds, including enantiomers, derivatives, analogs, and prodrugs thereof, and salts, hydrates, and solvates thereof.

The tigliane or phorbol class of PKC activating compounds comprise a partial structure of formula A:

A

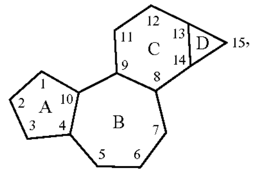

In some embodiments, the bond between carbon atoms 5 and 6, carbon atoms 6 and 7, and carbon atoms 1 and 2, are each independently a double bond, as illustrated in formula A1 and A2, below. In some embodiments, carbon atoms 5 and 6 or carbon atoms 6 and 7 are bonded to a common oxygen atom to form an epoxide, as illustrated in formula A3 and A4.

A1

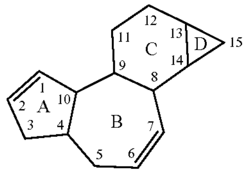

-continued

A2

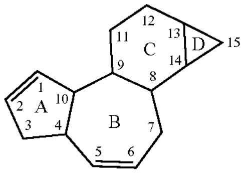

or

A3

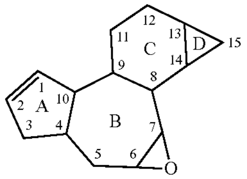

A4

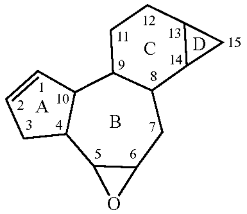

In various embodiments, substituents can be present on one or more of carbon atoms 2, 3, 4, 5, 6, 7, 9, 11, 12, 13, 14, and 15 of formula A, particularly of formula A1, A2, A3 or A4. PKC activating phorbol compounds and derivatives, analogs, and prodrugs thereof, and methods of their synthesis are described in, among others, U.S. Pat. Nos. 4,716,179; 5,145,842; 6,268,395; Kawamura et al., 2016, "Nineteen-step total synthesis of (+)-phorbol," Nature 532:90; Duran-Pena et al., 2014, Natural Product Reports 31:940-952; Shi et al., 2008, Chem. Rev. 108:4295-4327; all of which are incorporated herein by reference.

Deoxyphorbols comprise a partial structure of formula A, particularly the partial structures of formula A1, A2, A3 or A4, except that the carbon atom at position 12 of the structure formula is unsubstituted (i.e., H). In some embodiments, substituents can be present on one or more of carbon atoms 2, 3, 4, 5, 6, 7, 9, 11, 13, 14, and 15 of formula A, particularly of formula A1, A2, A3 or A4 where the PKC activating compound is deoxy at carbon atom 12. PKC activating deoxyphorbol compounds and derivatives, analogs, and prodrugs thereof, and methods of their synthesis are described in among others, U.S. Pat. Nos. 6,432,452; 8,022,103, 8,067,632; 8,431,612; 8,536,378; 8,816,122; US 20090187046; US 20110014699; US 20120101283; Wender, et al., 2008, "Practical Synthesis of Prostratin, DPP, and Their Analogs, Adjuvant Leads Against Latent HIV," Science. 320(5876):649-652; Beans et al., 2013, "Highly potent, synthetically accessible prostratin analogs induce latent HIV expression in vitro and ex vivo," Proc Natl Acad Sci USA 110(29):11698-11703; Tsai et al., 2016, "Isolation of Phorbol Esters from *Euphorbia grandicornis* and Evaluation of Protein Kinase C- and Human Platelet-Activating Effects of Euphorbiaceae Diterpenes," J Nat Prod. 79(10): 2658-2666; Duran-Pena et al., 2014, Natural Product Reports 31:940-952; Shi et al., 2008, Chem. Rev. 108:4295-4327; all publications incorporated herein by reference.

In some embodiments, the tigliane class of PKC activating compounds (e.g., phorbol and deoxyphorbol) have an alkyl (e.g., methyl) at carbon atoms 2, 11, and 15, and an optionally substituted alkyl, e.g., methyl or methylene at carbon atom 6. As will be understood by the skilled artisan, the numbering of the carbon atoms for such structures can use the following:

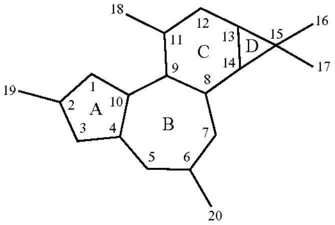

The ingenane or ingenol class of PKC modulating compounds comprise a partial structure of formula B:

B

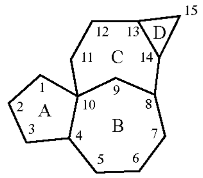

In some embodiments, the bond between carbon atoms 6 and 7 and carbon atoms 1 and 2 are each independently a double bond, as illustrated in formula B1 below. In some embodiments, carbon atom 9 is bonded to an oxygen atom to form a carbonyl, as illustrated in formula B2. In some embodiments, carbon atoms 6 and 7 are bonded to a common oxygen atom to form an epoxide, as illustrated in formula B3. In some embodiments, substituents can be present on one or more carbon atoms 2, 3, 4, 5, 6, 7, 9, 11, 12, 13, 14 and 15 of formula B, particularly of formula B1, B2 and B3.

B1

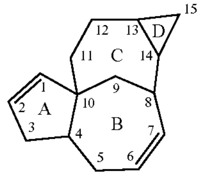

B2

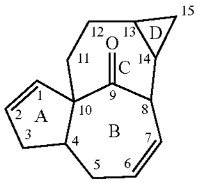

or

B3

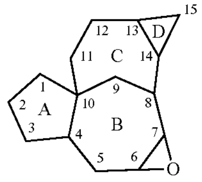

Ingenol compounds and derivatives, analogs, and prodrugs thereof, and methods of their synthesis are described in among others, U.S. Pat. Nos. 6,432,452; 8,022,103, 8,106,092; 8,431,612; 8,901,356; 9,102,687; US 20080069809; US 2010204318; US 20130324600; US 20130331446; US 20140371311; US 20150175622; WO20130182688; WO2014066967; Jorgensen et al., 2013, "14-Step Synthesis of (+)-Ingenol from (+)-3-Carene," Science 341(6148):878-882; McKerral et al., 2014, "Development of a Concise Synthesis of (+)-Ingenol," J. Am Chem Soc. 136 (15):5799-5810; Liang et al., 2013, Bioorg Med Chem Lett. 23:5624-5629; Grue-Sorensen et al., 2014, "Synthesis, biological evaluation and SAR of 3-benzoates of ingenol for treatment of actinic keratosis and non-melanoma skin cancer," Bioorg Med Chem Lett. 24:54-60; Duran-Pena et al., 2014, Natural Product Reports 31:940-952; Shi et al., 2008, Chem. Rev. 108:4295-4327; all of which are incorporated herein by reference.

In some embodiments, the ingenane class of PKC activating compounds (e.g., ingenols) have an alkyl (e.g., methyl) at carbon atoms 2, 11, and 15, and an optionally substituted alkyl, e.g., methyl or methylene at carbon atom 6. As will be understood by the skilled artisan, the numbering of the carbon atoms for such structures can use the following:

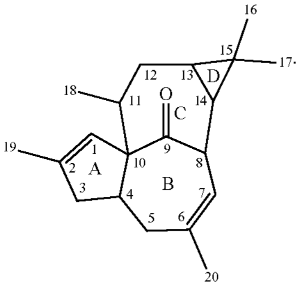

The daphnane class of PKC modulating compounds comprise a partial structure of formula C:

C

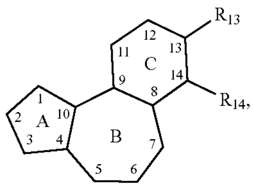

wherein one of $R_{13}$ and $R_{14}$ is an optionally substituted lower alkenyl of structure:

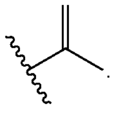

The daphnane class of diterpenoid PKC modulators constitutes a diverse group of compounds. In some embodiments, the bond between carbon atoms 6 and 7 and the bond between carbon atoms 1 and 2 are each independently a double bond, as illustrated in formula C1 and C3 below. In some embodiments, the carbon atoms 6 and 7 are bonded to a common oxygen atom to form an epoxide, as illustrated in formula C2 and C4.

C1

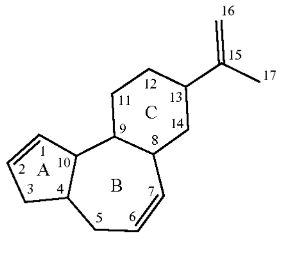

C2

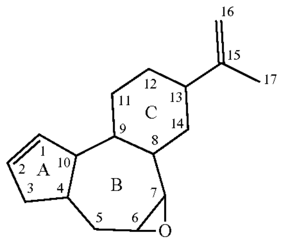

C3

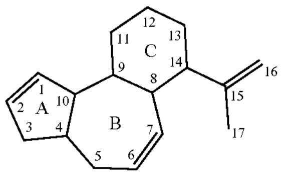

C4

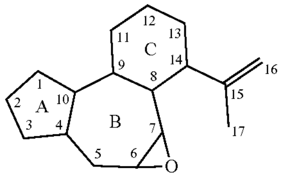

In some embodiments, substituents can be present on one or more carbon atoms 1, 2, 3, 4, 5, 6, 7, 9, 12, 13, and 14 of formula C, and additionally at carbon atom 17 for compounds of formula C1, C2, C3 and C4. Exemplary daphnane diterpenoid PKC activators include, among others, GD-1, yuanhuacine, mezerein, sapintoxin D, thymeleatoxin A, simplexin, gnidimacrin, pimelea factor S7, genididin, geniditrin and gnidilatin. Daphnane PKC activating compounds, and derivatives and analogs thereof, are described in among others, U.S. Pat. No. 5,145,842; Wender et al., 2011, Nat Chem. 3(8):615-619; Yoshida et al., 1996, Int J Cancer 66(2):268-73; and Brooks et al., 1989, Carcinogenesis 10(2):283-8; all publications incorporated herein by reference.

In some embodiments, the PKC activating tigliane, ingenane or daphnane compound for use in the methods herein is a non-tumor promoting tigliane, ingenane, or daphnane diterpenoid compound. "Tumor promoting" refers to the ability of a compound to promote tumorigenesis, while a "non-tumor promoting" characteristic refers to the absence or insignificant activity in promoting tumorigenesis.

In some embodiments, the PKC activating tigliane, ingenane, or daphnane compound for use in the methods does not significantly down-regulate expression of PKC protein. While many tigliane, ingenane and daphnane diterpenoids have PKC activating activity, some of the compounds also down-regulate expression of PKC protein. In some instances, this down-regulation could reduce or negate the advantageous effects of PKC activation. For example, PKC activating compounds that have tumor-promoting properties, such as 12-O-Tetradecanoylphorbol-13-acetate (TPA), also known as phorbol 12-myristate 13-acetate (PMA), have been shown to down-regulate PKC expression following extended exposure of cells to compounds (see, e.g., Lu et al., Mol Cell Biol., 17(6):3418-3428). In some embodiments, PKC activating tigliane, ingenane or daphnane compound can be selected for low or minimal PKC down-regulating characteristics. In some embodiments, PKC activating compounds are selected which does not downregulate PKC activity by more than 20%, 30%, 40%, 50%, 60%, or 70% of activity present in the absence of the PKC activating compound. In some embodiments, the down-regulation (or absence of down-regulation) is for global PKC expression. In some embodiments, the down-regulation is with respect to one or more of PKC isoforms selected from PKC α, β, γ, δ, ε, η, θ, ι/λ, μ, and ζ. Exemplary non-tumor promoting diterpenoid PKC activating compounds are based on 12-deoxyphorbol compounds, such as prostratin.

In some embodiments, the PKC activator is a compound of structural formula (I):

(I)

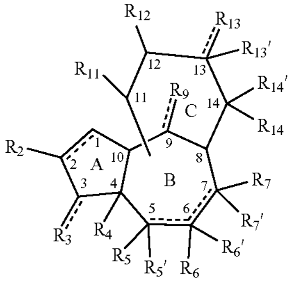

or an enantiomer, hydrate, solvate, or pharmaceutically acceptable salt thereof wherein Ring C is attached to Ring B at carbon atom 9 or 10;

$R_2$ is selected from H or lower alkyl;

$R_3$ is H, or O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl, —$S(O)_2R_b$, —$S(O)_2OR_b$, or —P(O)$(OR_b)_2$;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —$S(O)_2R_b$, —$S(O)_2OR_b$, and —P(O)$(OR_b)_2$;

$R_5$' and $R_6$' are H, or $R_5$' and $R_6$' together form a bond or are bonded to a common oxygen atom to form an epoxide;

$R_6$ is —$NR_bR_b$, —NHC(O)$R_b$, —$SR_b$, $SOR_b$, —$S(O)_2R_b$, —$S(O)_2OR_b$, —P(O)$(OR_b)_2$, —$SeR_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$C_{1-4}$alkyl-O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, —$S(O)_2R_b$, —$S(O)_2OR_b$, —P(O)$(OR_b)$, or $R_d$ is a promoiety which is hydrolyzable under biological conditions to yield an -alkyl-OH.

$R_6$' and $R_7$' are H, or $R_6$' and $R_7$' together form a bond or are bonded to a common oxygen atom to form an epoxide;

$R_7$ is H or OH;

$R_9$ is H, oxo, or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl, or $R_9$', is an O atom which is bonded to an optionally substituted common C atom bonded to $R_{13}$' and $R_{14}$', wherein $R_{13}$' and $R_{14}$' each is an O atom;

$R_{11}$ is lower alkyl;

$R_{12}$ is H, halo, —$NR_bR_b$, —NHC(O)$R_b$, —$SR_b$, $SOR_b$, —$S(O)_2R_b$, —$S(O)_2OR_b$, —P(O)$(OR_b)_2$, —$SeR_b$, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or $R_{12}$ is —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, $—S(O)_2R_b$, $—S(O)_2OR_b$, and $—P(O)(OR_b)_2$;

$R_{13}$ is H, halo, oxo, $—NR_bR_b$, $—NHC(O)R_b$, $—SR_b$, $SOR_b$, $—S(O)_2R_b$, $—S(O)_2OR_b$, $—P(O)(OR_b)_2$, $—SeR_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or $—OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, $—S(O)_2R_b$, $—S(O)_2OR_b$, and $—P(O)(OR_b)_2$;

$R_{13}'$ and $R_{14}'$ are independently H, OH, or are bonded to a common carbon atom to form a cyclopropyl ring, wherein the cyclopropyl ring is optionally mono- or disubstituted with OH, halo, $—NR_bR_b$, $—NHC(O)R_b$, $—SR_b$, $SOR_b$, $—S(O)_2R_b$, $—S(O)_2OR_b$, and $—OP(O)(OR_b)_2$, $—SeR_b$, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, carbamate, phosphine, phosphoramide, phosphoramidite, phosphoramidate, phosphonate, sulfonamide, amide, guanidine, urea; or a progroup which is hydrolysable under biological conditions to yield an -alkyl-OH group, or $R_{13}'$ and $R_{14}'$ are each an O atom which is bonded to an optionally substituted common C atom bonded to $R_9$, wherein $R_9$ is an O atom;

$R_{14}$ is H, OH or optionally substituted alkenyl;

wherein each $R_b$ is independently H, optionally substituted alkyl, optionally substituted alkenyl, alkynyl, optionally substituted aryl, optionally substituted heteroaryl, optionally substituted arylalkyl, or optionally substituted heteroarylalkyl; and the dashed line ( ..... ) represents an optional bond.

In some embodiments of structural formula (I), $R_6$ is $CH_2R_h$, wherein $R_h$ is $—O—C(O)—R_i$, wherein $R_i$ is a moiety which bears a permanent charge or which is ionizable at a pH in the range of about 2 to 8, and wherein the $—O—C(O)—R_i$ is hydrolyzable under biological conditions to yield an —OH group. In some embodiments, $R_i$ is an optionally substituted carboxyalkyl, wherein the carboxy is COOM, and wherein M is an H or a counterion. In some embodiments, the alkyl of $R_i$ is a $C_{1-6}$alkyl. In some embodiments, $R_j$ is an amino acid of structure $—(CH_2)_n—CH(CH_2)_n—NH_2)—(CH_2)_n—C(O)OM$ or $—(CH_2)_n—CHNH_2—(CH_2)_n—C(O)OM$, wherein n is 0, 1, 2, 3 or 4. In some embodiments, $R_i$ is an aminoalkyl, wherein the amino group is $—NR_jR_j$ or $—NR_kR_kR_k$, wherein each $R_j$ and $R_k$ is independently H, lower alkyl, lower alkyloxyalkyl, heteroalkyl, or two $R_j$ taken together with the nitrogen atom to which they are bonded form a 5-7 membered heteroatomic ring. In some embodiments, the alkyl of the aminoalkyl is a $C_{1-6}$alkyl. In some embodiments, $—NR_jR_j$ is N-morpholinyl, piperazinyl, 1-piperazinyl, 1-methyl-piperazinyl, or 1-methyl-4-piperazinyl.

In some embodiments, the PKC activator is a compound of structural formula (II):

(II)

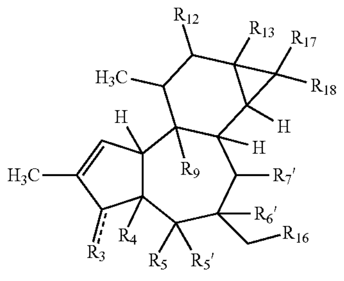

or an enantiomer, hydrate, solvate, or pharmaceutically acceptable salt thereof, wherein $R_3$ is O, S or N double bonded to the ring carbon, or $R_3$ is $—OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_5$' and $R_6$' are H, or $R_5$' and $R_6$' together form a bond or are bonded to a common oxygen atom to form an epoxide;

$R_6$' and $R_7$' are H, or $R_6$' and $R_7$' together form a bond or are bonded to a common oxygen atom to form an epoxide;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{12}$ is H, halo, or —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{16}$; and $R_{17}$ and $R_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted aryloxy, optionally substituted arylalkyloxy, optionally substituted alkylcarbonyloxy, optionally substituted alkenylcarbonyloxy, optionally substituted arylcarbonyloxy, optionally substituted arylalkylcarbonlyoxy, phosphine, phosphate, phosphoramide, phosphoramidite, phosphoramidate, phosphonate, sulfate, sulfonate, sulfonamide, sulfone, sulfite, amide, guanidine, or urea.

In some embodiments of structural formula (II), $R_{16}$ is —O—C(O)—$R_i$, wherein $R_i$ is a moiety which bears a permanent charge or which is ionizable at a pH in the range of about 2 to 8, and wherein the —O—C(O)—$R_i$ is hydrolyzable under biological conditions to yield an —OH group. In some embodiments, $R_i$ is an optionally substituted carboxyalkyl, wherein the carboxy is COOM, and wherein M is an H or a counterion. In some embodiments, the alkyl of $R_i$ is a $C_{1-6}$alkyl. In some embodiments, $R_i$ is an amino acid of structure —$(CH_2)_n$—$CH(CH_2)_n$—$NH_2$)—$(CH_2)_n$—C(O)OM or —$(CH_2)_n$—$CHNH_2$—$(CH_2)_n$—C(O)OM, wherein n is 0, 1, 2, 3 or 4. In some embodiments, $R_1$ is an aminoalkyl, wherein the amino group is —$NR_jR_j$, or —$NR_kR_kR_k$, wherein each $R_j$ and $R_k$ is independently H, lower alkyl, lower alkyloxyalkyl, heteroalkyl, or two $R_j$ taken together with the nitrogen atom to which they are bonded form a 5-7 membered heteroatomic ring. In some embodiments, the alkyl of the aminoalkyl is a $C_{1-6}$alkyl. In some embodiments, —$NR_jR_j$ is N-morpholinyl, piperazinyl, 1-piperazinyl, 1-methyl-piperazinyl, or 1-methyl-4-piperazinyl.

In some embodiments, the PKC activator comprises the compound of formula (IIa):

(IIa)

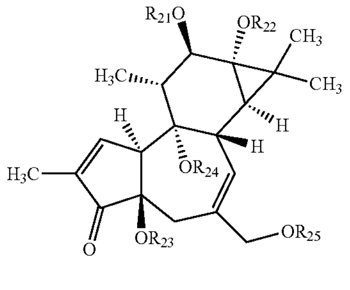

or an enantiomer, hydrate, solvate, or pharmaceutically acceptable salt thereof, wherein $R_{21}$, $R_{22}$, $R_{23}$, and $R_{24}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{25}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{25}$ is a promoiety which is hydrolyzable under biological conditions to yield an —OH group at the C20 carbon atom.

In some embodiments, the PKC activator comprises a compound of formula (IIb):

(IIb)

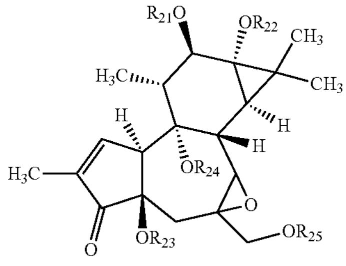

or an enantiomer, hydrate, solvate, or pharmaceutically acceptable salt thereof, wherein, $R_{21}$, $R_{22}$, $R_{23}$, $R_{24}$ and $R_{25}$ are as defined for formula (IIa).

In some embodiments, the PKC activator comprises a compound of formula (IIc):

(IIc)

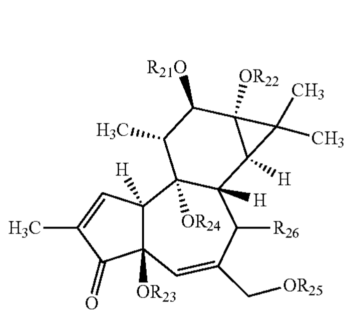

or an enantiomer hydrate, solvate, or pharmaceutically acceptable salt thereof, wherein, $R_{21}$, $R_{22}$, $R_{23}$, $R_{24}$ and $R_{25}$ are as defined for formula (IIa), and $R_{26}$ is H or OH.

In some embodiments, the PKC activator comprises a compound of formula (IId):

(IId)

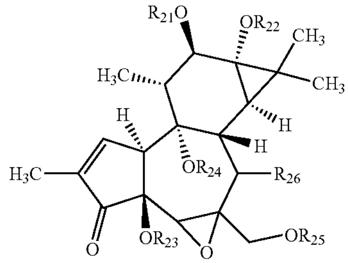

or an enantiomer, hydrate, solvate, or pharmaceutically acceptable salt thereof, wherein, $R_{21}$, $R_{22}$, $R_{23}$, $R_{24}$ and $R_{25}$ are as defined for formula (IIa), and $R_{26}$ is H or OH.

In some embodiments of structural formula (IIa), (IIb), (IIc) or (IId), the aryl is an optionally substituted phenyl.

In some embodiments of structural formula (IIa), (IIb), (IIc) and (IId), $R_{25}$ forms a promoiety as described in formula (II) above. In some embodiments of structural formula (IIa), (IIb), (IIc) and (IId), $R_{25}$ is an optionally substituted carboxyalkylcarbonyl, wherein the carboxy is COOM, wherein M is an H or a counterion. In some embodiments, the alkyl is a $C_{1-6}$alkyl. In some embodiments, $R_{25}$ is an amino acid carbonyl, where the amino acid portion has the structure $-(CH_2)_n-CH(CH_2)_n-NH_2)-(CH_2)_n-C(O)OM$ or $-(CH_2)_n-CHNH_2-(CH_2)_n-C(O)OM$, wherein n is 0, 1, 2, 3, or 4. In some embodiments, $R_{25}$ is an aminoalkylcarbonyl, wherein the alkyl is a $C_{1-6}$alkyl and the amino group is $-NR_jR_j$ or $-NR_kR_kR_k$, wherein each $R_j$ and $R_k$ is independently H, lower alkyl, lower alkyloxyalkyl, heteroalkyl, or two $R_j$ taken together with the nitrogen atom to which they are bonded form a 5-7 membered heteroatomic ring. In some embodiments, $-NR_jR_j$ is N-morpholinyl, piperazinyl, 1-piperazinyl, 1-methyl-piperazinyl, or 1-methyl-4-piperazinyl.

In some embodiments, the PKC activator is selected from the exemplary phorbol compounds presented below, including, among others, phorbol 13-butyrate; phorbol 12-decanoate; phorbol 13-decanoate; phorbol 12,13-diacetate, phorbol 13,20-diacetate, phorbol 12,13-dibenzoate, phorbol 12,13 dibutyrate, phorbol 12,13 didecanoate; phorbol 12,13-dihexanoate; phorbol 12,13 dipropionate, phorbol 12-myristate; phorbol 13-myristate, phorbol 12-myristate-13-acetate (TPA), phorbol 12,13,20-triacetate; phorbol 12-acetate, phorbol 13-acetate, phorbol-12-tigliate 13-decanoate, or salts, hydrates, solvates, or prodrugs thereof. In some embodiments, the prodrugs for the specified phorbol compounds contain a biohydrolyzable carbonate, biohydrolyzable ureide, biohydrolyzable carbamate, biohydrolyzable ester, biohydrolyzable amide, or biohydrolyzable phosphate group. In particular, the prodrug for the specified compound contains a biohydrolyzable ester, more particularly at the C20 carbon.

Phorbol Compounds
(1)
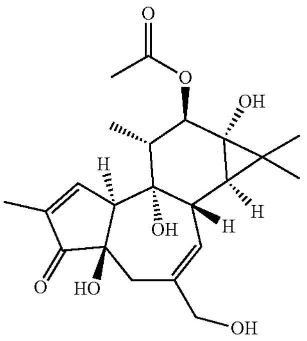
phorbol 12-acetate
(2)
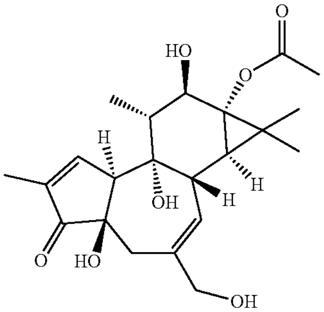
Phorbol 13-acetate
(3)
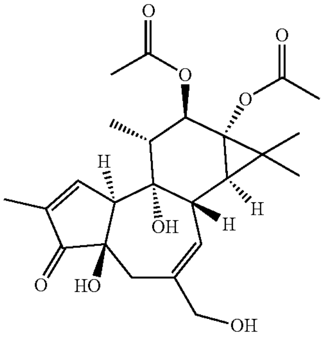
phorbol 12,13-diacetate
(4)
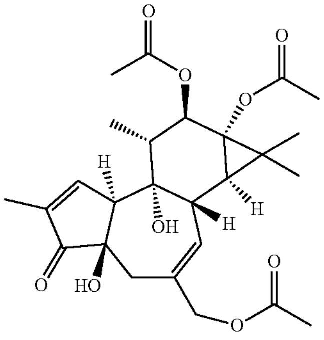
phorbol 12,13,20-triacetate
-continued
(5)
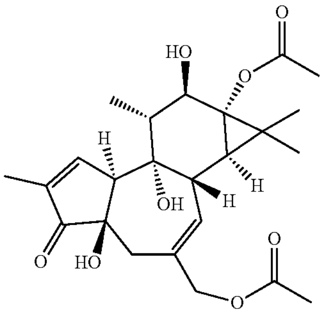
Phorbol 13,20-diacetate
(6)
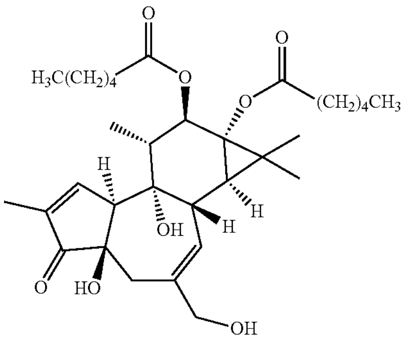
Phorbol 12,13-dihexanoate
(7)
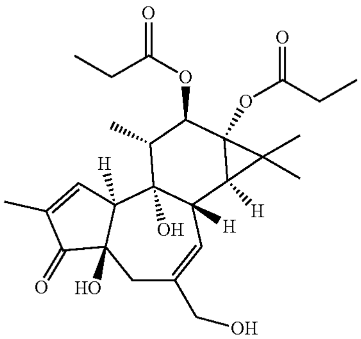
phorbol 12,13-dipropionate
(8)
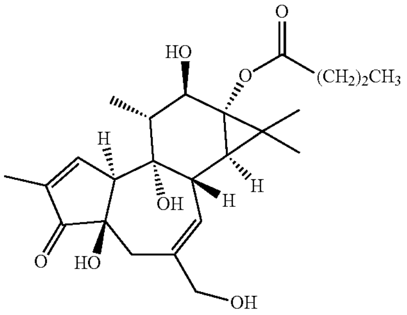
phorbol 13-butyrate -continued
(9)
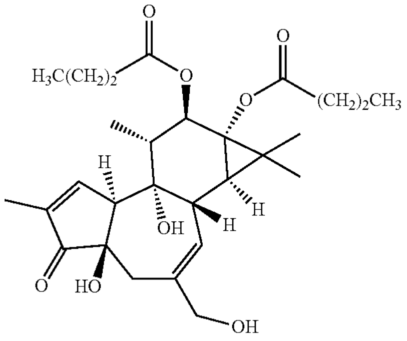
phorbol 12,13-dibutyrate
(10)
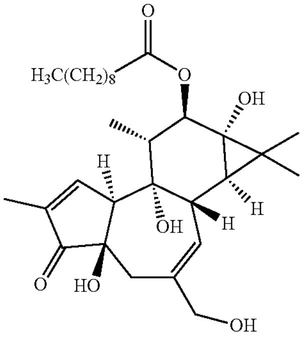
phorbol 12-decanoate
(11)
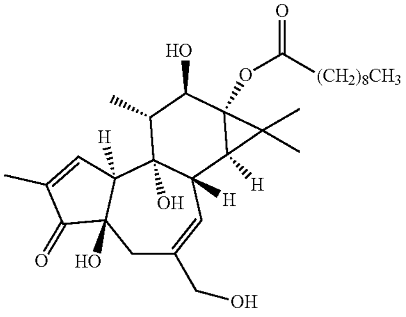
phorbol 13-decanoate
(12)
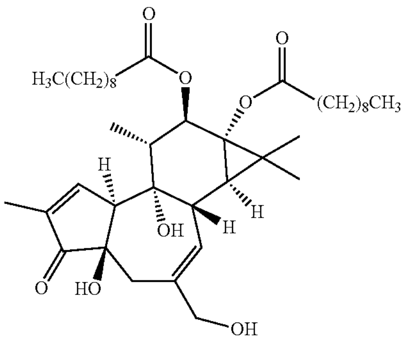
phorbol-12,13-decanoate
-continued
(13)
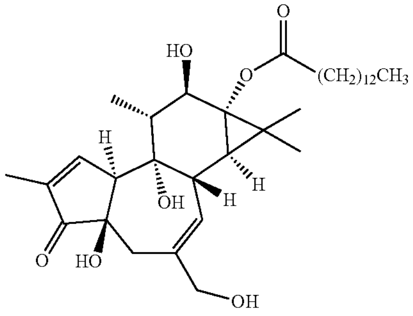
phorbol 13-myristate
(14)
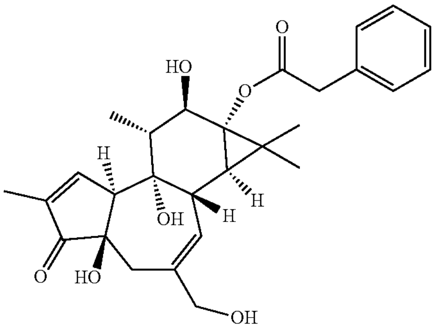
phorbol 13-phenylacetate
(15)
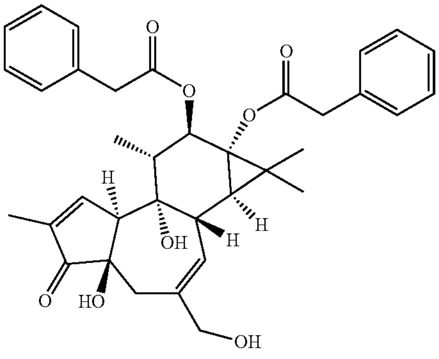
phorbol 12,13-diphenylacetate
(16)
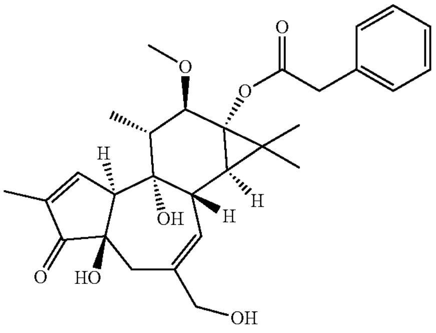
phorbol 12-methoxy-13-phenylacetate -continued
(17)
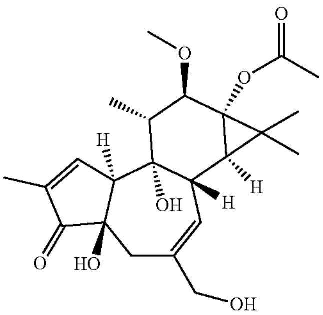
Phorbol 12-methoxy-13-acetate
(18)
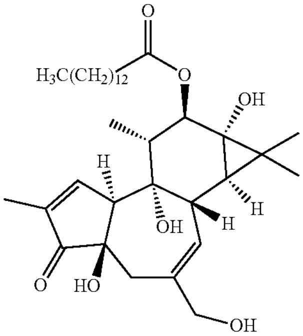
Phorbol 12-myristate
(18)
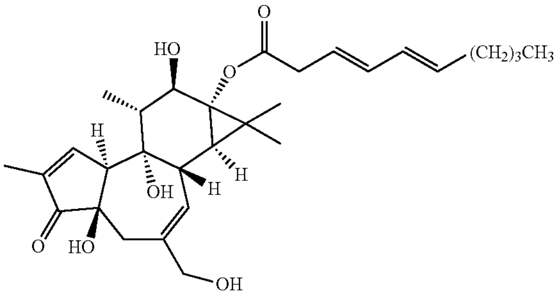
(19)
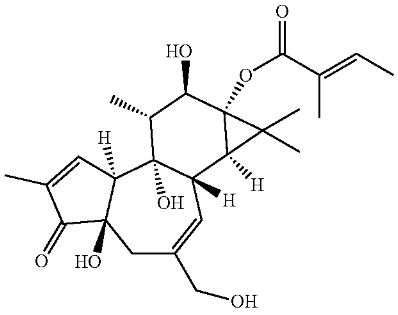
phorbol 13-tiglate
-continued
(20)
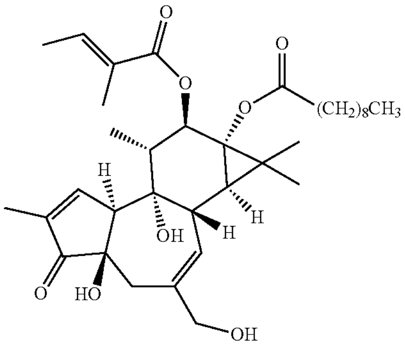
phorbol-12-tiglate-13-decanoate
(21)
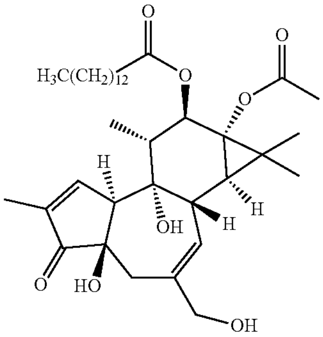
phorbol-12-myristate-13-acetate
(22)
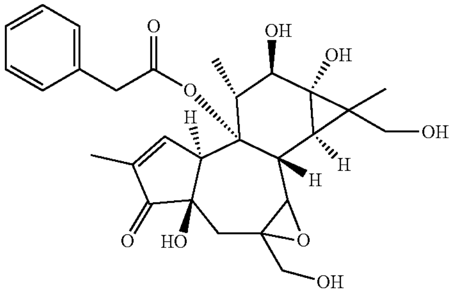
(23)
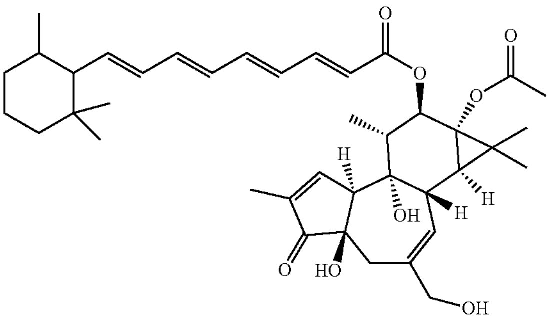
In some embodiments, the PKC activator is compound of structural formula (III):

(III)

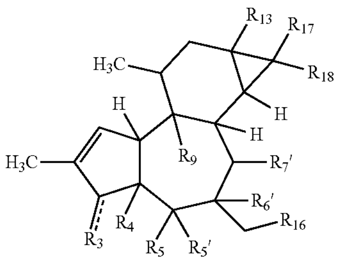

or an enantiomer, hydrate, solvate, or pharmaceutically acceptable salt thereof, wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_5'$ and $R_6'$ are H, or $R_5'$ and $R_6'$ together form a bond or are bonded to a common oxygen atom to form an epoxide;

$R_6'$ and $R_7'$ are H, or $R_6'$ and $R_7'$ together form a bond or are bonded to a common oxygen atom to form an epoxide;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{16}$ is H, halo, or —O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group—at the C20 carbon atom; and $R_{17}$ and $R_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, phosphine, phosphate, phosphoramide, phosphoramidite, phosphoramidate, phosphonate, sulfate, sulfonate, sulfonamide, sulfone, sulfite, amide, guanidine, urea, or a progroup which is hydrolyzable under biological conditions to yield an -alkyl-OH group.

In some embodiments of structural formula (III), $R_{16}$ is —O—C(O)—$R_i$, wherein $R_i$ is a moiety which bears a permanent charge or which is ionizable at a pH in the range of about 2 to 8, and wherein the —O—C(O)—$R_i$ is hydrolyzable under biological conditions to yield an —OH group. In some embodiments, $R_i$ is an optionally substituted carboxyalkyl, wherein the carboxy is COOM, and wherein M is an H or a counterion. In some embodiments, the alkyl of $R_i$ is a lower alkylene. In some embodiments, $R_i$ is an amino acid of structure $—(CH_2)_n—CH(CH_2)_n—NH_2)—(CH_2)_n—C(O)OM$ or $—(CH_2)_n—CHNH_2—(CH_2)_n—C(O)OM$, wherein n is 0, 1, 2, 3 or 4. In some embodiments, $R_i$ is an aminoalkyl, wherein the amino group is $—NR_jR_j$ or $—NR_kR_kR_k$, wherein each $R_j$ and $R_k$ is independently H, lower alkyl, lower alkyloxyalkyl, heteroalkyl, or two $R_j$ taken together with the nitrogen atom to which they are bonded form a 5-7 membered heteroatomic ring. In some embodiments, the alkylene of the aminoalkyl is a lower alkyl. In some embodiments, $—NR_jR_j$ is N-morpholinyl, piperazinyl, 1-piperazinyl, 1-methyl-piperazinyl, or 1-methyl-4-piperazinyl.

In some embodiments, the PKC activator comprises a compound of formula (IIIa) or (IIIb):

(IIIa)

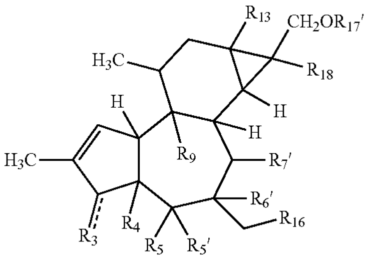

, or (IIIb)

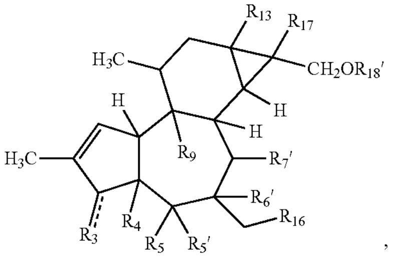

, or an enantiomer, hydrate, solvate, or pharmaceutically acceptable salt thereof, wherein $R_3$, $R_4$, $R_5$, $R_5$' $R_6$', $R_7$', $R_9$, $R_{13}$, and $R_{16}$ are as defined for formula (III);

$R_{17}$ or $R_{18}$ is H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted aryloxy, optionally substituted arylalkyloxy, phosphine, phosphate, phosphoramide, phosphoramidite, phosphoramidate, phosphonate, sulfate, sulfonate, sulfonamide, sulfone, sulfite, amide, guanidine, or urea; and $R_{17}$' or $R_{18}$' is H, optionally substituted alkyl, optionally substituted cycloalkyl, optionally substituted heteroalkyl, optionally substituted aryl, optionally substituted heteroaryl, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a progroup which is hydrolyzable under biological conditions to yield an —OH group.

In some embodiments, the PKC activator comprises a compound of formula (IIIc):

(IIIc)

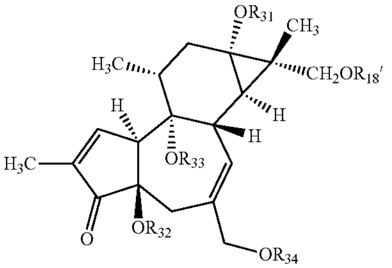

or an enantiomer, hydrate, solvate, or pharmaceutically acceptable salt thereof, wherein, $R_{18}$' is H, optionally substituted alkyl, optionally substituted cycloalkyl, optionally substituted heteroalkyl, optionally substituted aryl, optionally substituted heteroaryl, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group;

$R_{31}$, $R_{32}$, and $R_{33}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{34}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{34}$ is a pro-moiety which is hydrolyzable under biological conditions to yield an —OH group at the C20 carbon atom.

In some embodiments, the PKC activator comprises a compound of formula (IIId):

(IIId)

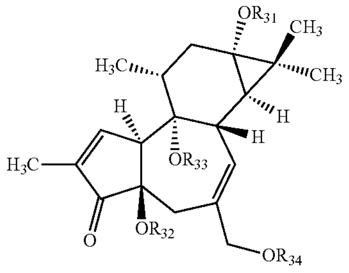

or an enantiomer, hydrate, solvate, or pharmaceutically acceptable salt thereof, wherein $R_{31}$, $R_{32}$, and $R_{33}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{34}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{34}$ is a pro-moiety which is hydrolyzable under biological conditions to yield an —OH group at the C20 carbon atom.

In some embodiments, the PKC activator comprises a compound of formula (IIIe):

(IIIe)

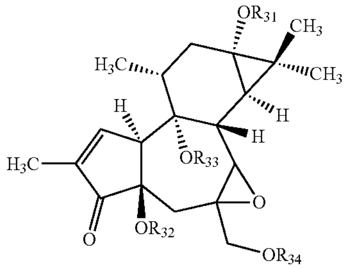

or an enantiomer, hydrate, solvate, or pharmaceutically acceptable salt thereof, wherein, $R_{31}$, $R_{32}$, $R_{33}$, and $R_{34}$ are as defined for formula (IIIc).

In some embodiments of the compound of formula (IIIc), (IIId) and (IIIe), $R_{34}$ is an optionally substituted carboxyalkylcarbonyl, wherein the carboxy is —COOM, wherein M is an H or a counterion. In some embodiments, the alkyl is a $C_{1-6}$alkyl. In some embodiments, $R_{34}$ is an amino acid carbonyl of structure $—C(O)—(CH_2)_n—CH(CH_2)_n—NH_2)—(CH_2)_n—C(O)OM$ or $—C(O)—CH_2)_n—CHNH_2—(CH_2)_n—C(O)OM$, wherein n is 0, 1, 2, 3, or 4. In some embodiments, $R_{34}$ is an aminoalkyl, wherein the amino group is $—NR_jR_j$ or $—NR_kR_kR_k$, wherein each $R_j$ and $R_k$ are independently H, lower alkyl, lower alkyloxyalkyl, heteroalkyl, or two $R_j$ taken together with the nitrogen atom to which they are bonded form a 5-7 membered heteroatomic ring. In some embodiments, the alkyl of $R_{34}$ is a $C_{1-6}$alkyl. In some embodiments, the $—NR_jR_j$ is N-morpholinyl, piperazinyl, 1-piperazinyl, 1-methyl-piperazinyl, or 1-methyl-4-piperazinyl.

In some embodiments, the PKC activator is selected from the exemplary deoxyphorbol compounds presented below, including, among others, 12-deoxyphorbol 13-angelate, 12-deoxyphorbol 13-angelate 20-acetate, 12-deoxyphorbol 13-isobutyrate, 12-deoxyphorbol 13-isobutyrate 20-acetate, 12-deoxyphorbol 13-phenylacetate, 12-deoxyphorbol 13-phenylacetate 20-acetate, 12-deoxyphorbol 13-tetradecanoate, 12-deoxyphorbol 13-acetate (prostratin), or salts, hydrates, solvates, or prodrugs thereof. In some embodiments, the prodrugs for the specified deoxyphorbol compounds contain a biohydrolyzable carbonate, biohydrolyzable ureide, biohydrolyzable carbamate, biohydrolyzable ester, biohydrolyzable amide, or biohydrolyzable phosphate group. In particular, the prodrug for the specified deoxyphorbol compound contains a biohydrolyzable ester, more particularly at the C20 carbon.

Deoxyphorbol Compounds
(1')
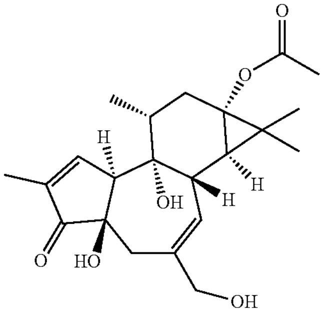
12-deoxyphorbol-13-acetate (prostratin)
(2')
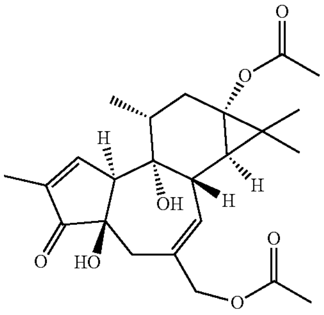
12-deoxyphorbol-13,20-diacetate
(3')
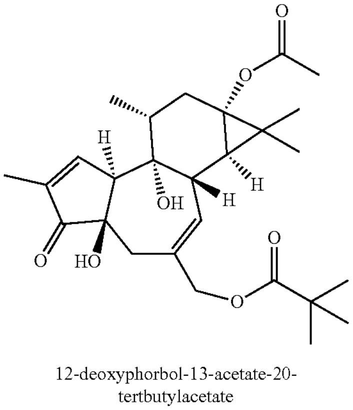
12-deoxyphorbol-13-acetate-20-tertbutylacetate
(4')
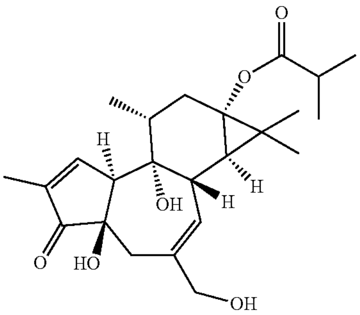
12-deoxyphorbol-13-isobutyrate
-continued
(5')
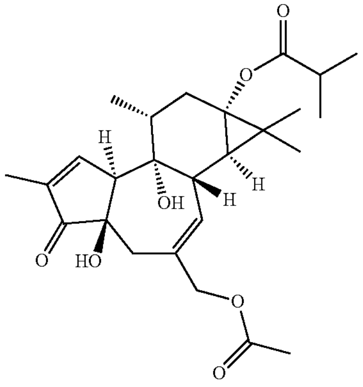
12-deoxyphorbol-13-isobutyrate-20-acetate
(6')
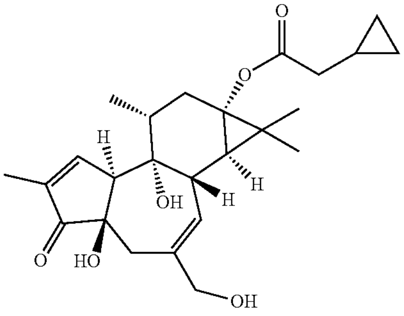
12-deoxyphorbol-13-cycloproylacetate
(7')
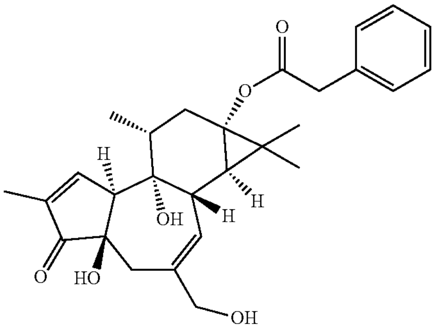
12-deoxyphorbol-13-benzoate
(8')
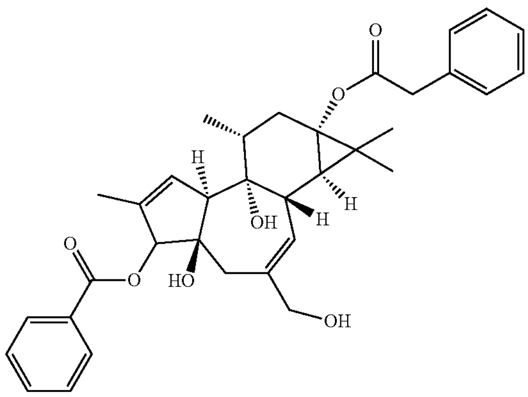
12-deoxyphorbol-3-benzoate-13-phenylacetate -continued
(9')
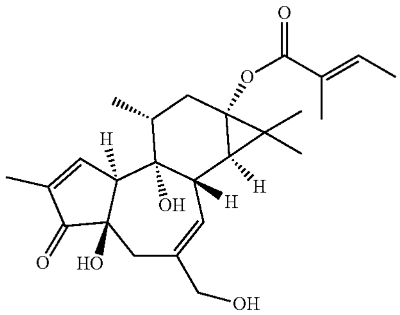
12-deoxyphorbol-13-angelate
(10')
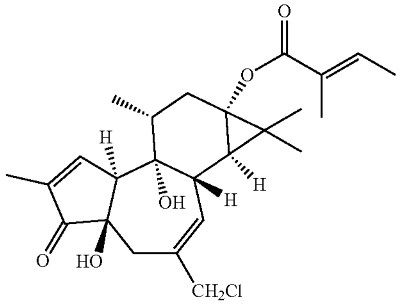
12-deoxyphorbol-6-chloromethyl-13-angelate
(11')
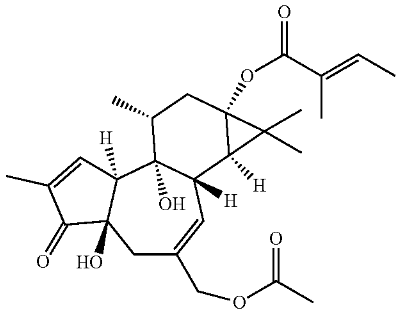
12-deoxyphorbol 13-angelate 20-acetate
(12')
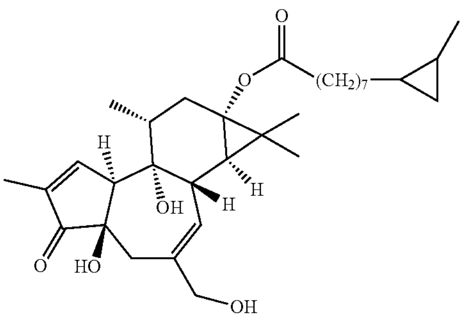
-continued
(13')
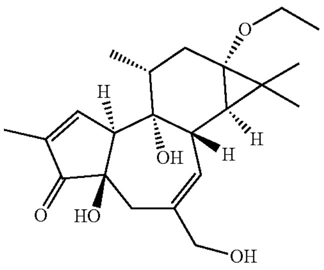
(14')
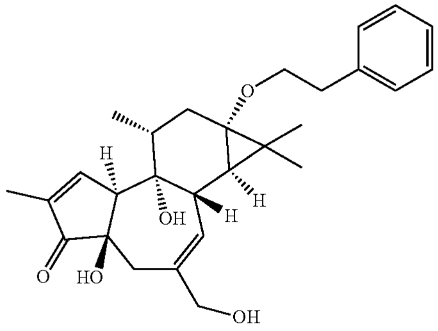
(15')
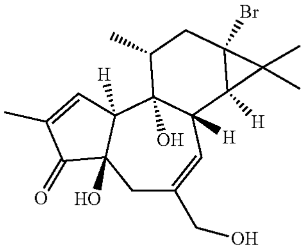
(16')
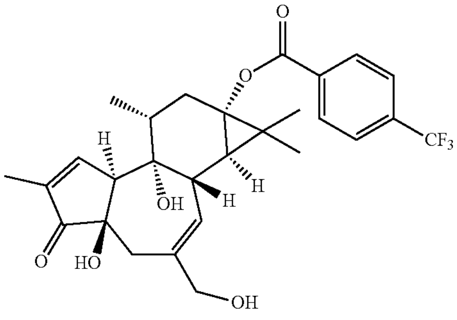
(17')
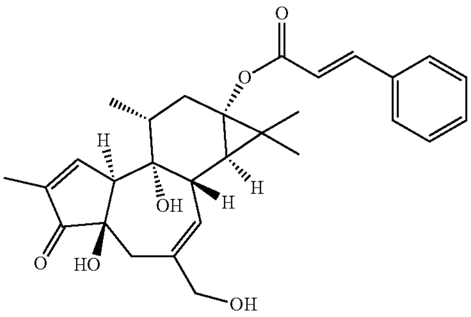

-continued (18')

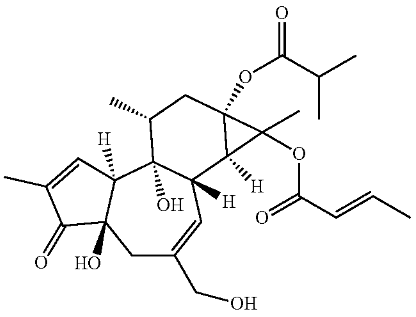

(19')

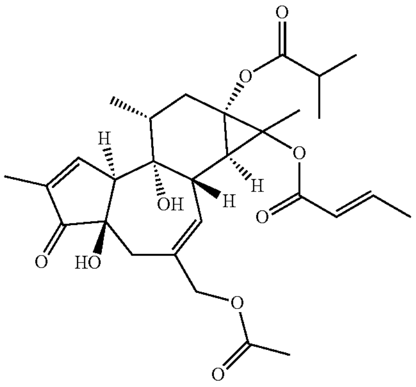

(20')

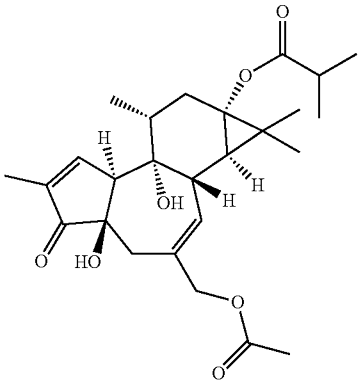

(21')

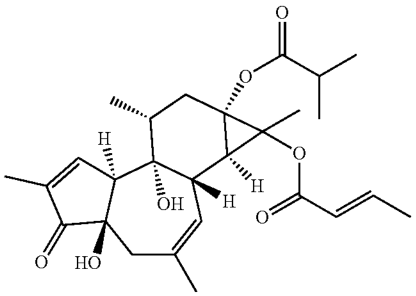

-continued (22')

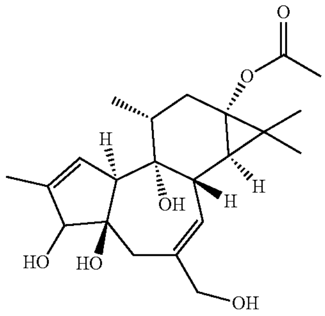

(23')

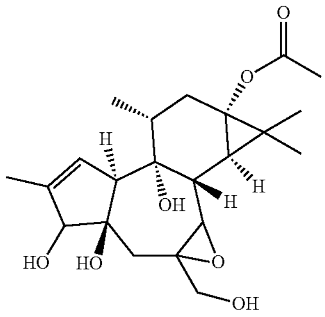

(24')

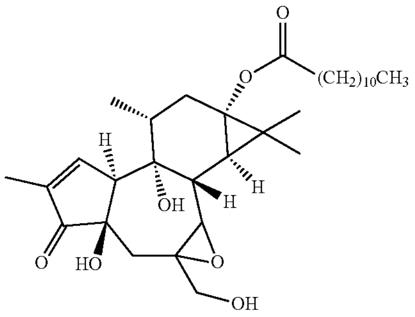

In some embodiments, the PKC activating compound is prostratin, or derivatives thereof, such as compounds K101B, K101C, K101D, K101E, K101F, and K101I, described herein and in the Examples.

In some embodiments, the PKC activator comprises a compound of formula (IV):

(IV)

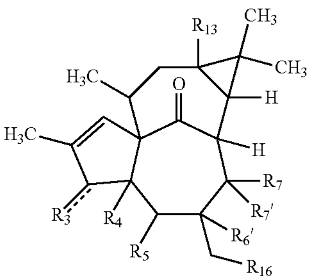

or an enantiomer, hydrate, solvate, or pharmaceutically acceptable salt thereof, wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_6$' and $R_7$' are H, or $R_6$' and $R_7$' together form a bond or are bonded to a common oxygen atom to form an epoxide;

$R_7$ is H or OH;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{16}$.

In some embodiments, the PKC activator comprises a compound of formula (IVa):

(IVa)

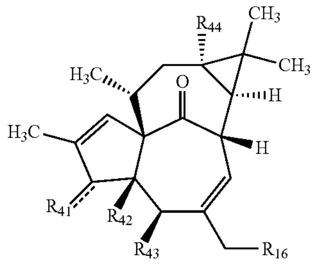

or an enantiomer, hydrate, solvate, or pharmaceutically acceptable salt thereof, wherein $R_{41}$ is O double bonded to the ring carbon, or $R_{41}$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_{42}$ and $R_{43}$ are independently H, halo, or —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{44}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a biohydrolyzable promoiety which is hydrolyzable under biological conditions to yield an —OH group at $R_{16}$.

In some embodiments, the PKC activator comprises a compound of formula (IVb):

(IVb)

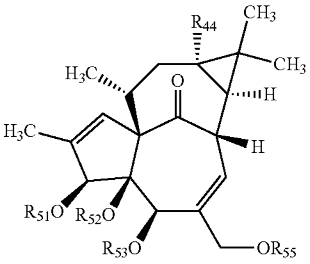

or an enantiomer, hydrate, solvate, or pharmaceutically acceptable salt thereof, wherein $R_{44}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{51}$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl; and $R_{52}$ and $R_{53}$ are independently H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{55}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group at the C20 carbon atom.

In some embodiments, the PKC activator comprises a compound of formula (IVc):

(IVc)

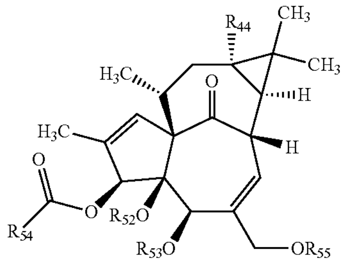

or an enantiomer, hydrate, solvate, or pharmaceutically acceptable salt thereof, wherein $R_{44}$ is H or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{52}$ and $R_{53}$ are independently H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{54}$ is H, an optionally substituted alkyl, optionally substituted alkenyl, optionally substituted cycloalkyl, optionally substituted aryl, optionally substituted heteroaryl, optionally substituted arylalkyl, optionally substituted arylalkenyl, optionally substituted heteroarylalkyl, optionally substituted heteroarylalkenyl; and $R_{55}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group at the C20 carbon atom.

In some embodiments of the compound of formula (IVb) and (IVc), $R_{55}$ is an optionally substituted carboxyalkylcarbonyl, wherein the carboxy is —COOM, wherein M is an H or a counterion. In some embodiments, the alkyl is a lower alkyl. In some embodiments, $R_{55}$ is an amino acid carbonyl of structure $—C(O)—(CH_2)_n—CH(CH_2)_n—NH_2)—(CH_2)_n—C(O)OM$ or $—C(O)—CH_2)_n—CHNH_2—(CH_2)_n—C(O)OM$, wherein n is 0, 1, 2, 3, or 4. In some embodiments, $R_{55}$ is an aminoalkyl, wherein the amino group is $—NR_jR_j$ or $—NR_kR_kR_k$, wherein each $R_j$ and $R_k$ are independently H, lower alkyl, lower alkyloxyalkyl, heteroalkyl, or two $R_j$ taken together with the nitrogen atom to which they are bonded form a 5-7 membered heteroatomic ring. In some embodiments, the alkyl of $R_{55}$ is a lower alkyl. In some embodiments, the $—NR_jR_j$ is N-morpholinyl, piperazinyl, 1-piperazinyl, 1-methyl-piperazinyl, or 1-methyl-4-piperazinyl.

In some embodiments, the PKC activator comprises a compound of formula (IVd):

(IVd)

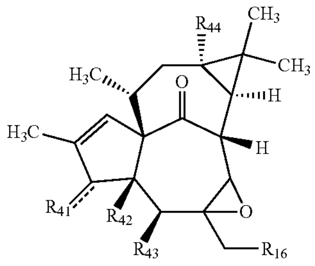

or an enantiomer, hydrate, solvate, or pharmaceutically acceptable salt thereof, wherein $R_{41}$, $R_{42}$, $R_{43}$, $R_{44}$ and $R_{16}$ are as defined for formula (IVa).

In some embodiments, the PKC activator is selected from the exemplary ingenane compounds presented below, including, among others, ingenol-3-angelate, ingenol-5-angelate, ingenol-3,20-dibenzoate, 20-O-acetyl-ingenol-3-angelate, ingenol-30-(3,5-diethyl-4-isoxazolecarboxylate), or 20-deoxy-ingenol-3-angelate, ingenol-20-benzoate, or solvates, hydrates, and prodrugs thereof. In some embodiments, the prodrugs for the specified ingenol compounds contain a biohydrolyzable carbonate, biohydrolyzable ureide, biohydrolyzable carbamate, biohydrolyzable ester, biohydrolyzable amide, or biohydrolyzable phosphate group. In particular, the prodrug for the specified ingenane compounds contains a biohydrolyzable ester, more particularly at the C20 carbon atom.

Ingenane Compounds (1″)

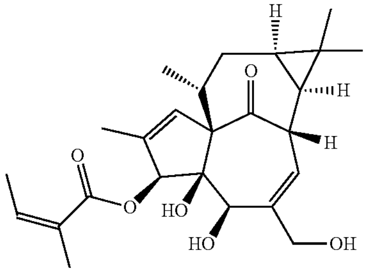

Ingenol 3-angelate (2″)

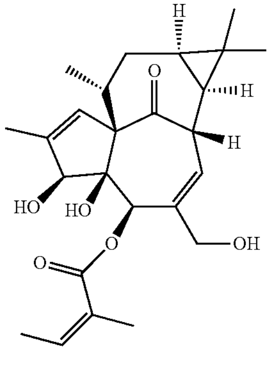

Ingenol 5-angelate

-continued
(3″)
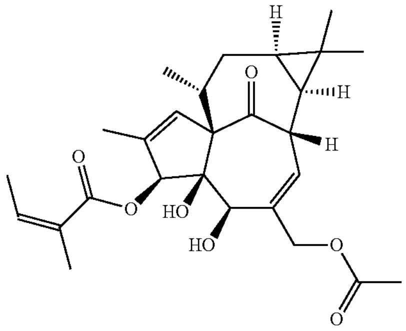
20-O-acetyl-ingenol-3-angelate
(4″)
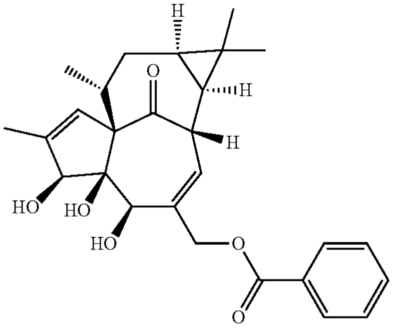
Ingenol 20-benzoate
(5″)
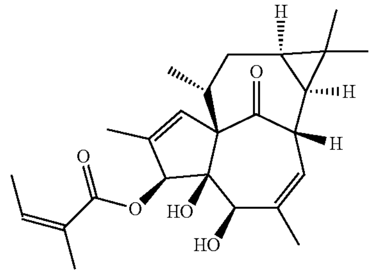
20-deoxy-ingenol-3-angelate
(6″)
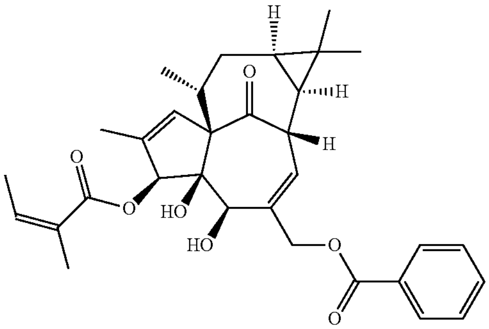
-continued
(7″)
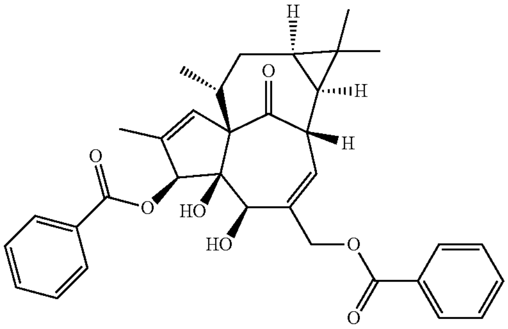
ingenol-3,20-dibenzoate
(8″)
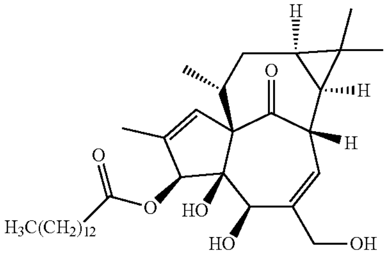
ingenol-3-tetradecanoate
(9″)
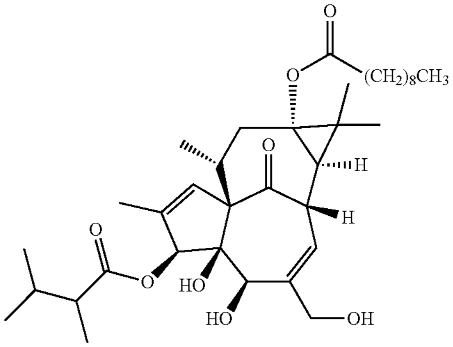
(10″)
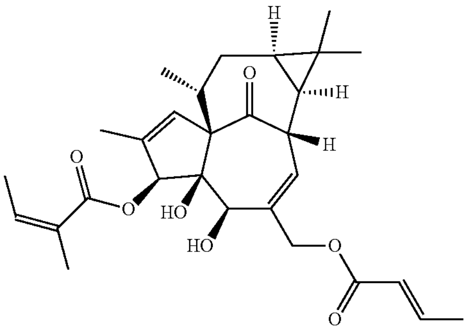
(11″)
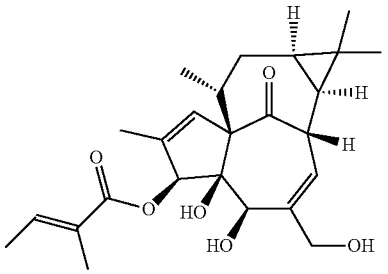

-continued (12″)

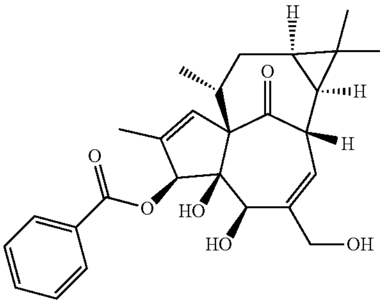

(13″)

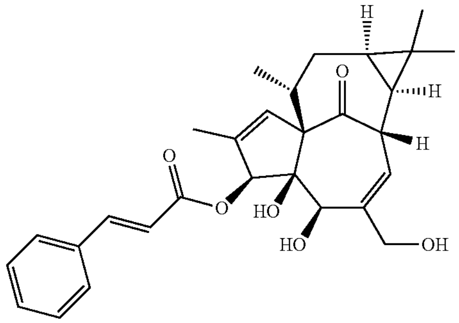

(14″)

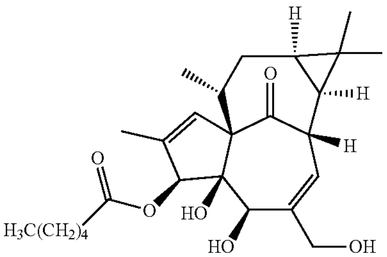

(15″)

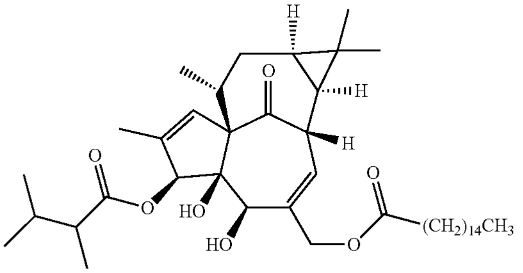

(16″)

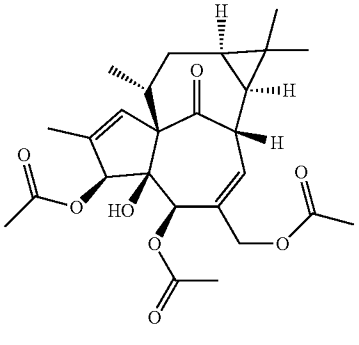

ingenol 3,5,20-triacetate

-continued (17′)

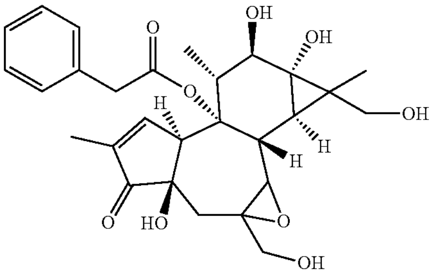

In some embodiments, the PKC activator comprises a compound of formula (V):

(V)

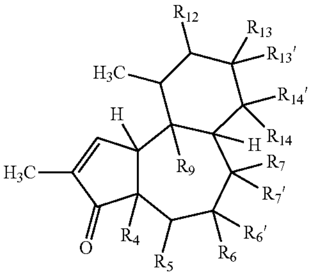

or an enantiomer, hydrate, solvate, or pharmaceutically acceptable salt thereof, wherein, $R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, or $R_9$' is an O atom which is bonded to an optionally substituted common C atom bonded to $R_{13}$' and $R_{14}$', wherein $R_{13}$' and $R_{14}$' each is an O atom;

$R_6$ is —$NR_bR_b$, —$NHC(O)R_b$, —$SR_b$, —$SOR_b$, —$S(O)_2R_b$, —$S(O)_2OR_b$, —$P(O)(OR_b)_2$, —$SeR_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or -alkyl-O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, —$S(O)_2R_b$, —$S(O)_2OR_b$, —$P(O)(OR_b)$, or $R_d$ is a promoiety which is hydrolyzable under biological conditions to yield an -alkyl OH;

$R_6'$ and $R_7'$ are H, or $R_6'$ and $R_7'$ together form a bond or are bonded to a common oxygen atom to form an epoxide;

$R_7$ is H or OH;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{12}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or $R_{12}$ is —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{13}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_i$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, or optionally substituted heteroarylalkenylcarbonyl;

$R_{13}'$ and $R_{14}'$ are independently H or OH, or $R_{13}'$ and $R_{14}'$ are each an O atom which is bonded to an optionally substituted common C atom which is bonded to $R_9$, wherein $R_9$ is an O atom; and $R_{14}$ is H, OH or optionally substituted alkenyl;

wherein one of $R_{13}$ and $R_{14}$ is an alkenyl of structure

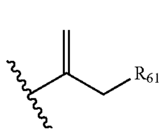

wherein $R_{61}$ is H or OH.

In some embodiments, the PKC activator comprises a compound of formula (Va):

(Va)

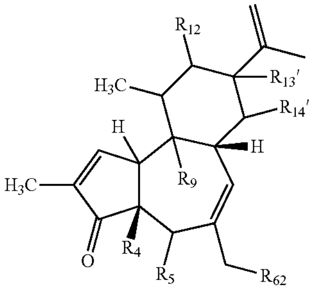

or an enantiomer, hydrate, solvate, or pharmaceutically acceptable salt thereof, wherein, $R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, or $R_9'$ is an O atom which is bonded to an optionally substituted common C atom bonded to $R_{13}'$ and $R_{14}'$, wherein $R_{13}'$ and $R_{14}'$ each is an O atom;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, optionally substituted arylalkyloxycarbonyl, or $R_9$ is an O atom which is bonded to an optionally substituted common C atom bonded to $R_{13}'$ and $R_{14}'$, wherein $R_{13}'$ and $R_{14}'$ each is an O atom;

$R_{12}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or $R_{12}$ is —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{13}$' and $R_{14}$' are independently H or OH, or $R_{13}$' and $R_{14}$' are each an O atom which is bonded to an optionally substituted common C atom which is bonded to $R_9$, wherein $R_9$ is an O atom; and $R_{62}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{62}$.

In some embodiments, the PKC activator comprises a compound of formula (Vb):

(Vb)

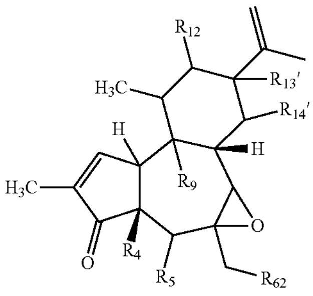

or an enantiomer, hydrate, solvate, or pharmaceutically acceptable salt thereof, wherein $R_4$, $R_5$, $R_9$, $R_{12}$, $R_{13}$', $R_{14}$', and $R_{62}$ are as defined for the compound of formula (Va).

In some embodiments, the PKC activator comprises a compound of formula (Vc):

(Vc)

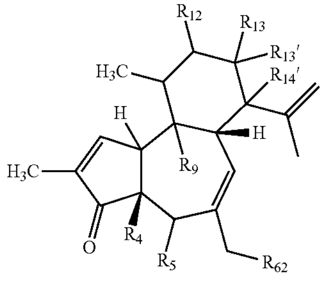

or an enantiomer, hydrate, solvate, or pharmaceutically acceptable salt thereof wherein, $R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, or $R_9$' is an O atom which is bonded to an optionally substituted common C atom bonded to $R_{13}$' and $R_{14}$', wherein $R_{13}$' and $R_{14}$' each is an O atom;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, optionally substituted arylalkyloxycarbonyl, or $R_9$ is an O atom which is bonded to an optionally substituted common C atom bonded to $R_{13}$' and $R_{14}$', wherein $R_{13}$' and $R_{14}$' each is an O atom;

$R_{12}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or $R_{12}$ is —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{13}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, or optionally substituted heteroarylalkenylcarbonyl;

$R_{13}$' and $R_{14}$' are independently H or OH, or $R_{13}$' and $R_{14}$' are each an O atom which is bonded to an optionally substituted common C atom which is bonded to $R_9$, wherein $R_9$ is an O atom; and $R_{62}$ is H, halo, or —O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{62}$.

In some embodiments, the PKC activator comprises a compound of formula (Vd):

(Vd)

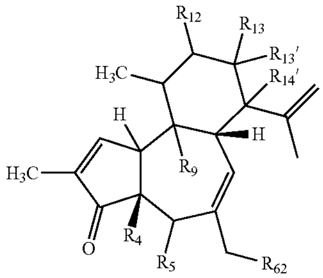

or an enantiomer, hydrate, solvate, or pharmaceutically acceptable salt thereof, wherein $R_4$, $R_5$, $R_9$, $R_{12}$, $R_{13}$, $R_{13}'$, $R_{14}'$ and $R_{62}$ are as defined for formula (Vc).

In some embodiments, the PKC activator comprises a compound of formula (Ve):

(Ve)

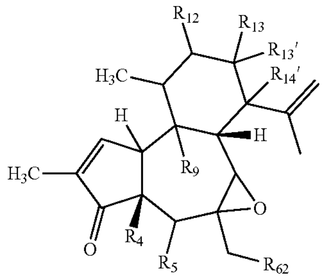

or an enantiomer, hydrate, solvate, or pharmaceutically acceptable salt thereof, wherein $R_4$, $R_5$, $R_9$, $R_{12}$, $R_{13}$, $R_{13}'$, $R_{14}'$ and $R_{62}$ are as defined for formula (Vc).

In some embodiments, the daphnane PKC activator is a compound selected from GD-1, yuanhuacine, sapintoxin D, thymeleatoxin A, simplexin, gnidimacrin, pimelea factor S7, genididin, geniditrin and gnidilatin. In some embodiments, the prodrugs for the specified daphnane compounds contain a biohydrolyzable carbonate, biohydrolyzable ureide, biohydrolyzable carbamate, biohydrolyzable ester, biohydrolyzable amide, or biohydrolyzable phosphate group. In particular, the prodrug for the specified daphnane compounds contains a biohydrolyzable ester, more particularly at the C20 carbon of formula (V).

In some embodiments, the PKC activity-modulating diterpenoid compound, e.g., tigliane (phorbol, deoxyphorbol), ingenane, and daphnane diterpenoids, including derivatives, analogs, and prodrugs thereof, and salts, hydrates, and solvates thereof, is administered in combination with a second anti-cancer chemotherapeutic agent. Accordingly, each and every embodiment of the PKC activating diterpenoid compounds described herein can be used in combination with a second anti-cancer chemotherapeutic agent.

In some embodiments, the combination is administered to a subject in need thereof based on the K-ras status of the cancer, i.e., a cancer which has been determined or identified as overexpressing K-ras, or a cancer determined or identified as having an oncogenic or activating K-ras mutation, including each and every K-ras mutation as described herein and known in the art.

In some embodiments, the combination is administered to a subject in need thereof based on an identified PKC activation potential of the cancer, as discussed above. In some embodiments, the combination is administered to a subject in need thereof based on the absence of loss of function mutations in one or more PKC isoforms, as described herein.

In some embodiments, the combination is administered to a subject in need thereof, where the cancer has been determined or identified as expressing K-ras or having an activation K-ras mutation, and an identified PKC activation potential.

In some embodiments, the second therapeutic agent is selected from an alkylating agent, anthracycline, cytoskeletal disruptor, topoisomerase inhibitor, kinase inhibitor, nucleoside analog, nucleoside metabolite inhibitor, peptide antibiotic, platinum-based agent, 26S proteasome inhibitor, and plant alkaloid used as an anti-cancer agent.

Alkylating agents can be selected from cyclophosphamide, ifosfamide, chlorambucil, busulfan, melphalan, mechlorethamine, uramustine, thiotepa, nitrosoureas, and temozolomide. Anthracyclines can be selected from doxorubicin, adriamycin, daunorubicin, epirubicin, and mitoxantrone. Cytoskeletal disruptors can be selected from paclitaxel and docetaxel. Histone deacetylase inhibitors can be selected from vorinostat and romidepsin. Topoisomerase inhibitors can be selected from irinotecan, topotecan, amsacrine, etoposide, and teniposide. Kinase inhibitors can be selected from erlotinib, gefitinib, imatinib, vemurafenib, and vismodegib. Nucleoside analogs can be selected from azacitidine, azathioprine, capecitabine, cytarabine, fluorouracil, gemcitabine, hydroxyurea, mercaptopurine, methotrexate, and thioguanine. Peptide antibiotics can be selected from actinomycin and bleomycin. Platinum-based anti-cancer compounds can be selected from cisplatin, oxaloplatin, and carboplatin. Plant alkaloids can be selected from vincristine, vinblastine, vinorelbine, vindesine, podophyllotoxin, paclitaxel, and docetaxel. An exemplary 26S proteasome inhibitor is bortezomib.

In some embodiments, the diterpenoid PKC activators can be administered with one or more of the second anti-cancer therapeutic agent sequentially or concurrently, either by the same route or by different routes of administration. When administered sequentially, the time between administrations is selected to benefit, among others, the therapeutic efficacy and/or safety of the combination treatment. In some embodiments, the diterpenoid PKC activator can be administered first followed by a second therapeutic agent, or alternatively, the second therapeutic agent is administered first followed by the PKC activating diterpenoid. By way of example and not limitation, the time between administrations is about 1, about 2, about 3, about 4, about 5, about 6, or about 7 more days apart. In some embodiments, the time between administrations is about 1 week, 2 weeks, 3 weeks, or 4 weeks or more. In some embodiments, the time between administrations is about 1 month, 2 months or 3 months or more.

When administered concurrently, the diterpenoid PKC modulator can be administered separately at the same time as the second therapeutic agent, by the same or different routes, or administered in a single composition by the same route.

The amount and frequency of administration of the second anti-cancer therapeutic agent can employ standard dosages and standard administration frequencies used for the particular anti-cancer agent. See, e.g., Physicians' Desk Reference, $70^{th}$ Ed., PDR Network, 2015; incorporated by reference herein.

5.4. Formulations and Administration

The PKC activating compounds, such as the tigliane (e.g., phorbol, deoxyphorbol, etc.), ingenane and daphnane compounds can be prepared as a pharmaceutical composition or a medicament with excipients or carriers suitable for administration.

In some embodiments, the pharmaceutical compositions of the PKC activators can be formulated by standard techniques using one or more physiologically acceptable carriers or excipients. Suitable pharmaceutical carriers are described herein and in Remington: The Science and Practice of Pharmacy, $21^{st}$ Ed. (2005). The PKC activating compounds and their physiologically acceptable salts, hydrates and solvates can be formulated for administration by any suitable route, including, among others, topically, nasally, orally, parenterally, rectally or by inhalation. In some embodiments, the pharmaceutical composition can be administered by intradermal, subdermal, intravenous, intramuscular, intranasal, intracerebral, intratracheal, intraarterial, intraperitoneal, intravesical, intrapleural, intracoronary and intratumoral route. Transdermal administration is also contemplated, as are inhalation or aerosol administration. Tablets and capsules can be administered orally, rectally or vaginally.

For oral administration, a pharmaceutical composition or a medicament can take the form of, for example, a tablet or a capsule prepared by conventional means with a pharmaceutically acceptable excipient. Tablets and capsules comprising the active ingredient, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (including potato starch or sodium starch), glycolate, agar, alginic acid or its sodium salt, or effervescent mixtures; (e) wetting agents, e.g., sodium lauryl sulphate; and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for reconstitution with water or other suitable vehicle before use. Such liquid preparations can be prepared by conventional means with pharmaceutically acceptable additives, for example, suspending agents, e.g., sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds of the present disclosure can be formulated for parenteral administration by injection, for example by bolus injection or continuous infusion. Formulations for injection can be presented in unit dosage form, for example, in ampoules or in multi-dose containers, with an added preservative. Injectable compositions can be aqueous isotonic solutions or suspensions. In some embodiments for parenteral administration, the compounds can be prepared with a surfactant, such as Cremaphor, or lipophilic solvents, such as triglycerides or liposomes. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound of the present disclosure with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

5.5. Therapeutically Effective Amount and Dosing

In some embodiments, a pharmaceutical composition or medicament is administered to a subject, preferably a human, at a therapeutically effective dose to prevent, treat, or control a condition or disease as described herein. The pharmaceutical composition or medicament is administered to a subject in an amount sufficient to elicit an effective therapeutic response in the subject. An effective therapeutic response is a response that at least partially arrests or slows the symptoms or complications of the condition or disease. An amount adequate to accomplish this is defined as "therapeutically effective dose."

The dosage of active compounds administered is dependent on the species of warm-blooded animal (mammal), the body weight, age, condition being treated, the severity of the condition being treated, surface area of the area to be treated, the form of administration, and route of administration. The size of the dose also will be determined by the existence, nature, and extent of any adverse effects that accompany the administration of a particular small molecule compound in a particular subject. A unit dosage for oral administration to a mammal of about 50 to 70 kg may contain between about 0.1 mg and 500 mg of the active ingredient. Typically, a dosage of the active compounds of the present invention, is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies and repetition rates.

In some embodiments, a pharmaceutical composition or medicament comprising compounds of the present disclosure is administered in a daily dose in the range from about 0.001 mg per kg of subject weight (0.001 mg/kg) to about 1 g/kg. In some embodiments, the daily dose is a dose in the range of about 0.1 mg/kg to about 500 mg/kg. In some embodiments, the daily dose is a dose in the range of about 1 mg/kg to about 500 mg/kg. In some embodiments, the daily dose is about 2 mg/kg to about 250 mg/kg. In some embodiments, the daily dose is about 0.001 mg/kg, 0.002 mg/kg, 0.01 mg/kg, 0.05 mg/kg, 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/kg, 10 mg/kg, 20 mg/kg, 40 mg/kg, 50 mg/kg, 100 mg/kg, 200 mg/kg or 500 mg/kg. The daily dose can be administered once per day or divided into subdoses and administered in multiple doses, e.g., twice, three times, or four times per day. However, as will be appreciated by a skilled artisan, the compounds may be administered in different amounts and at different times.

In some embodiments, where a second therapeutic agent is used, either in a composition with the diterpenoid PKC activating compound, or separately from the PKC activating compound, the second therapeutic agent is administered in a daily dose that corresponds to the therapeutically effective dose for the particular compound. In some embodiments, the second therapeutic agent is administered in a daily dose in the range from about 0.001 mg per kg of subject weight (0.001 mg/kg) to about 1 g/kg. In some embodiments, the daily dose is a dose in the range of about 0.01 mg/kg to about 1 g/kg. In some embodiments, the daily dose is a dose in the range of about 0.1 mg/kg to about 500 mg/kg. In some embodiments, the daily dose is a dose in the range of about 1 mg/kg to about 500 mg/kg. In some embodiments, the daily dose is about 2 mg/kg to about 250 mg/kg. In some embodiments, the daily dose is about 0.001 mg/kg, 0.002 mg/kg, 0.005 mg/kg, 0.01 mg/kg, 0.05 mg/kg, 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/kg, 10 mg/kg, 20 mg/kg, 40 mg/kg, 50 mg/kg, 100 mg/kg, 200 mg/kg or 500 mg/kg. The daily dose can be administered once per day or divided into subdoses and administered in multiple doses, e.g., twice, three times, or four times per day. In some embodiments, the doses for approved drugs are available in the Physician's Desk Reference, $70^{th}$ Ed. 2016, incorporated herein by reference.

To achieve the desired therapeutic effect, compounds may be administered for multiple days at the therapeutically effective daily dose. Thus, therapeutically effective administration of compounds to treat a condition or disease described herein in a subject requires periodic (e.g., daily) administration that continues for a period ranging from three days to two weeks or longer. Typically, compounds can be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the compounds in the subject. For example, the compounds can be administer every other day, every third day, or, if higher dose ranges are employed and tolerated by the subject, once a week. A preferred dosing schedule, for example, is administering daily for a week, one week off and repeating this cycle dosing schedule for 3-4 cycles.

Optimum dosages, toxicity, and therapeutic efficacy of such compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from, for example, cell culture assays and animal studies can be used to formulate a dosage range for use in humans. In some embodiments, the dosage of such small molecule compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

6. EXAMPLES

Example 1: Proliferation Assays

PKC activator compounds were tested in a panel of K-Ras mutant pancreatic, lung, and colon cancer cell lines as well as a few leukemia cell lines with either mutant K-Ras or N-Ras. The cell lines, tumor types, and their K- and N-Ras mutation status are listed in Table 1.

TABLE 1

Cancer Cell Lines and Ras Status

| Cell Line Name | Tumor Type | Ras Mutation |
|---|---|---|
| CaPan-1 | Pancreatic, adenocarcinoma, liver metastasis | K-ras: G12V |
| MiaPaCa-2 | Pancreatic, carcinoma | K-ras: G12C |
| KP-4 | Pancreatic carcinoma | K-ras: G12C |
| Panc2.03 | Pancreatic, adenocarcinoma | K-ras: G12D |
| Panc2.13 | Pancreatic, adenocarcinoma | K-ras: Q61H |
| AsPC1 | Pancreatic, ascites | K-ras: G12D |
| A549 | Lung, adenocarcinoma | K-ras: G12S |
| H358 | Lung, carcinoma | K-ras: G12C |
| H441 | Lung, papillary adenocarcinoma | K-ras: G12V |
| H727 | Lung, bronchial carcinoids | K-ras: G12V |
| AGS | Gastric, adenocarcinoma | K-ras: G12D |
| HCT116 | Colon, carcinoma | K-ras: G13D |
| LS180 | Colon, adenocarcinoma | K-ras: G12D |
| SW620 | Colon, adenocarcinoma, lymph node mets | K-ras: G12V |
| CCRF-CEM | Leukemia, acute lymphoblastic leukemia | K-ras: G12D |
| HL-60 | Leukemia, acute promyelocytic leukemia | N-ras: Q61L |
| THP-1 | Leukemia, acute monocytic leukemia | N-ras: G12D |

Other cancer cell lines with either wild-type or mutant K-Ras were also examined with various PKC activators. These cell lines, tumor types, and their K-Ras mutation status are listed in Table 1B.

TABLE 1B

Cancer Cell Lines and K-ras Status

| Cell Line Name | Tumor Type | Ras Status |
|---|---|---|
| BxPC-3 | Pancreatic, adenocarcinoma | WT |
| SW900 | Lung, squamous cell carcinoma | K-ras: G12V |
| H838 | Lung, adenocarcinoma | WT |
| H1915 | Lung, carcinoma | WT |
| HT29 | Colon, adenocarcinoma | WT |
| Colo205 | Colon, adenocarcinoma, ascites | WT |
| RPMI8226 | Blood, plasmacytoma, myeloma | K-ras: G12A |

The PKC activator compounds, including prostratin, prostratin analogs and prodrugs, ingenol-3-angelate, TPA (PMA), and Bryostatin-1, tested on the cell lines are listed in Table 2.

TABLE 2

| Compound | Structure | Compound | |
|---|---|---|---|
| K101A, or K-101 Prostratin | 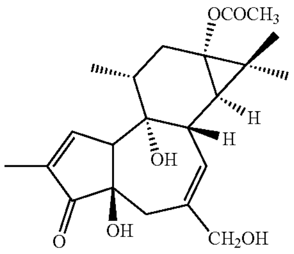 | K101B or K-101B succinate prodrug R = prodrug moiety sodium salt | 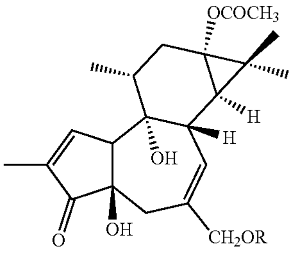 R = $COCH_2CH_2COOH$ |

TABLE 2-continued

| Compound | Structure | Compound | |
|---|---|---|---|
| K101C or K-101C R = substituent | 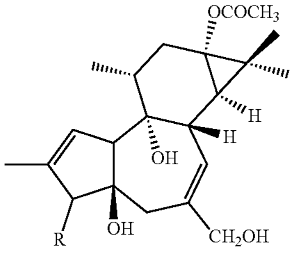 R = OH | K101D or K-101D | 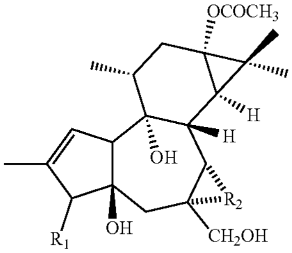 $R_1$ = OH $R_2$ = O |
| K101E, F or K-101E, F R1, R2 = substituents | 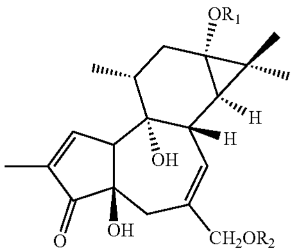 E: R1 = Ac, $R_2$ = Ac F: $R_1$ = H, $R_2$ = H | K101I or K-101I (amino acid prodrug) R = prodrug moiety, sodium salt | 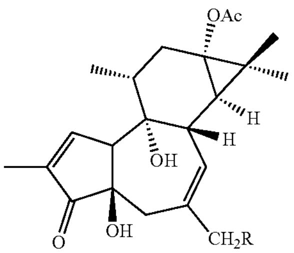 R = $OCOCH_2CH(NH_2)COO^-Na^+$ |
| K101 or K-102 Ingenol-3-angelate | 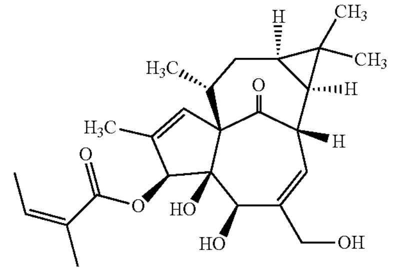 [SMILES: C/C=C(/C)C(=O)O[C@H]1C(C)=C[C@]23C(=O)[C@@H](C=C(CO)[C@@H](O)[C@]12O)[C@H]1[C@@H](C[C@H]3C)C1(C)C] | K103 or K-103 12-O-tetra-decanoylphorbol-13-acetate (TPA) | 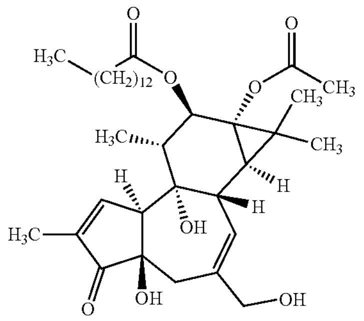 |
| K104 or K-104 Bryostatin 1 | 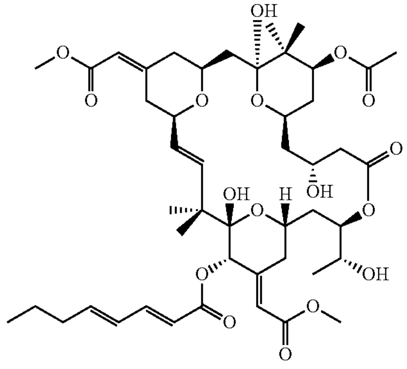 | | |

Briefly, cells at a density of 1,000-10,000 cells/well were seeded in 96-well plates and incubated at 37'C for 24 hours. A series of 9 different concentrations of compound stocks (500×) were created by 3-fold serial dilution in DMSO. These compounds were further diluted in culture media and then added to cells so that the final DMSO concentration was 0.2%. After 96 hours of incubation, 50 μL of CellTiter Glo reagent (Promega) was added to each well and luminescence was measured after 10 minutes using EnVision (PerkinElmer). Paclitaxel was used as the reference compound and the dose range was 0.08 nM-0.5 μM. The dose range for most compounds was 4.6 nM-30 μM. The dose ranges for some compounds were adjusted downward to 0.46 nM-3 μM or 0.08 nM-0.5 μM or 0.03 nM-0.2 μM. Luminescence from cells treated with 0.02% DMSO alone was set as Max and % of inhibition was calculated as follows: Inhibition %=(Max-Sample value)/Max*100. Data was analyzed using XL-fit software (ID Business Solutions Ltd.) and EC50, relative EC50, and % of top inhibition were calculated. The results are shown in Tables 3-6 for pancreatic cancer, lung cancer, colon/gastric cancer, and leukemia cell lines. Table 5 shows absolute EC50, relative EC50, and % of top inhibition of testing agents in blocking cell proliferation in colon (5A) and gastric (5B) cancer cell lines harboring various K-Ras mutations. Table 6 shows absolute EC50, relative EC50, and % of top inhibition of testing agents in blocking cell proliferation in leukemia cell lines harboring N-Ras or K-Ras mutations.

The screening results from 17 cell lines of 5 different cancer types indicated that prostratin and prostratin analogs showed good inhibitory activities in pancreatic and lung cancer cell lines harboring K-Ras mutations. Cell lines with different types of K-Ras mutations, including G12V, G12D, G12C, G12S, and Q61H, were sensitive to prostratin and analogs. Unexpectedly, these compounds did not inhibit proliferation of the colon cancer cell lines harboring K-Ras mutations at the highest concentration tested. The types of K-Ras mutations in given cell lines did not seem to be the factors determining the sensitivity. Interestingly, all three leukemia cell lines tested were sensitive to prostratin and analogs, regardless of their K-Ras mutation status. Nevertheless, two of the sensitive leukemia cell lines have N-Ras mutations. Such sensitivity can be verified by the methods described in this application.

In addition, some PKC activator compounds, such as ingenol-3-angelate and PMA showed similar activity patterns as the prostratin and analogs whereas other PKC activator compounds such as bryostatin-1 showed different activity patterns. In general, the potency of these compounds to inhibit proliferation correlated with the known potency of PKC activation. For example, PMA and ingenol-3-angelate are more potent PKC activators than prostratin and they are also more potent in proliferation inhibition than prostratin. However, there are exceptions to this. For example, bryostatin 1 is more potent PKC activator but it is less potent in proliferation inhibition than prostratin. Furthermore, a prostratin prodrug was active in this assay even though it was less potent than its parent compound prostratin. Since the prodrug is not expected to bind PKC, it is possible that tumor cells have the ability to convert the prostratin prodrug to the parent compound.

Other cancer cell lines having wild-type K-ras status and K-ras mutation at G12 were also screened using the PKC activator compounds. As in the studies with the 17 cancer cell lines discussed above, paclitaxel was used as the reference compound, and its dose range was 0.08 nM-0.5 μM. K-104 was tested in a range of 0.03 nM-0.2 μM. The dose range selected for most compounds (e.g., K-101A, K-101C, K-101D, K-101E, K-101I, K102, and K-103) was 4.6 nM-30 μM. The dose ranges were adjusted downward to 0.46 nM-3 μM for K-102 and 0.08 nM-0.5 μM for K-103 for some cell lines. The results of the screening of cancer cells lines with wild-type K-ras status and K-ras mutations at the G12 positions are presented in Table 7. Consistent with the observation made in the other cells lines above, prostratin, prostratin analogs, ingenol-3-angelate, and PMA showed similar activity patterns, which in general correlated with their known PKC activation potencies. However, bryostatin 1 showed different activity patterns and had much lower activity in cancer cell lines.

In Table 7, the % of top inhibition appears to be a good indication whether a cell line is sensitive or refractory to inhibition by these compounds. Data from all 24 cell lines against four different compounds (e.g., K-101A, K-101E, K-102 and K-103) were graphed together and the data is shown on FIG. 8.

Figure 7:
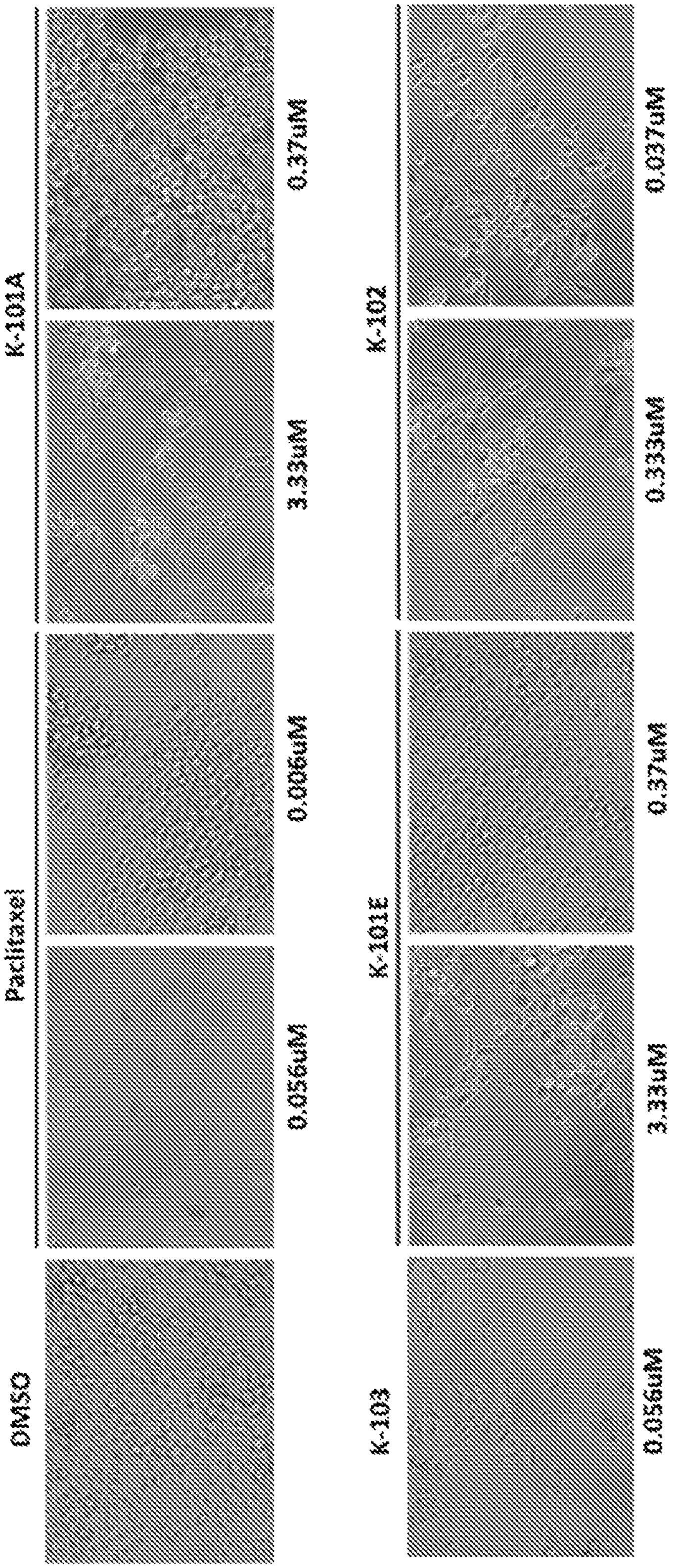
FIG. 7 shows photographs of morphology change upon treatment with compounds prostratin (K-101A), K-101E, ingenol-3-angelate (K102), and PMA (K103) in Colo205 cells (colon carcinoma).
Figure 8A:
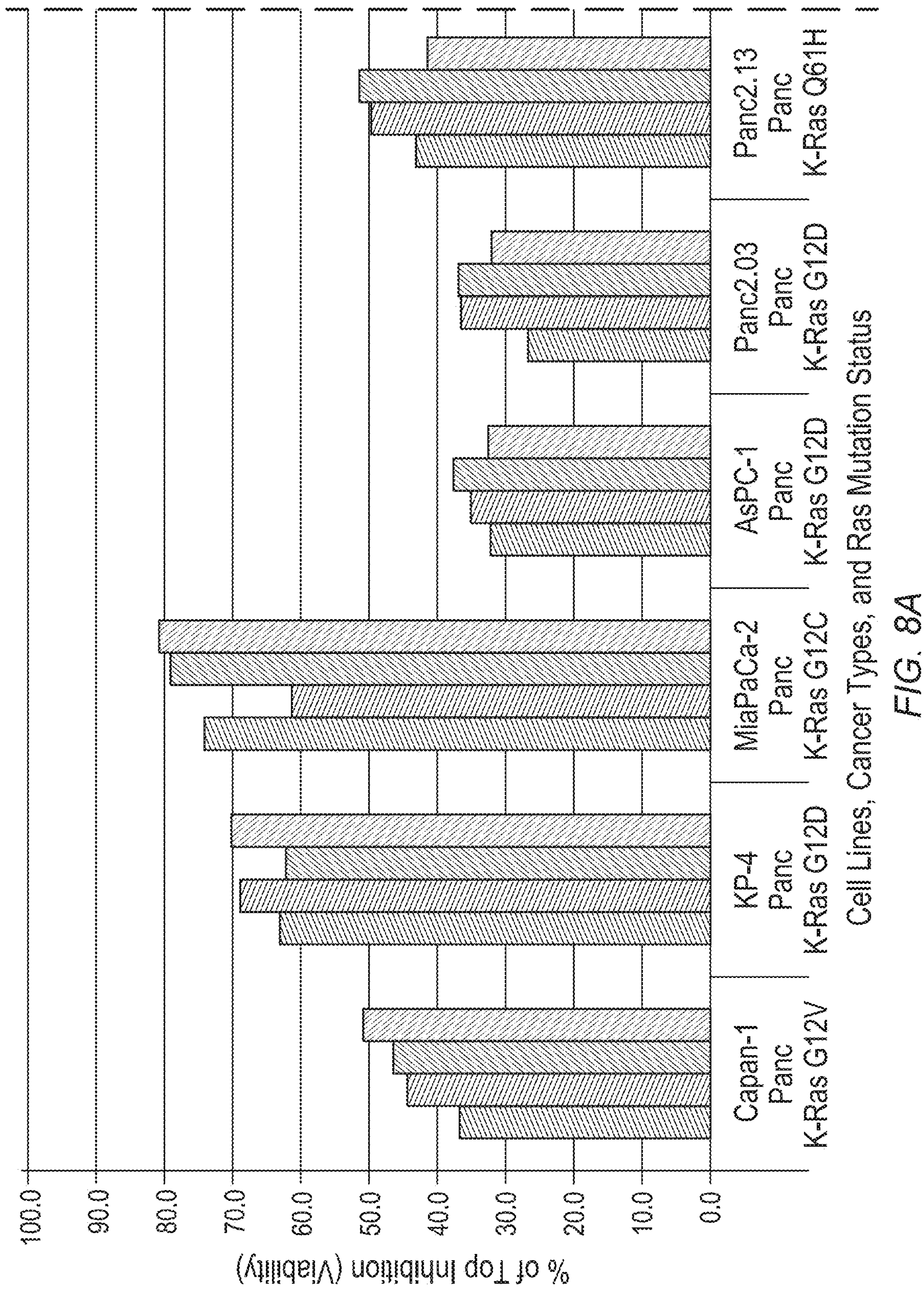
FIG. 8A, FIG. 8B, FIG. 8C and FIG. 8D show a summary of viability data (% Top inhibition) for compounds prostratin (K101A), K101E, ingenol-3-angelate (K102), and PMA (K103) in 24 different cell lines.
Figure 8B:
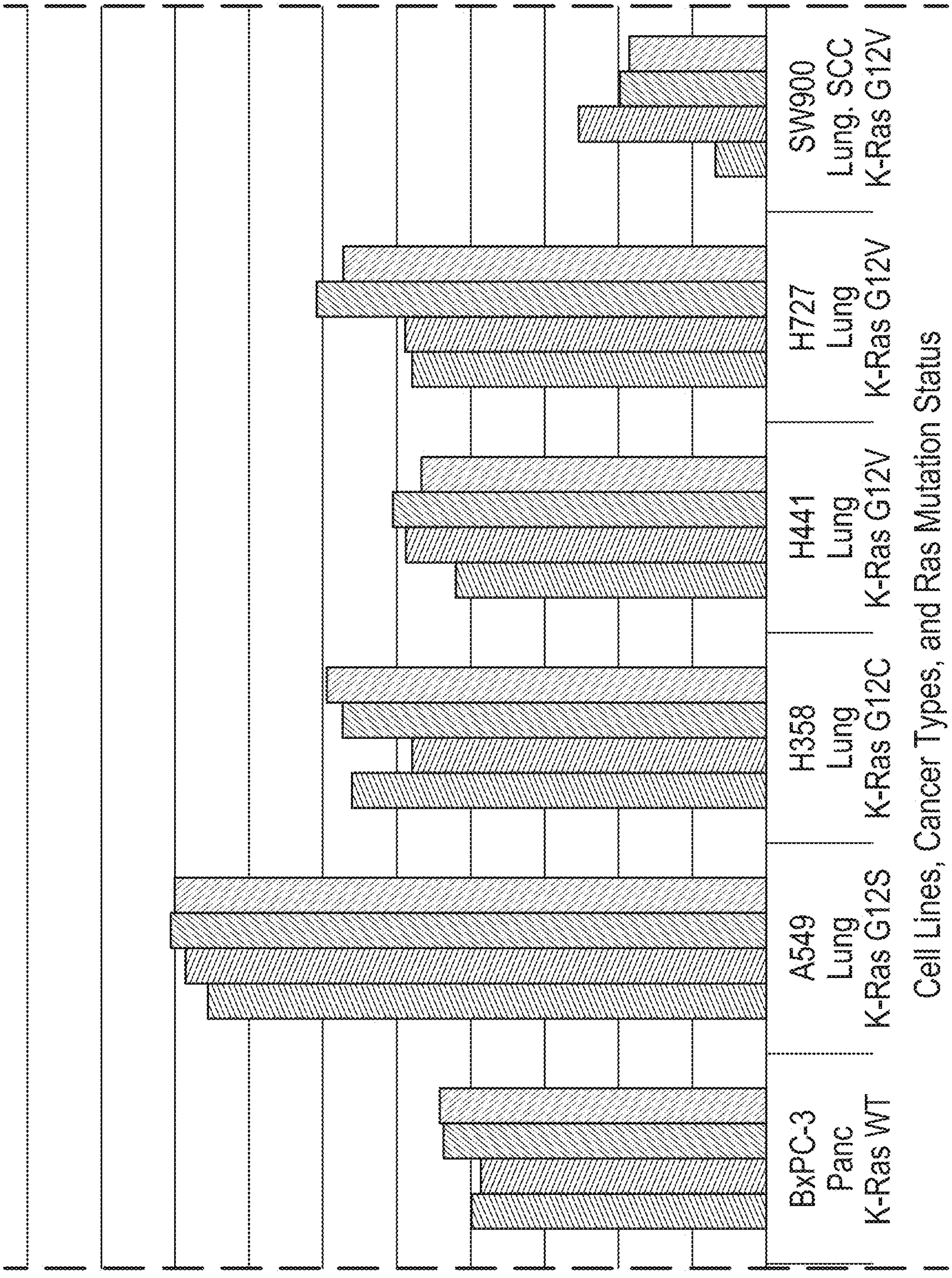
Figure 8C:
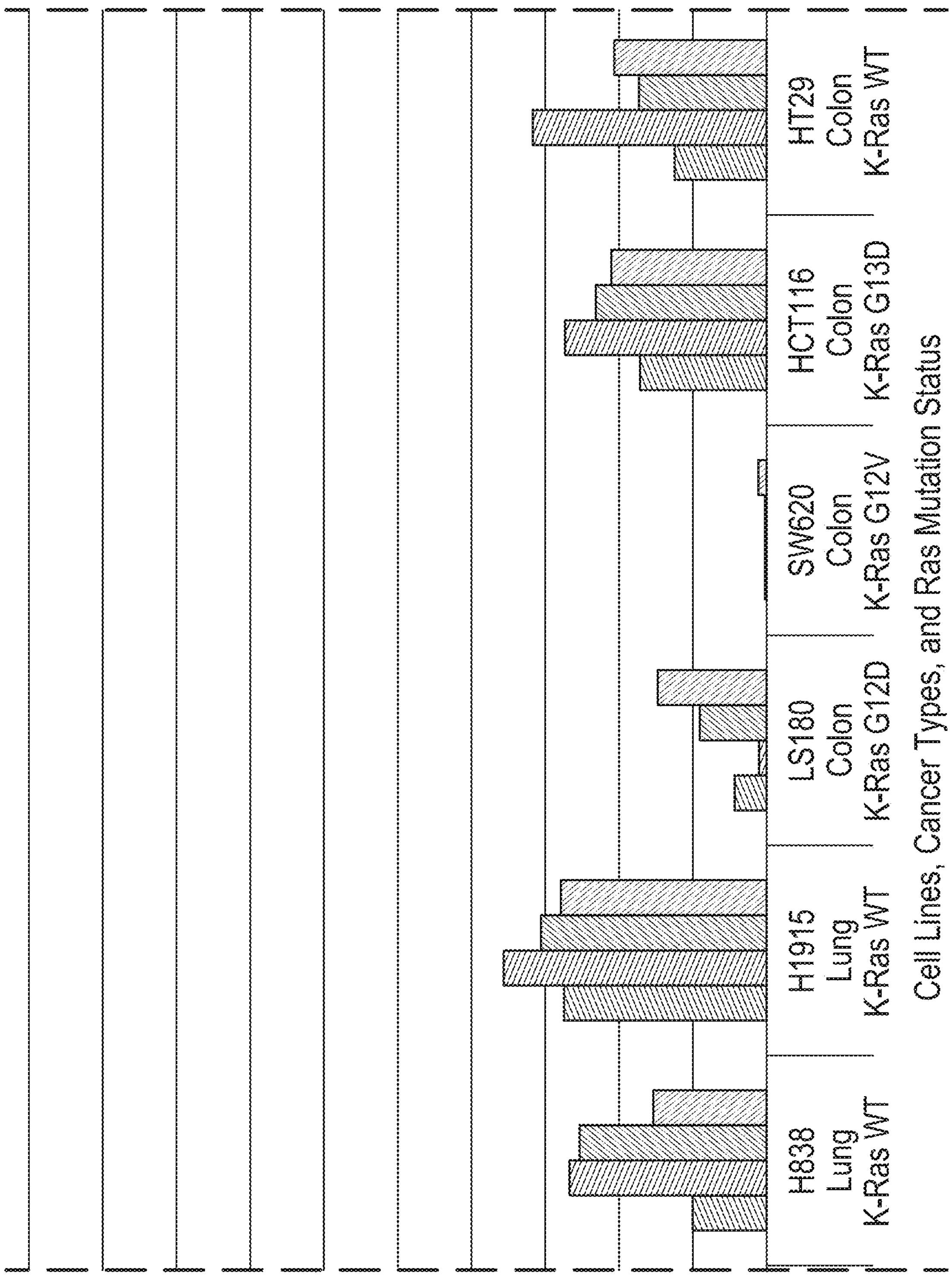
Figure 8D:
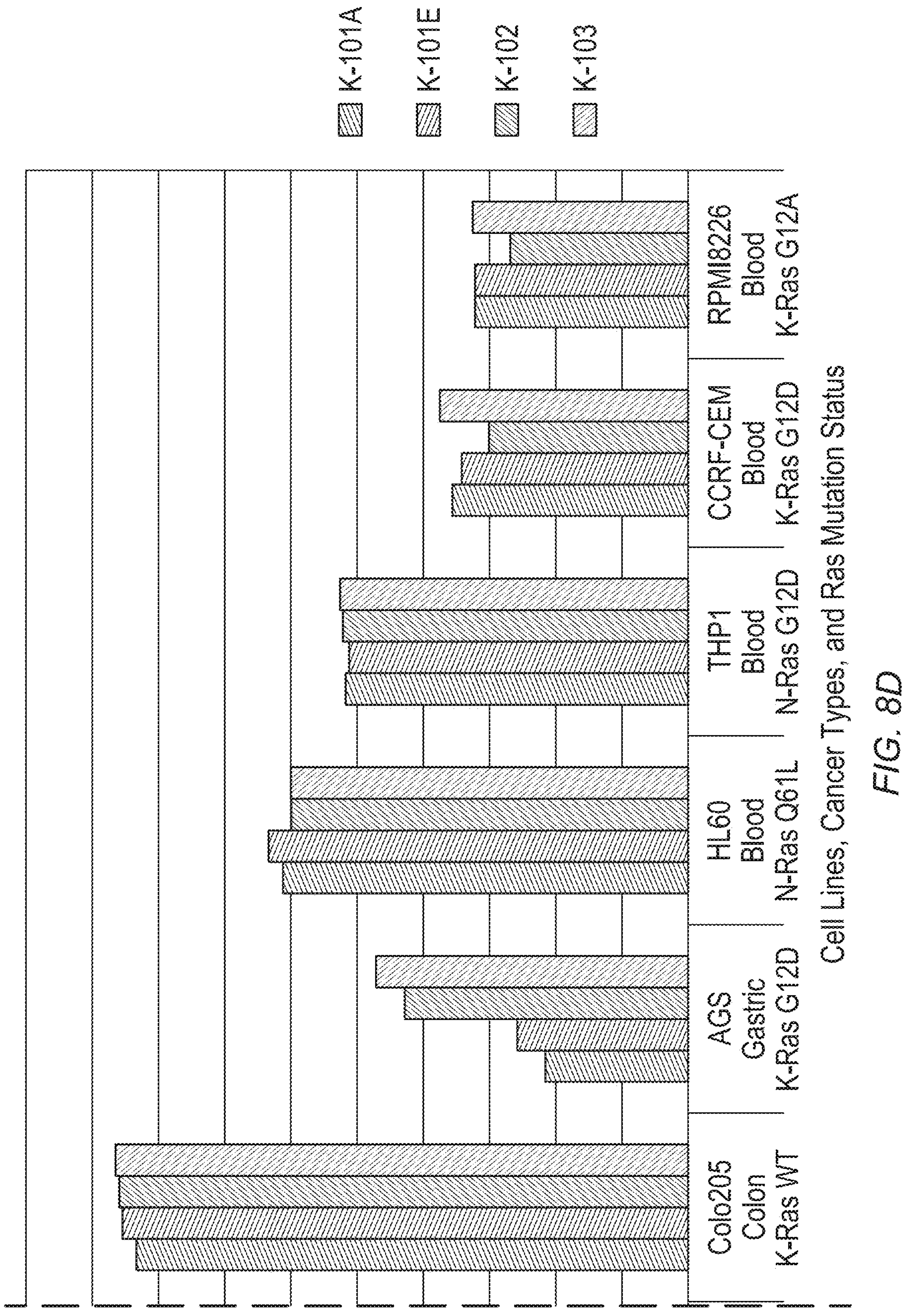

The data indicate that a number of pancreatic, lung, and leukemia cell lines tested are sensitive to phorbol family of PKC activators (e.g. prostratin and analogs, prostratin prodrugs, ingenol-3-angelate, and PMA, etc.). In general, it appears that the cancer cell lines harboring mutant K-Ras are more sensitive than those harboring wild-type K-Ras. However, some cell lines with wild-type K-Ras are sensitive to inhibition by the PKC activator compounds to some extent (e.g., BxPC-3 and Colo205). In addition, as noted above, colon cancer cell lines (4 out of 5 tested) regardless of K-Ras mutation status appear to be somewhat resistant to these compounds. The exception was colon cancer cell line Colo205, which has wild-type K-Ras and was very sensitive to inhibition by these compounds. Interestingly, Colo205 cells changed their morphology dramatically, from round to more extended and flat morphology, upon treatment of these compounds (FIG. 7).

Results from these experiments allow identification of most sensitive cell lines to the inhibition of the prostratin analogs and selected other PKC activators. In addition, such screen also identifies potent analogs from different classes of PKC activators for potential treatment of cancers with K-Ras mutations and leukemias.

Tables 3A and 3B: Absolute EC50, relative EC50, and % of top inhibition of testing agents in blocking cell proliferation in pancreatic cancer cell lines harboring various K-Ras mutations.

TABLE 3A

| | Capan-1 | | | KP-4 | | | MiaPaCa-2 | | |
|---|---|---|---|---|---|---|---|---|---|
| Compound ID | Ab EC50 (μM) | Re EC50 (μM) | Top inhibition % | Ab EC50 (μM) | Re EC50 (μM) | Top inhibition % | Ab EC50 (μM) | Re EC50 (μM) | Top inhibition % |
| Paclitaxel | 0.011 | 0.0072 | 73.5 | 0.0019 | 0.0018 | 96.2 | 0.0034 | 0.0033 | 94.6 |
| K-101A | >30 | 0.31 | 37.1 | 0.40 | 0.19 | 63.3 | 0.30 | 0.18 | 74.4 |
| K-101C | >30 | 5.40 | 35.7 | 11 | 6.77 | 70.4 | >30 | 4.37 | 40.1 |
| K-101D | >30 | 8.66 | 22.3 | >30 | 5.47 | 47.9 | >30 | — | 18.6 |
| K-101E | >30 | 0.83 | 44.6 | 1.28 | 0.68 | 69.1 | 1.88 | 0.86 | 61.4 |
| K-102 | >30 | 0.013 | 46.9 | 0.015 | 0.015 | 62.2 | 0.013 | 0.0090 | 79.3 |
| K-103 | 0.014 | — | 51.0 | <0.0046 | — | 70.3 | 0.00028 | 0.00024 | 81.1 |

TABLE 3B

| Compound ID | AsPC-1 Ab EC50 (μM) | AsPC-1 Re EC50 (μM) | AsPC-1 Top inhibition % | Panc2.03 Ab EC50 (μM) | Panc2.03 Re EC50 (μM) | Panc2.03 Top inhibition % | Panc2.13 Ab EC50 (μM) | Panc2.13 Re EC50 (μM) | Panc2.13 Top inhibition % |
|---|---|---|---|---|---|---|---|---|---|
| Paclitaxel | 0.010 | 0.0038 | 60.9 | 0.0033 | 0.0018 | 64.6 | 0.065 | 0.0027 | 53.2 |
| K-101A | >30 | 0.27 | 32.4 | >30 | 0.12 | 27.0 | >30 | 0.017 | 43.4 |
| K-101I | >30 | 6.64 | 25.0 | >30 | 6.04 | 26.3 | >30 | 0.16 | 48.3 |
| K-104 | >0.2 | — | 4.2 | >0.2 | — | 0.0 | >0.2 | — | 32.2 |
| K-101E | >30 | 2.78 | 35.2 | >30 | 1.92 | 36.5 | >30 | 0.044 | 49.8 |
| K-102 | >3 | 0.014 | 37.8 | >3 | 0.0033 | 36.9 | 0.0039 | 0.0012 | 51.7 |
| K-103 | >0.5 | 0.0013 | 32.7 | >0.5 | 0.00090 | 32.2 | >0.5 | 0.00066 | 41.9 |

TABLE 4

Absolute EC50, relative EC50, and % of top inhibition of testing agents in blocking cell proliferation in lung cancer cell lines harboring various K-Ras mutations.

| Compound ID | A549 Ab EC50 (μM) | A549 Re EC50 (μM) | A549 Top inhibition % | H358 Ab EC50 (μM) | H358 Re EC50 (μM) | H358 Top inhibition % | H441 Ab EC50 (μM) | H441 Re EC50 (μM) | H441 Top inhibition % | H727 Ab EC50 (μM) | H727 Re EC50 (μM) | H727 Top inhibition % |
|---|---|---|---|---|---|---|---|---|---|---|---|---|
| Paclitaxel | 0.0026 | 0.0023 | 86.0 | 0.0024 | 0.0018 | 89.2 | 0.0358 | 0.0035 | 51.9 | >0.5 | 0.0023 | 49.0 |
| K-101A | 0.49 | 0.27 | 76.0 | 4.90 | 0.16 | 56.4 | >30 | 0.32 | 42.1 | >30 | 0.19 | 48.3 |
| K-101C | 13 | 6.68 | 70.3 | >30 | 4.98 | 44.0 | >30 | 7.44 | 37.0 | >30 | 3.61 | 42.8 |
| K-101D | >30 | 7.72 | 44.4 | >30 | 11 | 23.0 | >30 | — | 11.6 | >30 | 8.37 | 31.8 |
| K-101E | 2.64 | 1.56 | 78.7 | >30 | 1.25 | 47.9 | >30 | 2.61 | 49.1 | >30 | 0.62 | 49.1 |
| K-102 | 0.017 | 0.017 | 80.8 | 0.097 | 0.0045 | 57.5 | 1.01 | 0.0024 | 50.6 | 0.022 | 0.0043 | 61.0 |
| K-103 | <0.0046 | — | 80.6 | 0.0022 | 0.0004 | 59.6 | >0.5 | 0.00075 | 46.7 | 0.0022 | 0.00037 | 57.4 |

Table 5A and 5B. Absolute EC50, relative EC50, and % of top inhibition of testing agents in blocking cell proliferation in colon (a) and gastric (b) cancer cell lines harboring various K-Ras mutations.

TABLE 5A

| Compound ID | LS180 Ab EC50 (μm) | LS180 Re EC50 (μM) | LS180 Top inhibition % | SW620 Ab EC50 (μM) | SW620 Re EC50 (μM) | SW620 Top inhibition % | HCT116 Ab EC50 (μM) | HCT116 Re EC50 (μM) | HCT116 Top inhibition % |
|---|---|---|---|---|---|---|---|---|---|
| Paclitaxel | 0.014 | 0.0088 | 67.1 | 0.012 | 0.0094 | 92.1 | 0.0022 | 0.0021 | 94.8 |
| K-101A | >30 | — | 4.4 | >30 | — | 0.0 | >30 | — | 17.4 |
| K-101C | >30 | — | 6.8 | >30 | — | 0.0 | >30 | — | 12.2 |
| K-101D | >30 | — | 8.2 | >30 | — | 0.0 | >30 | — | 3.0 |
| K-101E | >30 | — | 1.3 | >30 | — | 0.0 | >30 | 6.64 | 27.4 |
| K-102 | >30 | — | 9.3 | >30 | — | 0.0 | >3 | 0.021 | 23.2 |
| K-103 | >10 | — | 14.7 | >10 | — | 1.2 | >0.5 | 0.0012 | 21.4 |

TABLE 5B

| Compound ID | AGS Ab EC50 (μM) | AGS Re EC50 (μM) | AGS Top inhibition % |
|---|---|---|---|
| Paclitaxel | 0.0047 | 0.0039 | 87.7 |
| K-101A | >30 | 0.49 | 21.7 |
| K-101C | >30 | 11 | 25.3 |
| K-101D | >30 | — | 13.5 |
| K-101E | >30 | 4.38 | 25.9 |

TABLE 5B-continued

| Compound ID | AGS Ab EC50 (μM) | AGS Re EC50 (μM) | AGS Top inhibition % |
|---|---|---|---|
| K-102 | >3 | 0.012 | 42.9 |
| K-103 | >0.5 | 0.0011 | 47.2 |

Table 6A and 6B. Absolute EC50, relative EC50, and % of top inhibition of testing agents in blocking cell proliferation in leukemia cell lines harboring N-Ras or K-Ras mutations.

TABLE 6A

| | HL60 | | | THP1 | | |
|---|---|---|---|---|---|---|
| Compound ID | Ab EC50 (μM) | Re EC50 (μM) | Top inhibition % | Ab EC50 (μM) | Re EC50 (μM) | Top inhibition % |
| Paclitaxel | 0.0052 | 0.0052 | 98.7 | 0.0083 | 0.0076 | 91.2 |
| K-101A | 0.47 | 0.40 | 61.3 | 0.87 | 0.30 | 51.8 |
| K-101C | 17 | 13 | 63.9 | 16 | 8.11 | 51.4 |
| K-101D | >30 | — | 14.4 | >30 | 14 | 33.6 |
| K-101E | 3.05 | 1.92 | 63.4 | 3.60 | 1.02 | 51.6 |
| K-102 | 0.015 | 0.014 | 60.1 | 0.015 | 0.012 | 52.4 |
| K-103 | <0.0046 | — | 60.0 | <0.0046 | — | 52.9 |

TABLE 6B

| | CCRF-CEM | | |
|---|---|---|---|
| Compound ID | Ab EC50 (μM) | Re EC50 (μM) | Top inhibition % |
| Paclitaxel | 0.0040 | 0.0039 | 97.8 |
| K-101A | >30 | 0.051 | 35.9 |
| K-101I | >30 | 1.51 | 37.4 |
| K-104 | >0.2 | — | 6.0 |
| K-101E | >30 | 0.27 | 34.3 |
| K-102 | >3 | 0.0009 | 30.3 |
| K-103 | >0.5 | 0.00024 | 37.7 |

TABLE 7

% of top inhibition of testing agents in blocking cell proliferation in cancer cell lines with wild-type K-ras status and K-Ras mutations at G12.

| | Top Inhibition % | | | | | | |
|---|---|---|---|---|---|---|---|
| Compound ID | BxPC-3 | SW900 | H838 | H1915 | HT29 | Colo205 | RPMI8226 |
| Paclitaxel | 91.93% | 81.0% | 96.5% | 80.6% | 93.8% | 97.4% | 98.98% |
| K-101A | 40.11% | 7.1% | 10.1% | 27.7% | 12.8% | 83.6% | 32.39% |
| K-101C | 36.67% | 10.9% | 20.2% | 28.9% | 4.8% | 73.2% | 22.72% |
| K-101D | 37.49% | not converged | 27.7% | 28.6% | 10.0% | 42.3% | not converged |
| K-101E | 38.87% | 25.4% | 26.8% | 35.6% | 31.7% | 85.8% | 32.25% |
| K-102 | 44.13% | 20.1% | 25.5% | 30.8% | 17.3% | 86.0% | 27.06% |
| K-103 | 44.46% | 18.7% | 15.5% | 27.9% | 20.9% | 86.8% | 32.75% |
| K-104 | 3.99% | not converged | 20.0% | 25.1% | 4.3% | 49.4% | not converged |
| K-101I | 38.12% | 10.8% | 29.3% | 16.4% | 11.8% | 82.2% | 17.60% |

Example 2: Analysis of Expression of PKC Signaling Pathway Elements

Figure 1:
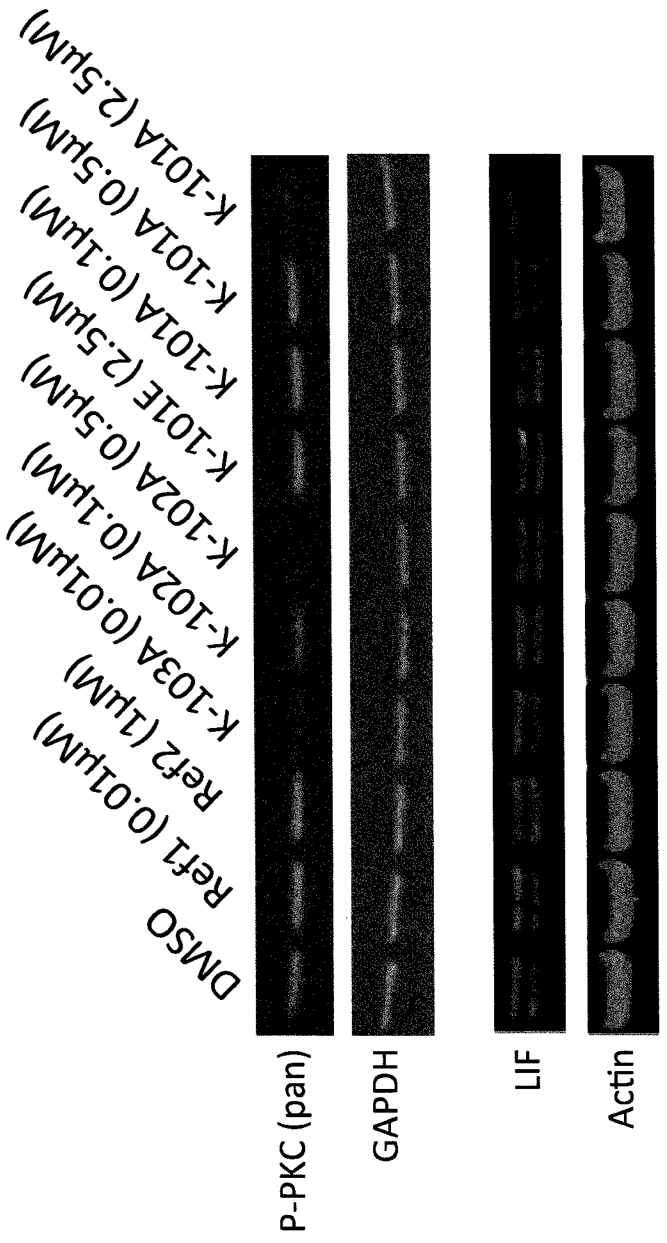
FIG. 1 shows Western blot analysis of phospho-PKC (pan) and leukemia inhibitory factor (LIF) in lung cancer cell line A549 treated with different PKC activators for 48 hours.
Figure 2A:
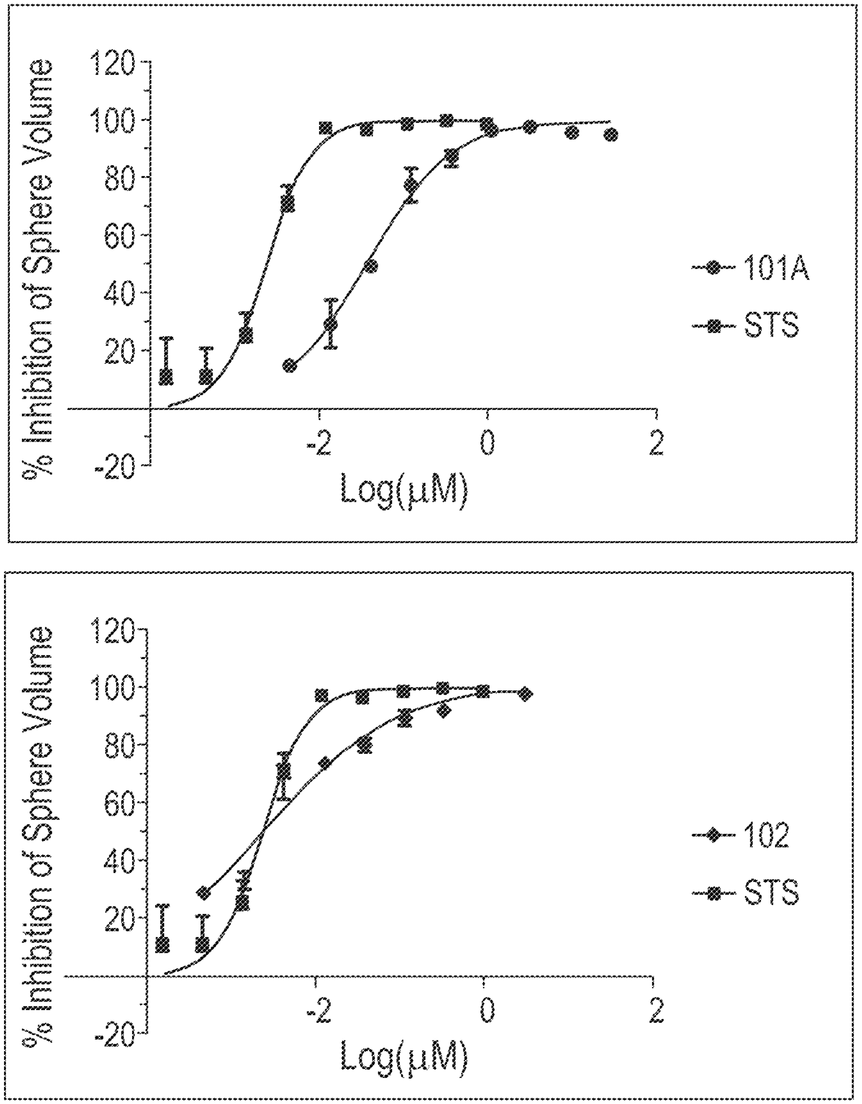
FIG. 2A and FIG. 2B show soft agar assays of PKC activators in A549 lung cancer cells. STS and staurosporin used as reference compounds.
Figure 2B:
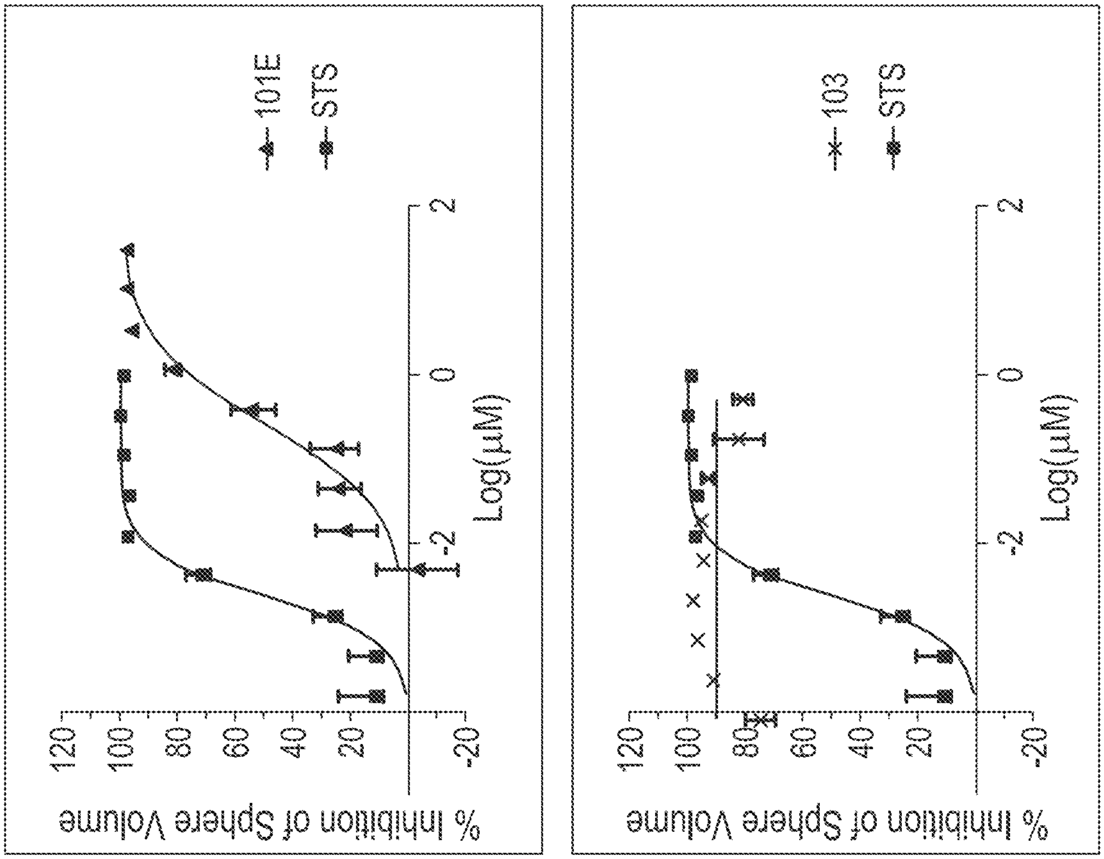
Figure 3:
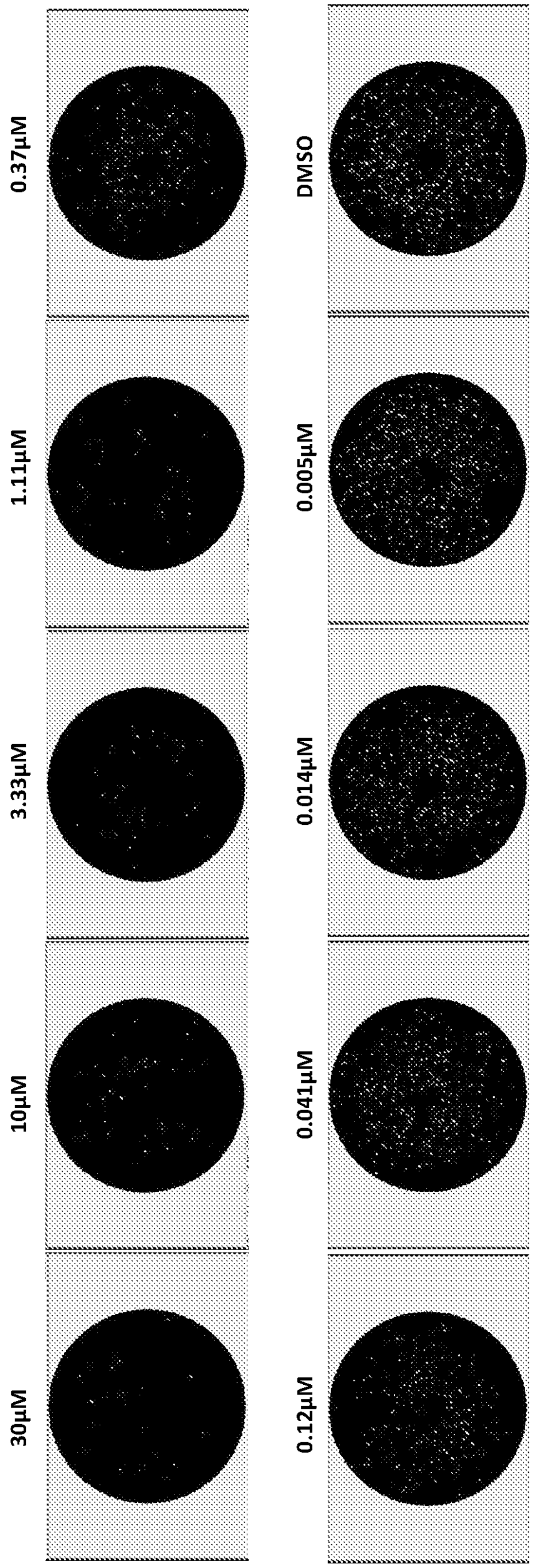
FIG. 3 shows soft agar assay of prostratin (K101A, also coded as K-101A) in A549 lung cancer cells.
Figure 4:
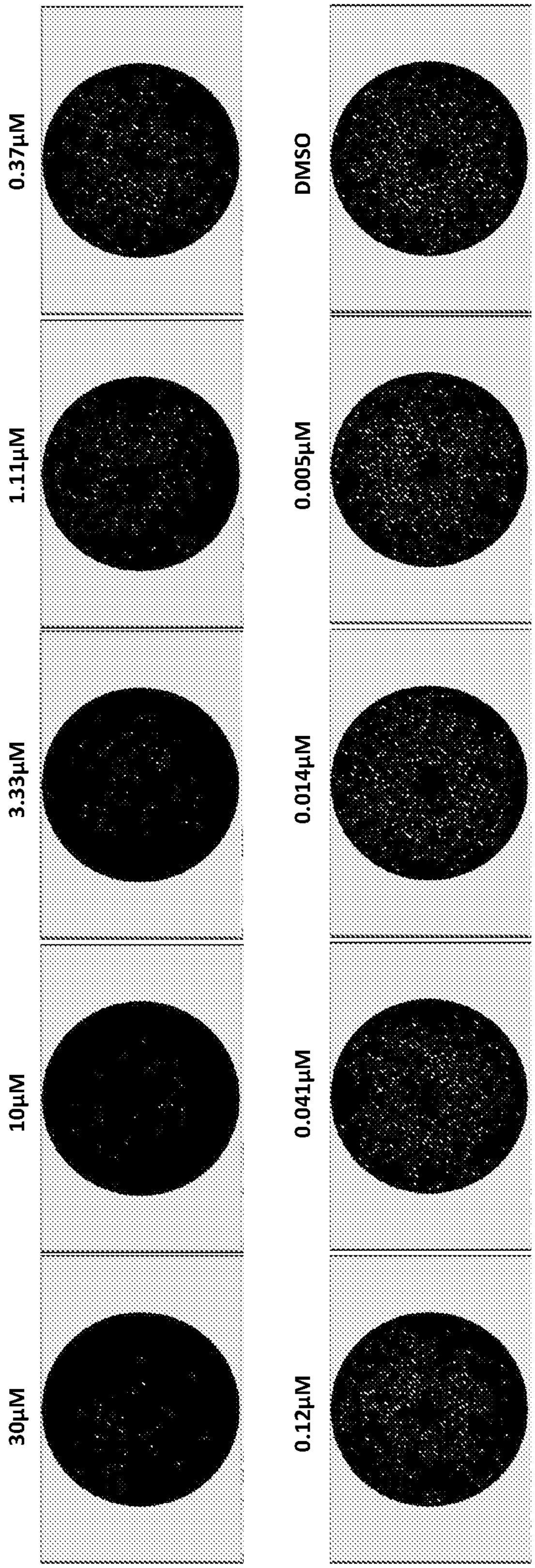
FIG. 4 shows soft agar assay of PKC activator K-101E in A549 lung cancer cells.
Figure 5:
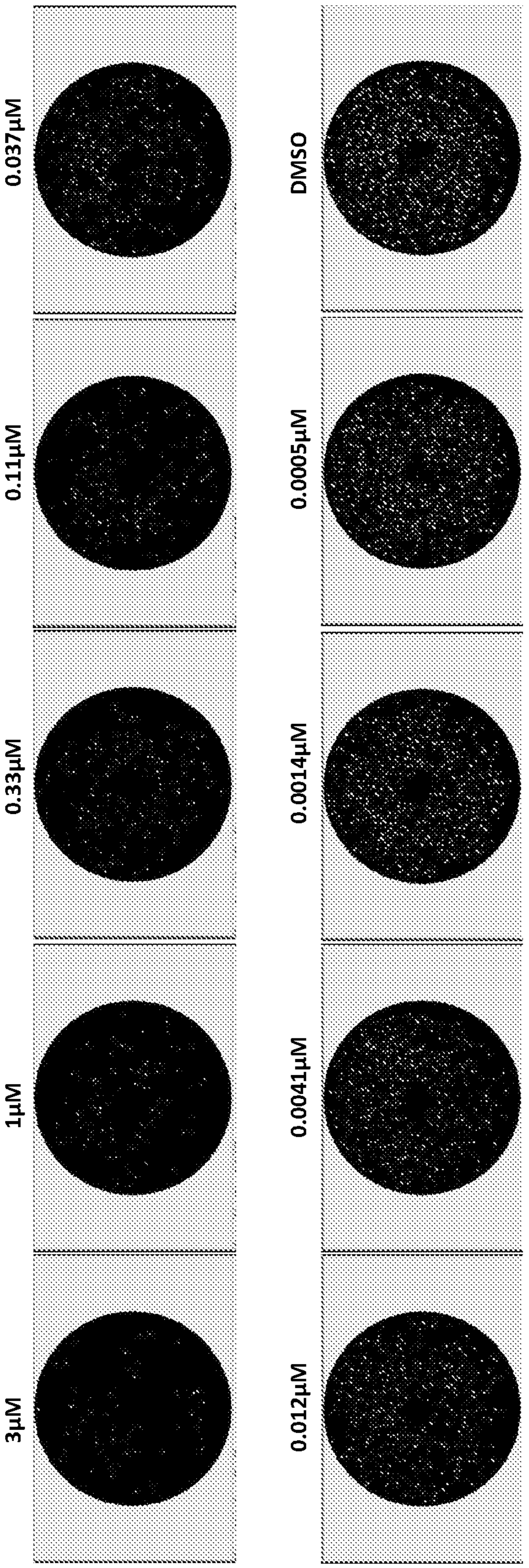
FIG. 5 shows soft agar assay of PKC activator ingenol-3-angelate (K102, also coded as K-102) in A549 lung cancer cells.
Figure 6:
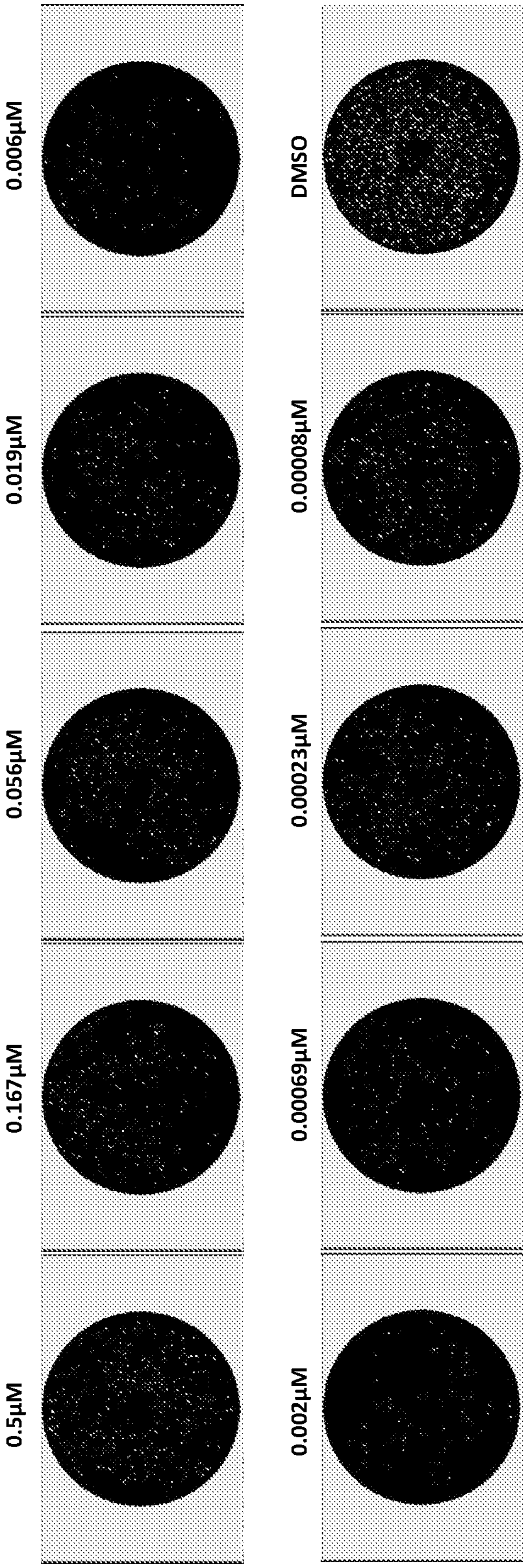
FIG. 6 shows soft agar assay of PKC activator PMA (K103, also coded as K-103) in A549 lung cancer cells.

Cancer cells (2-8 million cells) were seeded in 10 cm dishes and grown overnight. For A549 lung cancer cell line, about 3 million cells were seeded. Cells were then treated with different drugs at indicated concentrations (see Table 8) for a period of time up to 48 hours. Cells were lysed in 0.3-0.5 mL of RIPA buffer (Sigma) supplemented with protease inhibitors (Roche) and phosphatase inhibitors (Sigma). Lysates were assayed for protein concentration using BCA kit (Pierce). Normalized amount of lysates (20-30 μg protein/lane) were run on 4-12% NuPage gel (Life Technologies) and the proteins were transferred to the PVDF or nitrocellulose membrane using iBlot® Transfer Stack (Life Technologies). The membranes were probed with primary antibodies shown in Table 8 at 4° C. overnight after blocking with 1×TBST containing 5% non-fat milk. Antibodies from other vendors could also be used in Western blot analysis. After washing 5 times with 1×TBS containing 0.1% Tween20, the membranes were probed with $2^{nd}$ antibodies Anti-mouse IgG Dylight 800 conjugate or Anti-rabbit IgG DyLight 680 conjugate (1:10000; Cell signaling or similar IR $2^{nd}$ antibodies from different vendors) at room temperature for one hour. After washing 5 times, the membranes were scanned using Odyssey® Imaging System (Licor Biosciences). The results are shown in FIG. 1.

Treatment of A549 cells with K-101A resulted in dose-dependent reduction in the protein levels of the leukemia inhibitory factor (LIF) (lower band is the LIF and upper band is a non-specific band), a member of the IL-6 family. As expected, negative control compounds (Ref1 and Ref2) did not affect the levels of LIF. Interestingly, K-103, K-102, and K-101E also did not affect the levels of LIF at the concentrations tested. Since LIF has a well-established role in preventing stem-cell differentiation and maintaining stem cells in a pluripotent state and LIF is one of the major cytokines that activates STAT3 and other stem cell factors such as SOX2, NANOG, OCT3/4, thus, reduction in LIF by selected PKC activators can cause loss of stemness of treated cancer cells.

Treatment of A549 cells with PKC activators (K-103, K-102 at 0.5 μM, and K-101A at 2.5 μM) for 48 hours resulted in reduction of the phospho-PKC (pan) levels. This is consistent with the notion that chronic treatment of cells with TPA results in downregulation of PKC. However, it is worth noting that treatment with 0.5 uM of K-101A lowered the LIF protein level without affecting the phospho-PKC (pan) level.

TABLE 8

Compounds and their concentrations used in WB analysis

| No. | Compound ID | Concentration | DMSO final conc. |
|---|---|---|---|
| 1 | DMSO | 0.2% | 0.2% |
| 2 | K-101A | 0.1 μM | 0.2% |

TABLE 8-continued

| Compounds and their concentrations used in WB analysis | | | |
|---|---|---|---|
| No. | Compound ID | Concentration | DMSO final conc. |
| 3 | K-101A | 0.5 μM | 0.2% |
| 4 | K-101A | 2.5 μM | 0.2% |
| 5 | K-101E | 2.5 μM | 0.2% |
| 6 | K-102 | 0.1 μM | 0.2% |
| 7 | K-102 | 0.5 μM | 0.2% |
| 8 | K-103 | 0.01 μM | 0.2% |
| 9 | Ref1* | 1 μM | 0.2% |
| 10 | Ref2* | 0.01 μM | 0.2% |

*Ref1 and Ref2 are natural products unrelated to the PKC activators used in the present disclosure and do not display PKC activation activity. Ref1 and Ref2 are negative controls for PKC pathway activities.

The antibodies used to detect various PKC signaling elements are described in Table 9 below.

TABLE 9

| Primary antibodies used for Western blot analysis | | | | | |
|---|---|---|---|---|---|
| Antibody Name | Vendor | Cat No. | Species | MW | Dilution |
| GAPDH (loading control) | Millipore | MAB374 | Mouse | 37 kd | 1:10000 |
| β-Actin (loading control) | Sigma | A5441 | Mouse | 43 kd | 1:10000 |
| FZD8 | Abcam | ab75235 | Rabbit | ~73 kd | 1:500 |
| Phosph-CaMKii (Thr286) | Abcam | ab32678 | Rabbit | ~50 & 60 kd | 1:1000 |
| CaMKii | Abcam | ab52476 | Rabbit | ~50 & 60 kd | 1:1000 |
| Phospho-PKC (pan) | Cell signaling | 9371 | Rabbit | 78-85 kd | 1:1000 |
| LIF | Abcam | ab34427 | Mouse | 20 kD (~34 kd) | 1:500 |

Example 3: Soft Agar Assays

Soft agar colony formation is one of the hallmarks (anchorage-independent growth) of cancer cells. Three-dimensional (3D) assay models have been shown to have advantages over conventional two-dimensional (2D) monolayer assay models. Many drugs active in 2D model do not show efficacy in preclinical models or in clinical trials. Such 3D model represents a more biologically relevant system, bridging the gaps between the 2D assays with in vivo models.

To prepare the base agar layer (0.6%), melted 1.2% agar solution was mixed 1:1 (v/v) with 2×DMEM/20% FBS medium in a tube by inverting several times and 50 μL of the mixture was immediately transferred to a well in a 96-well flat-bottom microplate. The plate was placed at 4° C. for 30 minutes to allow the base agar layer to solidify. Then, the cell agar layer (agar 0.4%) was prepared by transferring 75 μL of the cell and agar mixture containing 1:1:1 (v/v/v) of 1.2% agar solution, 2×DMEM/20% FBS and cell suspension (0.4-4×$10^5$/mL) to each well of the plates so that each well contained 1000-10000 cells per well. The plates were placed at 4° C. for 15 minutes and then 75 μL of media were added to each well. After incubating the plates overnight in a $CO_2$ incubator, 50 μL of media with or without 5× final concentrations of compounds were added to each well. Each compound was tested in 9-point 3-fold dilution series. The plates were incubated for 7-10 days at 37° C. At the end of incubation period, 28 μL of Calcein AM solution (5 μM) was added to the center of each well. The plates were incubated at 37° C. for 45 minutes before scanning on Acumen (TTP Labtech). Each compound was tested in triplicates. Data was analyzed and compound EC50s were calculated using GraphPad Prism 5. The results are shown in FIGS. 2-6.

The results indicated that selected PKC activators (K101A, K101E, K102, and K103) reduced the number of colonies formed by A549 cells in a dose-dependent manner. Most potent compound in this assay was K103, followed by K102, K101A, and K101E. Reduction in colony formation in soft agar reflected loss of anchorage-independent growth.

Example 4: Activation of Global PKC and PKC Isoforms by Diterpenoid PKC Activators A549 lung cancer cells (~3 million cells) were seeded in 10 cm tissue culture dishes and grown overnight. Cells were then treated with different drugs at indicated concentrations (see FIG. 9A for global activation of PKC and FIG. 10 for activation of PKC isoforms) for 30 minutes. Panc2.13 pancreatic cells (~5 million) were seeded and treated as in FIG. 9B for global activation of PKC. Cell lysate preparation, protein quantitation, SDS-PAGE, and Western blotting procedures are described in Example 2. Primary antibodies used in this Example and later Examples of this application are shown in Table A. Western blot membranes were scanned using Odyssey® Imaging System (Licor Biosciences) if secondary antibodies Anti-mouse IgG Dylight 800 conjugate or Anti-rabbit IgG DyLight 680 conjugate (1:10000)(Cell signaling or similar IR $2^{nd}$ antibodies from different vendors) were used. Alternatively, Imagequant LAS4000 (GE) was used to scan membranes if secondary antibodies Anti-mouse IgG HRP conjugate or Anti-rabbit IgG HRP conjugate (dilutions from 1:2000-1:10000) were used. The results are shown in FIG. 9 and FIG. 10.

Prostratin (K101A) and ingenol-3-angelate (K102) induced dose-dependent phosphorylation of PKC substrates in A549 cells (probed with Phospho-PKC substrate Motif [(R/KXpSX(R/K)] MultiMab™; FIG. 9A) and in Panc2.13 cells (probed with Phospho-(Ser) PKC Substrate Antibody; FIG. 9B). Phosphorylation levels of PKC substrates reflect the extent of the total/global activation of PKC. K103 potently elevated the levels of phosphorylated PKC substrates in both cell lines whereas K101E, a much less potent analog of K-101A, had nearly no effect. Two reference compounds (Ref1 and Ref2), which are unrelated to PKC activators, had no effect at all on global activation of PKC. Therefore, Phospho-PKC substrate Motif [(R/KXpSX(R/K)] MultiMab™ and Phospho-(Ser) PKC Substrate Antibody can be used to monitor the total activation of PKC in cells.

Treatment of A549 cells with K101A and K102 resulted in dose-dependent increases in P-PKCδ (Thr505) and P-PKCδ/θ (Ser643/676). Phosphorylation of these sites has been linked to acute activation of these PKC isoforms. K103 also potently increased phosphorylation of these PKC isoforms whereas K101E had no effects. In contrast, high levels of P-PKC (pan)(βII Ser660), as detected by a phospho-PKC antibody that recognizes a number of phosphorylated isoforms of PKC, and P-PKCα/β (Thr638/641), as detected by a phospho-PKC antibody that recognizes PKCα and β when Thr638/641 are phosphorylated, were present in DMSO treated cells; no further increases of these phosphorylated isoforms of PKC were observed upon treatment of K101A, K102, or K103. Thus, P-PKCδ (Thr505) and P-PKCδ/θ

(Ser643/676) antibodies are very useful for monitoring PKC isoform specific phosphorylation and activation.

Example 5: Activation of PKC Isoforms in Non-Cancerous Cells, and PKC Activator Sensitive and Resistant Cancer Cells Non-cancerous lung fibroblast cell line HFL-1 or cancer cells (2-8 million cells) were seeded in 10 cm dishes and grown overnight so that the cells were about 40-80% confluent before treatment with the compound. Cells were then treated with different drugs at indicated concentrations (see descriptions for FIG. 11 and FIG. 12) for 30 minutes. Cell lysate preparation, protein quantitation, SDS-PAGE, and Western blotting procedures are described in Example 2 and 4. Primary antibodies used in this Example and later Examples of this application are shown in Table A. Secondary antibodies Anti-mouse IgG HRP conjugate or Anti-rabbit IgG HRP conjugate (dilutions from 1:2000-1:10000) were used. Western blot membranes were scanned using Imagequant LAS4000 (GE). The results are shown in FIG. 11A and FIG. 11B for HFL-1 cells and FIG. 11C and FIG. 12 for A549 cells.

In non-cancerous lung fibroblast HFL-1 cells, treatment of K101A and K102 resulted in phosphorylation of PKC isoforms PKCμ at both Ser916 and Ser744/748, and PKCδ at Thr505 and Tyr311. PKCμ activation with PKC activators K101A, K102, or K103 was observed for all four cancer cell lines, as assessed by detecting phosphorylation at Ser744/748 while PKCμ activation was observed primarily in cell lines A549 and Panc02.13 cells when assessed by detecting phosphorylation at Ser916. PKCδ activation by K101A, K102, or K103 was observed for cell lines HCT116 and SW620 but not as significantly for cell lines A549 and Panc02.13 when assessed by detecting phosphorylation at Tyr311. Phosphorylation of PKCδ at Tyr311 has been indicated as a redox/src-activated site (Newton et al., 2016, Clin Sci (Lond). 130(17): 1499-1510). HCT116 and SW620 are insensitive while A549 and Panc02.13 are sensitive to the anti-cell proliferative effects of K101A, K102, or K103. Interestingly, phosphorylation of PKCμ at Ser916 appears to correlate with the anti-proliferation effects while phosphorylation of PKCδ at Tyr311 appears to inversely correlate with the anti-proliferation effects of the PKC activator compounds.

Example 6: Activation of PKC Isoforms in Pancreatic Cancer Cell Lines

Cells from four pancreatic cancer cell lines xMiaPaCa-2 (a variant of MiaPaCa-2 passaged through immune-compromised mice), MiaPaCa-2, Panc6.03, and Pane 1 (FIG. 13A), as well as mouse bladder cancer line MBT-2 and mouse hepatoma cell line MH22A (FIG. 13B) were seeded, treated with DMSO, K101A (1 μM), or K102 (0.1 μM), and processed for Western blot analysis as described above in Examples 2 and 5.

The results indicate that both diterpenoid PKC activators K101A or K102 increased phosphorylations of PKCδ at Thr505 and PKCμ at Ser744/748 in all four pancreatic cell lines. The degree of phosphorylation of PKCμ at Ser916 induced by these PKC activators in four pancreatic cell lines is ordered as follows (from most to least): Panc1>Panc2.13>MiaPaCa-2>xMiaPaCa-2. This order is roughly correlated with the sensitivity of these cell lines in proliferation assays. Interestingly, xMiaPaCa-2, less sensitive to proliferation inhibition by K-101A or K-102 compared to MiaPaCa-2, induced robust phosphorylation of PKCδ at Tyr311. As expected, K101A and K102 induced phosphorylation of c-Raf at Ser338 (Zang et al., 2008, J Biol Chem. 283(46):31429-37). In mouse bladder cell line MBT-2, treatment of K101A and K102 induced phosphorylations of various PKC isoforms, e.g. PKCδ at Thr505, PKCμ at Ser744/748, and PKCμ at Ser916, and phosphorylation of c-Raf at Ser338. In mouse liver cancer cell line MH22A, basal phosphorylation levels of PKCδ at Thr505, PKCμ at Ser744/748, PKCμ at Ser916, and c-Raf at Ser338 were high and treatment of K101A or K102 did not induce further phosphorylation of these proteins. MH22A is insensitive while MBT-2 is sensitive to the anti-cell proliferative effects of K101A and K102.

Example 7: Time Course of Activation of PKC Isoforms by Diterpenoid PKC Activators Cells of pancreatic cancer cell line Panc2.13 were seeded as described above, and the cell confluence was between 40-80% the next day. Cells were treated with K101A (1 μM), K102 (0.1 μM) and K103 (0.01 μM) for 30', 2 h, 6 h (FIG. 14A) and for 30', 16 h, and 24 h (FIG. 14B). Phosphorylation at multiple PKC isoforms, such as Ser744/748 or Ser916 for PKCμ, phosphorylation at Thr638/641 for PKCα/β, phosphorylation at Ser660 for PKCβII (pan-PKC), phosphorylation at Ser643/676 for PKCδ/θ, and phosphorylation at Thr505 for PKCδ, were detected. Extended activation by the diterpenoid PKC activators are observed for PKCδ (via both phosphorylation sites). However, phosphorylation of PKCδ at Thr505 was transient and subsided after 2 h. Treatment with diterpenoid PKC activators for extended periods (16 h and 24 h) resulted in loss of basal phosphorylation levels of PKCα/β at Thr638/641, pan-PKCβII at Ser660, and PKCδ/θ at Ser643/676. It is known that TPA displays biphasic effects on PKCs in concentration and time-dependent manner and can down-regulate various PKC isoforms upon treatment for extended periods. While K101A is more potent in reducing the phosphorylation at Ser643/676 of PKCδ/θ, K102 and K103 (TPA or PMA) are more potent in reducing the phosphorylation at βII Ser660 of PKC (pan) and to a lesser extent, phosphorylation at Thr638/641 of PKCα/β. Literature reports that TPA is tumor-promoting while prostratin is non-tumor-promoting.

Example 8: Effect of Broad Spectrum PKC Inhibitor on PKC Activator Inhibition of Lung Cancer and Pancreatic Cancer Cell Proliferation To assess if activation of different classes of PKC is required for anti-proliferation effect of PKC activators, Sotrastaurin, a PKC inhibitor targeting both conventional and novel classes of PKC, was tested in combination with PKC activators in the proliferation assays. Proliferation assay in lung cancer cell line A549 (FIG. 15) and in pancreatic cell line MiaPaCa-2 (FIG. 16) was performed as described in Example 1. Sotrastaurin was first tested alone in 9-point serial dilutions to identify concentration range where Sotrastaurin has minimal effects on proliferation. Then, K101A or K102 was tested in 8- or 9-point titrations in the presence of DMSO or Sotrastaurin (0.1 μM or 1 μM). The results showed that Sotrastaurin (1 μM) completely abolished the PKC activator-mediated anti-proliferation effects in both cell lines. Thus, PKC activator-mediated anti-proliferation effects are dependent on activation of PKC isoforms from conventional, or novel, or both classes of PKCs.

Example 9: Effect of Broad Pan PKC Inhibitor Go6983 on PKC Activator Inhibition of Lung Cancer and Pancreatic Cancer Cell Proliferation To assess if PKC activation is required for anti-proliferation effect of PKC activators in cancer cell lines that are sensitive to these activators, a pan-PKC inhibitor Go6983, targeting classes of PKCs (conventional, novel, atypical, and PKCμ), was tested in combination with PKC activators in the proliferation assays. Proliferation assay in lung cancer cell line A549 (FIG. 17) and in pancreatic cell line MiaPaCa-2 (FIG. 18) was performed as described in Example 1. Go6983 was first tested in 9-point serial dilutions to identify concentration range where it has minimal effects on proliferation alone. Then, K101A or K102 was tested in 8- or 9-point titrations in the presence of DMSO or Go6983 (0.1 μM or 1 μM). The results showed that Go6983 inhibited the PKC activator-mediated anti-proliferation effects in a dose-dependent manner in both cell lines. Thus, PKC activation is required for anti-proliferation effect of PKC activators.

Example 10: Effect of Different PKC Inhibitors on PKC Activator Inhibition of Lung Cancer and Pancreatic Cancer Cell Proliferation To further assess which classes of PKC are required for anti-proliferation effect of PKC activators, PKC inhibitors targeting mainly the conventional PKCs, such as Go6976 (PKCα & β inhibitor; Ki 2.3-6.2 nM) (FIG. 19), GF109203X (PKCα, β, & γ inhibitor; Ki ~20 nM) (FIG. 20), or Enzastaurin (PKCα, β, γ inhibitor; Ki 6-83 nM and PKCε inhibitor; Ki 110 nM) (FIG. 21), were tested in combination with PKC activators in the proliferation assays using the A549 lung cancer cell line. Proliferation assay was performed as described in Example 1. All three PKC inhibitors were first tested alone in 9-point serial dilutions to identify concentration range having minimal effects on proliferation. Then, K101A was tested in serial titrations in the presence of DMSO or Go6976 (0.1 μM or 0.3 μM), or GF109203X (0.3 μM or 1 μM), or Enzastaurin (0.3 μM or 1 μM). The results showed that these inhibitors of conventional PKCs had minimal effects on the PKC activator-mediated proliferation inhibition. Slight inhibition of K101A anti-proliferative effects observed with higher concentrations of GF109203X or Enzastaurin may due to inhibition of novel PKC isoforms. Thus, PKC activator-mediated anti-proliferation effects appear mainly dependent on activation of novel PKC isoforms.

Example 11: Effect of PKC Inhibitor on PKC Activator-Mediated Phosphorylation of PKC Enzymes and Erk1/2

To assay if PKC inhibitors have any effects on the PKC activator-mediated phosphorylation of PKCs, A549 cells were pre-treated with DMSO, PKC inhibitors Go6983 (0.3 μM or 1 μM) or Sotrastaurin (0.3 μM or 1 μM) for 30 minutes before adding PKC activators K101A (1 μM) or K102 (0.1 μM) for another 30 minutes (FIG. 22). Cell lysis, protein quantitation, and Western blot analysis were performed as described above in Example 2 and 4. K101A- or K102-induced phosphorylation of various PKC isoforms detected using phospho-antibodies P-PKCμ (Ser916), P-PKCμ (Ser744/748), or P-PKCδ (Thr505) was blocked in a dose-dependent manner by the pre-treatment of both inhibitors. Phosphorylation of PKCα/β at Thr638/641 was not affected by the inhibitors (FIG. 22A). Interestingly, K101A- and K102-induced phosphorylation of Erk1/2 was also blocked dose-dependently by the pre-treatment of both inhibitors (FIG. 22B). These PKC inhibitor studies indicate that blocking phosphorylation and activation of various isoforms of PKC is correlated with inhibition of the anti-proliferative effects of the PKC activators.

Example 12: Effect of PKC Inhibitor on PKC Activator-Mediated Phosphorylation of PKC Enzymes To determine which PKC inhibitors have effects on the PKC activator-mediated phosphorylation of PKCs, A549 cells were pre-treated with 1 μM of a pan-PKC inhibitor Go6983, a conventional and novel (broad-spectrum) PKC inhibitor Sotrastaurin, or conventional PKC inhibitors GF109203X, Enzastaurin, or Go6976 for 30 minutes before adding PKC activators K101A (1 μM) or K102 (0.1 μM) for another 30 minutes (FIG. 23). Cell lysis, protein quantitation, and Western blot analysis were performed as described above in Example 2 and 4. Pre-treatment of the cells with pan- or broad-spectrum PKC inhibitors completely abolished prostratin (K101A) or ingenol-3-angelate (K102)-induced phosphorylation of PKCμ at Ser916 or Ser744/748, PKCδ at Thr505, and the downstream target Erk. Interestingly, these PKC inhibitors induced phosphorylation of PKCδ at Tyr311. In contrast, pre-treatment with Go6976 and two other conventional PKC inhibitors had minimal effects on the K101A- or K102-induced phosphorylation of PKCμ at Ser916 or Ser744/748, PKCδ at Thr505, and the downstream target Erk. Go6976, which had no inhibition on the anti-proliferative effects of PKC activators, induced no phosphorylation of PKCδ at Tyr311. GF109203X and Enzastaurin, which had weak inhibition on the anti-proliferative effects of PKC activators, induced phosphorylation of PKCδ at Tyr311 partially. These PKC inhibitor studies also indicate that phosphorylation and activation of novel PKC isoforms and PKCμ is required for the anti-proliferative effects of the PKC activators whereas phosphorylation of PKCδ at Tyr311 is correlated with inhibition of the anti-proliferative effects of PKC activators.

Example 13: Inhibitory Effect of Diterpenoid PKC Activators on Different Cancer Cell Lines Cancer cell lines (161 different lines) from various cancer types, such as bladder, brain, breast, cervical, colon, duodenal, esophageal, gastric, head and neck, leukemia, liver, lung (NSCLC), lung (SCLC), lymphoma, melanoma, myeloma, ovarian, pancreatic, prostate, renal, sarcoma, and skin cancers, were screened with prostratin (K-101A) in proliferation assays as described in Example 1 with slight modifications. Cells were treated for 72 hours instead of 96 hours. Thus, cell numbers from individual cell line were optimized so that cells were ~70-80% confluent in 72 hours when treated with vehicle only. The results are shown in FIGS. 24A, B and C. Roughly 50% of the cell lines (83 out 161) showed top inhibition above 30% while ~25% of the cell lines showed top inhibition above 50%. Cell lines from pancreatic cancer (5 out 6 lines having a top inhibition above 30%), leukemia (10 out of 11), lymphoma (13 out 16), and lung cancer (NSCLC) (16 out 26) are the most sensitive to K-101A. Cell lines from breast (9 out of 18) and colon (5 out 19) cancers are moderately sensitive to K-101A. A number of other cancer cell lines from bladder, ovarian, myeloma, prostrate, and renal cancers are also sensitive to K-101A. Most cell lines from liver and lung (SCLC) are resistant to K101A.

Example 14: Inhibition of Lymphoma Cell Growth by Diterpenoid PKC Activators PKC activators were tested in 9 lymphoma cell lines (Table 10). Proliferation assays were performed as described in Example 1. Seven lymphoma cell lines were very sensitive to prostratin (K101A) and ingenol-3-angelate (K102) whereas two lymphoma cell lines (Daudi and Raji) were not sensitive. Responses of two sensitive cell lines, NAMALWA and Mino, and two resistant cells lines, Raji and Daudi are shown in FIG. 25A and FIG. 25B. Among the sensitive lines, $IC_{50}$ ranges for K101A are 0.077-0.284 μM while those for K102 are 0.0008-0.005 μM. It is worth noting that top inhibition by K101A or K102 reached 80-95% in certain lymphoma cell lines (e.g., SU-DHL-2, Z138, Mino, and NAMALWA), indicating the PKC activators may induce apoptosis or differentiation in addition to proliferation inhibition.

TABLE 10

| | |
|---|---|
| SU-DHL-2 | Large cell lymphoma; diffuse histiocytic lymphoma |
| Farage | Non-Hodgkin's B cell lymphoma |
| DoHH-2 | Non-Hodgkin's B cell lymphoma |
| Z-138 | Mantel cell lymphoma (B cell non-Hodgkin's lymphoma) |
| Daudi | Burkitt's lymphoma |
| Mino | Mantel cell lymphoma (B cell non-Hodgkin's lymphoma) |
| NAMALWA | Burkitt's lymphoma |
| Raji | Burkitt's lymphoma |
| U937 | histiocytic lymphoma; myeloid |

To study activation of PKC isoforms, four lymphoma cell lines were treated with DMSO or 1 μM K101A for 30 minutes. Western blot analysis was performed as described in Example 2 and 4. As shown in FIG. 25C, phosphorylation of PKCμ at Ser744/748 and Ser916 and PKCδ at Thr505 was induced in all cell lines by K101A, however, proportion of phosphorylated PKCμ at Ser916/total PKCμ was much greater in two sensitive cell lines (NAMALMA and Mino) than in two insensitive cell lines (Raji and Daudi). In addition, the levels of phospho-PKCδ (Tyr311) were much higher in two insensitive cell lines than in sensitive cell lines (both untreated or K101A treated conditions). It appears that phosphorylation of PKCμ at Ser916 may be associated with sensitivity to K101A whereas phosphorylation of PKCδ at Tyr311 may be associated with insensitivity.

Example 15: Effect of PKC Inhibitors on PKC Activator Inhibition of Lymphoma Mino Cell Proliferation PKC inhibitor studies were performed as described in Example 8, 9, and 10. PKC inhibitors were first tested alone in 9-point serial dilutions to identify concentration range with minimal effects on proliferation. To assess if activation of different classes of PKC is required for anti-proliferation effect of PKC activators in Mino cells, various PKC inhibitors, i.e., Sotrastaurin (0.3 μM and 1 μM), Go6983 (0.1 μM and 1 μM), Go6976 (0.3 μM and 1 μM), and Enzastaurin (1 μM and 3 μM), were tested in combination with PKC activators in the proliferation assays. The results showed that two broad-spectrum PKC inhibitors Sotrastaurin (FIG. 26) and Go6983 (FIG. 27) dose-dependently blocked the PKC activator-mediated anti-proliferation effects, whereas Go6976 (FIG. 28), a conventional PKC inhibitor, did not block, and Enzastaurin (FIG. 29), a potent conventional PKC inhibitor and a weak PKCε inhibitor, partially blocked the PKC activator-mediated anti-proliferative effects. Thus, PKC activator-mediated anti-proliferation effects may be dependent on activation of PKC isoforms from the novel PKC class.

Example 16: Effect of PKC Inhibitors on PKC Activator Inhibition of Lymphoma Namalwa Cell Proliferation PKC inhibitor studies were performed as described in Example 15. PKC inhibitors were first tested alone in 9-point serial dilutions to identify concentration range with minimal effects on proliferation. To assess if activation of different classes of PKC is required for anti-proliferation effect of PKC activators in Namalwa cells, various PKC inhibitors, i.e., Sotrastaurin (0.3 μM and 1 μM), Go6983 (0.1 μM and 1 μM), Go6976 (0.3 μM and 1 μM), and Enzastaurin (3 μM and 10 μM), were tested in combination with PKC activators in the proliferation assays. The results showed that two broad-spectrum PKC inhibitors Sotrastaurin (FIG. 30) and Go6983 (FIG. 31) dose-dependently blocked the PKC activator-mediated anti-proliferation effects, whereas Go6976 (FIG. 32), a conventional PKC inhibitor, did not block, and Enzastaurin (FIG. 32), a potent conventional PKC inhibitor and a weak PKCε inhibitor, marginally blocked the PKC activator-mediated anti-proliferative effects at very high concentration of 10 μM. Thus, PKC activator-mediated anti-proliferation effects may be dependent on activation of novel PKC isoforms.

Example 17: Effect of PKC Inhibitor on PKC Activator-Mediated Phosphorylation of PKC Enzymes and Erk1/2 in Lymphoid Cancer Cell Lines To determine if PKC inhibitors have effects on the PKC activator-mediated phosphorylation of PKCs and downstream target Erk1/2, Mino cells were pre-treated with DMSO, Sotrastaurin (0.3 μM and 1 μM), Go6983 (0.1 μM and 1 μM), Go6976 (0.3 μM and 1 μM), or Enzastaurin (1 μM and 3 μM) for 30 minutes before adding prostratin (K-101A) (1 μM) for another 30 minutes (FIG. 34A). Namalwa cells were pre-treated similarly as described above for Mino cells except that higher concentrations of Enzastaurin (3 μM and 10 μM) were used (FIG. 34B). Cell lysis, protein quantitation, and Western blot analysis were performed as described above in Example 2 and 4. Pre-treatment with 1 μM of pan- or broad-spectrum PKC inhibitor Go6983 or Sotrastaurin completely abolished K101A-induced phosphorylation of PKCμ at Ser916 or Ser744/748, PKCδ at Thr505, and phosphorylation of the downstream target Erk. Interestingly, these PKC inhibitors induced robust phosphorylation of PKCδ at Tyr311. In contrast, pre-treatment with Go6976, an inhibitor of conventional PKCs, had little effect on the K101A-induced phosphorylation of PKCμ at Ser916 or Ser744/748, PKCδ at Thr505, and Erk1/2. It did not induce phosphorylation of PKCδ at Tyr311. Enzastaurin, which partially inhibits the anti-proliferative effects of PKC activators, induced moderate phosphorylation of PKCδ at Tyr311. Again, these PKC inhibitor studies indicate the anti-proliferative effects of the PKC activators appear to be positively associated with phosphorylation and activation of novel PKC isoforms and PKCγ, and negatively associated with the phosphorylation of PKCδ at Tyr311.

Example 18: Effect of Diterpenoid PKC Activators on CaMKii Phosphorylation in Pancreatic Cancer Cell Lines Panc1 or Panc2.13 cells (~5-8 millions) were seeded in 10 cm dishes and were treated next day with prostratin (K-101A) (0.5 μM and 2.5 μM) or ingenol-3-angelate (K-102) (0.1 μM and 0.5 μM) for 24 hours or 48 hours. Cells were lysed in a protein lysis buffer (1 ml of 10×TNE [20 mL 1M Tris pH7.5; 30 mL 5M NaCl; 2 mL 0.5M EDTA; 48 mL $d2H_2O$], 1 ml of 10% NP40, 7.7 mL of $dH_2O$, 100 μL of 10× Protease inhibitors, 100 μL of 10× Phosphatase inhibitors, and 10 μl DTT). Protein quantification, SDS-PAGE, and Western blot procedures were performed as described in Example 2. As shown in FIG. 35, both K-101A and K-102 induced phosphorylation on CaMKii at Thr286. The effect was more apparent at 48 hours. Phospho-CaMKii (T286) is a marker for activation of CaMKii kinase in the Wnt/$Ca^{2+}$ signaling pathway when K-Ras and CaM are dissociated (Wang et al., 2015, Cell. 163(5):1237-51). This result indicate that PKC activators may activate CaMKii through disruption of the interaction between K-Ras and CaM and that the phospho-specific antibody of CaMKii can be used as a marker to monitor the effects of PKC activators.

Example 19: Effect of Diterpenoid PKC Activators on Wnt Signaling

A549 cells (20K cells/well) were seeded in 96-well plates on Day 1. Cells were transfected with a mixture of TOPFlash firefly luciferase reporter plasmid M50 (300 ng/well) (Addgene) and an internal control plasmid pRL-TK-Renilla luciferase (20 ng/well) (Promega) using FuGene transfection reagent (plasmid:FuGene=1:4) (Promega) on Day 2. After overnight incubation, transfected cells were treated with DMSO, prostratin (K101A) (1 μM, 3 μM, and 10 μM) or ingenol-3-angelate (K102) (0.03 μM, 0.1 μM, and 0.3 μM) for 24 hours. Luciferase activities in treated cells were measured using Dual-Glo Luciferase Kit according to manufacturer's instructions (Promega) on Envision (Perkin Elmer). TOPFlash has been used as a reporter for activation of Wnt signaling pathway. As shown in FIG. 36, K-101A and K-102 inhibited TOPFlash activity at all doses tested with the maximal inhibition about 60%. It has been reported that PKC activators, via suppression of K-Ras stemness pathway, can block canonical Wnt signaling in pancreatic cancer cells. The data here indicate that PKC activator can also block canonical Wnt signaling in lung cancer cells.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating a patient with cancer, comprising: treating cancer cells of a patient with a diterpenoid protein kinase C (PKC) activator, determining phosphorylation status of one or more human PKC proteins, identifying the cancer having cancer cells that have increased phosphorylation of the one or more human PKC proteins following treatment with the diterpenoid PKC activator, and administering to the patient with the identified cancer a therapeutically effective amount of the diterpenoid PKC activator, wherein the one or more of human PKC proteins is selected from the group consisting of PKCδ, PKCε, PKCη, PKCθ and PKCμ and the cancer is selected from the group consisting of bladder cancer, breast cancer, cervical cancer, colorectal cancer, esophageal cancer, gastric cancer, head and neck cancer, leukemia, liver cancer, non-small cell lung cancer, lymphoma, skin cancer, melanoma, myeloma, ovarian cancer, pancreatic cancer, prostate cancer, and renal cancer, and wherein the diterpenoid PKC activator is a compound of structural formula (III):

(III)

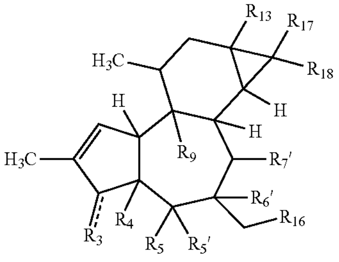

or an enantiomer, hydrate, solvate, or pharmaceutically acceptable salt thereof, wherein $R_3$ is O, S or N double bonded to the ring carbon, or $R_3$ is-$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_5$' and $R_6$' are H, or $R_5$' and $R_6$' together form a bond or are bonded to a common oxygen atom to form an epoxide;

$R_6$' and $R_7$' are H, or $R_6$' and $R_7$' together form a bond or are bonded to a common oxygen atom to form an epoxide;

$R_9$ is H or -$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or -$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{16}$ is H, halo, or -O-$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an -OH group—at the C20 carbon atom; and $R_{17}$ and $R_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, phosphine, phosphate, phosphoramide, phosphoramidite, phosphoramidate, phosphonate, sulfate, sulfonate, sulfonamide, sulfone, sulfite, amide, guanidine, urea, or a progroup which is hydrolyzable under biological conditions to yield an -alkyl-OH group.

2. The method of claim 1, wherein the cancer is selected for treatment based on phosphorylation status of PKCδ or PKCμ.

3. The method of claim 2, wherein the one or more human PKC proteins is PKCμ, wherein the increased phosphorylation is at amino acid position Ser910, and wherein the cancer identified as having an increase in phosphorylation at amino acid position Ser910 in presence of the diterpenoid PKC activator is selected for treatment.

4. The method of claim 2, wherein the cancer is selected for treatment based on phosphorylation status of PKCμ at amino acid position Ser738 and/or Ser742, wherein the cancer identified as having an increase in phosphorylation at amino acid position Ser738 and/or Ser742 in presence of the diterpenoid PKC activator is selected for treatment.

5. The method of claim 2, wherein the cancer is selected for treatment based on phosphorylation status of PKCδ at amino acid position Thr507, wherein the cancer identified as having an increase in phosphorylation at amino acid position Thr507 in presence of the diterpenoid PKC activator is selected for treatment.

6. The method of claim 1, wherein the cancer selected for treatment is further identified as having an oncogenic or activating K-ras and/or N-ras mutation.

7. The method of claim 1, wherein the PKC activator comprises a compound of formula (IIIa) or (IIIb):

(IIIa)

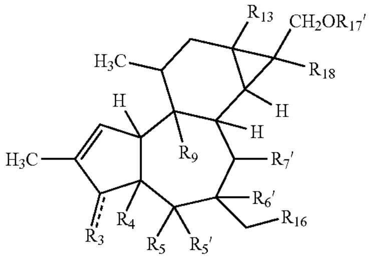

or (IIIb)

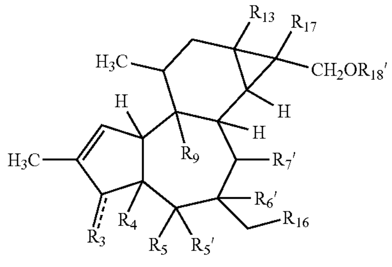

or an enantiomer, hydrate, solvate, or pharmaceutically acceptable salt thereof, wherein $R_3$; $R_4$, $R_5$, $R_5'$, $R_6'$, $R_7'$, $R_9$, $R_{13}$, and $R_{16}$ are as defined for formula (III);

$R_{17}$ or $R_{18}$ is H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted aryloxy, optionally substituted arylalkyloxy, phosphine, phosphate, phosphoramide, phosphoramidite, phosphoramidate, phosphonate, sulfate, sulfonate, sulfonamide, sulfone, sulfite, amide, guanidine, or urea; and $R_{17}$' or $R_{18}$' is H, optionally substituted alkyl, optionally substituted cycloalkyl, optionally substituted heteroalkyl, optionally substituted aryl, optionally substituted heteroaryl, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a progroup which is hydrolyzable under biological conditions to yield an -OH group.

8. The method of claim 1, wherein the PKC activator comprises a compound of formula (IIIc):

(IIIc)

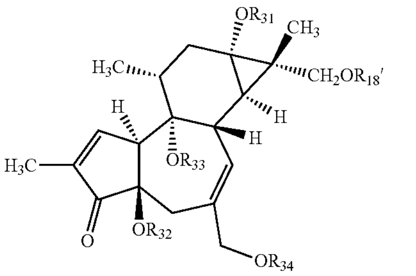

or an enantiomer, hydrate, solvate, or pharmaceutically acceptable salt thereof, wherein, $R_{18}$' is H, optionally substituted alkyl, optionally substituted cycloalkyl, optionally substituted heteroalkyl, optionally substituted aryl, optionally substituted heteroaryl, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an -OH group;

$R_{31}$, $R_{32}$, and $R_{33}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{34}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{34}$ is a promoiety which is hydrolyzable under biological conditions to yield an -OH group—at the C20 carbon atom.

9. The method of claim 1, wherein the PKC activator comprises a compound of formula (IIId):

(IIId)

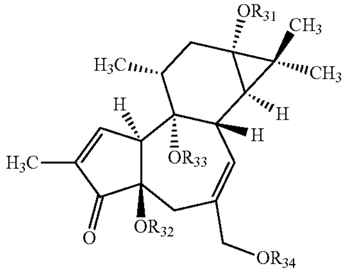

or an enantiomer, hydrate, solvate, or pharmaceutically acceptable salt thereof, wherein $R_{31}$, $R_{32}$, and $R_{33}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{34}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{34}$ is a promoiety which is hydrolyzable under biological conditions to yield an -OH group—at the C20 carbon atom.

10. The method of claim 1, the PKC activator comprises a compound of formula (IIIe):

(IIIe)

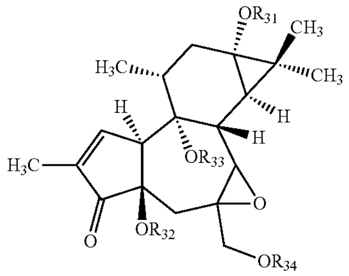

or an enantiomer, hydrate, solvate, or pharmaceutically acceptable salt thereof, wherein, $R_{31}$, $R_{32}$, $R_{33}$, and $R_{34}$ are as defined for formula (IIIc).

11. The method of claim 1, wherein the cancer is bladder cancer, breast cancer, cervical cancer, colorectal cancer, esophageal cancer, gastric cancer, head and neck cancer, liver cancer, non-small cell lung cancer, skin cancer, melanoma, ovarian cancer, pancreatic cancer, prostate cancer, or renal cancer.

12. The method of claim 1, wherein the cancer is pancreatic cancer.

13. The method of claim 1, wherein the cancer is breast cancer.

14. The method of claim 1, wherein the cancer is colorectal cancer.

15. The method of claim 1, wherein the cancer is non-small cell lung cancer.

16. The method of claim 1, wherein the cancer is prostate cancer.

17. The method of claim 1, wherein the cancer is head and neck cancer.

18. The method of claim 1, wherein the cancer is skin cancer.

19. The method of claim 1, wherein the cancer is melanoma.

20. The method of claim 1, wherein the cancer is leukemia, lymphoma, or myeloma.

21. The method of claim 1, wherein the treatment of the cancer with the compound of formula (III) is conducted on a biological sample of the cancer obtained from the patient.

* * * * *